US012297194B2

(12) United States Patent
Kim et al.

(10) Patent No.: US 12,297,194 B2
(45) Date of Patent: May 13, 2025

(54) N2-PHENYLPYRIMIDINE-2,4-DIAMINE COMPOUNDS, AND PREPARATION METHODS AND METHODS OF USE THEREOF

(71) Applicant: BRIDGE BIOTHERAPEUTICS, INC., Seongnam-si (KR)

(72) Inventors: Chulwon Kim, Seongnam-si (KR); Koo Lee, Yongin-si (KR); GwangHee Lee, Seongnam-si (KR); Taiguang Jin, Wallesley, MA (US); Yong-Hee Lee, Flemington, NJ (US); Jeong-Hyun Ryou, Seongnam-si (KR); Jehrod Brenneman, Newton, MA (US); Sang Uk Kang, Seongnam-si (KR)

(73) Assignee: BRIDGE BIOTHERAPEUTICS, INC., Seongnam-si (KR)

( * ) Notice: Subject to any disclaimer, the term of this patent is extended or adjusted under 35 U.S.C. 154(b) by 0 days.

(21) Appl. No.: 17/710,050

(22) Filed: Mar. 31, 2022

(65) Prior Publication Data

US 2022/0332711 A1    Oct. 20, 2022

Related U.S. Application Data

(60) Provisional application No. 63/170,098, filed on Apr. 2, 2021.

(51) Int. Cl.
| | |
|---|---|
| C07D 413/14 | (2006.01) |
| A61K 45/06 | (2006.01) |
| C07D 401/14 | (2006.01) |
| C07D 403/12 | (2006.01) |
| C07D 487/10 | (2006.01) |
| C07D 487/18 | (2006.01) |

(52) U.S. Cl.
CPC .......... *C07D 413/14* (2013.01); *A61K 45/06* (2013.01); *C07D 401/14* (2013.01); *C07D 403/12* (2013.01); *C07D 487/10* (2013.01); *C07D 487/18* (2013.01)

(58) Field of Classification Search
CPC ............. C07D 413/14; C07D 401/14; C07D 403/12; C07D 487/10; C07D 487/18; A61K 45/06; A61K 31/506; A61K 31/5377
See application file for complete search history.

(56) References Cited

U.S. PATENT DOCUMENTS

| | | | |
|---|---|---|---|
| 7,947,698 B2 | 5/2011 | Atuegbu et al. | |
| 10,781,218 B2 | 9/2020 | Wu et al. | |
| 2011/0098288 A1 | 4/2011 | Major et al. | |
| 2011/0130401 A1 | 6/2011 | Sapountzis et al. | |
| 2020/0179384 A1 | 6/2020 | Lee et al. | |
| 2020/0207768 A1 | 7/2020 | Wu et al. | |
| 2021/0330669 A1 | 10/2021 | Yang et al. | |

FOREIGN PATENT DOCUMENTS

| | | | | |
|---|---|---|---|---|
| CN | 202010450437 | * | 5/2020 | ........... C07D 413/12 |
| CN | 202110524157.4 | * | 5/2021 | ........... C07D 413/12 |
| CN | 202110901100.1 | * | 8/2021 | ........... C07D 405/12 |
| KR | 10-2019-0114910 A | | 10/2019 | |
| WO | 2005/016894 A1 | | 2/2005 | |
| WO | 2009/112490 A1 | | 9/2009 | |
| WO | 2017/041771 A1 | | 3/2017 | |
| WO | 2018/230934 A1 | | 12/2018 | |
| WO | 2019/015655 A1 | | 1/2019 | |
| WO | 2019/112344 A1 | | 6/2019 | |
| WO | WO 2019/190259 A1 | * | 10/2019 | ........... C07D 401/04 |
| WO | 2020/216371 A1 | | 10/2020 | |
| WO | 2020/253862 A1 | | 12/2020 | |
| WO | 2020/256477 A1 | | 12/2020 | |
| WO | WO 2021/238827 A1 | * | 2/2021 | ........... C07D 413/12 |

OTHER PUBLICATIONS

International Search Report dated Jun. 30, 2022 from the International Searching Authority in International Application No. PCT/IB2022/053051.
Written Opinion dated Jun. 30, 2022 from the International Searching Authority in International Application No. PCT/IB2022/053051.
Extended European Search Report issued Jan. 8, 2025 in Application No. 22779298.3.

* cited by examiner

*Primary Examiner* — Matthew P Coughlin
*Assistant Examiner* — David M Shim
(74) *Attorney, Agent, or Firm* — Sughrue Mion, PLLC

(57) ABSTRACT

Novel N2-phenylpyrimidine-2,4-diamine compounds, method for preparing the same, and pharmaceutical composition or health functional food are disclosed. The novel N2-phenylpyrimidine-2,4-diamine compounds show potent inhibitory efficacies on EGFR mutations and thus, can be effectively used for the treatment of cancer with EGFR mutations.

8 Claims, 6 Drawing Sheets

N2-PHENYLPYRIMIDINE-2,4-DIAMINE COMPOUNDS, AND PREPARATION METHODS AND METHODS OF USE THEREOF

CROSS REFERENCE TO RELATED APPLICATIONS

This application claims benefit of and right of priority based on U.S. Provisional Application No. 63/170,098 filed Apr. 2, 2021, of which content is incorporated by reference in its entirety.

FIELD

The present disclosure generally relates to N2-phenylpyrimidine-2,4-diamine compounds, methods for preparing the same, and pharmaceutical compositions comprising the same, and uses of the same in the prevention or treatment of cancer.

BACKGROUND ART

The occurrence of cancers is related to a variety of environmental factors including chemical substances, viruses, radiation and changes of oncogenes, tumor suppressor genes, genes associated with apoptosis, DNA repair and the like.

A traditional approach to fight cancer is chemotherapy using cytotoxic drugs. But these agents are often poorly selective for cancer cells, subsequently leading to damage to normal cells that divide rapidly. Other treatment options include radiation therapy, targeted therapy, immunotherapy, hormonal therapy, and surgery. The choice of therapy depends upon various factors including the cancer type, severity of the tumor, the stage of the disease and general state of the patients. Currently, a large number of experimental cancer treatments are under development.

Targeted therapeutic agents are generally prepared to show efficacy in patients by targeting malfunctioning proteins that cancer cells characteristically have. There are targeted therapies for lung cancer, colorectal cancer, head and neck cancer, breast cancer, multiple myeloma, lymphoma, prostate cancer, melanoma and other cancers (www.cancer.gov/about-cancer/treatment/types/targeted-therapies/targeted-therapies-fact-sheet).

Among them, EGFR (epidermal growth factor receptor, also known as ErbB-1 or HER1 in humans) inhibitors have achieved remarkable outcomes in the treatment for patients with EGFR mutant cancers. EGFR is a transmembrane protein that is a receptor for members of the epidermal growth factor family (EGF family) of extracellular protein ligands and is known to be abnormally activated in a number of epithelial cell tumors including non-small cell lung carcinoma (NSCLC), breast cancer, glioma, squamous cell carcinoma of head and neck, colorectal cancer, rectal adenocarcinoma, head and neck cancer, gastric cancer, and prostate cancer. The activation of the EGFR-tyrosine kinase causes persistent cell proliferation, invasion of the surrounding tissue, remote metastasis, and angiogenesis, and increases tumor cell survival.

In particular, EGFR is overexpressed in at least half of non-small cell lung cancers (NSCLC) and thus numerous studies targeting the EGFR have been carried out for NSCLC patients. In this regard, EGFR TKIs (tyrosine kinase inhibitors) which inhibit the activity of EGFR tyrosine kinase, have been developed and the representative examples are Gefitinib (IRESSA™), erlotinib (TARCEVA™), lapatinib (TYKERB™, TYVERB™).

However, despite the improvement in clinical outcomes with the use of EGFR-TKIs in the treatment of patients with NSCLC whose tumors harbor EGFR-activating mutations, prognosis remains unfavorable due to the occurrence of either intrinsic or acquired resistance. The two most common EGFR-activating mutations are deletions in exon 19 and L858R point mutation of exon 21, which collectively account for >90% of known activating EGFR mutations (Science 2004; 304: 1497-1500).

Additionally, despite an early clinical effect of gefitinib/erlotinib in NSCLC patients with an EGFR mutation, a progressive cancer develops in most patients eventually. In an early study of recurred cancer samples, a secondary EGFR mutation (T790M) was identified which caused gefitinib and erlotinib to be ineffective inhibitors toward EGFR mutant kinase (Kobayashi et al. NEJM 2005 and Pao et al. PLOS Medicine 2005).

To overcome the T790M mutation, osimertinib (TAGRISSO™) was developed by AstraZeneca as a third-generation EGFR-TKI, which was approved as a cancer treatment in 2017 by both the Food and Drug Administration and the European Commission. Unfortunately, EGFR C797S mutation was reported to be a leading mechanism of resistance to third-generation inhibitors (Thress et al, Nature Medicine 2015) and research groups have reported study results to overcome EGFR C797S mutation, including PCT Publication Nos. WO2018230934, WO2019015655 and WO2019112344, of which contents are incorporated herein by reference in their entities.

Thus, there is a need for the development of inhibitors exhibiting a potent inhibition on EGFR specific activating or resistance mutants.

SUMMARY

One aspect of the present disclosure relates to novel EGFR inhibitors, solvates, stereoisomers thereof or pharmaceutically acceptable salts thereof which can be used for the prevention and/or treatment of diseases characterized by excessive or abnormal cell proliferation. In another aspect of the present disclosure, novel N2-phenylpyrimidine-2,4-diamine compounds, solvates, stereoisomers thereof or pharmaceutically acceptable salts thereof have an inhibitory effect on EGFR activation or mutation in vitro and/or in vivo and/or ex vivo.

Another aspect of the present disclosure relates to a method for preparing novel EGFR inhibitors.

Another aspect of the present disclosure relates to a pharmaceutical composition for the prevention or treatment of cancer containing novel EGFR inhibitors, solvates, stereoisomers thereof or pharmaceutically acceptable salts thereof as active ingredient.

Another aspect of the present disclosure relates to a health functional food composition for the prevention or amelioration of cancer containing novel EGFR inhibitors, solvates, stereoisomers thereof, or pharmaceutically acceptable salts thereof as active ingredient.

Another aspect of the present disclosure relates to methods for the prevention or treatment by administering an effective amount of the novel EGFR inhibitors, solvates, stereoisomers thereof or pharmaceutically acceptable salts thereof.

Accordingly, one or more embodiments of the present disclosure provides novel N2-phenylpyrimidine-2,4-diamine compounds as novel EGFR inhibitors with high efficacy against a variety of EGFR mutations including, but not limited thereto, EGFR L858R, EGFR L858R/T790M, EGFR L858R/C797S, L858R/T790M/C797S, EGFR Del19, EGFR Del19/T790M, EGFR Del19/C797S, and EGFR Del19/T790M/C797S.

Novel compounds are represented by the following Formula 1, a prodrug thereof, a hydrate thereof, a solvate thereof, an isomer thereof, an isotope labeled thereof, or a pharmaceutically acceptable salt thereof:

Formula 1

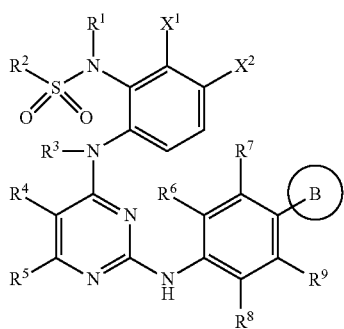

wherein
$R^1$ and $R^3$ are independently hydrogen or C1-C3 alkyl,
$R^2$ is linear or branched C1-C6 alkyl, C3-C6 cycloalkyl, or amino,
$R^4$-$R^9$ are independently hydrogen, —$OR^{10}$, —$CF_3$, halogen, hydroxy, amino, silyl ether, linear or branched C1-C6 alkyl, or C3-C6 cycloalkyl,
$X^1$ and $X^2$ are independently hydrogen, —$OR^{11}$, —$CF_3$, halogen, hydroxy, amino, silyl ether, linear or branched C1-C6 alkyl, C3-C6 cycloalkyl, or $X^1$ and $X^2$ taken together form 4-8 membered heterocycloalkyl or a heteroaryl ring(s), with proviso that $X^1$ and $X^2$ are not simultaneously hydrogen, B is a 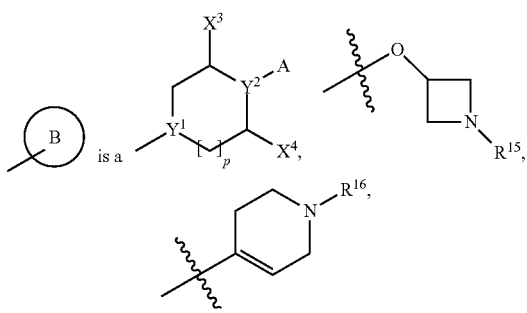

spiro C3-C12 heterocycloalkyl, or bridged C4-C12 heterocycloalkyl,
$X^3$ and $X^4$ are independently hydrogen, $OR^{12}$, —$CF_3$, halogen, hydroxy, amino, silyl ether, linear or branched C1-C6 alkyl, or C3-C6 cycloalkyl;
p is an integer of 0 or 1,
$Y^1$ is N or CH,
$Y^2$ is N or CH, or O when A is not present,
A is hydrogen, linear or branched C1-C6 alkyl, C3-C6 cycloalkyl, aryl, heteroaryl, spiro C3-C12 cycloalkyl, or bridged C4-C12 cycloalkyl, wherein the above linear or branched C1-C6 alkyl, C3-C6 cycloalkyl, aryl, heteroaryl, spiro C3-C12 cycloalkyl, or bridged C4-C12 cycloalkyl may optionally contain hetero atoms instead of carbon atoms thus forming a heteroalkyl, heterocycloalkyl, and A can be independently substituted with —$OR^{13}$, —$CF_3$, halogen, hydroxy, amino, silyl ether, linear or branched C1-C6 alkyl, or C3-C6 cycloalkyl;
$R^{10}$-$R^{13}$, $R^{15}$ and $R^{16}$ are independently hydrogen, linear or branched C1-C6 alkyl, C3-C6 cycloalkyl, or amino.

In an embodiment, the novel compounds are represented by the following Formula 1-1, a prodrug thereof, a hydrate thereof, a solvate thereof, an stereoisomer thereof, an isotope labeled thereof, or a pharmaceutically acceptable salt thereof:

Formula 1-1

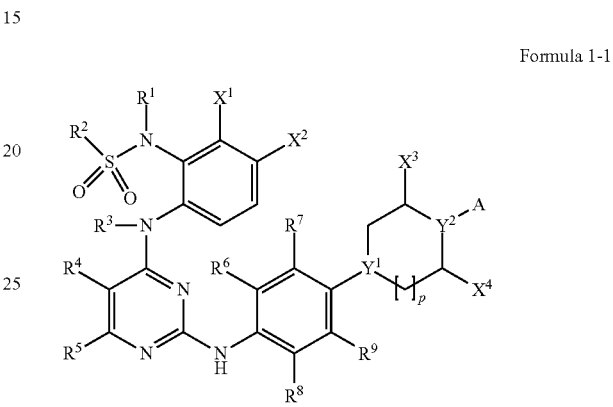

wherein the $R^1$-$R^9$, $X^1$-$X^4$, p, and A has the same meaning as defined above. In an embodiment, one or both of $Y^1$ and $Y^2$ is(are) N. In an embodiment, in Formulas 1 and 1-1, A is linear or branched C1-C6 alkyl, C1-C3 haloalkyl, —$NH_2$, —$N(R^{11})(R^{11})$, C3-C6 cycloalkyl, aryl, heteroaryl, spiro 3-12 membered heterocycloalkyl, or bridged 4-12 membered heterocycloalkyl, 3-8 membered heterocycloalkyl, 4-14 membered heterocycloalkyl, or 5-12 membered heterocycloalkyl, and A can be independently substituted with hydrogen, —$OR^{13}$, —$CF_3$, halogen, hydroxy, amino, silyl ether, linear or branched C1-C6 alkyl, or C3-C6 cycloalkyl, wherein $R^{11}$ and $R^{13}$ are a linear or branched C1-5 alkyl. In an embodiment, in Formulas 1 and 1-1, $X^1$ and $X^2$ together form a ring that optionally contains a heteroatom.

In an embodiment, the novel compounds are represented by the following Formula 1-2, a prodrug thereof, a solvate thereof, an isomer thereof, an isotope labeled thereof, or a pharmaceutically acceptable salt thereof:

Formula 1-2

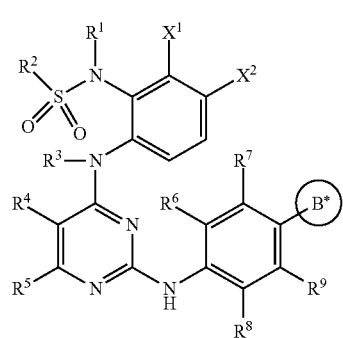

wherein the

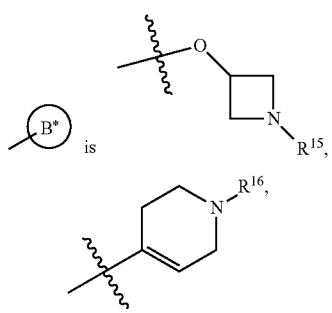

spiro 3-12 membered heterocycloalkyl, or bridged 6-12 membered heterocycloalkyl, wherein hetero atom is N.

According to one aspect, in Formulas 1, 1-1, and 1-2,

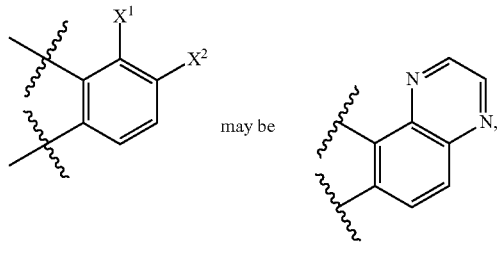

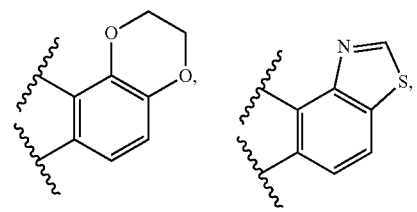

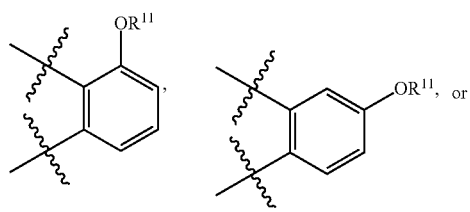

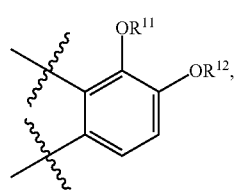

wherein $R^{11}$ and $R^{12}$ are independently a linear or branched C1-5 alkyl.

According to one aspect, in Formula 1-1,

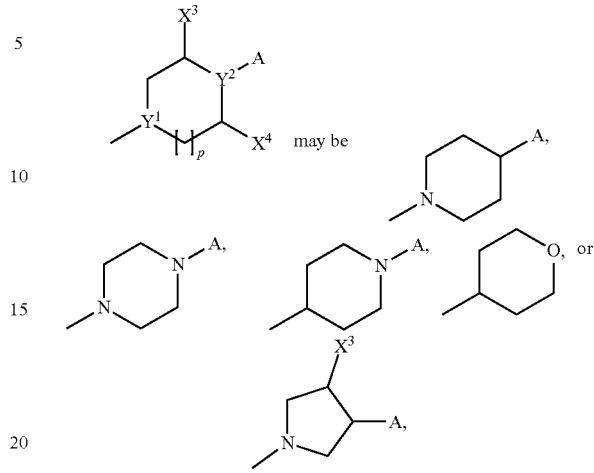

wherein A and $X^3$ have the same meaning as defined above. In certain embodiments, A is hydrogen, C1-C5 linear or branched alkyl, C1-C5 haloalkyl, —NH$_2$, —N($R^{11}$)($R^{12}$), substituted or unsubstituted C3-C8 heterocycloalkyl, substituted or unsubstituted spiro C3-C12 heterocycloalkyl, or substituted or unsubstituted bridged C4-C12 heterocycloalkyl, wherein $R^{11}$ and $R^{12}$ are independently hydrogen or a linear or branched C1-5 alkyl; and $X^3$ is a halogen. In certain embodiments, the C3-C8 heterocycloalkyl, spiro C3-C12 heterocycloalkyl, or bridged C4-C12 heterocycloalkyl may contain one, two, or three heteroatoms selected from N and O.

According to some aspects, in Formulas 1, 1-1, and 1-2, $R^6$ and $R^9$ each may be hydrogen. In some other aspects, in Formulas 1, 1-1, and 1-2, $R^7$ may be hydrogen or liner or branched C1-C4 alkyl. In some other aspects, in Formulas 1, 1-1, and 1-2, $R^8$ is —$OR^{10}$ or —N($R^{11}$)($R^{12}$), wherein $R^{10}$ is linear or branched C1-C4 alkyl, and $R^{11}$ and $R^{12}$ are independently hydrogen or linear or branched C1-C4 alkyl. In some other aspects, in Formulas 1, 1-1, and 1-2, $R^6$ and $R^9$ each may be hydrogen, $R^7$ may be hydrogen or liner or branched C1-C4 alkyl, and $R^8$ is —$OR^{10}$ or —N($R^{11}$)($R^{12}$), wherein $R^{10}$ is linear or branched C1-C4 alkyl, and $R^{11}$ and $R^{12}$ are independently hydrogen or linear or branched C1-C4 alkyl. In some other aspects, in Formulas 1, 1-1, and 1-2, $R^5$ may be hydrogen. In some other aspects, in Formulas 1, 1-1, and 1-2, $R^4$ may be halo, C1-C3 alkyl, or C1-C3 haloalkyl.

In an embodiments, in Formulas 1, 1-1, and 1-2, C1-C5 haloalkyl may be CF$_3$, CHF$_2$, CH$_2$CHF$_2$, and CH$_2$F.

In embodiments, A is selected from the group consisting of hydrogen, C1-C3 alkyl, C1-C3 haloalkyl,

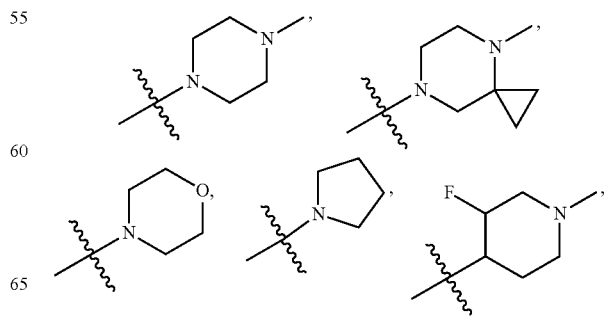

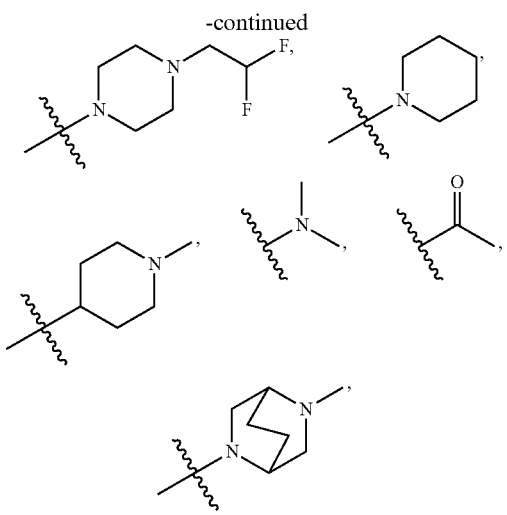

and —N(R$^{11}$)(R$^{12}$) wherein R$^{11}$ and R$^{12}$ are independently hydrogen or linear or branched C1-C6 alkyl.

According to one aspect, in Formulas 1, 1-1, and 1-2, substituted or unsubstituted spiro C3-C12 heterocycloalkyl may be 7-membered, 8-membered, or 9-membered. In certain embodiments, spiro-heterocycloalkyl may be

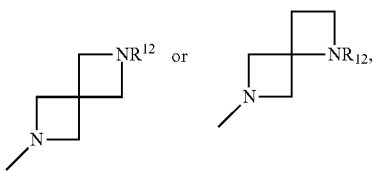

wherein R$^{12}$ is hydrogen, C1-C6 linear or branched alkyl, or C1-C6 haloalkyl.

According to one aspect, in Formulas 1, 1-1, and 1-2, substituted or unsubstituted bridged C4-C12 heterocycloalkyl may be 7-membered, 8-membered, 9-membered, or 10-membered. In certain embodiments, bridged heterocycloalkyl may be

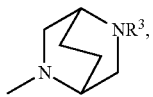

wherein R$^{12}$ is hydrogen, C1-C6 linear or branched alkyl, or C1-C6 haloalkyl.

In certain embodiments, the compound of formula 1 is:
(1) N-(6-((5-chloro-2-((5-ethyl-2-methoxy-4-(4-(4-methylpiperazin-1-yl)piperidin-1-yl)phenyl)amino)pyrimidin-4-yl)amino)quinoxalin-5-yl)methanesulfonamide;
(2) N-(6-((5-bromo-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide;
(3) N-(6-((5-bromo-2-((5-ethyl-2-methoxy-4-(4-(4-methylpiperazin-1-yl)piperidin-1-yl)phenyl)amino)pyrimidin-4-yl)amino)quinoxalin-5-yl)-N-methylmethanesulfonamide;
(4) N-(6-((5-chloro-2-((4-((2-(dimethylamino)ethyl)(methyl)amino)-5-ethyl-2-methoxyphenyl)amino)pyrimidin-4-yl)amino)quinoxalin-5-yl)methanesulfonamide;
(5) N-(6-((5-bromo-2-((4-(4-(dimethylamino)piperidin-1-yl)-2-methoxy-5-methylphenyl)amino)pyrimidin-4-yl)amino)quinoxalin-5-yl)-N-methylmethanesulfonamide;
(6) N-(2-((5-bromo-2-((2-methoxy-5-methyl-4-(4-(4-methylpiperazin-1-yl)piperidin-1-yl)phenyl)amino)pyrimidin-4-yl)amino)-6-methoxyphenyl)methanesulfonamide;
(7) N-(6-((5-chloro-2-((4-(3-(dimethylamino)propyl)(methyl)amino)-5-ethyl-2-methoxyphenyl)amino)pyrimidin-4-yl)amino)quinoxalin-5-yl)methanesulfonamide;
(8) N-(2-((5-bromo-2-((2-methoxy-5-methyl-4-(4-(4-methylpiperazin-1-yl)piperidin-1-yl)phenyl)amino)pyrimidin-4-yl)amino)-5-methoxyphenyl)methanesulfonamide;
(9) N-(6-((5-bromo-2-((4-(4-(dimethylamino)piperidin-1-yl)-2-methoxy-5-propylphenyl)amino)pyrimidin-4-yl)amino)quinoxalin-5-yl)methanesulfonamide;
(10) N-(6-((5-bromo-2-((5-ethyl-2-methoxy-4-(4-morpholinopiperidin-1-yl)phenyl)amino)pyrimidin-4-yl)amino)quinoxalin-5-yl)methanesulfonamide;
(11) N-(6-((5-bromo-2-((5-ethyl-2-methoxy-4-(4-(pyrrolidin-1-yl)piperidin-1-yl)phenyl)amino)pyrimidin-4-yl)amino)quinoxalin-5-yl)methanesulfonamide;
(12) N-(6-((5-bromo-2-((4-(4-(dimethylamino)piperidin-1-yl)-5-ethyl-2-methoxyphenyl)amino)pyrimidin-4-yl)amino)quinoxalin-5-yl)-N-methylmethanesulfonamide;
(13) N-(6-((5-chloro-2-((5-ethyl-2-methoxy-4-(4-(pyrrolidin-1-yl)piperidin-1-yl)phenyl)amino)pyrimidin-4-yl)amino)quinoxalin-5-yl)methanesulfonamide;
(14) N-(2-((5-bromo-2-((5-ethyl-2-methoxy-4-(4-(4-methylpiperazin-1-yl)piperidin-1-yl)phenyl)amino)pyrimidin-4-yl)amino)-6-methoxyphenyl)-N-methylmethanesulfonamide;
(15) N-(2-((5-chloro-2-((5-ethyl-2-methoxy-4-(4-morpholinopiperidin-1-yl)phenyl)amino)pyrimidin-4-yl)amino)-5-methoxyphenyl)methanesulfonamide;
(16) N-(6-((5-chloro-2-((5-ethyl-2-methoxy-4-(4-morpholinopiperidin-1-yl)phenyl)amino)pyrimidin-4-yl)amino)-2,3-dihydrobenzo[b][1,4]dioxin-5-yl)methanesulfonamide;
(17) N-(2-((5-chloro-2-((2-methoxy-5-methyl-4-(4-(4-methylpiperazin-1-yl)piperidin-1-yl)phenyl)amino)pyrimidin-4-yl)amino)-6-methoxyphenyl)ethanesulfonamide;
(18) N-(2-((5-chloro-2-((2-methoxy-5-methyl-4-(4-(4-methylpiperazin-1-yl)piperidin-1-yl)phenyl)amino)pyrimidin-4-yl)amino)-5-methoxyphenyl)ethanesulfonamide;
(19) N-(6-((5-chloro-2-((5-ethyl-2-methoxy-4-(4-(4-methylpiperazin-1-yl)piperidin-1-yl)phenyl)amino)pyrimidin-4-yl)amino)quinoxalin-5-yl)-N-methylmethanesulfonamide;
(20) N-(2-((5-bromo-2-((2-methoxy-5-methyl-4-(4-(4-methylpiperazin-1-yl)piperidin-1-yl)phenyl)amino)pyrimidin-4-yl)amino)-6-methoxyphenyl)-N-methylmethanesulfonamide;
(21) N-(2-((5-bromo-2-((5-ethyl-2-methoxy-4-(4-(4-methylpiperazin-1-yl)piperidin-1-yl)phenyl)amino)pyrimidin-4-yl)amino)-6-methoxyphenyl)methanesulfonamide;
(22) N-(2-((5-chloro-2-((2-methoxy-5-methyl-4-(4-(4-methylpiperazin-1-yl)piperidin-1-yl)phenyl)amino)pyrimidin-4-yl)amino)-6-methoxyphenyl)methanesulfonamide
(23) N-(6-((5-chloro-2-((5-ethyl-2-methoxy-4-(4-(pyrrolidin-1-yl)piperidin-1-yl)phenyl)amino)pyrimidin-4-yl)amino)quinoxalin-5-yl)-N-methylmethanesulfonamide;

(24) N-(6-((5-bromo-2-((5-ethyl-2-methoxy-4-(4-(4-methylpiperazin-1-yl)piperidin-1-yl)phenyl)amino)pyrimidin-4-yl)amino)-2,3-dihydrobenzo[b][1,4]dioxin-5-yl)-N-methylmethanesulfonamide;

(25) N-(6-((5-chloro-2-((5-ethyl-2-methoxy-4-(4-morpholinopiperidin-1-yl)phenyl)amino)pyrimidin-4-yl)amino)-2,3-dihydrobenzo[b][1,4]dioxin-5-yl)-N-methylmethanesulfonamide;

(26) N-(6-((5-chloro-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide;

(27) N-(6-((5-chloro-2-((2-methoxy-4-(4-(4-methylpiperazin-1-yl)piperidin-1-yl)-5-propylphenyl)amino)pyrimidin-4-yl)amino)quinoxalin-5-yl)methanesulfonamide;

(28) N-(6-((5-bromo-2-((4-(4-(dimethylamino)piperidin-1-yl)-2-methoxy-5-methylphenyl)amino)pyrimidin-4-yl)amino)quinoxalin-5-yl)methanesulfonamide;

(29) N-(6-((5-bromo-2-((2-methoxy-5-methyl-4-(4-(4-methylpiperazin-1-yl)piperidin-1-yl)phenyl)amino)pyrimidin-4-yl)amino)quinoxalin-5-yl)cyclopropanesulfonamide;

(30) N-(6-((2-((2-methoxy-5-methyl-4-(4-(4-methylpiperazin-1-yl)piperidin-1-yl)phenyl)amino)-5-methylpyrimidin-4-yl)amino)quinoxalin-5-yl)methanesulfonamide;

(31) N-(6-((5-bromo-2-((2-methoxy-5-methyl-4-(4-morpholinopiperidin-1-yl)phenyl)amino)pyrimidin-4-yl)amino)quinoxalin-5-yl)methanesulfonamide;

(32) N-(6-((5-bromo-2-((2-methoxy-5-methyl-4-(4-(4-methylpiperazin-1-yl)piperidin-1-yl)phenyl)amino)pyrimidin-4-yl)amino)quinoxalin-5-yl)ethanesulfonamide;

(33) N-(6-((5-chloro-2-((2-methoxy-5-methyl-4-(4-(4-methylpiperazin-1-yl)piperidin-1-yl)phenyl)amino)pyrimidin-4-yl)amino)quinoxalin-5-yl)ethanesulfonamide;

(34) N-(2-((5-bromo-2-((4-(4-(dimethylamino)piperidin-1-yl)-2-methoxy-5-methylphenyl)amino)pyrimidin-4-yl)amino)-6-methoxyphenyl)methanesulfonamide;

(35) N-(6-((5-chloro-2-((4-(4-(dimethylamino)piperidin-1-yl)-2-methoxy-5-propylphenyl)amino)pyrimidin-4-yl)amino)quinoxalin-5-yl)methanesulfonamide;

(36) N-(6-((5-chloro-2-((5-ethyl-2-methoxy-4-(4-morpholinopiperidin-1-yl)phenyl)amino)pyrimidin-4-yl)amino)quinoxalin-5-yl)methanesulfonamide;

(37) N-(6-((5-chloro-2-((2-methoxy-5-methyl-4-(4-(pyrrolidin-1-yl)piperidin-1-yl)phenyl)amino)pyrimidin-4-yl)amino)quinoxalin-5-yl)methanesulfonamide;

(38) N-(6-((5-chloro-2-((2-methoxy-5-methyl-4-(4-morpholinopiperidin-1-yl)phenyl)amino)pyrimidin-4-yl)amino)quinoxalin-5-yl)methanesulfonamide;

(39) N-(6-((5-bromo-2-((4-(4-(dimethylamino)piperidin-1-yl)-5-ethyl-2-methoxyphenyl)amino)pyrimidin-4-yl)(methyl)amino)quinoxalin-5-yl)-N-methylmethanesulfonamide;

(40) N-(2-((5-chloro-2-((2-methoxy-5-methyl-4-(4-(pyrrolidin-1-yl)piperidin-1-yl)phenyl)amino)pyrimidin-4-yl)amino)-6-methoxyphenyl)methanesulfonamide;

(41) N-(2-((5-chloro-2-((2-methoxy-5-methyl-4-(4-(pyrrolidin-1-yl)piperidin-1-yl)phenyl)amino)pyrimidin-4-yl)amino)-5-methoxyphenyl)methanesulfonamide:

(42) N-(2-((5-chloro-2-((4-(4-(dimethylamino)piperidin-1-yl)-2-methoxy-5-propylphenyl)amino)pyrimidin-4-yl)amino)-5-methoxyphenyl)methanesulfonamide;

(43) N-(6-((5-chloro-2-((4-(4-(dimethylamino)piperidin-1-yl)-2-methoxy-5-propylphenyl)amino)pyrimidin-4-yl)amino)-2,3-dihydrobenzo[b][1,4]dioxin-5-yl)methanesulfonamide;

(44) N-(2-((5-chloro-2-((4-(4-(dimethylamino)piperidin-1-yl)-2-methoxy-5-propylphenyl)amino)pyrimidin-4-yl)amino)-6-methoxyphenyl)methanesulfonamide;

(45) N-(6-((5-bromo-2-((5-ethyl-2-methoxy-4-(4-morpholinopiperidin-1-yl)phenyl)amino)pyrimidin-4-yl)amino)quinoxalin-5-yl)-N-methylmethanesulfonamide;

(46) N-(6-((5-chloro-2-((5-ethyl-2-methoxy-4-(4-morpholinopiperidin-1-yl)phenyl)amino)pyrimidin-4-yl)amino)quinoxalin-5-yl)-N-methylmethanesulfonamide;

(47) N-(2-((5-bromo-2-((2-methoxy-5-methyl-4-(4-(pyrrolidin-1-yl)piperidin-1-yl)phenyl)amino)pyrimidin-4-yl)amino)-6-methoxyphenyl)methanesulfonamide;

(48) N-(2-((5-chloro-2-((2-methoxy-5-methyl-4-(4-(4-methylpiperazin-1-yl)piperidin-1-yl)phenyl)amino)pyrimidin-4-yl)amino)-5-methoxyphenyl)methanesulfonamide;

(49) N-(6-((5-chloro-2-((2-methoxy-5-methyl-4-(4-(pyrrolidin-1-yl)piperidin-1-yl)phenyl)amino)pyrimidin-4-yl)amino)-2,3-dihydrobenzo[b][1,4]dioxin-5-yl)methanesulfonamide;

(50) N-(6-((2-((4-([1,4'-bipiperidin]-1'-yl)-5-ethyl-2-methoxyphenyl)amino)-5-bromopyrimidin-4-yl)amino)quinoxalin-5-yl)-N-methylmethanesulfonamide;

(51) N-(2-((5-chloro-2-((4-(4-(dimethylamino)piperidin-1-yl)-2-methoxy-5-propylphenyl)amino)pyrimidin-4-yl)amino)-6-methoxyphenyl)-N-methylmethanesulfonamide;

(52) N-(6-((5-bromo-2-((5-ethyl-2-methoxy-4-(4-(5-methyl-2,5-diazabicyclo[2.2.2]octan-2-yl)piperidin-1-yl)phenyl)amino)pyrimidin-4-yl)amino)quinoxalin-5-yl)methanesulfonamide;

(53) N-(6-((5-bromo-2-((5-ethyl-2-methoxy-4-(4-(5-methyl-2,5-diazabicyclo[2.2.2]octan-2-yl)piperidin-1-yl)phenyl)amino)pyrimidin-4-yl)amino)quinoxalin-5-yl)-N-methylmethanesulfonamide;

(54) N-(6-((5-chloro-2-((5-ethyl-4-(5-isopropyl-2,5-diazabicyclo[2.2.2]octan-2-yl)-2-methoxyphenyl)amino)pyrimidin-4-yl)amino)quinoxalin-5-yl)-N-methylmethanesulfonamide;

(55) N-(6-((5-bromo-2-((5-ethyl-4-(6-isopropyl-2,6-diazaspiro[3.3]heptan-2-yl)-2-methoxyphenyl)amino)pyrimidin-4-yl)amino)quinoxalin-5-yl)-N-methylmethanesulfonamide;

(56) N-(6-((5-bromo-2-((5-ethyl-4-(5-isopropyl-2,5-diazabicyclo[2.2.2]octan-2-yl)-2-methoxyphenyl)amino)pyrimidin-4-yl)amino)quinoxalin-5-yl)-N-methylmethanesulfonamide;

(57) N-(6-((5-bromo-2-((5-ethyl-4-(1-isopropyl-1,6-diazaspiro[3.3]heptan-6-yl)-2-methoxyphenyl)amino)pyrimidin-4-yl)amino)quinoxalin-5-yl)-N-methylmethanesulfonamide

(58) N-(6-((5-bromo-2-((5-ethyl-2-methoxy-4-(4-(1-methylpiperidin-4-yl)piperazin-1-yl)phenyl)amino)pyrimidin-4-yl)amino)quinoxalin-5-yl)-N-methylmethanesulfonamide;

(59) N-(6-((5-chloro-2-((2-methoxy-4-(4-(4-methylpiperazin-1-yl)piperidin-1-yl)phenyl)amino)pyrimidin-4-yl)amino)quinoxalin-5-yl)methanesulfonamide;

(60) N-(6-((5-chloro-2-((5-cyclopropyl-2-methoxy-4-(4-(4-methylpiperazin-1-yl)piperidin-1-yl)phenyl)amino)pyrimidin-4-yl)amino)quinoxalin-5-yl)methanesulfonamide

(61) N-(6-((5-chloro-2-((2-methoxy-4-(4-(4-methylpiperazin-1-yl)piperidin-1-yl)-5-(trifluoromethyl)phenyl)amino)pyrimidin-4-yl)amino)quinoxalin-5-yl)methanesulfonamide

(62) N-(6-((5-bromo-2-((5-ethyl-2-methoxy-4-(4-(4-methylpiperazin-1-yl)piperidin-1-yl)phenyl)amino)pyrimidin-4-yl)amino)quinoxalin-5-yl)methanesulfonamide;

(63) N-(6-((2-((5-ethyl-2-methoxy-4-(4-(4-methylpiperazin-1-yl)piperidin-1-yl)phenyl)amino)-5-fluoropyrimidin-4-yl)amino)quinoxalin-5-yl)methanesulfonamide;

(64) N-(6-((5-bromo-2-((4-(4-(dimethylamino)piperidin-1-yl)-5-ethyl-2-methoxyphenyl)amino)pyrimidin-4-yl)amino)quinoxalin-5-yl)methanesulfonamide;

(65) N-(6-((5-bromo-2-((4-(4-(dimethylamino)piperidin-1-yl)-2-methoxyphenyl)amino)pyrimidin-4-yl)amino)quinoxalin-5-yl)methanesulfonamide;

(66) N-(6-((5-chloro-2-((4-(4-(dimethylamino)piperidin-1-yl)-2-methoxy-5-methylphenyl)amino)pyrimidin-4-yl)amino)quinoxalin-5-yl)methanesulfonamide;

(67) N-(6-((5-chloro-2-((4-(4-(dimethylamino)piperidin-1-yl)-5-ethyl-2-methoxyphenyl)amino)pyrimidin-4-yl)amino)quinoxalin-5-yl)methanesulfonamide;

(68) N-(6-((5-chloro-2-((2-methoxy-5-methyl-4-(4-(4-methylpiperazin-1-yl)piperidin-1-yl)phenyl)amino)pyrimidin-4-yl)amino)quinoxalin-5-yl)cyclopropanesulfonamide;

(69) N-(6-((5-bromo-2-((5-fluoro-2-methoxy-4-(4-(4-methylpiperazin-1-yl)piperidin-1-yl)phenyl)amino)pyrimidin-4-yl)amino)quinoxalin-5-yl)methanesulfonamide;

(70) N-(2-((5-chloro-2-((4-(4-(dimethylamino)piperidin-1-yl)-2-methoxy-5-methylphenyl)amino)pyrimidin-4-yl)amino)-5-methoxyphenyl)methanesulfonamide;

(71) N-(6-((5-fluoro-2-((2-methoxy-4-(4-(4-methylpiperazin-1-yl)piperidin-1-yl)-5-propylphenyl)amino)pyrimidin-4-yl)amino)quinoxalin-5-yl)methanesulfonamide;

(72) N-(2-((5-bromo-2-((4-(4-(dimethylamino)piperidin-1-yl)-2-methoxy-5-methylphenyl)amino)pyrimidin-4-yl)amino)-6-methoxyphenyl)-N-methylmethanesulfonamide;

(73) N-(6-((5-chloro-2-((5-ethyl-2-methoxy-4-(4-morpholinopiperidin-1-yl)phenyl)amino)pyrimidin-4-yl)amino)-2,3-dimethoxyphenyl)methanesulfonamide;

(74) N-(2-((5-chloro-2-((5-ethyl-2-methoxy-4-(4-morpholinopiperidin-1-yl)phenyl)amino)pyrimidin-4-yl)amino)-6-methoxyphenyl)methanesulfonamide;

(75) N-(6-((5-chloro-2-((2-methoxy-4-(4-morpholinopiperidin-1-yl)-5-propylphenyl)amino)pyrimidin-4-yl)amino)quinoxalin-5-yl)-N-methylmethanesulfonamide

(76) N-(2-((5-chloro-2-((2-methoxy-4-(4-morpholinopiperidin-1-yl)-5-propylphenyl)amino)pyrimidin-4-yl)amino)-6-methoxyphenyl)methanesulfonamide;

(77) N-(6-((5-chloro-2-((2-methoxy-5-propyl-4-(4-(pyrrolidin-1-yl)piperidin-1-yl)phenyl)amino)pyrimidin-4-yl)amino)quinoxalin-5-yl)-N-methylmethanesulfonamide;

(78) N-(6-((5-bromo-2-((4-(4-(dimethylamino)piperidin-1-yl)-2-methoxy-5-propylphenyl)amino)pyrimidin-4-yl)amino)quinoxalin-5-yl)-N-methylmethanesulfonamide;

(79) N-(6-((5-chloro-2-((5-ethyl-2-methoxy-4-(5-methyl-2,5-diazabicyclo[2.2.2]octan-2-yl)piperidin-1-yl)phenyl)amino)pyrimidin-4-yl)amino)quinoxalin-5-yl)methanesulfonamide;

(80) N-(6-((5-chloro-2-((5-ethyl-2-methoxy-4-(5-methyl-2,5-diazabicyclo[2.2.2]octan-2-yl)piperidin-1-yl)phenyl)amino)pyrimidin-4-yl)amino)quinoxalin-5-yl)-N-methylmethanesulfonamide;

(81) N-(6-((5-chloro-2-((5-ethyl-4-(5-isopropyl-2,5-diazabicyclo[2.2.2]octan-2-yl)-2-methoxyphenyl)amino)pyrimidin-4-yl)amino)quinoxalin-5-yl)methanesulfonamide;

(82) N-(6-((5-chloro-2-((5-ethyl-2-methoxy-4-(4-morpholinopiperidin-1-yl)phenyl)amino)pyrimidin-4-yl)amino)-2,3-dimethoxyphenyl)-N-methylmethanesulfonamide;

(83) N-(6-((5-chloro-2-((5-ethyl-4-(6-isopropyl-2,6-diazaspiro[3.3]heptan-2-yl)-2-methoxyphenyl)amino)pyrimidin-4-yl)amino)quinoxalin-5-yl)methanesulfonamide;

(84) N-(6-((5-chloro-2-((5-ethyl-4-(6-isopropyl-2,6-diazaspiro[3.3]heptan-2-yl)-2-methoxyphenyl)amino)pyrimidin-4-yl)amino)quinoxalin-5-yl)-N-methylmethanesulfonamide;

(85) N-(6-((5-bromo-2-((5-ethyl-2-isopropoxy-4-(1-methylpiperidin-4-yl)phenyl)amino)pyrimidin-4-yl)amino)quinoxalin-5-yl)-N-methylmethanesulfonamide;

(86) N-(6-((5-chloro-2-((5-ethyl-2-methoxy-4-(4-(4-methylpiperazin-1-yl)piperidin-1-yl)phenyl)amino)pyrimidin-4-yl)(methyl)amino)quinoxalin-5-yl)methanesulfonamide;

(87) N-(6-((2-((5-ethyl-2-methoxy-4-(4-(4-methylpiperazin-1-yl)piperidin-1-yl)phenyl)amino)-5-(trifluoromethyl)pyrimidin-4-yl)amino)quinoxalin-5-yl)methanesulfonamide;

(88) N-(6-((5-chloro-2-((5-methyl-2-(methylamino)-4-(4-(4-methylpiperazin-1-yl)piperidin-1-yl)phenyl)amino)pyrimidin-4-yl)amino)quinoxalin-5-yl)methanesulfonamide;

(89) N-(6-((5-bromo-2-((2-(dimethylamino)-5-methyl-4-(4-(4-methylpiperazin-1-yl)piperidin-1-yl)phenyl)amino)pyrimidin-4-yl)amino)quinoxalin-5-yl)methanesulfonamide;

(90) N-(6-((5-bromo-2-((2-(dimethylamino)-4-(4-(dimethylamino)piperidin-1-yl)-5-methylphenyl)amino)pyrimidin-4-yl)amino)quinoxalin-5-yl)methanesulfonamide;

(91) N-(6-((5-chloro-2-((2-(dimethylamino)-5-methyl-4-(4-(4-methylpiperazin-1-yl)piperidin-1-yl)phenyl)amino)pyrimidin-4-yl)amino)quinoxalin-5-yl)methanesulfonamide;

(92) N-(6-((5-chloro-2-((2-(dimethylamino)-5-ethyl-4-(4-(4-methylpiperazin-1-yl)piperidin-1-yl)phenyl)amino)pyrimidin-4-yl)amino)quinoxalin-5-yl)methanesulfonamide;

(93) N-(6-((2-((2-methoxy-5-methyl-4-(4-(4-methylpiperazin-1-yl)piperidin-1-yl)phenyl)amino)-5-(trifluoromethyl)pyrimidin-4-yl)amino)quinoxalin-5-yl)methanesulfonamide;

(94) N-(6-((2-((4-(4-(dimethylamino)piperidin-1-yl)-2-methoxy-5-methylphenyl)amino)-5-(trifluoromethyl)pyrimidin-4-yl)amino)quinoxalin-5-yl)methanesulfonamide;

(95) N-(6-((5-fluoro-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide;

(96) N-(6-((5-bromo-2-((2-methoxy-5-methyl-4-morpholinophenyl)amino)pyrimidin-4-yl)amino)quinoxalin-5-yl)methanesulfonamide;

(97) N-(6-((5-bromo-2-((2-methoxy-5-methyl-4-(piperidin-4-yl)phenyl)amino)pyrimidin-4-yl)amino)quinoxalin-5-yl)methanesulfonamide;

(98) N-(6-((5-chloro-2-((4-((3R,4S)-3-fluoro-4-(4-methylpiperazin-1-yl)piperidin-1-yl)-2-methoxyphenyl)amino)pyrimidin-4-yl)amino)quinoxalin-5-yl)methanesulfonamide;

(99) N-(6-((5-chloro-2-((4-(4-((3S,4R)-3-fluoro-1-methylpiperidin-4-yl)piperazin-1-yl)-2-methoxyphenyl)amino)pyrimidin-4-yl)amino)quinoxalin-5-yl)methanesulfonamide;

(100) N-(6-((5-chloro-2-((4-(4-(4-(2,2-difluoroethyl)piperazin-1-yl)piperidin-1-yl)-2-methoxyphenyl)amino)pyrimidin-4-yl)amino)quinoxalin-5-yl)methanesulfonamide;
(101) N-(6-((5-chloro-2-((2-methoxy-4-(piperazin-1-yl)phenyl)amino)pyrimidin-4-yl)amino)quinoxalin-5-yl)methanesulfonamide;
(102) N-(2-((5-chloro-2-((2-methoxy-4-(piperazin-1-yl)phenyl)amino)pyrimidin-4-yl)amino)-6-methoxyphenyl)methanesulfonamide;
(103) N-(5-((5-chloro-2-((2-methoxy-4-(4-(4-methylpiperazin-1-yl)piperidin-1-yl)phenyl)amino)pyrimidin-4-yl)amino)benzo[d]thiazol-4-yl)methanesulfonamide;
(104) N-(6-((5-chloro-2-((2-methoxy-4-(4-(4-methylpiperazin-1-yl)piperidin-1-yl)phenyl)amino)pyrimidin-4-yl)amino)-2,3-dihydrobenzo[b][1,4]dioxin-5-yl)methanesulfonamide;
(105) N-(6-((5-chloro-2-((2-methoxy-4-(4-(4-methyl-4,7-diazaspiro[2.5]octan-7-yl)piperidin-1-yl)phenyl)amino)pyrimidin-4-yl)amino)quinoxalin-5-yl)methanesulfonamide;
(106) N-(6-((5-chloro-2-((5-fluoro-2-methoxy-4-(piperidin-4-yl)phenyl)amino)pyrimidin-4-yl)amino)quinoxalin-5-yl)methanesulfonamide;
(107) N-(6-((5-chloro-2-((2-methoxy-4-(1-methylpiperidin-4-yl)phenyl)amino)pyrimidin-4-yl)amino)quinoxalin-5-yl)methanesulfonamide;
(108) N-(6-((2-((4-(1-acetylpiperidin-4-yl)-2-methoxyphenyl)amino)-5-chloropyrimidin-4-yl)amino)quinoxalin-5-yl)methanesulfonamide;
(109) N-(6-((5-bromo-2-((2-methoxy-5-methyl-4-(1,2,3,6-tetrahydropyridin-4-yl)phenyl)amino)pyrimidin-4-yl)amino)quinoxalin-5-yl)methanesulfonamide;
(110) N-(6-((5-chloro-2-((2-methoxy-4-(piperidin-4-yl)phenyl)amino)pyrimidin-4-yl)amino)quinoxalin-5-yl)methanesulfonamide;
(111) N-(6-((5-chloro-2-((4-((3R,4R)-3-fluoro-4-(methylamino)pyrrolidin-1-yl)-2-methoxyphenyl)amino)pyrimidin-4-yl)amino)quinoxalin-5-yl)methanesulfonamide;
(112) N-(6-((5-fluoro-2-((2-methoxy-4-(piperidin-4-yl)phenyl)amino)pyrimidin-4-yl)amino)quinoxalin-5-yl)methanesulfonamide;
(113) N-(6-((5-bromo-2-((2-methoxy-4-(piperidin-4-yl)phenyl)amino)pyrimidin-4-yl)amino)quinoxalin-5-yl)methanesulfonamide;
(114) N-(6-((5-cyclopropyl-2-((2-methoxy-4-(piperidin-4-yl)phenyl)amino)pyrimidin-4-yl)amino)quinoxalin-5-yl)methanesulfonamide;
(115) N-(6-((5-chloro-2-((2-isopropoxy-4-(piperidin-4-yl)phenyl)amino)pyrimidin-4-yl)amino)quinoxalin-5-yl)methanesulfonamide;
(116) N-(6-((2-((4-(azetidin-3-yloxy)-2-methoxyphenyl)amino)-5-chloropyrimidin-4-yl)amino)quinoxalin-5-yl)methanesulfonamide; or
(117) N-(6-((5-chloro-2-((2-methoxy-4-(2,6-diazaspiro[3.3]heptan-2-yl)phenyl)amino)pyrimidin-4-yl)amino)quinoxalin-5-yl)methanesulfonamide.

The present disclosure further relates to hydrates, solvates, stereoisomers, polymorphs, metabolites, derivatives, and prodrugs of compounds of Formulas 1, 1-1, or 1-2 or pharmaceutically acceptable salts of the compounds.

In another aspect, the disclosure relates to uses of the compounds of Formulas 1, 1-1, or 1-2, or pharmaceutically acceptable salts thereof as medicaments.

In another aspect, the disclosure relates to the compounds of Formulas 1, 1-1, or 1-2, or pharmaceutically acceptable salts thereof for use in the treatment and/or prevention of cancer. In an embodiment, the cancer is associated with one, two, three, or more mutations in EGFR that activates EGFR or causes resistance to EGFR. In an embodiment, the EGFR mutations may include del19, L858R, T790M, C797S, or a combination thereof. In an embodiment, the EGFR mutations may be del19, del19/L858R, del19/T790M, del19/C797S, L858/T790M, L858R/C797S, T790M/C797S, del19/T790M/C797S (DTC) or L858R/T790M/C797S (LTC).

In another aspect, the disclosure relates to the compounds of Formulas 1, 1-1, or 1-2, a prodrug thereof, a hydrate thereof, a solvate thereof, an isomer thereof, an isotope labeled thereof, or pharmaceutically acceptable salts thereof for use in the treatment and/or prevention of cancer including pseudomyxoma, intrahepatic cholangiocarcinoma, hepatoblastoma, liver cancer, thyroid cancer, colon cancer, testis cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian seminoma, male breast cancer, brain cancer, pituitary adenoma, multiple myeloma, gallbladder cancer, cholangiocarcinoma, colorectal cancer, chronic myeloid leukemia, chronic lymphocytic leukemia, retinoblastoma, choroidal melanoma, ampullar of vater cancer, bladder cancer, peritoneal cancer, parathyroid cancer, adrenal cancer, nasal and paranasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal tumor, Wilms' tumor, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, and thymic cancer; and more preferably, the cancer may be a cancer with mutation on one or more selected from the group consisting of EGFR. In certain embodiment, the cancer is non-small cell lung cancer. In still another aspect, the disclosure relates to uses of the compounds of Formulas 1, 1-1, or 1-2, a prodrug thereof, a hydrate thereof, a solvate thereof, an isomer thereof, an isotope labeled thereof, or pharmaceutically acceptable salts thereof in manufacturing a medicament for treatment and/or prevention of cancer including those listed above.

In another aspect, the disclosure is related to a process for the treatment and/or prevention of cancer comprising administering a therapeutically effective amount of a compound of Formulas 1, 1-1, or 1-2, a prodrug thereof, a hydrate thereof, a solvate thereof, an isomer thereof, an isotope labeled thereof, or a pharmaceutically acceptable salts thereof to a subject in need thereof.

In another aspect, the disclosure relates to a pharmaceutical preparation comprising as active ingredient one or more compounds of Formulas 1, 1-1, or 1-2, a prodrug thereof, a hydrate thereof, a solvate thereof, an isomer thereof, an isotope labeled thereof, or a pharmaceutically acceptable salt thereof, optionally in combination with conventional excipients and/or carriers.

BRIEF DESCRIPTION OF THE DRAWINGS

So that the manner in which the above recited features of the present disclosure can be understood in detail, a more particular description of the disclosure, briefly summarized above, may be had by reference to the embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Definitions

Figure 1A:
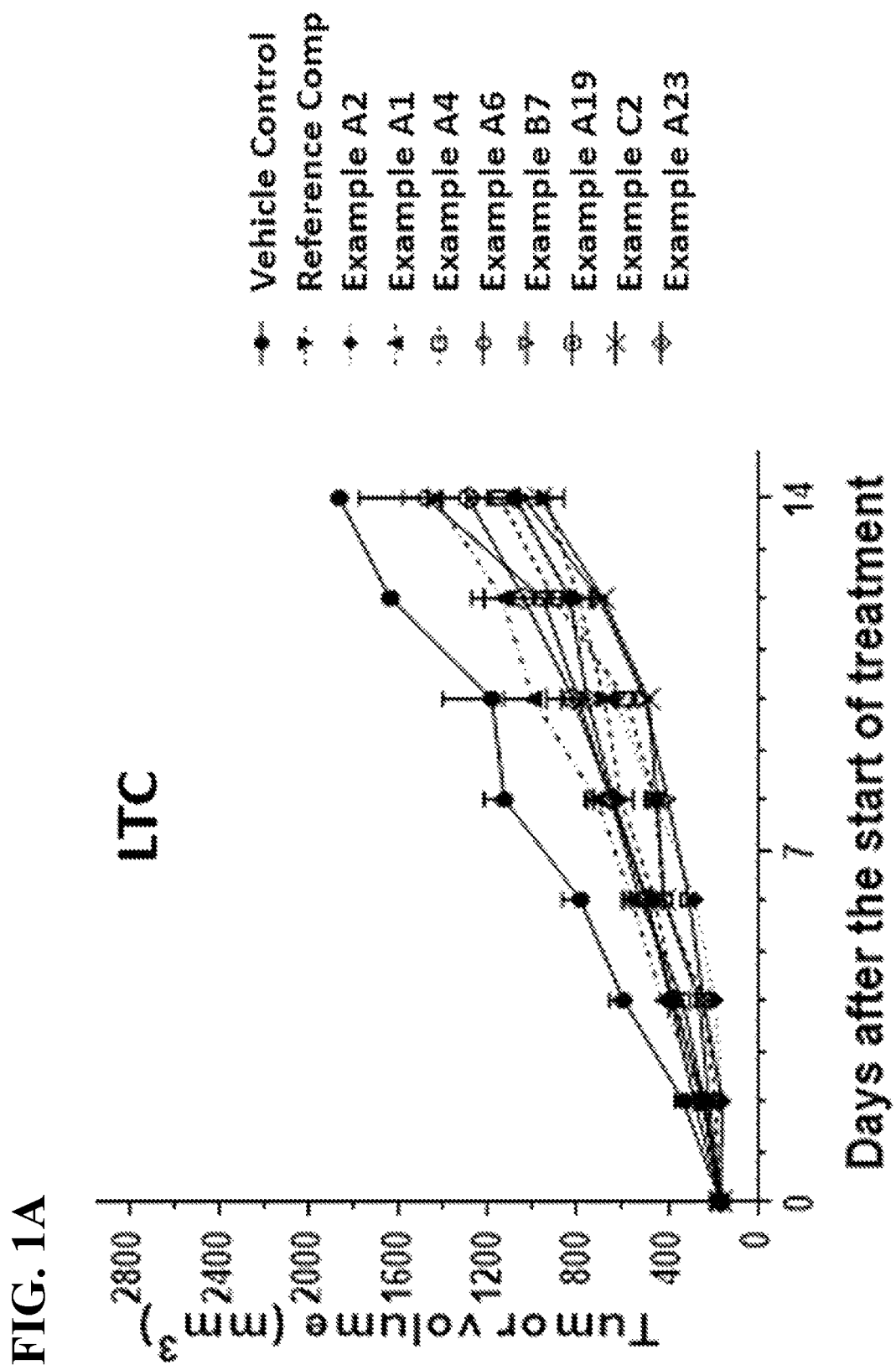
FIG. 1A and FIG. 1B show tumor growth curves of different treatment groups of female BALB/c nude mice bearing Ba/F3 EGFR L/T/C murine pro-B cell tumor models (FIG. 1A) and Ba/F3 EGFR D/T/C murine pro-B cell tumor models (FIG. 1B). Data points represent group mean, error bars represent standard error of the mean (SEM).

The term "halogen" or the word "halo" of "haloalkyl" herein may be F, Cl, Br, or I.

As used herein, the term "alkyl" refers to a straight, or branched hydrocarbon moiety that may be substituted or unsubstituted unless otherwise noted. The alkyl group may include without limitation all possible isomers thereof, such as, for example, methyl, ethyl, propyl, butyl, pentyl, hexyl, or isopropyl, isobutyl, and t-butyl.

As used herein, the term "aryl" refers to an aromatic group which may be substituted or unsubstituted unless otherwise indicated, including, for example, C3-C30 aryl, C3-C20 aryl, C3-C12 aryl, or C3-C8 aryl. For example, phenyl, biphenyl, naphthyl, toluyl, naphthalenyl, anthracenyl, or all possible isomers thereof may be included without limitation.

As used herein, the term "heteroaryl," unless stated otherwise, refers to monocyclic or bicyclic or more, including one or more heteroatoms selected from B, N, O, S, Si and P, wherein nitrogen and sulfur atoms are optionally oxidized, and nitrogen atom is optionally quaternized. Examples of monocyclic heteroaryls include, but are not limited to, pyrazolyl, pyrrolyl, thiazolyl, oxazolyl, thiophenyl, furanyl, imidazolyl, isoxazolyl, triazolyl, thiadiazolyl, tetrazolyl, oxazozolyl, pyridinyl, pyridazinyl, pyrimidinyl, pyrazinyl, thiazolyl and similar groups. Examples of bicyclic heteroaryl include, but are not limited to, indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, purinyl, puropyridinyl, oxochromen, dioxoisoindolin, pyrazolopyridinyl, and the like.

As used herein, the term "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups, spirocycles, and bridged rings (e.g., a bridged bicycloalkyl group). In some embodiments, the cycloalkyl is a C4-10 spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

The term "heterocycloalkyl" used herein is substituted or unsubstituted of a monocyclic or bicyclic including one or more heteroatoms selected from N, O, S, Si and P, unless stated otherwise. Heterocycloalkyl groups can also include spirocycles and bridged rings (e.g., a 5-14 membered bridged biheterocycloalkyl ring optionally substituted with 0 to 2 additional heteroatoms independently selected from N, O, S or B). Heterocycloalkyl include, but are not limited to, C3-C30 heterocycloalkyl, C3-C20 heterocycloalkyl, C3-C12 heterocycloalkyl, or C3-C8 heterocycloalkyl. Examples include, but are not limited to, piperidinyl, piperazinyl, morpholinyl, pyrrolidinyl, thiomorpholinyl, imidazolidinyl, tetrahydrofuryl, 1,3-isoxazolidin-2-one, pyranyl, oxetanyl, azetidinyl, isoxazolidinyl, oxazolidinyl, thiazolidinyl, imidazolidinyl, azepanyl, benzazapene, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxaadamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like.

The term "leaving group" refers to a functional group or atom which can be replaced by another functional group or atom through a substitution reaction (for example an affinity substitution reaction). For example, representative leaving groups include triflate; chlorine, bromine and iodine; sulfonate, such as mesylate, tosylate, p-bromobenzenesulfonate, p-toluenesulfonate and the like; acyloxy, such as acetoxy, trifluoroacetoxy and the like.

As used herein, the term "solvate" may refer to a compound of the present invention or a salt thereof that includes a stoichiometric or nonstoichiometric amount of solvent bound by non-covalent intermolecular forces. Preferred solvents therein may be volatile, non-toxic, and/or solvents suitable for administration to humans. When the solvent is water, hydrate(s) of the compound is/are formed, and such hydrate(s) is/are intended to be included in the disclosure.

As used herein, the term "stereoisomers" may refer to a compound of the present invention or a salt thereof having the same chemical formula or molecular formula, but which is optically or sterically different, and specifically, diastereomers, enantiomers, geometric isomers, or shapes It may be an isomer. The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. Formulas 1, 1-1, and 1-2 provided herein include stereoisomers of the compounds. Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

As used herein, the term "derivative" refers to a compound obtained by substituting a part of the structure of the compound with another atom or group of atoms.

The compounds according to the invention can also be used in the form of pharmaceutically acceptable salts derived from inorganic or organic acids, for example the salts are hydrochloric acid, hydrobromic acid, sulfuric acid, phosphoric acid, nitric acid, acetic acid, glycolic acid, lactic acid, Pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, Salts derived from salicylic acid, methanesulfonic acid, benzenesulfonic acid, toluenesulfonic acid and the like. Pharmaceutically acceptable salts of the compounds according to the disclosure are prepared by dissolving a compound of Formula 1 in a water miscible organic solvent, such as acetone, methanol, ethanol, or acetonitrile and adding an excess of an organic acid or an aqueous acid solution of an inorganic acid. It can then be prepared by precipitation or crystallization. The solvent or excess acid may then be evaporated and dried in this mixture to obtain an addition salt or the precipitated salt may be prepared by suction filtration.

Preparation Method

The compounds of the present disclosure can be prepared by a variety of synthetic methods well known by those skilled in the art, including the following exemplified embodiments, the embodiments formed by combining them with other chemical synthesis methods, and equivalent alternatives known to those skilled in the art. Preferred embodiments include, but are not limited to, the examples of the present disclosure. General processes of the preparation methods are illustrated in Reaction Schemes 1-3 below.

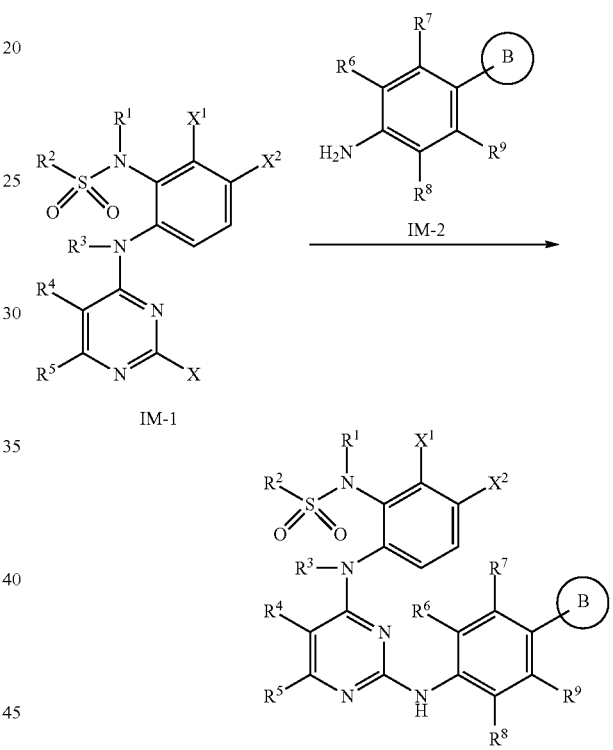

In the Reaction Scheme 1, X of compound IM-1 serves as a leaving group when reacting with compound IM-2 and thus forming a covalent bond between IM-1 and IM-2. The reaction can be conducted in a solvent, which includes, but is not particularly limited to, lower alcohols including iso-propanol, methanol, ethanol, propanol, iso-butanol, tert-butanol, sec-butanol and n-butanol; tetrahydrofuran (THF); dioxane; ether solvents including ethyl ether, 1,2-dimethoxyethane and the like; dimethylformamide (DMF); dimethyl sulfoxide (DMSO); methylene chloride; dichloroethane; water; acetonitrile; ethyl acetate; N-Methyl-2-pyrrolidone (NMP). The variables can be further modified when necessary.

Additionally, the present disclosure provides a method for preparing the compound IM-1 as indicated in Reaction Scheme 2 in which the variables can be further modified when necessary. Further, sulfonyl group can be introduced later after reacting IM-A and IM-B.

[Reaction Scheme 2]

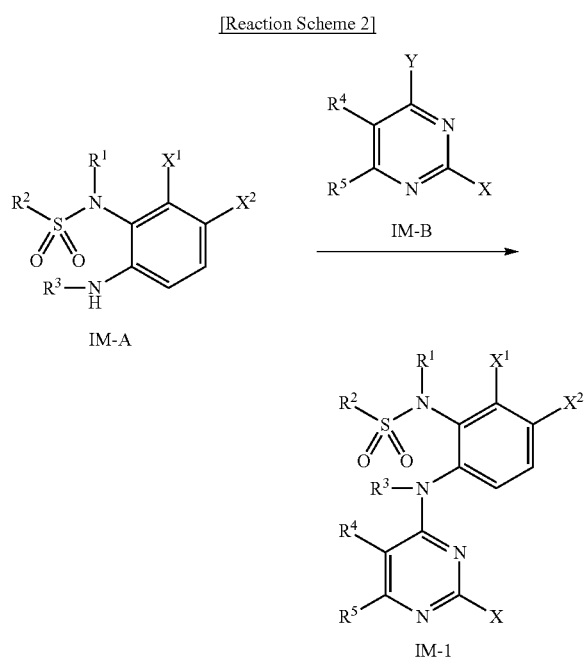

In Reaction Scheme 2, variables X and Y each represent a halogen.

In Reaction Scheme 2, Y of compound IM-B serves as a leaving group when reacting with compound IM-A and thus forming a covalent bond between IM-A and IM-B. The reaction may be performed in a solvent which may include, but is not particularly limited to, lower alcohols including isopropanol, methanol, ethanol, propanol, iso-butanol, tert-butanol, sec-butanol and n-butanol; tetrahydrofuran (THF); dioxane; ether solvents including ethyl ether, 1,2-dimethoxyethane and the like; dimethylformamide (DMF); dimethyl sulfoxide (DMSO); methylene chloride; dichloroethane; water; acetonitrile; ethyl acetate; or N-Methyl-2-pyrrolidone (NMP).

[Reaction Scheme 3]

Additionally, the compound IM-2 of Reaction Scheme 1 may be prepared according to Reaction Scheme 3 below, in which the variables can be further modified when necessary.

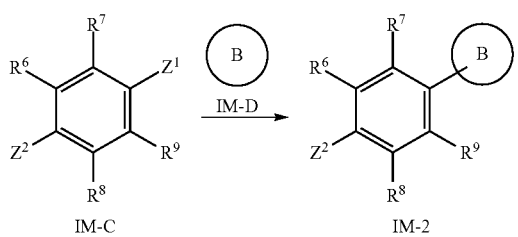

In Reaction Scheme 3, $Z^1$ represents a leaving group and $Z^2$ can be further modified as necessary by employing conditions known in the art.

In Reaction Scheme 3 above, the reaction can be carried out in the presence of a solvent, and the solvent may include, but is not particularly limited to, lower alcohols including isopropanol, methanol, ethanol, propanol, iso-butanol, tert-butanol, sec-butanol and n-butanol; tetrahydrofuran (THF); dioxane; ether solvents including ethyl ether, 1,2-dimethoxyethane and the like; dimethylformamide (DMF); dimethyl sulfoxide (DMSO); methylene chloride; dichloroethane; water; acetonitrile; ethyl acetate; or N-Methyl-2-pyrrolidone (NMP).

Formulations and Uses

Suitable pharmaceutical compositions or formulations include for example tablets, capsules, suppositories, solutions, particularly solutions for injection (s.c., i.v., i.m.) and infusion, syrups, elixirs, emulsions or dispersible powders. The content of the pharmaceutically active compound(s) may be in the range from 0.1 to 90 wt. %, preferably 0.5 to 50 wt. % of total weight or volume of the composition.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly, the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules comprising one or more active substances or combinations of active substances may for example be prepared by mixing the active substances with inert carriers such as lactose or sorbitol and packing them into gelatine capsules.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The compositions are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavor enhancers or colorings in addition to the excipients mentioned above.

For parenteral use, solutions of the active ingredients with suitable liquid carriers may be used.

The dosage of the pharmaceutical composition is an amount effective for treating or preventing an individual, a subject, or a patient, and may be orally or parenterally administered as desired. Upon oral administration, 0.01 to 1000 per kg of body weight per day based on the active ingredient mg, more specifically 0.1 to 1000 mg, to be administered in an amount of 0.01 to 100 mg per kg body weight per day, more specifically 0.1 to 50 mg based on the active ingredient during parenteral administration. It may be administered in divided doses of 1 to several times. Dosages for a particular individual, subject, or patient should be determined in light of several relevant factors such as the patient's weight, age, sex, health condition, diet, time of administration, mode of administration, severity of the disease and can be appropriately added or subtracted by a specialist. It is to be understood that such doses are not intended to limit the scope of the disclosure in any aspect. A physician or veterinarian having ordinary skill in the art can readily determine and prescribe the effective amount of the required pharmaceutical composition. For example, a physician or veterinarian may use a dose of a compound of the disclosure for use in a pharmaceutical composition, starting at a lower level than required to achieve the desired therapeutic effect, and gradually increasing the dosage until the desired effect is achieved.

As used herein, the term "treating" or "treatment" refers to inhibiting a disease, e.g., inhibiting a disease, condition or disorder in an individual experiencing or exhibiting the pathology or indication of the disease, condition or disorder, i.e., preventing further development of the pathology and/or signs, or ameliorating the disease, e.g., improving a disease, condition or disorder in an individual experiencing or exhibiting the pathology or sign of the disease, condition or disorder, i.e., reversing pathology and/or signs, such as reducing disease severity.

As used herein, the term "Individual," "subject," or "patient" refers to any animal, including mammals such as mice, rats, other rodents, rabbits, dogs, cats, pigs, cattle, sheep, horses or primates, and humans.

In one or more embodiments, the compound represented by Formula 1 shows a high inhibitory ability on EGFR mutation, and thus, can be added to health functional foods or dietary supplements, such as foods, beverages, and the like, as a health functional food composition for the prevention or amelioration of cancer, particularly cancer with EGFR mutation.

In one or more embodiments, the compound may be administered in combination with other anticancer treatments. The compounds of the present disclosure can be used in combination with one or more other enzyme/protein/receptor inhibitors or one or more therapies for the treatment of cancer. The compounds of the present disclosure can further be used in combination with other methods of treating cancers, for example by chemotherapy, irradiation therapy, tumor-targeted therapy, adjuvant therapy, immunotherapy or surgery.

Before describing several exemplary embodiments of the disclosure, it is to be understood that the disclosure is not limited to the details of construction or process steps set forth in the following description. The disclosure is capable of other embodiments and of being practiced or being carried out in various ways.

EXAMPLES

Hereinafter, various embodiments of the present invention will be described in detail through the Examples and Experimental Examples. However, the following Examples and Experimental Examples are only illustrations of the present invention, and the contents of the present invention are not limited to the following Examples and Experimental Examples. If there is no other definition available, they have a meaning that is commonly understood by a person who has common knowledge in the technical field.

The chemical structures of the compounds prepared as Examples were arranged and indicated in Tables 1 to 4 below.

TABLE 1

| Example | Chemical Structure |
| --- | --- |
| A1 | 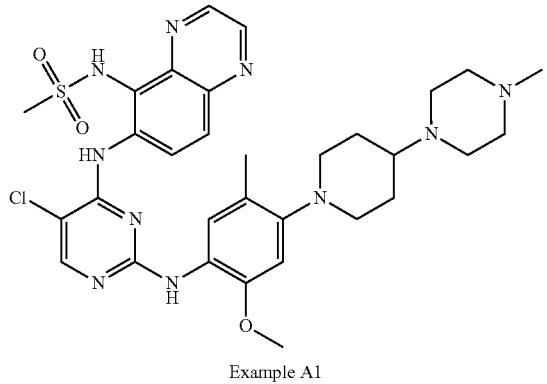 [SMILES: COc1cc(N2CCC(N3CCN(C)CC3)CC2)c(C)cc1Nc1ncc(Cl)c(Nc2ccc3nccnc3c2NS(C)(=O)=O)n1] |

Example A1

TABLE 1-continued
| Example | Chemical Structure |
|---|---|
| A2 | 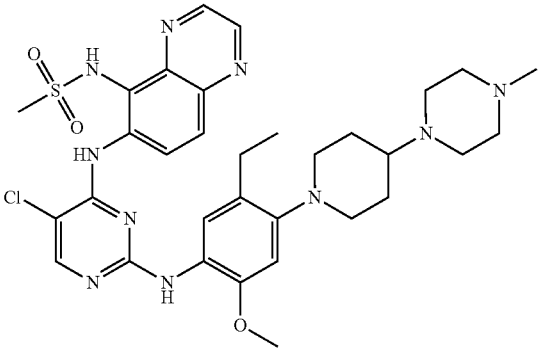<br>Example A2 |
| A3 | 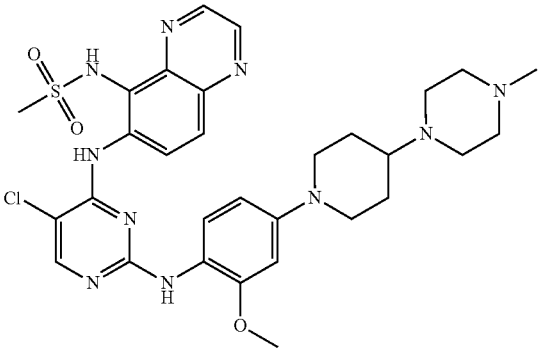<br>Example A3 |
| A4 | 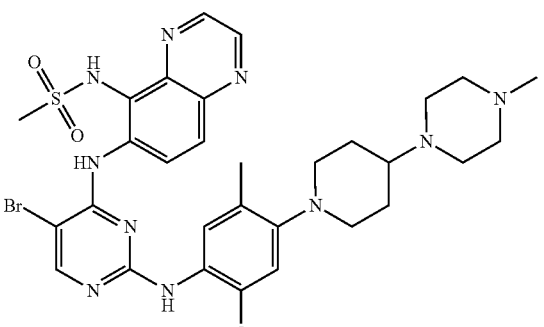<br>Example A4 |
| A5 | 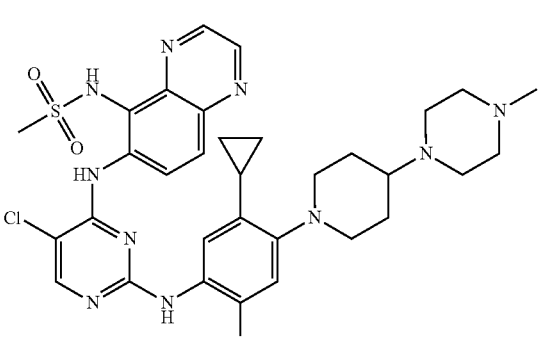<br>Example A5 |

TABLE 1-continued
| Example | Chemical Structure |
|---|---|
| A6 | 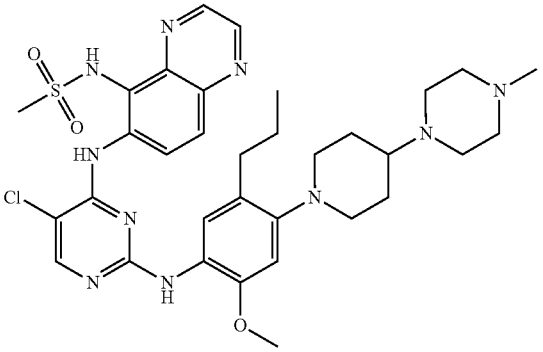<br>Example A6 |
| A7 | 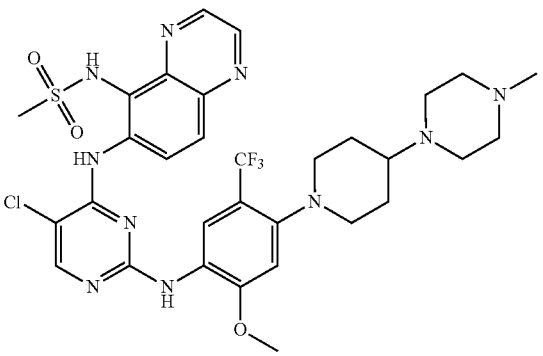<br>Example A7 |
| A8 | 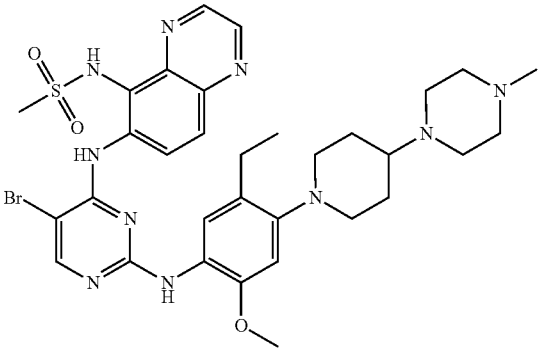<br>Example A8 |
| A9 | 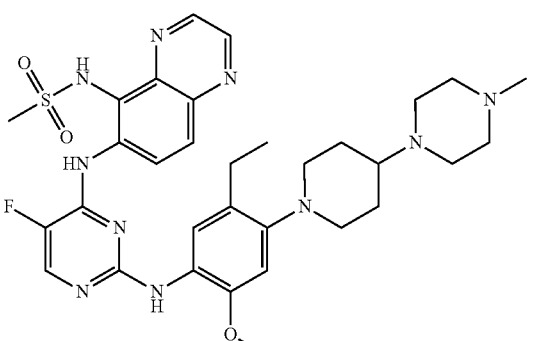<br>Example A9 |

TABLE 1-continued

| Example | Chemical Structure |
|---------|-------------------|
| A10 | Example A10 |
| A11 | Example A11 |
| A12 | Example A12 |
| A13 | Example A13 |

TABLE 1-continued
| Example | Chemical Structure |
| --- | --- |
| A14 | 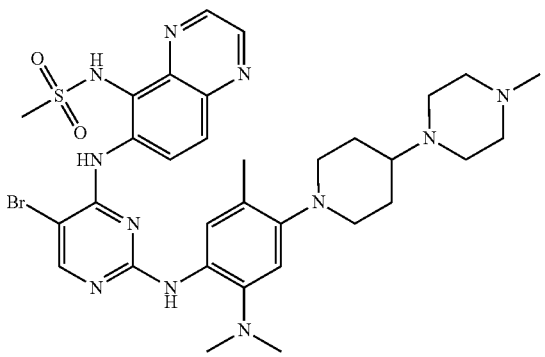Example A14 |
| A15 | 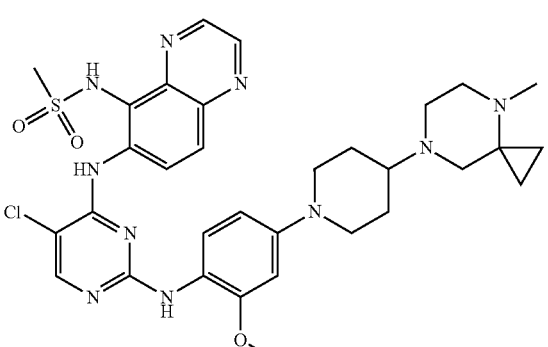Example A15 |
| A16 | 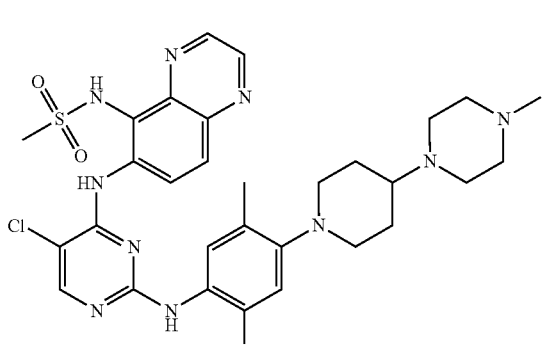Example A16 |
| A17 | 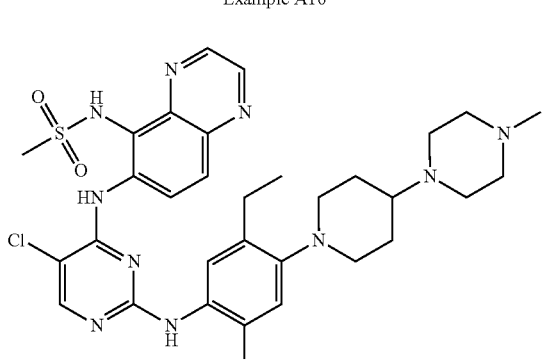Example A17 |

TABLE 1-continued
| Example | Chemical Structure |
| --- | --- |
| A19 | 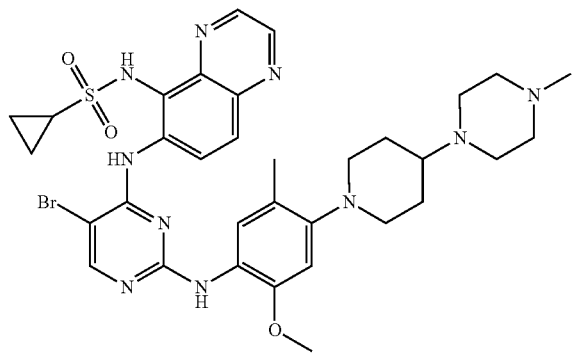<br>Example A19 |
| A20 | 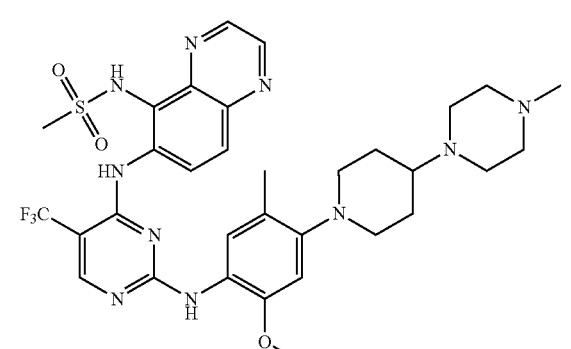<br>Example A20 |
| A21 | 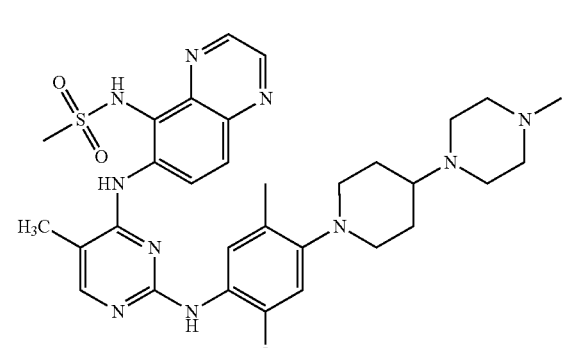<br>Example A21 |
| A22 | 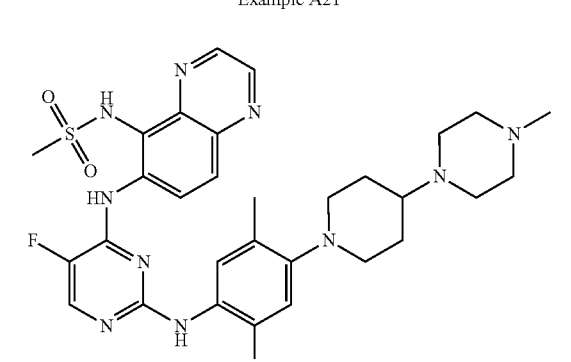<br>Example A22 |

TABLE 1-continued
| Example | Chemical Structure |
| --- | --- |
| A23 | 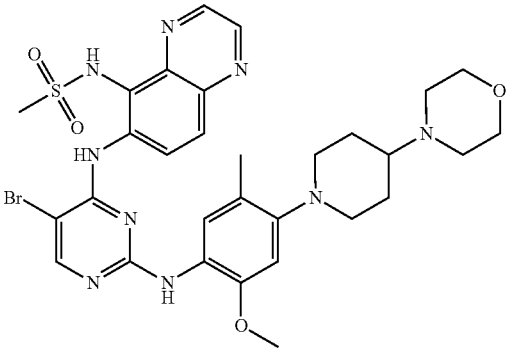
Example A23 |
| A24 | 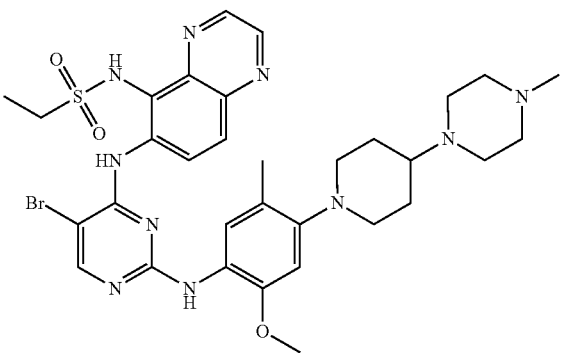
Example A24 |
| A25 | 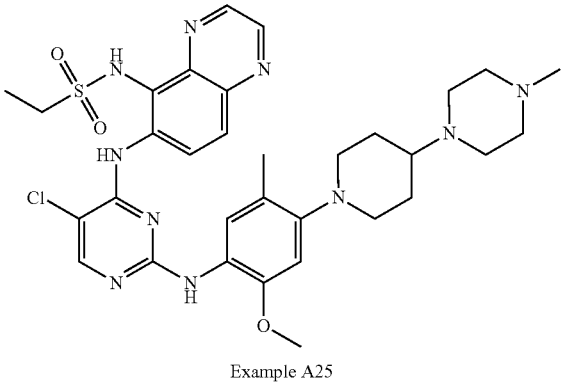 [SMILES: CCS(=O)(=O)Nc1c(Nc2nc(Nc3cc(C)c(N4CCC(N5CCN(C)CC5)CC4)cc3OC)ncc2Br)ccc2nccnc12]
Example A25 |
| A26 | 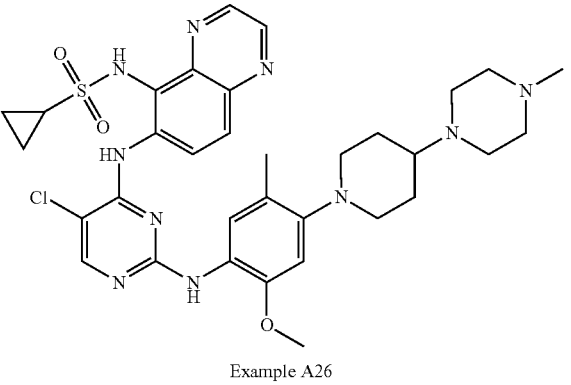 [SMILES: COc1cc(N2CCC(N3CCN(C)CC3)CC2)c(C)cc1Nc1ncc(Cl)c(Nc2ccc3nccnc3c2NS(=O)(=O)C2CC2)n1]
Example A26 |

TABLE 1-continued
| Example | Chemical Structure |
|---|---|
| A27 | 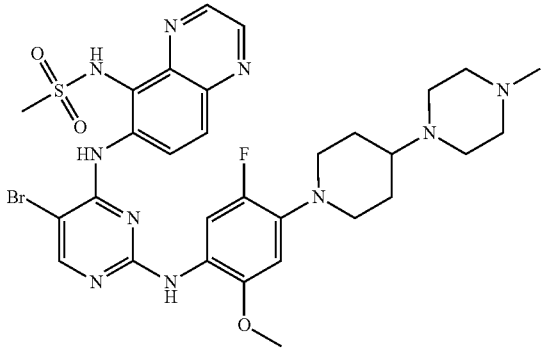<br>Example A27 |
| A28 | 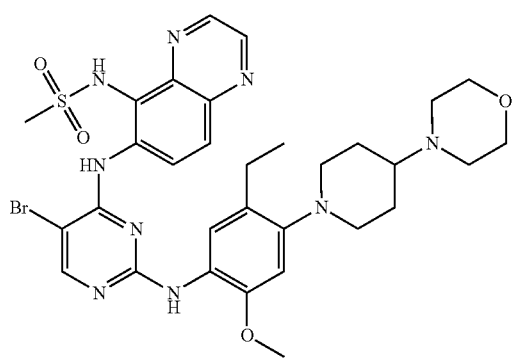<br>Example A28 |
| A29 | 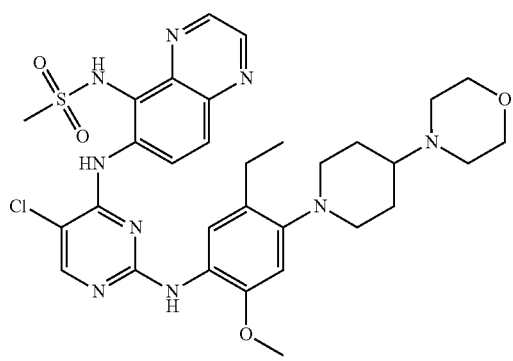<br>Example A29 |
| A30 | 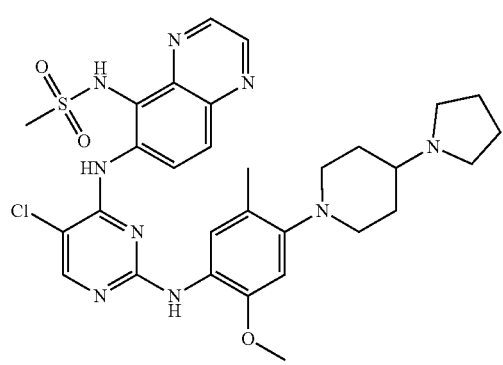<br>Example A30 |

TABLE 1-continued
| Example | Chemical Structure |
|---|---|
| A31 | 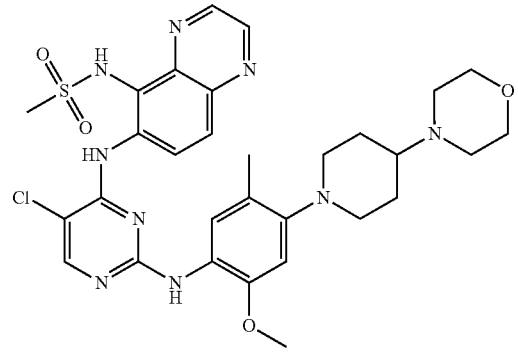<br>Example A31 |
| A32 | 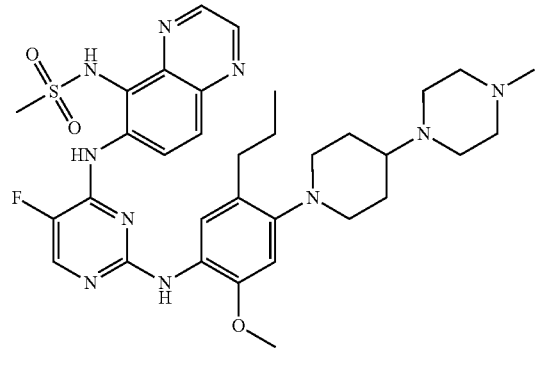<br>Example A32 |
| A33 | 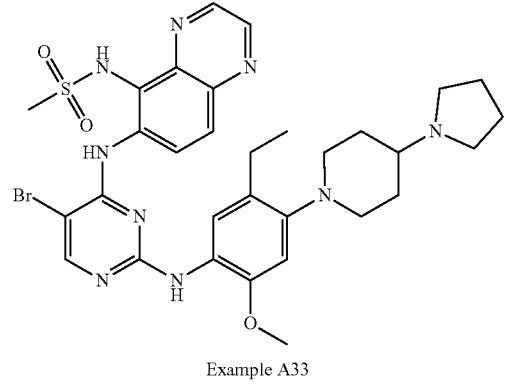 [SMILES: CCc1cc(Nc2ncc(Br)c(Nc3ccc4nccnc4c3NS(C)(=O)=O)n2)c(OC)cc1N1CCC(N2CCCC2)CC1]<br>Example A33 |
| A34 | 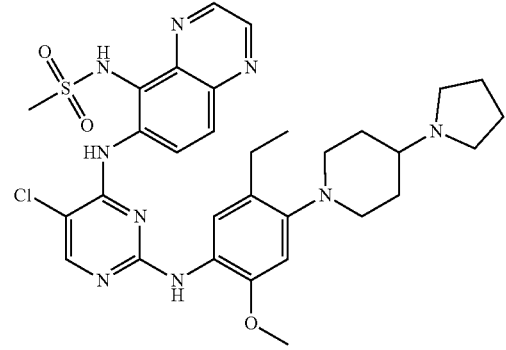<br>Example A34 |

TABLE 1-continued
| Example | Chemical Structure |
|---|---|
| A35 | 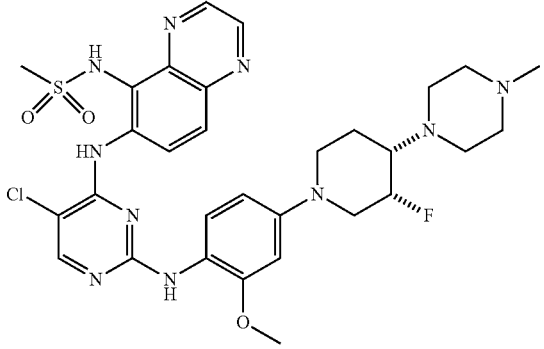<br>Example A35 |
| A36 | 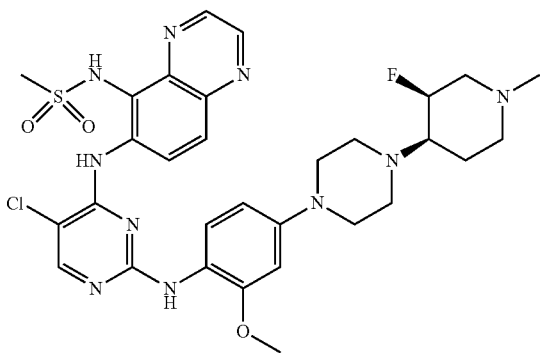<br>Example A36 |
| A37 | 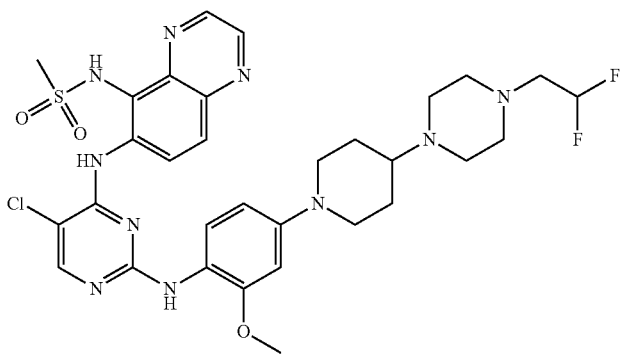<br>Example A37 |
| A38 | 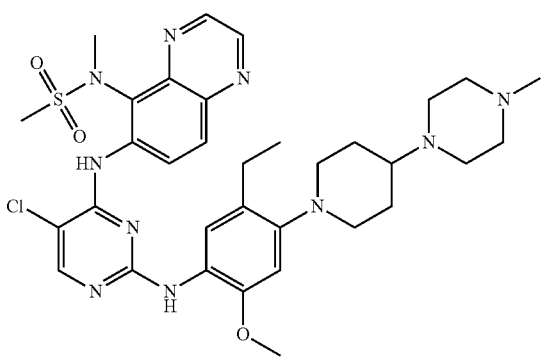<br>Example A38 |

TABLE 1-continued
| Example | Chemical Structure |
|---|---|
| A39 | 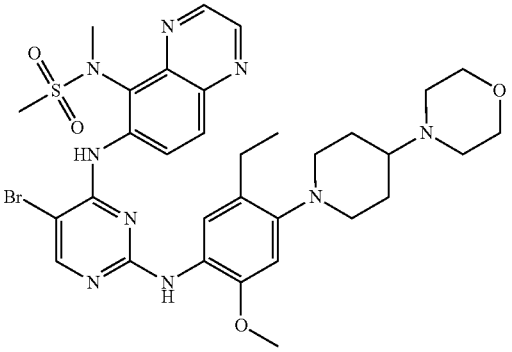<br>Example A39 |
| A40 | 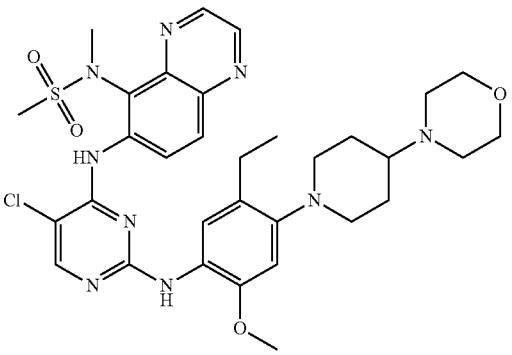<br>Example A40 |
| A41 | 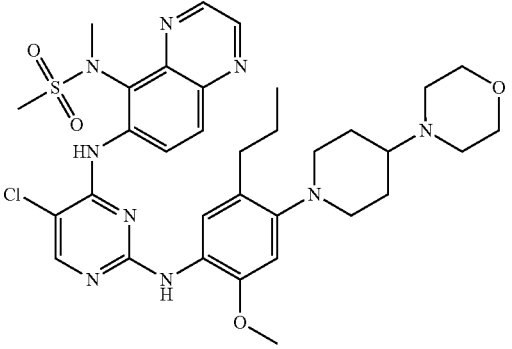<br>Example A41 |
| A42 | 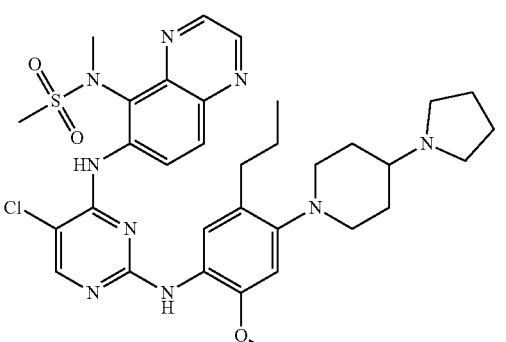<br>Example A42 |

TABLE 1-continued
| Example | Chemical Structure |
|---|---|
| A43 | 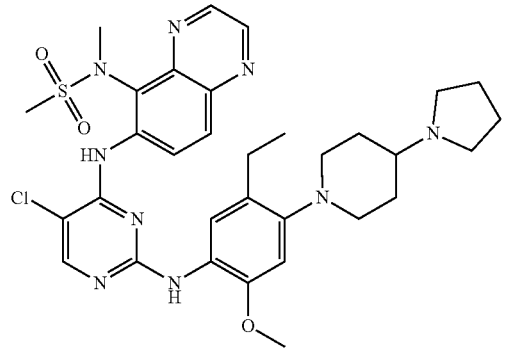<br>Example 43 |
| A44 | 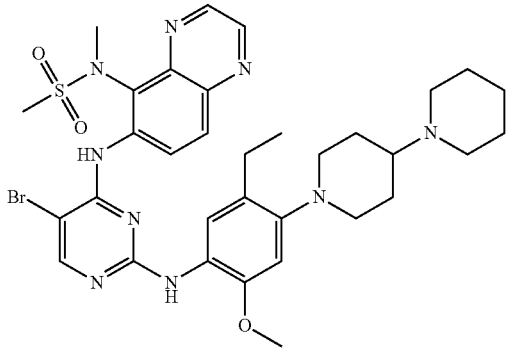<br>Example A44 |
| A45 | 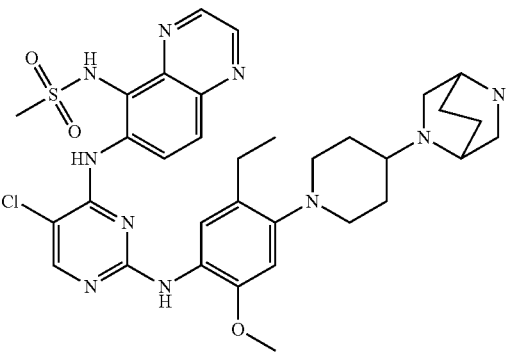<br>Example A45 |
| A46 | 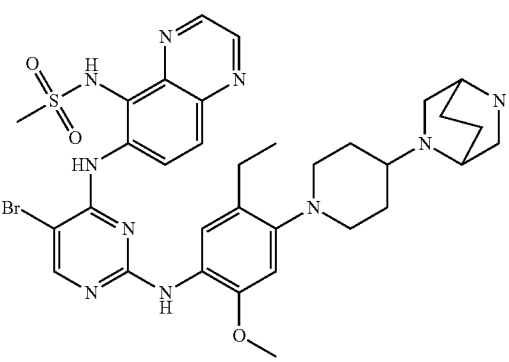<br>Example A46 |

TABLE 1-continued
| Example | Chemical Structure |
|---|---|
| A47 | 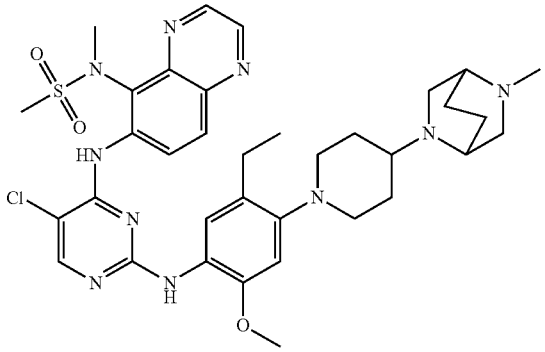<br>Example A47 |
| A48 | 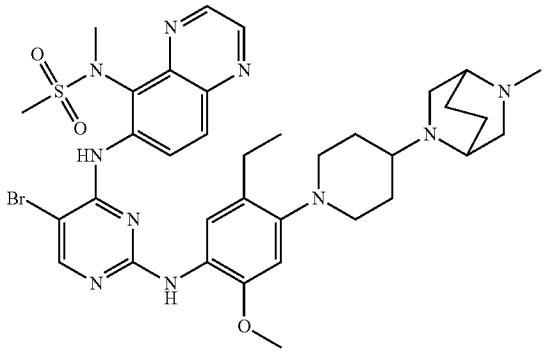<br>Example A48 |
| A49 | 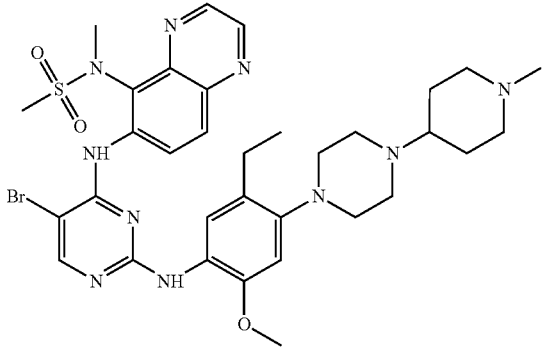<br>Example A49 |

TABLE 2

| Example | Chemical Structure |
|---|---|
| B1 | Example B1 |
| B2 | Example B2 |
| B3 | Example B3 |
| B4 | Example B4 |

TABLE 2-continued

| Example | Chemical Structure |
|---|---|
| B5 | Example B5 |
| B6 | Example B6 |
| B7 | Example B7 |
| B8 | Example B8 |

TABLE 2-continued

| Example | Chemical Structure |
|---------|-------------------|
| B9 | Example B9 |
| B10 | Example B10 |
| B11 | Example B11 |
| B12 | Example B12 |
| B13 | Example B13 |
| B14 | Example B14 |
| B15 | Example B15 |
| B16 | Example B16 |

TABLE 2-continued

| Example | Chemical Structure |
|---|---|
| B17 | Example B17 |
| B18 | Example B18 |
| B19 | Example B19 |
| B20 | Example B20 |
| B21 | Example B21 |
| B22 | Example B22 |
| B23 | Example B23 |

TABLE 2-continued

| Example | Chemical Structure |
|---|---|
| B24 | Example B24 |
| B25 | Example B25 |
| B26 | Example B26 |
| B27 | Example B27 |
| B28 | Example B28 |
| B29 | Example B29 |
| B30 | Example B30 |
| B31 | Example B31 |

TABLE 2-continued
| Example | Chemical Structure |
|---|---|
| B32 | 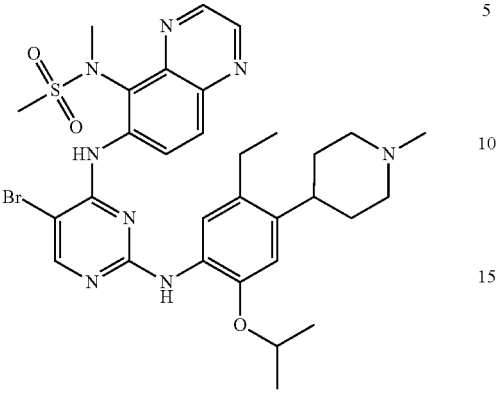<br>Example B32 |
TABLE 3
| Example | Chemical Structure |
|---|---|
| C1 | 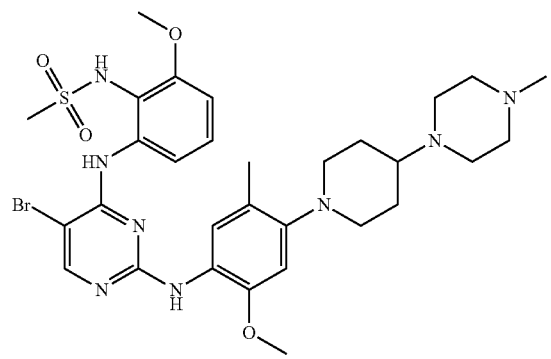<br>Example C1 |
| C2 | 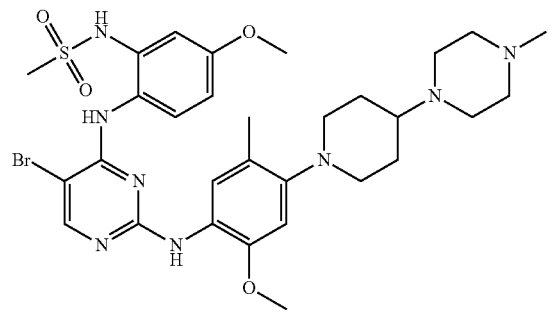<br>Example C2 |

TABLE 3-continued
| Example | Chemical Structure |
| --- | --- |
| C3 | 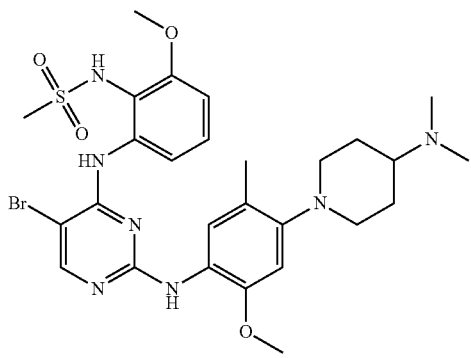
Example C3 |
| C4 | 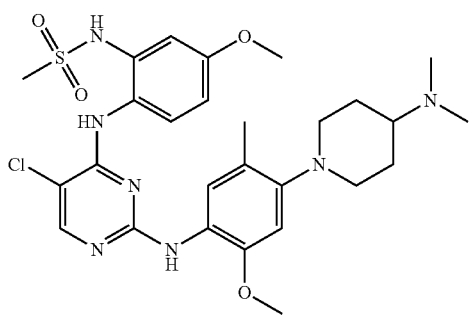
Example C4 |
| C5 | 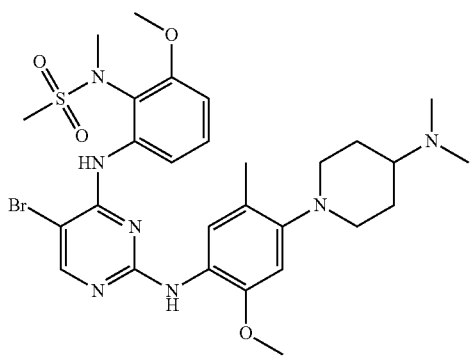
Example C5 |
| C6 | 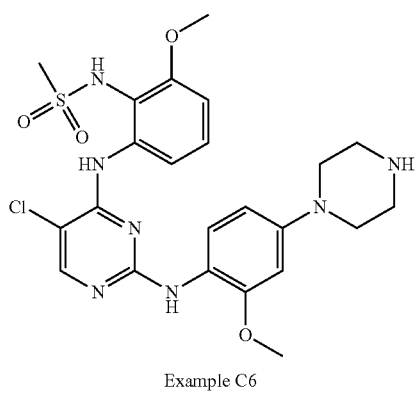 [SMILES: COc1cc(N2CCNCC2)ccc1Nc1ncc(Cl)c(Nc2cccc(OC)c2NS(C)(=O)=O)n1]
Example C6 |

TABLE 3-continued
| Example | Chemical Structure |
| --- | --- |
| C7 | 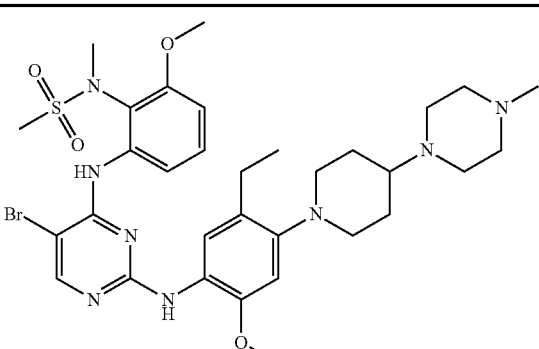
Example C7 |
| C8 | 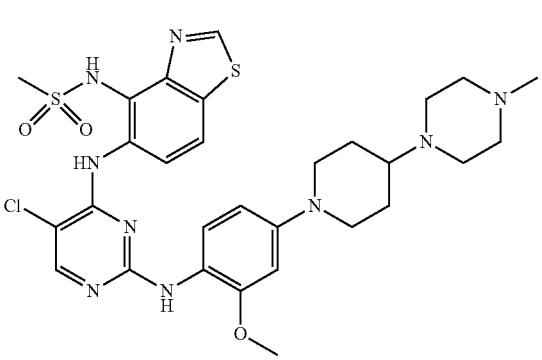
Example C8 |
| C9 | 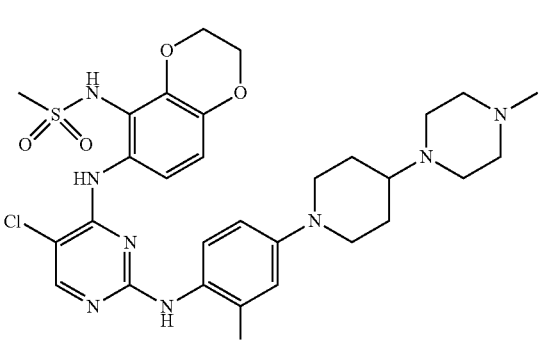
Example C9 |
| C10 | 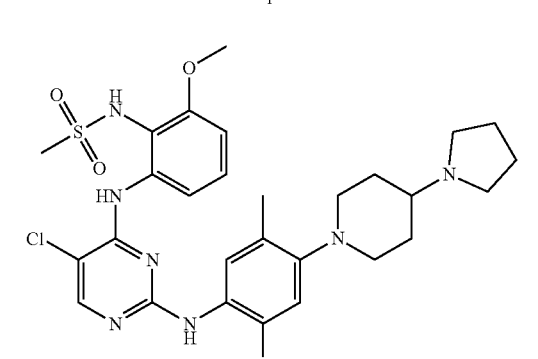
Example C10 |

TABLE 3-continued
| Example | Chemical Structure |
|---|---|
| C11 | 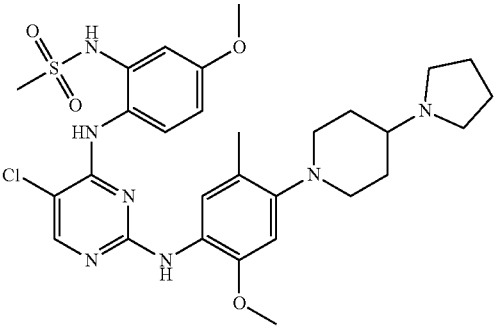
Example C11 |
| C12 | 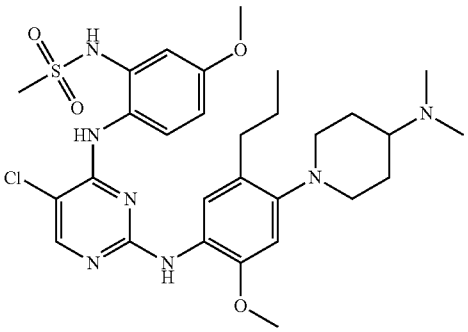
Example C12 |
| C13 | 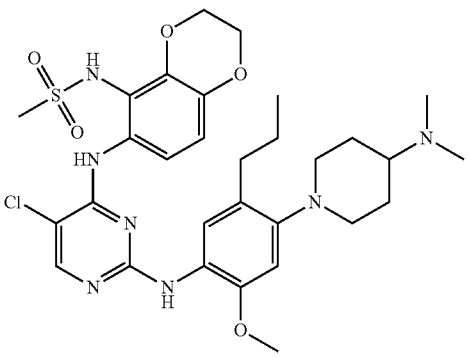
Example C13 |
| C14 | 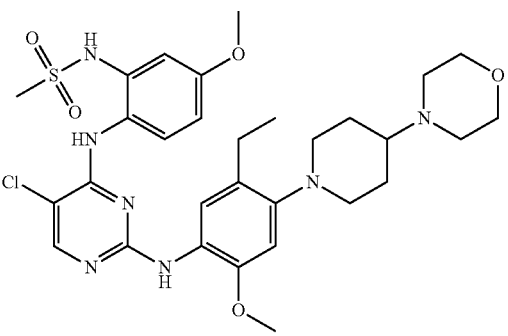
Example C14 |

TABLE 3-continued
| Example | Chemical Structure |
| --- | --- |
| C15 | 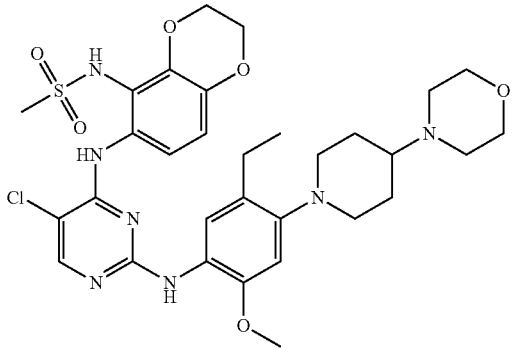<br>Example C15 |
| C16 | 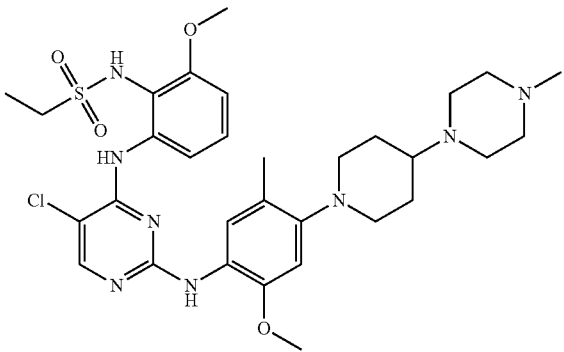<br>Example C16 |
| C17 | 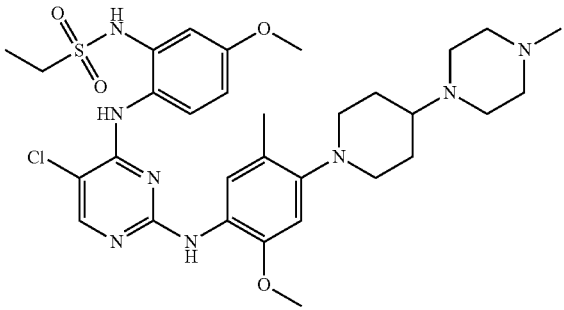<br>Example C17 |
| C18 | 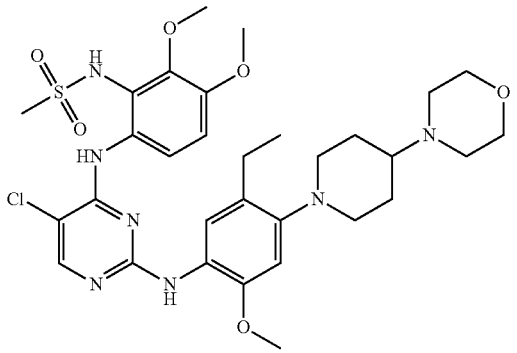<br>Example C18 |

TABLE 3-continued
| Example | Chemical Structure |
|---|---|
| C19 | 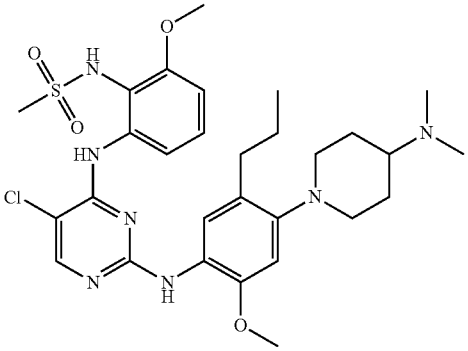<br>Example C19 |
| C20 | 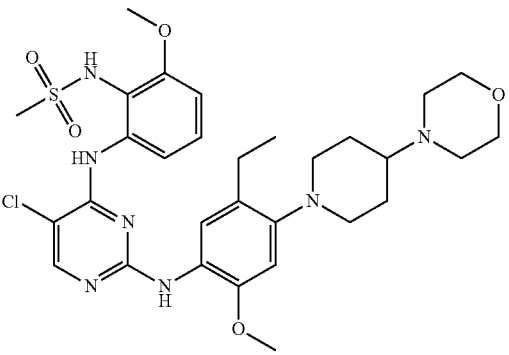<br>Example C20 |
| C21 | 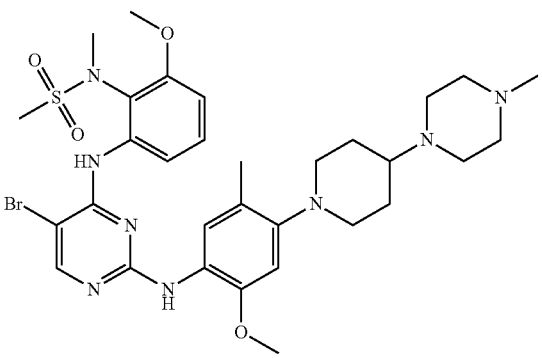<br>Example C21 |
| C22 | 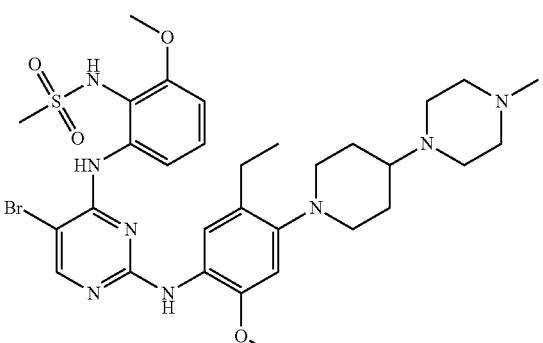<br>Example C22 |

TABLE 3-continued
| Example | Chemical Structure |
| --- | --- |
| C23 | 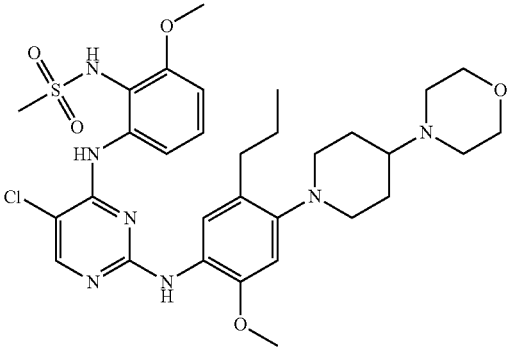
Example C23 |
| C24 | 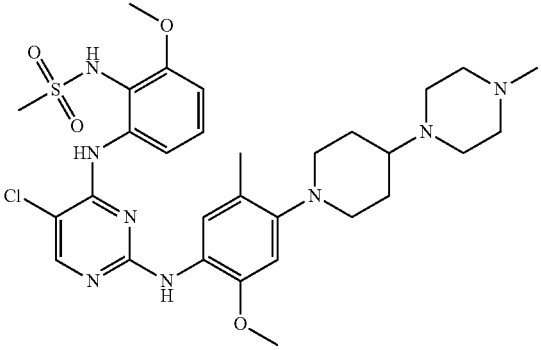
Example C24 |
| C25 | 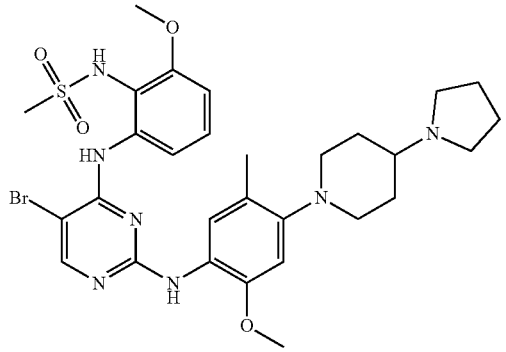
Example C25 |
| C26 | 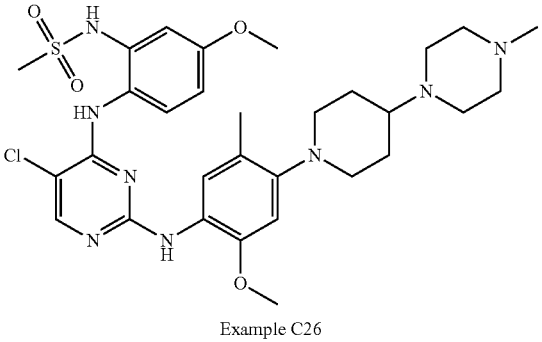 [SMILES: COc1ccc(Nc2nc(Nc3cc(C)c(N4CCC(N5CCN(C)CC5)CC4)cc3OC)ncc2Cl)c(NS(C)(=O)=O)c1]
Example C26 |

TABLE 3-continued
| Example | Chemical Structure |
|---|---|
| C27 | 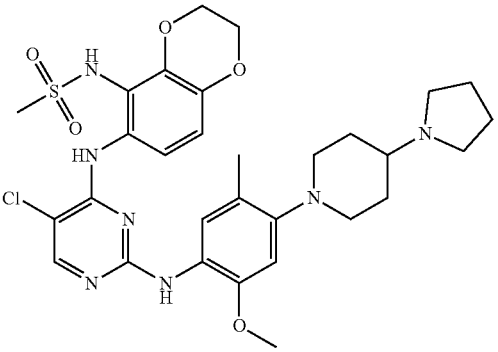<br>Example C27 |
| C28 | 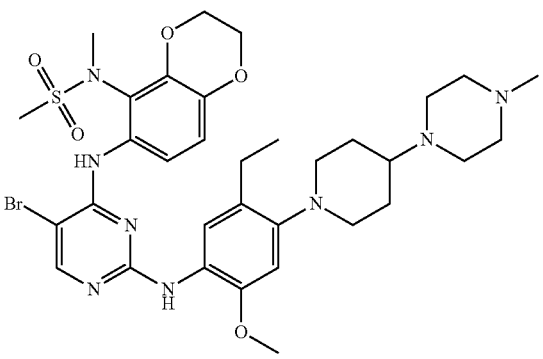<br>Example C28 |
| C29 | 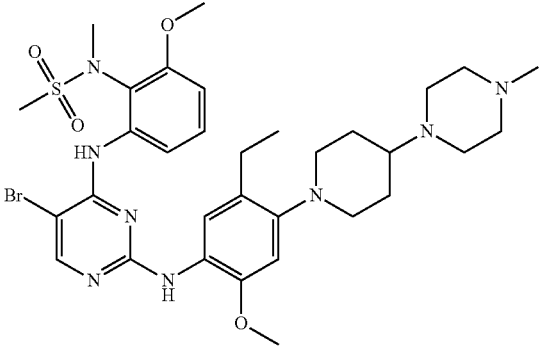<br>Example C29 |
| C30 | 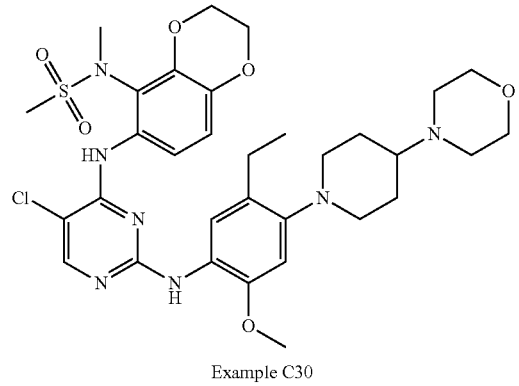 [SMILES: CCc1cc(Nc2ncc(Cl)c(Nc3ccc4c(c3N(C)S(C)(=O)=O)OCCO4)n2)c(OC)cc1N1CCC(N2CCOCC2)CC1]<br>Example C30 |

TABLE 3-continued
| Example | Chemical Structure |
|---|---|
| C31 | 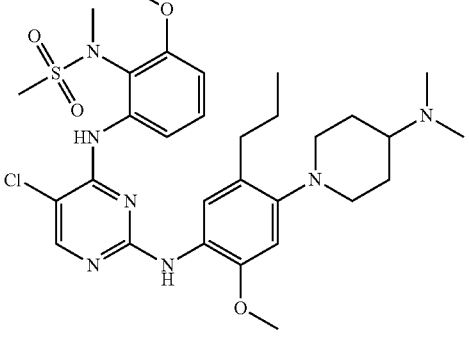
Example 31 |
| C32 | 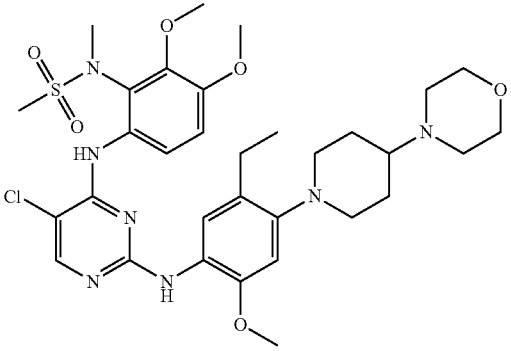
Example C32 |
TABLE 4
| Example | Chemical Structure |
|---|---|
| D1 (comparative) | 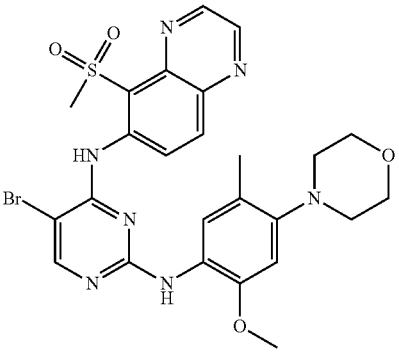 |
TABLE 4-continued
| Example | Chemical Structure |
|---|---|
| D2 | 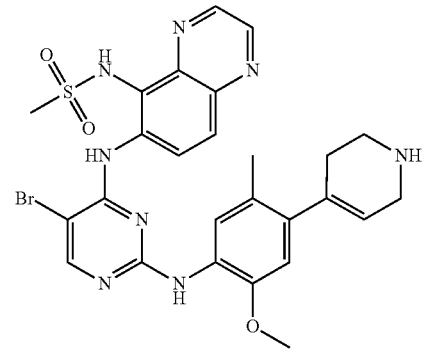 [SMILES: COc1cc(C2=CCNCC2)c(C)cc1Nc1ncc(Br)c(Nc2ccc3nccnc3c2NS(C)(=O)=O)n1] |

TABLE 4-continued

| Example | Chemical Structure |
|---|---|
| D3 (comparative) | 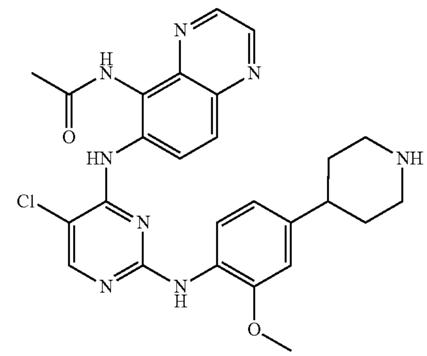 [SMILES: COc1cc(C2CCNCC2)ccc1Nc1ncc(Cl)c(Nc2ccc3nccnc3c2NC(C)=O)n1] |
| D4 (comparative) | 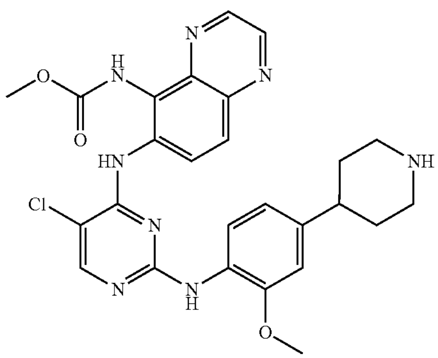 [SMILES: COC(=O)Nc1c(Nc2nc(Nc3ccc(C4CCNCC4)cc3OC)ncc2Cl)ccc2nccnc12] |
| D5 | 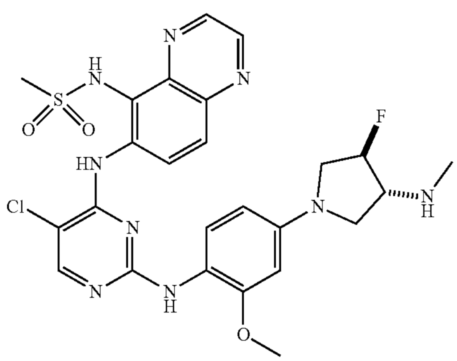 [SMILES: CN[C@@H]1CN(c2ccc(Nc3ncc(Cl)c(Nc4ccc5nccnc5c4NS(C)(=O)=O)n3)c(OC)c2)C[C@H]1F] |
| D6 | 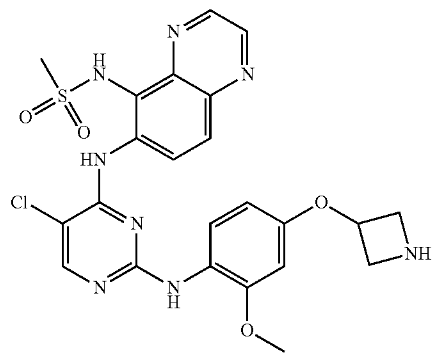 [SMILES: COc1cc(OC2CNC2)ccc1Nc1ncc(Cl)c(Nc2ccc3nccnc3c2NS(C)(=O)=O)n1] |
| D7 | 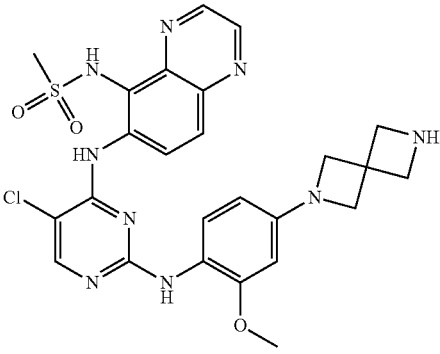 [SMILES: COc1cc(N2CC3(CNC3)C2)ccc1Nc1ncc(Cl)c(Nc2ccc3nccnc3c2NS(C)(=O)=O)n1] |

List of Abbreviations

| | |
|---|---|
| AcOH | Acetic acid |
| Boc | Tert-butyloxycarbonyl |
| BuOH | Butanol |
| EtOAc | Ethyl acetate |
| EtOH | Ethanol |
| MeOH | Methanol |
| DCM | Dichloromethane |
| DMSO | Dimethyl sulfoxide |
| MeCN | Acetonitrile |
| LC-MS | Liquid chromatography-mass spectrometry |
| NMP | N-Methyl-2-pyrrolidone |
| THF | Tetrahydrofuran |
| TFA | Trifluoroacetic acid |
| TEA | Triethylamine |
| TLC | Thin layer chromatography |
| TsOH | Tosylic acid |
| HPLC | High-performance liquid chromatography |

[Example A1] N-(6-((5-chloro-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide (Step 1) Preparation of 1-bromo-2-fluoro-4-methoxy-5-nitrobenzene (A1-2)

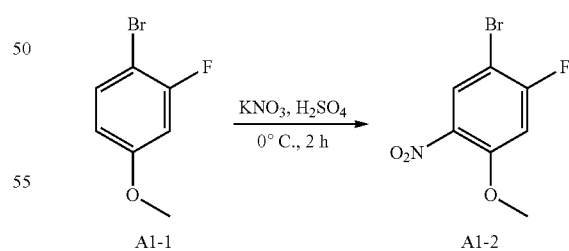

To a solution of Compound A1-1 (25.0 g, 122 mmol) in con. H₂SO₄ (125 mL) was added KNO₃ (12.3 g, 122 mmol) portion wise at 0° C. The reaction mixture was stirred at 0° C. for 1 h. The reaction mixture was added to ice water (200 mL) slowly under stirring. Then it was extracted with DCM (150 mL×3). The combined organic layer was washed with brine (200 mL), dried over Na₂SO₄, filtered and concentrated under reduced pressure to give a residue. The residue was purified by flash silica gel chromatography to afford compound A1-2 as a yellow solid.

$^1$H NMR (400 MHz, CDCl$_3$) δ 3.99 (3H, s), 6.90 (1H, d, J=9.6 Hz), 8.19 (1H, d, J=7.2 Hz).

(Step 2) Preparation of 1-(1-(2-bromo-5-methoxy-4-nitrophenyl)piperidin-4-yl)-4-methylpiperazine (A1-3)

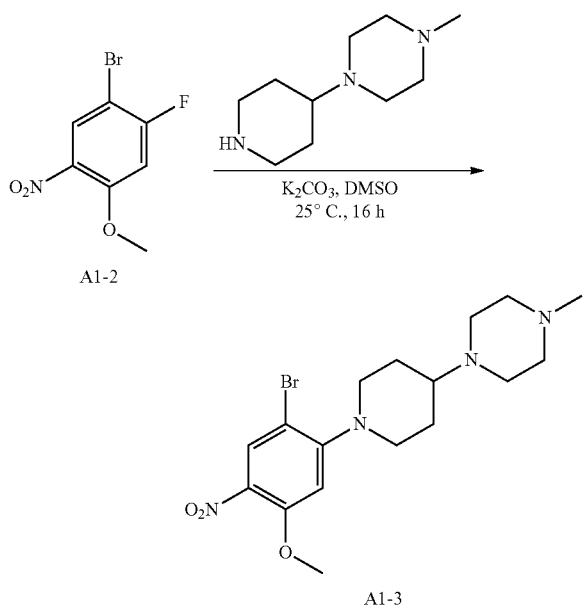

To a stirred solution of compound A1-2 (12.3 g, 49.2 mmol) in DMSO (150 mL) was added K$_2$CO$_3$ (10.2 g, 73.8 mmol) and 1-methyl-4-(4-piperidyl) piperazine (9.92 g, 54.1 mmol). The mixture was stirred at 25° C. for 16 h. The reaction mixture was diluted with water (400 mL) and extracted with EtOAc (200 mL×4). The combined organic layer was washed with brine (500 mL), dried over Na$_2$SO$_4$, filtered and concentrated under reduced pressure to give a residue. It was purified by reverse-phase chromatography to afford compound A1-3 as a yellow solid.

$^1$H NMR (400 MHz, CDCl$_3$) δ 1.75-1.85 (2H, m), 1.79-1.80 (2H, m), 2.24-2.26 (1H, m), 2.31 (3H, s), 2.40-2.77 (10H, m), 3.61 (2H, d, J=12.4 Hz), 3.96 (3H, s), 6.57 (1H, s), 8.21 (1H, s).

(Step 3) Preparation of 1-(1-(5-methoxy-2-methyl-4-nitrophenyl)piperidin-4-yl)-4-methylpiperazine (A1-4)

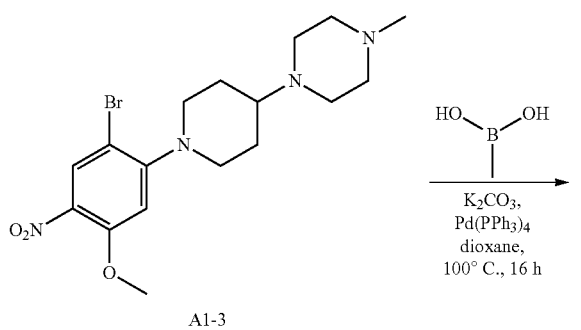

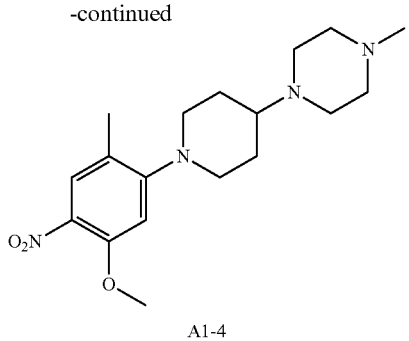

To a mixture of compound A1-3 (4.00 g, 9.68 mmol), methylboronic acid (3.48 g, 58.1 mmol) and K$_2$CO$_3$ (4.01 g, 29.0 mmol) in dioxane (150 mL) was added Pd(PPh$_3$)$_4$ (1.12 g, 0.970 mmol). The reaction mixture was stirred at 100° C. for 16 h. The reaction mixture was concentrated under reduced pressure to give a residue. The residue was diluted with water (100 mL) and extracted with EtOAc (100 mL×3). The combined organic layer was washed with brine (200 mL), dried over Na$_2$SO$_4$, filtered and concentrated under reduced pressure to give a residue. The residue was purified by flash silica gel chromatography to afford compound A1-4 as a yellow solid.

$^1$H NMR (400 MHz, CDCl$_3$) δ 1.71-1.75 (2H, m), 1.98-2.03 (2H, m), 2.25 (3H, s), 2.33 (3H, s), 2.38-2.76 (11H, m), 3.35 (2H, d, J=12.4 Hz), 3.95 (3H, s), 6.66 (1H, s), 7.84 (1H, s).

(Step 4) Preparation of 2-methoxy-5-methyl-4-(4-(4-methylpiperazin-1-yl)piperidin-1-yl)aniline (A1-5)

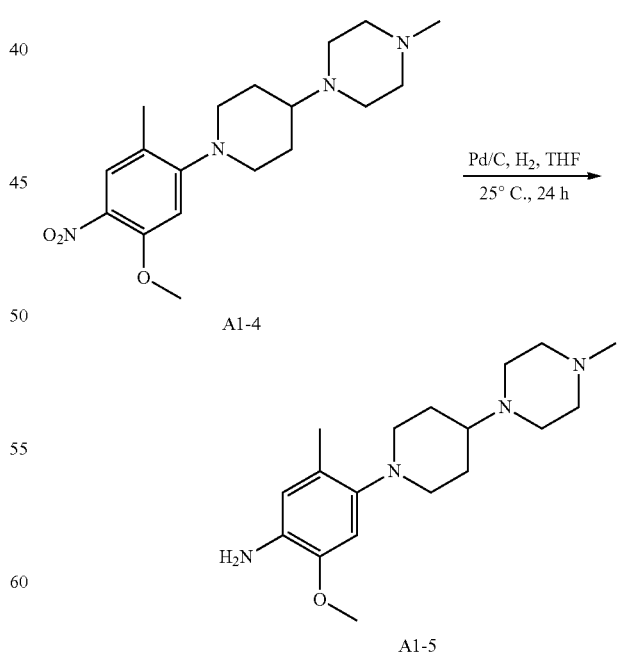

To a solution of compound A1-4 (2.06 g, 5.91 mmol) in THF (20 mL) was added Pd/C (200 mg, 10 mol %). The suspension was degassed under vacuum and purged with H$_2$ for several times. The mixture was stirred under H₂ (15 psi) at 25° C. for 24 hr. The reaction mixture was filtered and washed with THF (10 mL×3). The filtrate was concentrated under reduced pressure to afford compound A1-5 as a brown solid.

$^1$H NMR (400 MHz, CD$_3$OD) δ 1.64-1.69 (2H, m), 1.90-1.93 (2H, m), 2.25 (3H, s), 2.16 (3H, s), 2.34-2.37 (1H, m), 2.49-2.73 (8H, m), 2.85-2.88 (1H, m), 2.97-3.10 (3H, m), 3.82 (3H, s), 6.60-6.65 (2H, m).

(Step 5) Preparation of 6-nitroquinoxaline (A1-6)

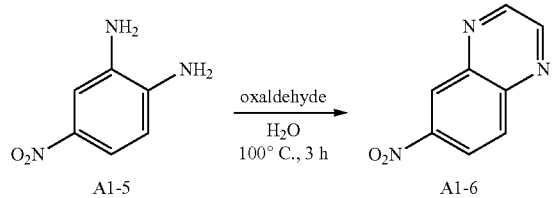 [SMILES: Nc1ccc([N+](=O)[O-])cc1N ; O=[N+]([O-])c1ccc2nccnc2c1]

To a solution of compound A1-5 (50.0 g, 327 mmol) in H₂O (200 mL) was added oxaldehyde (94.7 g, 653 mmol, 40% purity) dropwise. The reaction mixture was stirred at 100° C. for 3 h. The reaction mixture was filtered and washed with water (50 mL×3). The cake was dissolved in DCM (1,000 mL). It was washed with water (500 mL) and concentrated under vacuo to afford compound A1-6 as a red solid.

$^1$H NMR (400 MHz, CDCl$_3$) δ 8.30 (1H, d, J=9.2 Hz), 8.56-8.60 (1H, m), 9.04-9.06 (3H, m).

(Step 6) Preparation of 6-nitroquinoxalin-5-amine (A1-7)

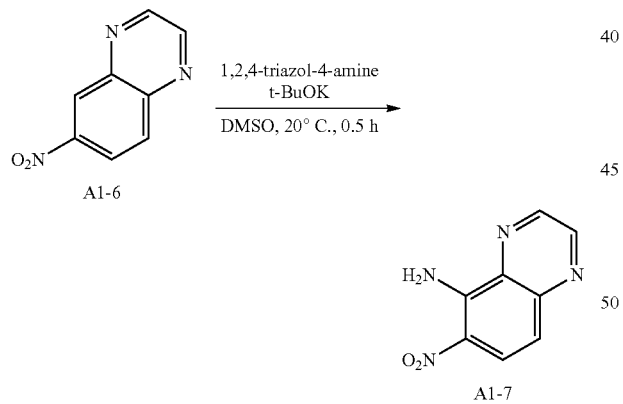

A solution of t-BuOK (3.84 g, 34.3 mmol) in DMSO (100 mL) was added dropwise to a solution of compound A1-6 (5.00 g, 28.6 mmol) and 1,2,4-triazol-4-amine (2.88 g, 34.3 mmol) in DMSO (20 mL). The reaction mixture was stirred at 20° C. for 0.5 h. The reaction mixture was poured into sat. aq. NH₄Cl (140 mL) and it was stirred for 2 h. The resulting yellow precipitate was filtered, washed with water (20 mL×3) and dried. The cake was purified by flash silica gel chromatography to afford compound A1-7 as a red solid.

$^1$H NMR (400 MHz, DMSO-d$_6$) δ 7.17 (1H, d, J=9.6 Hz), 8.29 (1H, d, J=9.6 Hz), 8.52 (2H, brs), 8.94 (1H, d, J=1.6 Hz), 9.10 (1H, d, J=2.0 Hz)

(Step 7) Preparation of quinoxaline-5,6-diamine (A1-8)

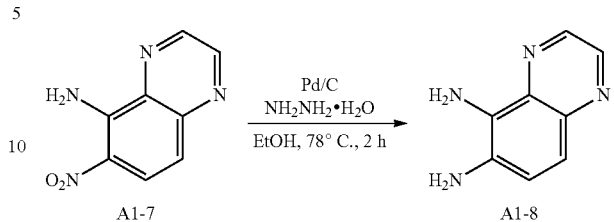

A mixture of compound A1-7 (789 mg, 4.15 mmol) and Pd/C (90 mg, 10 mol %) in EtOH (20 mL) was stirred at 78° C. for 1 h. Hydrazine monohydrate (8.31 g, 83.0 mmol, 50%) was added and the mixture was stirred at 78° C. for another 1 h. The reaction mixture was filtered and the resulting cake was washed with EtOH (10 mL×3). The filtrate was concentrated under reduced pressure to give a residue. The residue was purified by flash NH-silica gel chromatography to afford compound A1-8 as a red solid.

$^1$H NMR (400 MHz, CDCl$_3$) δ 5.15 (2H, brs), 5.27 (2H, brs), 7.19 (1H, d, J=8.8 Hz), 7.26 (1H, d, J=8.8 Hz), 8.50 (1H, d, J=2.0 Hz), 8.59 (1H, d, J=1.6 Hz).

(Step 8) Preparation of N6-(2,5-dichloropyrimidin-4-yl)quinoxaline-5,6-diamine (A1-9)

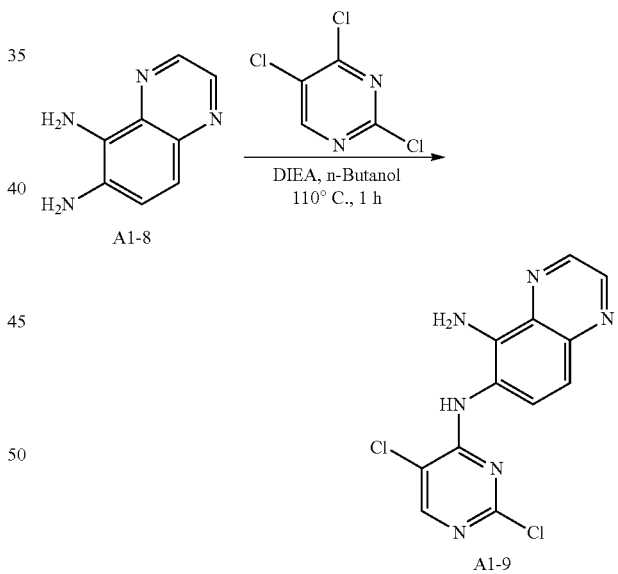

To a stirred solution of compound A1-8 (230 mg, 1.44 mmol) and 2,4,5-trichloropyrimidine (263 mg, 1.44 mmol) in n-butanol (3 mL) was added DIEA (371 mg, 2.87 mmol). The mixture was stirred at 110° C. for 1 h under microwave irradiation. The residue was poured into aq. NH₄Cl (0.1M, 20 mL) and stirred for 30 min, and then it was extracted with DCM (20 mL×3). The combined organic layer was washed with brine (50 mL), dried over Na₂SO₄, filtered and concentrated under reduced pressure to give a residue. The residue was purified by flash silica gel chromatography to afford compound A1-9 as a red solid.

¹H NMR (400 MHz, DMSO-d₆) δ 6.06 (2H, brs), 7.23 (1H, d, J=8.8 Hz), 7.51 (1H, d, J=8.8 Hz), 8.31 (1H, s), 8.79 (1H, d, J=1.6 Hz), 8.90 (1H, d, J=1.6 Hz), 9.37 (1H, brs).

(Step 9) Preparation of Compound A1-10

(Step 10) Preparation of N-(6-((5-chloro-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide (Example A1)

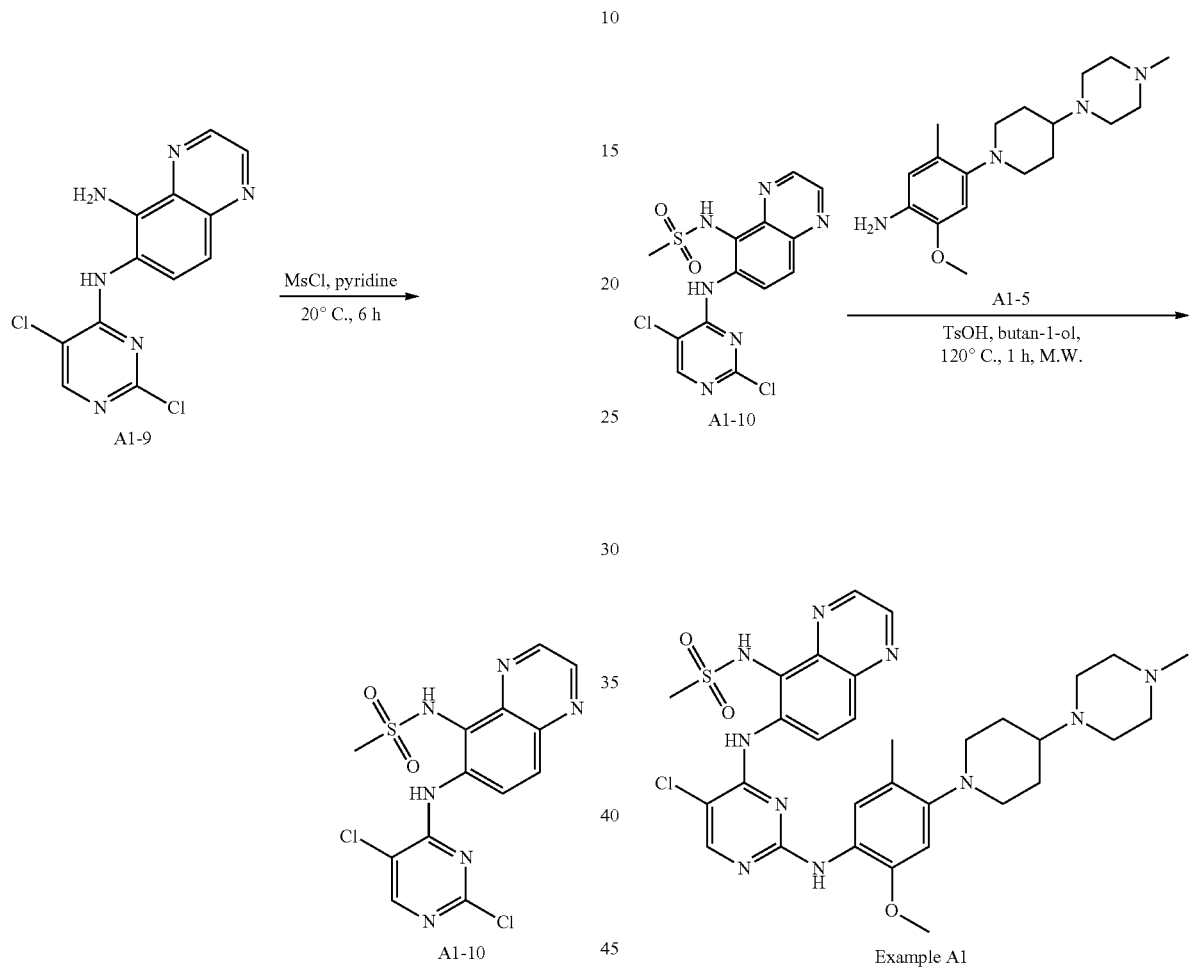

To a solution of compound A1-9 (178 mg, 0.58 mmol) in pyridine (5 mL) was added MsCl (246 mg, 2.14 mmol) at 0° C. It was stirred at 20° C. for 6 h. The mixture was diluted with ice-water (10 mL) and EtOAc (10 mL×3). The organic layer was collected and washed with brine (25 mL), dried over Na₂SO₄, filtered and concentrated under reduced pressure to give a residue. The residue was purified by flash NH-silica gel chromatography to afford compound A1-10 as a yellow solid.

¹H NMR (400 MHz, DMSO-d₆) δ 3.05 (3H, s), 8.17 (1H, d, J=9.2 Hz), 8.48 (1H, d, J=9.2 Hz), 8.58 (1H, s), 9.00 (1H, d, J=2.0 Hz), 9.05 (1H, d, J=1.6 Hz), 9.42 (1H, brs), 10.01 (1H, brs).

A mixture of compound A1-10 (30 mg, 0.080 mmol), compound A1-5 (30 mg, 0.090 mmol) and TsOH (20 mg, 0.12 mmol) in n-butanol (2 mL) was stirred at 120° C. for 1 h under microwave irradiation. The reaction mixture was concentrated under reduced pressure to give a residue that was purified by prep-HPLC to afford Example A1 as a yellow solid.

¹H NMR (400 MHz, CDCl₃) δ 1.70-1.76 (2H, m), 1.92-1.98 (2H, m), 2.06 (3H, s), 2.34 (4H, m), 2.45-2.72 (10H, m), 2.96 (3H, s), 3.13 (2H, d, J=11.6 Hz), 3.86 (3H, s), 6.61 (1H, brs), 7.40 (1H, s), 7.87 (1H, s), 8.08 (1H, d, J=6.8 Hz), 8.89 (1H, s), 8.09 (1H, d, J=9.2 Hz), 8.18 (1H, s), 8.85-8.88 (1H, m), 9.24 (1H, brs). LC-MS: Calculated 666.3, MS Found 667.3 [M+H]⁺.

[Example A2] Preparation of N-(6-((5-chloro-2-((5-ethyl-2-methoxy-4-(4-(4-methylpiperazin-1-yl)piperidin-1-yl)phenyl)amino)pyrimidin-4-yl)amino)quinoxalin-5-yl)methanesulfonamide (Step 1) Preparation of 1-(1-(5-methoxy-4-nitro-2-vinylphenyl)piperidin-4-yl)-4-methylpiperazine (A2-1)

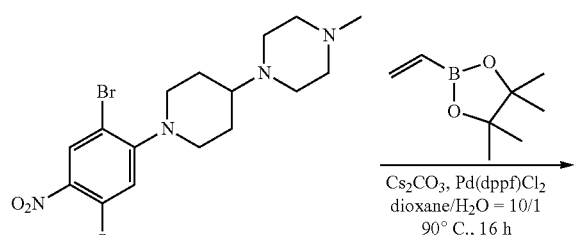

A1-3

Cs₂CO₃, Pd(dppf)Cl₂
dioxane/H₂O = 10/1
90° C., 16 h

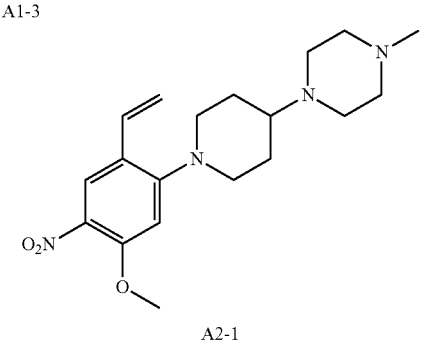

A2-1

To a mixture of compound A1-3 (2.00 g, 4.84 mmol) in dioxane (20 mL) and H₂O (2 mL) were added Cs₂CO₃ (4.73 g, 14.5 mmol), 4,4,5,5-tetramethyl-2-vinyl-1,3,2-dioxaborolane (1.12 g, 7.26 mmol) and Pd(dppf)Cl₂ (354 mg, 0.480 mmol). It was stirred at 90° C. for 16 h. The reaction mixture was filtered and the filtrate was concentrated under reduced pressure to give a residue. It was purified by reverse-phase chromatography to afford compound A2-1 as a brown solid.
¹H NMR (400 MHz, CDCl₃) δ 1.74-1.78 (2H, m), 1.98-2.03 (2H, m), 2.32 (3H, s), 2.42-2.78 (11H, m), 3.47 (1H, s), 3.51 (1H, s), 3.98 (3H, s), 5.28-5.31 (1H, m), 5.68-5.73 (1H, m), 6.52 (1H, s), 6.71-6.76 (1H, m), 8.21 (1H, s).

(Step 2) Preparation of 5-ethyl-2-methoxy-4-(4-(4-methylpiperazin-1-yl)piperidin-1-yl)aniline (A2-2)

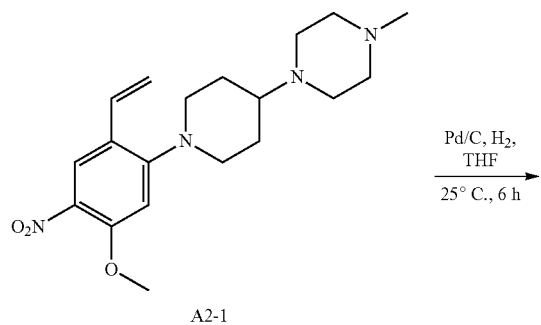

A2-1

Pd/C, H₂,
THF
25° C., 6 h

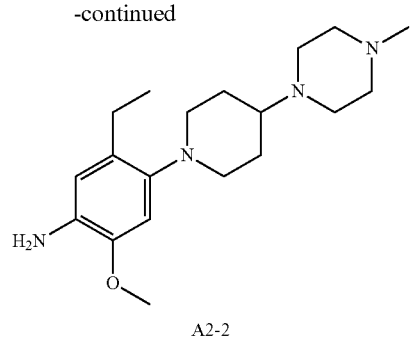

A2-2

To a solution of compound A2-1 (950 mg, 2.64 mmol) in THF (10 mL) was added Pd/C (100 mg, 10 mol %). The suspension was degassed under vacuum and purged with H₂ several times. The mixture was stirred under H₂ (15 psi) at 25° C. for 6 h. The reaction mixture was then filtered, and the collected solids were washed with THF (10 mL×3). The filtrate was concentrated under reduced pressure to give a residue. It was purified by reverse-phase chromatography to afford compound A2-2 as a brown solid.
¹H NMR (400 MHz, CDCl₃) δ 1.17 (3H, t, J=7.6 Hz), 1.69-1.73 (2H, m), 2.00-2.03 (2H, m), 2.47 (3H, s), 2.54-2.62 (3H, m), 2.69-2.91 (10H, m), 3.00 (2H, d, J=12.0 Hz), 3.83 (3H, s), 6.66 (1H, s), 6.69 (1H, s).

(Step 3) Preparation of N-(6-((5-chloro-2-((5-ethyl-2-methoxy-4-(4-(4-methylpiperazin-1-yl)piperidin-1-yl)phenyl)amino)pyrimidin-4-yl)amino)quinoxalin-5-yl)methanesulfonamide (Example A2)

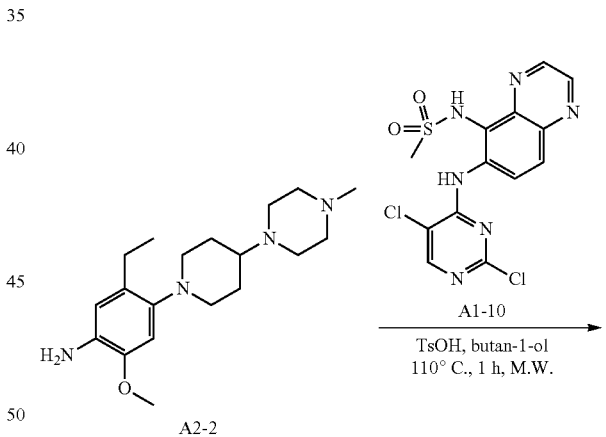

A2-2 + A1-10

TsOH, butan-1-ol
110° C., 1 h, M.W.

Example A2

A mixture of compound A1-10 (20 mg, 0.050 mmol), compound A2-2 (35 mg, 0.10 mmol) and TsOH (13 mg, 0.080 mmol) in n-butanol (2 mL) was stirred at 110° C. for 1 h under microwave irradiation. The reaction mixture was concentrated under reduced pressure to give a residue. It was purified by prep-HPLC to afford Example A2 as a yellow solid.

$^1$H NMR (400 MHz, CDCl$_3$) δ 0.84-0.87 (3H, m), 1.54-1.56 (2H, m), 1.83-1.85 (2H, m), 2.16 (4H, s), 2.27-2.40 (8H, m), 2.67-2.69 (4H, m), 2.97-3.01 (2H, m), 3.02 (3H, s), 3.77 (3H, s), 6.77-6.79 (1H, m), 7.41-7.43 (1H, m), 7.83-7.85 (1H, m), 8.18-8.20 (1H, m), 8.22-8.24 (1H, m), 8.67-8.69 (1H, m), 8.90-8.92 (1H, m), 8.97-8.99 (1H, m), 9.01-9.03 (1H, m). LC-MS: MS Calculated 680.3, MS Found 681.6 [M+H]$^+$.

[Example A3] Preparation of N-(6-((5-chloro-2-((2-methoxy-4-(4-(4-methylpiperazin-1-yl)piperidin-1-yl)phenyl)amino)pyrimidin-4-yl)amino)quinoxalin-5-yl)methanesulfonamide

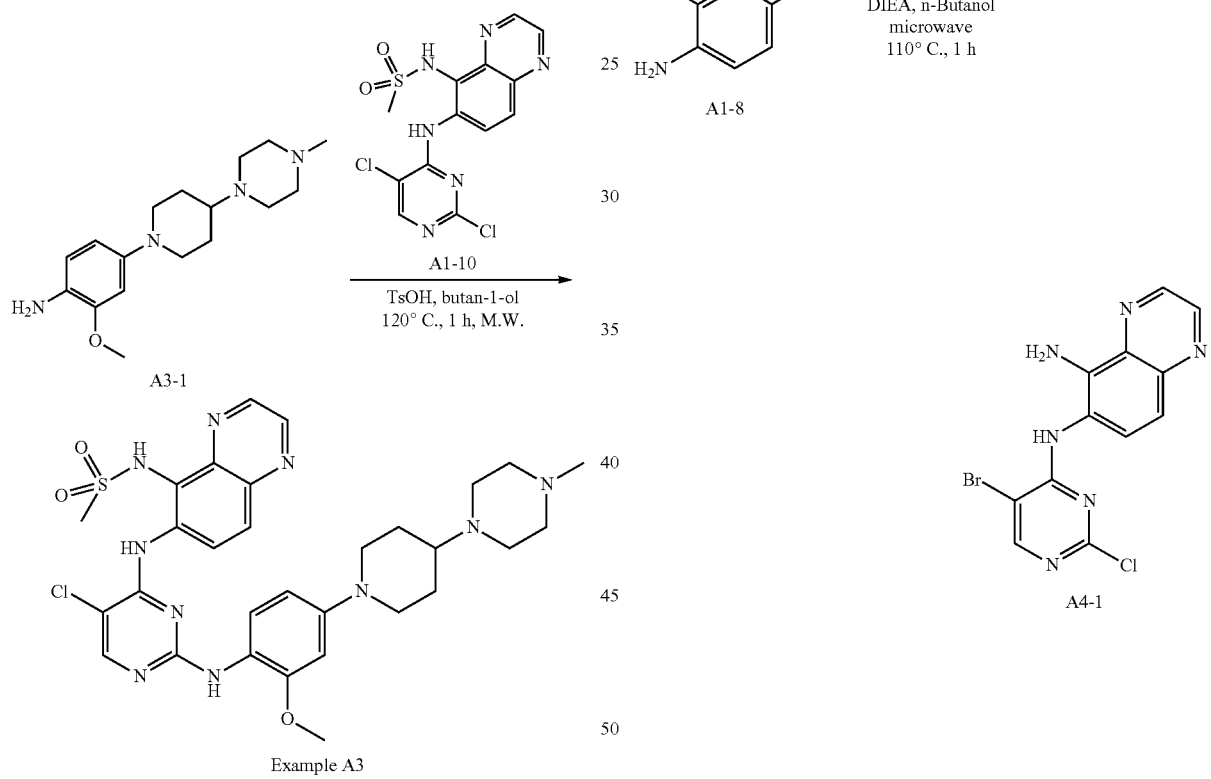

To a mixture of compound A1-10 (20 mg, 0.050 mmol), compound A3-1 (24 mg, 0.080 mmol) and TsOH (13 mg, 0.080 mmol) in n-butanol (2 mL) was stirred at 120° C. for 1 h under microwave irradiation. The reaction mixture was concentrated under reduced pressure to give a residue. It was purified by prep-HPLC to afford Example A3 as a yellow solid.

$^1$H NMR (400 MHz, CDCl$_3$) δ 1.69-1.71 (2H, m), 1.94-1.96 (2H, m), 2.34 (3H, s), 2.39-2.41 (1H, m), 2.45-2.75 (10H, m), 2.96 (3H, s), 3.63-3.65 (2H, m), 3.87 (3H, s), 6.43 (1H, d, J=8.8 Hz), 6.55 (1H, d, J=2.4 Hz), 7.33 (1H, s), 7.96 (1H, d, J=8.8 Hz), 8.10 (1H, d, J=9.6 Hz), 8.17 (1H, s), 8.85 (1H, d, J=2.0 Hz), 8.88-8.91 (2H, m), 9.23 (1H, s). LC-MS: MS Calculated 652.3, MS Found 653.3 [M+H]$^+$.

[Example A4] N-(6-((5-bromo-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide (Step 1) Preparation of N6-(5-bromo-2-chloropyrimidin-4-yl)quinoxaline-5,6-diamine (A4-1)

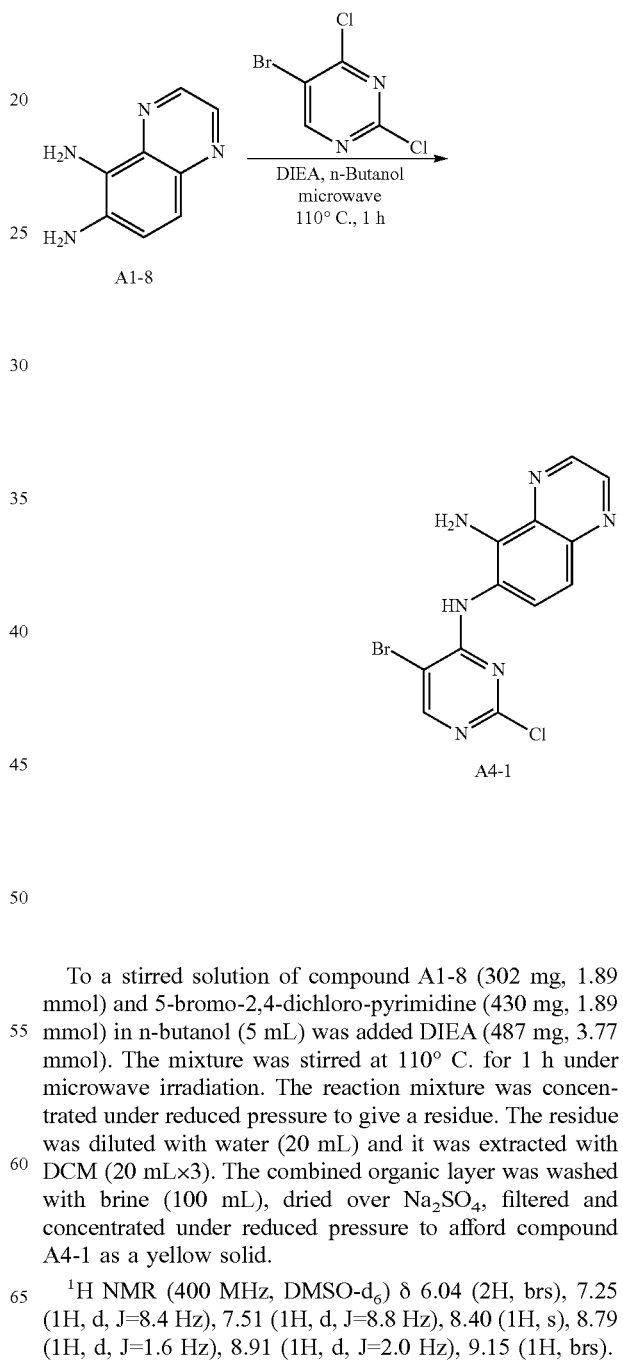

To a stirred solution of compound A1-8 (302 mg, 1.89 mmol) and 5-bromo-2,4-dichloro-pyrimidine (430 mg, 1.89 mmol) in n-butanol (5 mL) was added DIEA (487 mg, 3.77 mmol). The mixture was stirred at 110° C. for 1 h under microwave irradiation. The reaction mixture was concentrated under reduced pressure to give a residue. The residue was diluted with water (20 mL) and it was extracted with DCM (20 mL×3). The combined organic layer was washed with brine (100 mL), dried over Na$_2$SO$_4$, filtered and concentrated under reduced pressure to afford compound A4-1 as a yellow solid.

$^1$H NMR (400 MHz, DMSO-d$_6$) δ 6.04 (2H, brs), 7.25 (1H, d, J=8.4 Hz), 7.51 (1H, d, J=8.8 Hz), 8.40 (1H, s), 8.79 (1H, d, J=1.6 Hz), 8.91 (1H, d, J=2.0 Hz), 9.15 (1H, brs).

(Step 2) Preparation of N-(6-((5-bromo-2-chloropyrimidin-4-yl)amino)quinoxalin-5-yl) methane-sulfonamide (A4-2)

(Step 3) Preparation of N-(6-((5-bromo-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide (Example A4)

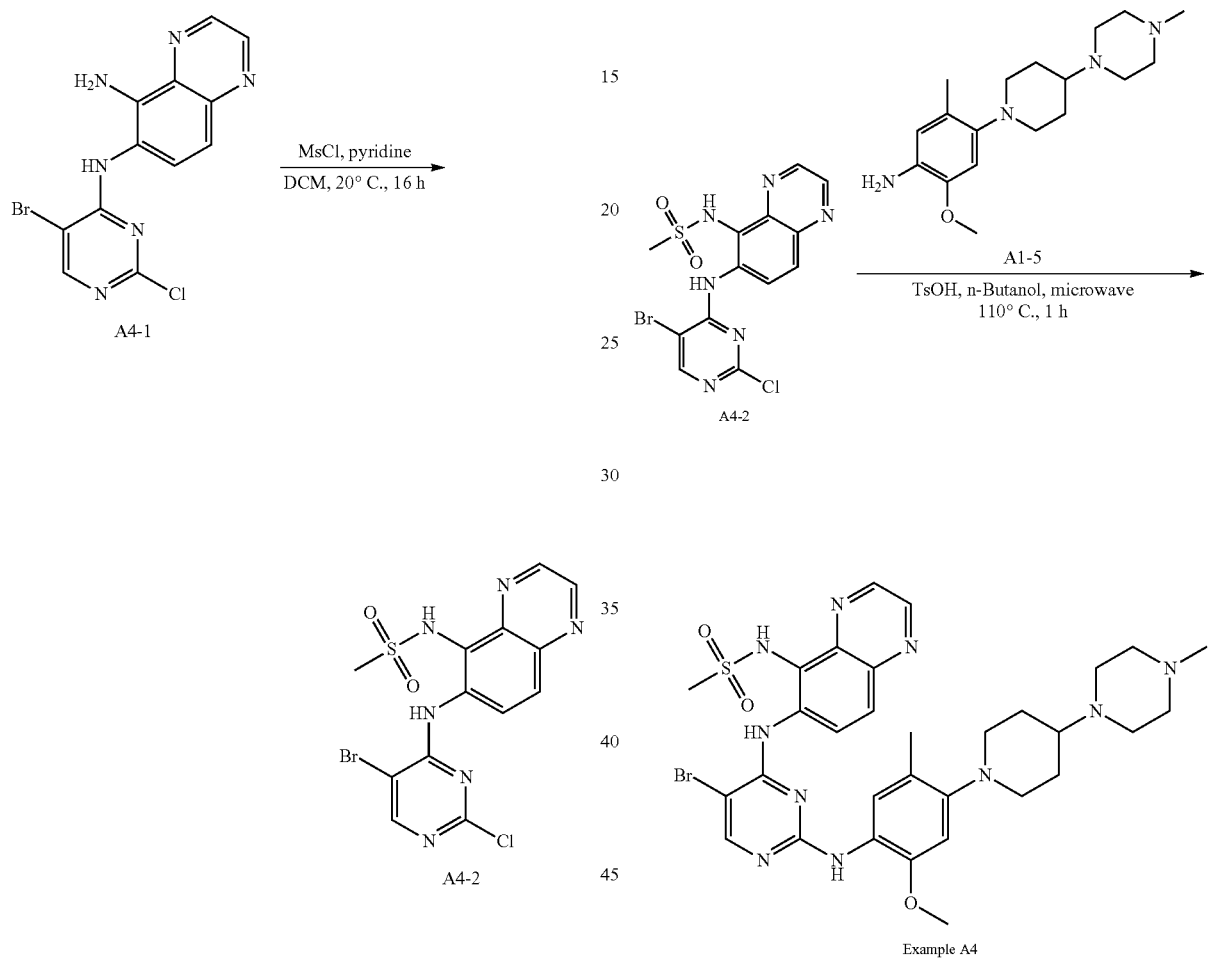

A solution of compound A4-1 (82 mg, 0.23 mmol) in pyridine (5 mL) was cooled to 0° C. before dropwise addition of MsCl (187 mg, 1.63 mmol). The solution was then stirred at 20° C. for 16 h. The resulting mixture was diluted with water (5 mL), aq. HCl (1M, 5 mL) and EtOAc (10 mL×3). The organic layer was separated and concentrated under reduced pressure to give a residue. The residue was purified by flash NH-silica gel chromatography (0-40% EtOAc in PE) to afford compound A4-2 as a yellow solid.

$^1$H NMR (400 MHz, DMSO-d$_6$) δ 3.04 (3H, s), 8.17 (1H, d, J=9.2 Hz), 8.50 (1H, d, J=9.2 Hz), 8.65 (1H, s), 9.00 (1H, d, J=0.8 Hz), 9.05 (1H, d, J=0.8 Hz), 9.30 (1H, brs), 10.04 (1H, brs).

A mixture of compound A4-2 (26 mg, 0.61 mmol), compound A1-5 (39 mg, 0.12 mmol) and TsOH (16 mg, 0.09 mmol) in n-butanol (2 mL) was stirred at 110° C. for 1 h under microwave irradiation. The resulting residue was purified by prep-HPLC to afford Example A4 as a yellow solid. $^1$H NMR (400 MHz, CDCl$_3$) δ 1.69 (2H, d, J=4.8 Hz), 1.91-1.93 (2H, m), 2.03 (3H, s), 2.34 (4H, s), 2.52-2.66 (10H, m), 2.97 (3H, s), 3.11-3.13 (2H, m), 3.86 (3H, s), 6.60 (1H, brs), 7.39 (1H, s), 7.87 (1H, s), 8.08 (1H, d, J=6.8 Hz), 8.27 (1H, s), 8.81 (1H, d, J=9.6 Hz), 8.55 (1H, d, J=1.6 Hz), 8.91 (1H, d, J=1.6 Hz), 9.16 (1H, brs). LC-MS: MS Calculated 710.2, MS Found 711.4 [M+H]$^+$.

[Example A5] Preparation of N-(6-((5-chloro-2-((5-cyclopropyl-2-methoxy-4-(4-(4-methylpiperazin-1-yl)piperidin-1-yl)phenyl)amino)pyrimidin-4-yl)amino)quinoxalin-5-yl)methanesulfonamide (Step 1) Preparation of 1-(1-(2-cyclopropyl-5-methoxy-4-nitrophenyl)piperidin-4-yl)-4-methylpiperazine (A5-1)

(Step 2) Preparation of 5-cyclopropyl-2-methoxy-4-(4-(4-methylpiperazin-1-yl)piperidin-1-yl)aniline (A5-2)

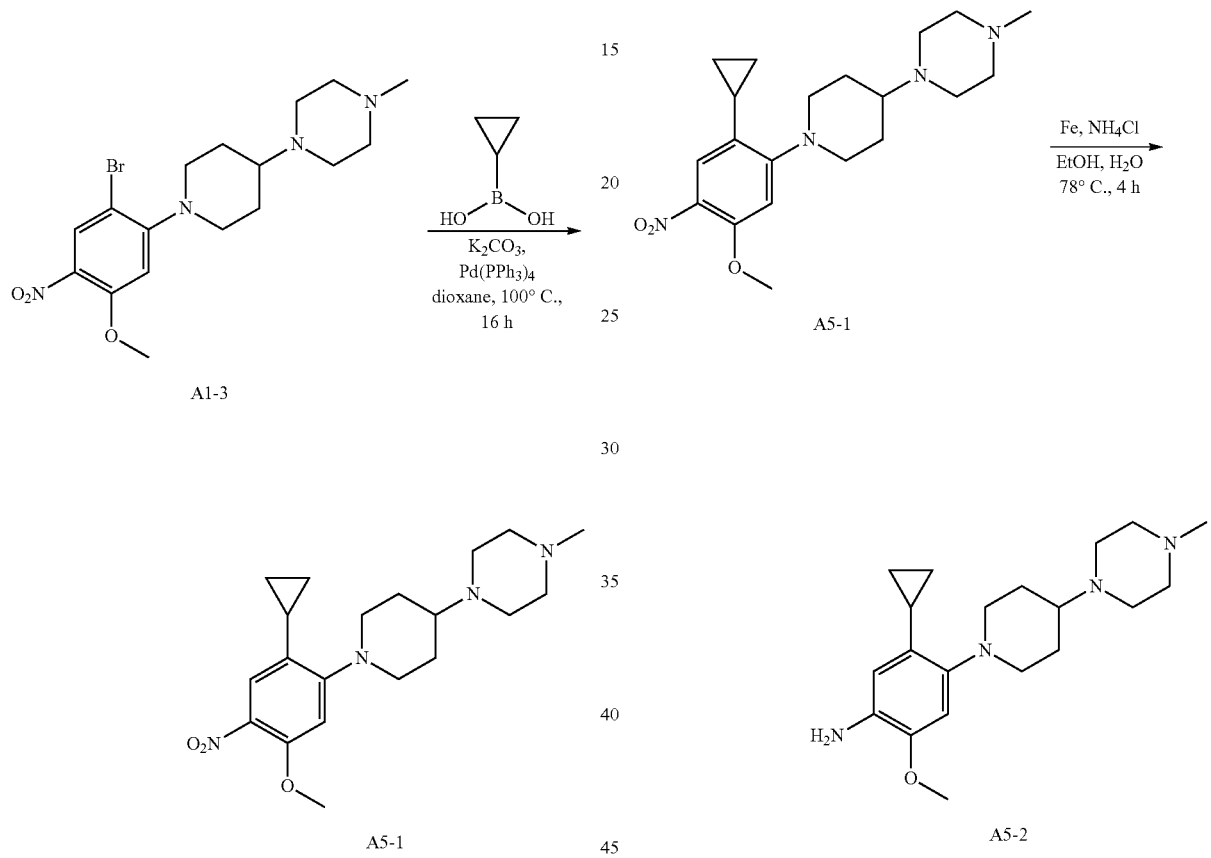

To a mixture of compound A1-3 (1.00 g, 2.42 mmol), cyclopropylboronic acid (1.25 g, 14.5 mmol) and $K_2CO_3$ (1.00 g, 7.26 mmol) in dioxane (30 mL) was added $Pd(PPh_3)_4$ (280 mg, 0.242 mmol). The reaction mixture was stirred at 100° C. under $N_2$ for 16 h. The reaction mixture was concentrated under reduced pressure to give a residue. The residue was diluted with water (20 mL) and extracted with EtOAc (20 mL×3). The combined organic layer was washed with brine (60 mL), dried over $Na_2SO_4$, filtered and concentrated under reduced pressure. The remaining residue was purified by reverse-phase column chromatography and concentrated under reduced pressure to afford compound A5-1 as a yellow solid.

$^1$H NMR (400 MHz, $CDCl_3$) δ 0.73-0.77 (2H, m), 1.00-1.05 (2H, m), 1.70-1.72 (2H, m), 1.97-2.02 (3H, m), 2.30 (3H, s), 2.40-2.78 (11H, m), 3.61-3.65 (2H, m), 3.94 (3H, s), 6.52 (1H, s), 7.51 (1H, s).

To a solution of compound A5-1 (456 mg, 1.22 mmol) in EtOH (15 mL) and $H_2O$ (5 mL) were added Fe powder (272 mg, 4.87 mmol) and $NH_4Cl$ (521 mg, 9.74 mmol). The mixture was stirred under $N_2$ at 78° C. for 4 h. The reaction mixture was then filtered and the solids were washed with THF (10 mL×3). The filtrate was concentrated under reduced pressure to give a residue. It was purified by reverse-phase column chromatography to afford compound A5-2 as a brown solid.

$^1$H NMR (400 MHz, $CDCl_3$) δ 0.48-0.52 (2H, m), 0.80-0.83 (2H, m), 1.64-1.72 (2H, m), 1.89-2.00 (2H, m), 2.12-2.19 (1H, m), 2.35 (3H, s), 2.39-2.46 (1H, m), 2.55-2.84 (10H, m), 3.19-3.22 (2H, m), 3.50 (2H, brs), 3.74 (3H, s), 6.05 (1H, s), 6.48 (1H, s).

(Step 3) Preparation of N-(6-((5-chloro-2-((5-cyclopropyl-2-methoxy-4-(4-(4-methylpiperazin-1-yl)piperidin-1-yl)phenyl)amino)pyrimidin-4-yl)amino)quinoxalin-5-yl)methanesulfonamide (Example A5)

[Example A6] Preparation of N-(6-((5-chloro-2-((2-methoxy-4-(4-(4-methylpiperazin-1-yl)piperidin-1-yl)-5-propylphenyl)amino)pyrimidin-4-yl)amino)quinoxalin-5-yl)methanesulfonamide (Step 1) Preparation of 1-(1-(5-methoxy-4-nitro-2-propylphenyl)piperidin-4-yl)-4-methylpiperazine (A6-1)

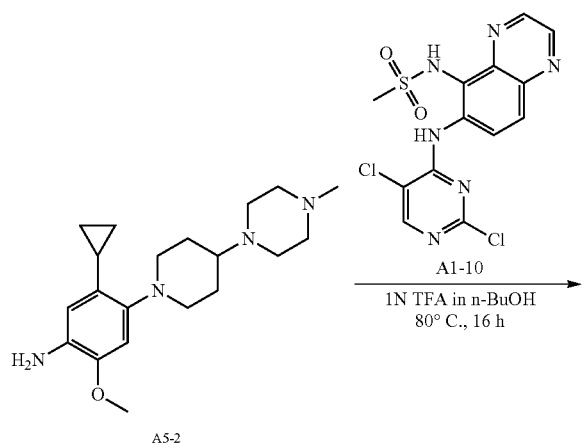

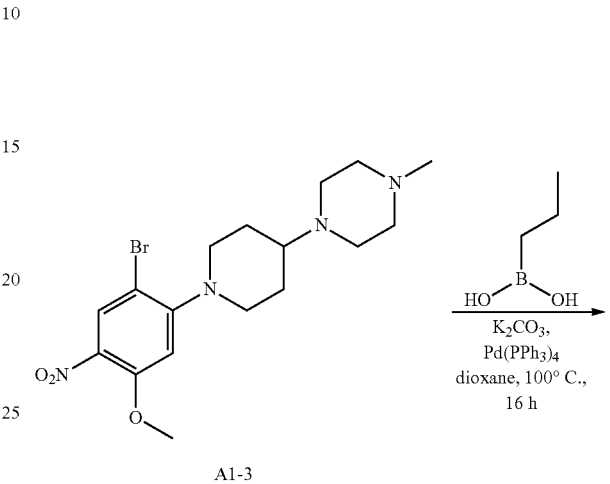

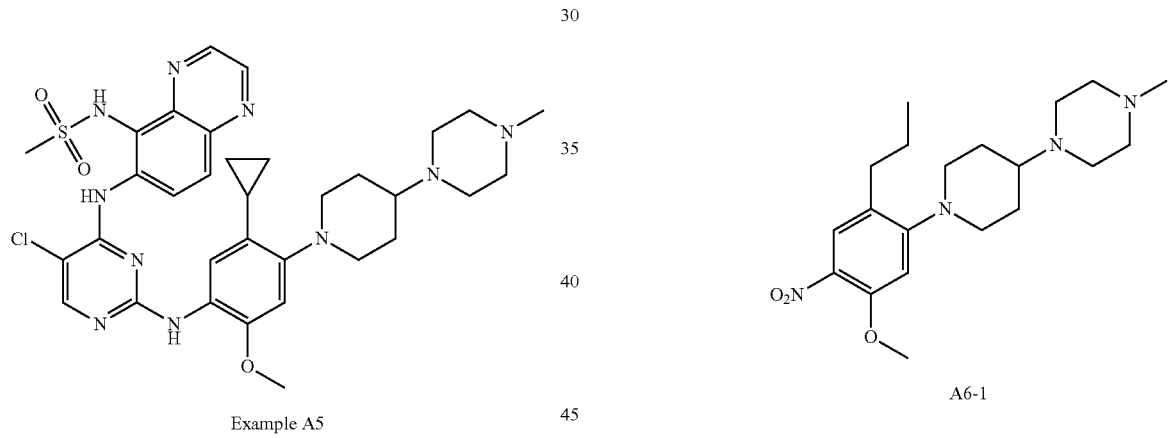

To a mixture of compound A1-10 (60 mg, 0.16 mmol) in n-butanol (1 mL) were added compound A5-2 (59 mg, 0.17 mmol) and TFA (53 mg, 0.47 mmol). The mixture was stirred at 80° C. under $N_2$ for 16 h. The reaction mixture was concentrated under reduced pressure to give a residue. The residue was purified by prep-HPLC to afford Example A5 as a yellow solid.

$^1$H NMR (400 MHz, DMSO-$d_6$) δ 0.34-0.36 (2H, m), 0.69-0.71 (2H, m), 1.57-1.67 (2H, m), 1.86-1.89 (2H, m), 2.04-2.13 (1H, m), 2.18 (3H, s), 2.30-2.40 (3H, m), 2.53-2.59 (3H, m), 2.65-2.73 (2H, m), 3.02 (3H, s), 3.28-3.32 (5H, m), 3.74 (3H, s), 6.72 (1H, s), 6.87 (1H, brs), 7.83 (1H, d, J=12.0 Hz), 8.16-8.21 (2H, m), 8.29 (1H, s), 8.67 (1H, brs), 8.90 (2H, d, J=4.0 Hz), 8.98 (1H, d, J=2.0 Hz).

LC-MS: MS Calculated 692.3, MS Found 693.1 [M+H]$^+$.

To a mixture of A1-3 (1.00 g, 2.42 mmol), propylboronic acid (1.28 g, 14.5 mmol) and $K_2CO_3$ (1.00 g, 7.26 mmol) in dioxane (30 mL) was added Pd(PPh$_3$)$_4$ (280 mg, 0.242 mmol). The reaction mixture was stirred under $N_2$ at 100° C. for 16 h. The reaction mixture was concentrated under reduced pressure to give a residue. The residue was diluted with water (20 mL) and extracted with EtOAc (20 mL×3). The combined organic layer was washed with brine (60 mL), dried over Na$_2$SO$_4$, filtered and concentrated under reduced pressure to give a residue. The residue was purified by reverse-phase column chromatography to afford compound A6-1 as a yellow solid.

$^1$H NMR (400 MHz, CDCl$_3$) δ 0.96 (3H, t, J=7.2 Hz), 1.60-1.74 (6H, m), 1.98-2.03 (2H, m), 2.33 (3H, s), 2.36-2.40 (1H, m), 2.50-2.75 (10H, m), 3.26-3.30 (2H, m), 3.94 (3H, s), 6.59 (1H, s), 7.84 (1H, s).

(Step 2) Preparation of 2-methoxy-4-(4-(4-methylpiperazin-1-yl)piperidin-1-yl)-5-propylaniline (A6-2)

(Step 3) Preparation of N-(6-((5-chloro-2-((2-methoxy-4-(4-(4-methylpiperazin-1-yl)piperidin-1-yl)-5-propylphenyl)amino)pyrimidin-4-yl)amino)quinoxalin-5-yl)methanesulfonamide (Example A6)

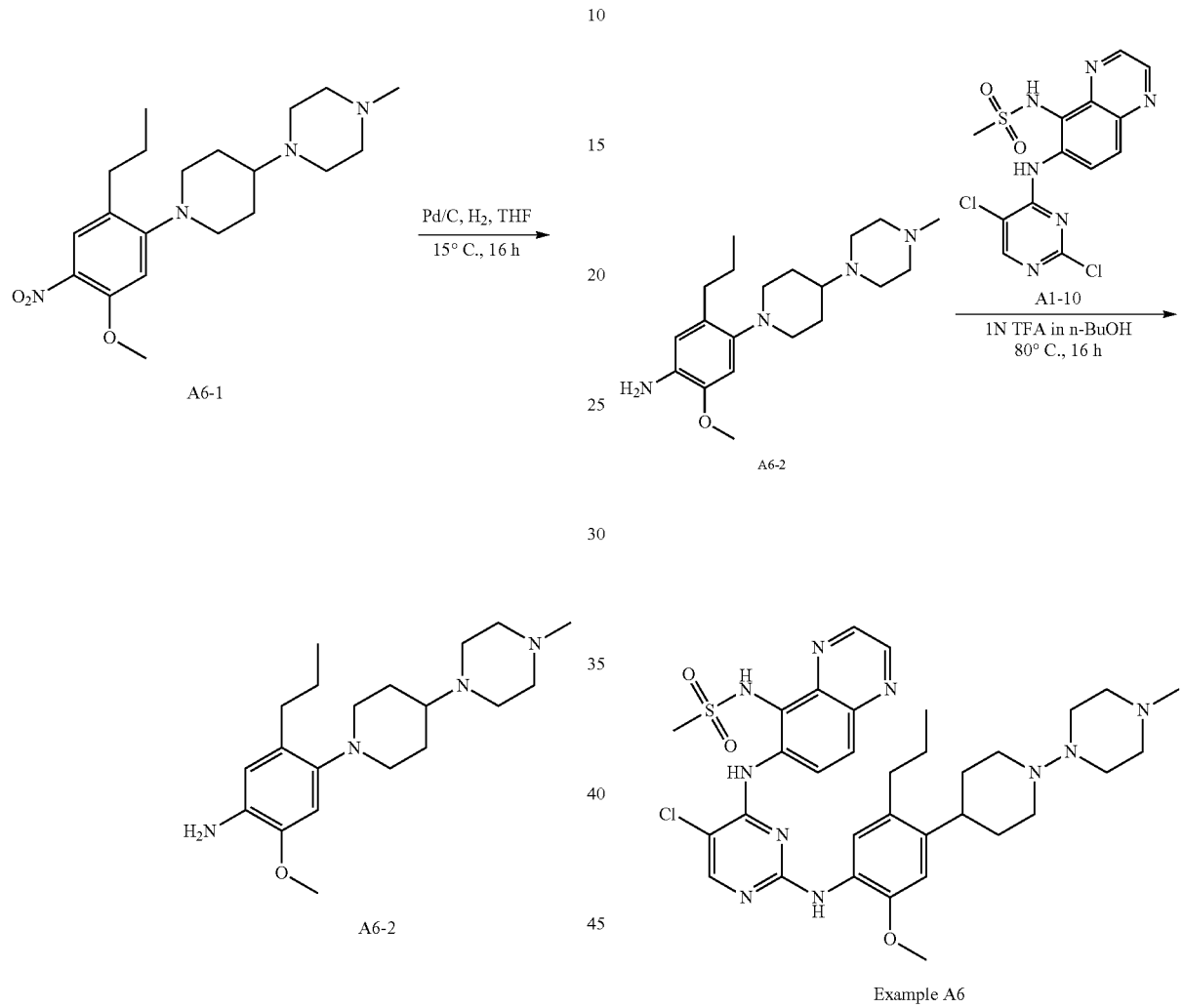

To a solution of compound A6-1 (189 mg, 0.500 mmol) in THF (2.0 mL) was added Pd/C (20 mg, 10 mol %). The suspension was degassed under vacuum and purged with $H_2$ for several times. The mixture was then stirred under $H_2$ (15 psi) at 15° C. for 16 h. The resulting mixture was filtered and the solids were washed with THF (10 mL×3). The filtrate was concentrated under reduced pressure to give a residue. It was purified by reverse-phase column chromatography to afford compound A6-2 as a brown solid.

$^1$H NMR (400 MHz, CDCl$_3$) δ 0.97 (3H, t, J=7.2 Hz), 1.55-1.75 (6H, m), 1.90-1.98 (2H, m), 2.33 (3H, s), 2.47-2.78 (11H, m), 3.00-3.03 (2H, m), 3.59 (2H, brs), 3.83 (3H, s), 6.55-6.65 (2H, m).

To a solution of TFA (625 mg, 5.48 mmol) in n-butanol (5 mL) was added compound A1-10 (50 mg, 0.130 mmol) and compound A6-2 (54 mg, 0.16 mmol). The mixture was stirred under $N_2$ at 80° C. for 16 h. The reaction mixture was concentrated under reduced pressure to give a residue. The residue was purified by prep-HPLC to afford Example A6 as a yellow solid.

$^1$H NMR (400 MHz, CDCl$_3$) δ 0.59 (3H, s), 1.18-1.22 (2H, m), 1.63-1.71 (2H, m), 1.90-1.98 (2H, m), 2.30-2.44 (6H, m), 2.50-2.77 (10H, m), 2.94 (3H, s), 3.03-3.06 (2H, m), 3.84 (3H, s), 6.64 (1H, brs), 7.41 (1H, s), 7.90 (1H, s), 8.05 (1H, d, J=9.6 Hz), 8.17 (1H, s), 8.76 (1H, d, J=9.6 Hz), 8.54 (1H, s), 8.90 (1H, s), 9.21 (1H, brs). LC-MS: MS Calculated 694.3, MS Found 695.4 [M+H]$^+$.

[Example A7] Preparation of N-(6-((5-chloro-2-((2-methoxy-4-(4-(4-methylpiperazin-1-yl)piperidin-1-yl)-5-(trifluoromethyl)phenyl)amino)pyrimidin-4-yl)amino)quinoxalin-5-yl)methanesulfonamide (Step 1) Preparation of 1-bromo-5-fluoro-4-nitro-2-(trifluoromethyl)benzene (A7-2)

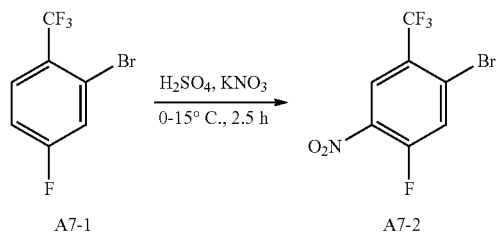 [SMILES: Fc1ccc(C(F)(F)F)c(Br)c1 ; O=[N+]([O-])c1cc(C(F)(F)F)c(Br)cc1F]

To a mixture of compound A7-1 (2.00 g, 8.23 mmol) in H₂SO₄ (20 mL) was added KNO₃ (920 mg, 9.10 mmol) slowly at 0° C. The mixture was stirred at 0° C. under N₂ for 0.5 h. Then the mixture was stirred at 15° C. under N₂ for 2 h. The mixture was then poured into ice water (200 mL) and extracted with EtOAc (50 mL×2). The combined organic layer was washed with brine (30 mL), dried over Na₂SO₄, filtered and concentrated under reduced pressure to afford compound A7-2 as a yellow solid. ¹H NMR (400 MHz, CDCl₃) δ 7.75 (1H, d, J=12.0 Hz), 8.46 (1H, d, J=8.0 Hz).

(Step 2) Preparation of 1-bromo-5-methoxy-4-nitro-2-(trifluoromethyl)benzene (A7-3)

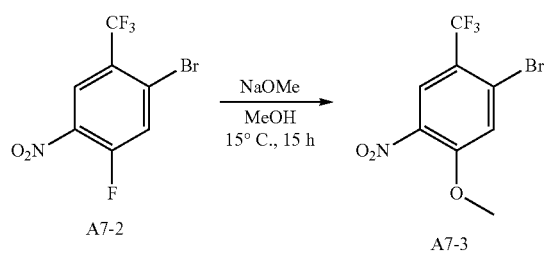 [SMILES: O=[N+]([O-])c1cc(C(F)(F)F)c(Br)cc1F ; COc1cc(Br)c(C(F)(F)F)cc1[N+](=O)[O-] ; "NaOMe"]

To a mixture of compound A7-2 (1.86 g, 6.46 mmol) in MeOH (15 mL) was added NaOMe (349 mg, 6.46 mmol). The mixture was stirred at 15° C. under N₂ for 15 h, then diluted with H₂O (20 mL) and extracted with EtOAc (30 mL×3). The combined organic layer was washed with brine (30 mL), dried over Na₂SO₄, filtered and concentrated under reduced pressure to afford compound A7-3 as a yellow solid. ¹H NMR (400 MHz, CDCl₃) δ 4.06 (3H, s), 7.45 (1H, s), 8.23 (1H, s).

(Step 3) Preparation of 1-(1-(5-methoxy-4-nitro-2-(trifluoromethyl)phenyl)piperidin-4-yl)-4-methylpiperazine (A7-4)

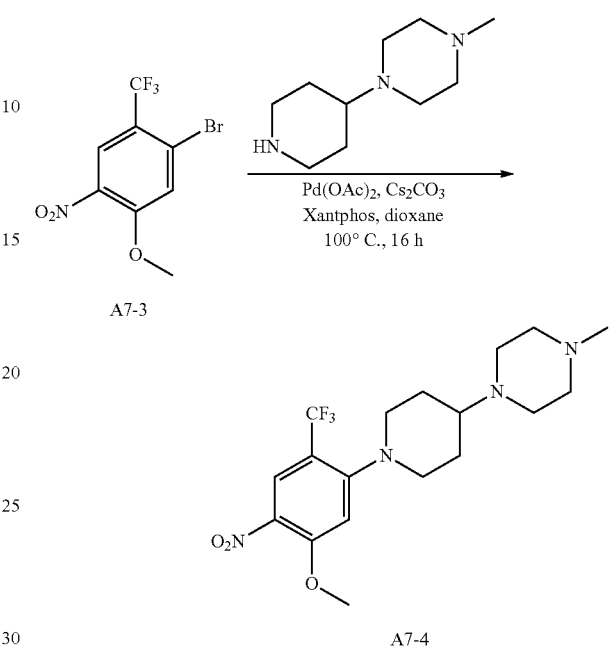

To a mixture of compound A7-3 (1.34 g, 4.47 mmol) in dioxane (13 mL) were added 1-methyl-4-(4-piperidyl)piperazine-HCl salt (1.08 g, 4.91 mmol), Cs₂CO₃ (4.37 g, 13.4 mmol), Pd(OAc)₂ (100 mg, 0.446 mmol) and Xantphos (516 mg, 0.893 mmol). The mixture was stirred at 100° C. under N₂ for 16 h, then diluted with H₂O (20 mL) and extracted with EtOAc (30 mL×3). The combined organic layer was washed with brine (10 mL×2), dried over Na₂SO₄, filtered and concentrated under reduced pressure to give a residue. The mixture was purified by reverse-phase column chromatography to afford compound A7-4 as a brown solid.

¹H NMR (400 MHz, CDCl₃) δ 1.47-1.59 (2H, m), 1.86-1.89 (2H, m), 2.18 (3H, s), 2.31-2.41 (4H, m), 2.53-2.54 (1H, m), 2.88-2.96 (2H, m), 3.27-3.34 (6H, m), 4.02 (3H, s), 7.03 (1H, s), 8.20 (1H, s).

(Step 4) Preparation of 2-methoxy-4-(4-(4-methylpiperazin-1-yl)piperidin-1-yl)-5-(trifluoromethyl)aniline (A7-5)

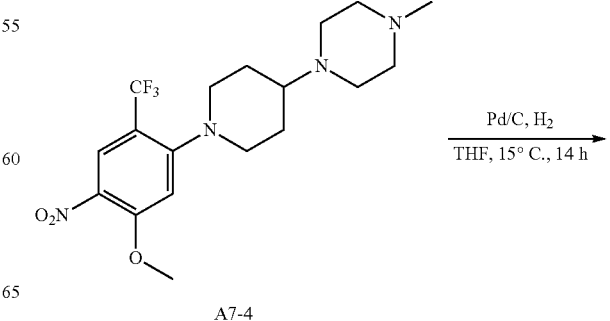

-continued

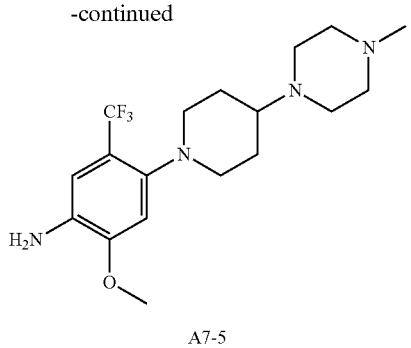

A7-5

To a mixture of compound A7-4 (210 mg, 0.522 mmol) in THF (5.0 mL) was added Pd/C (50 mg, 10 mol %). The suspension was degassed under vacuum and purged with $H_2$ several times. The mixture was stirred at 15° C. under $H_2$ (15 psi) for 14 h. The mixture was filtered and concentrated under reduced pressure to afford compound A7-5 as a brown solid.

$^1$H NMR (400 MHz, DMSO-$d_6$) δ 1.41-1.53 (2H, m), 1.76-1.78 (2H, m), 2.14 (3H, s), 2.22-2.34 (7H, m), 2.68-2.76 (3H, m), 2.80-2.89 (3H, m), 3.81 (3H, s), 4.89 (2H, s), 6.84 (1H, s), 6.92 (1H, s).

(Step 5) Preparation of N-(6-((5-chloro-2-((2-methoxy-4-(4-(4-methylpiperazin-1-yl)piperidin-1-yl)-5-(trifluoromethyl)phenyl)amino)pyrimidin-4-yl)amino)quinoxalin-5-yl)methanesulfonamide (Example A7)

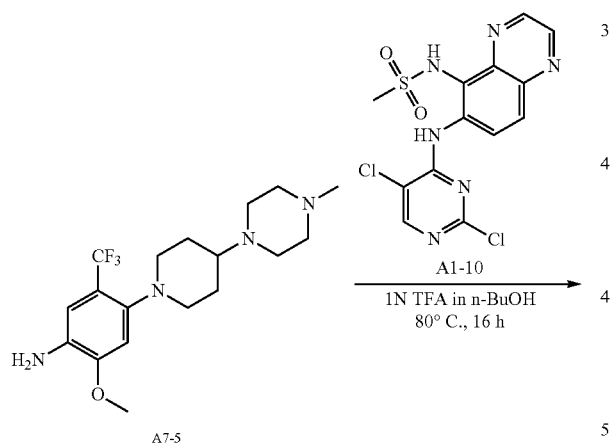

Example A7

To a solution of TFA (625 mg, 5.48 mmol) in n-butanol (5.0 mL) were added compound A1-10 (50 mg, 0.13 mmol) and compound A7-5 (58 mg, 0.16 mmol). The resulting mixture was stirred under $N_2$ at 80° C. for 16 h, and then concentrated under reduced pressure to give a residue. The residue was purified by prep-HPLC to afford Example A7 as a yellow solid.

$^1$H NMR (400 MHz, CDCl$_3$) 1.70-1.75 (2H, m), 1.87-1.92 (2H, m), 2.40 (4H, m), 2.58-2.82 (10H, m), 2.93 (3H, s), 3.06-3.10 (2H, m), 3.91 (3H, s), 6.81 (1H, brs), 7.42 (1H, s), 8.04 (1H, d, J=9.2 Hz), 8.21 (1H, s), 8.34 (1H, s), 8.64 (1H, d, J=9.6 Hz), 8.84 (1H, d, J=1.6 Hz), 8.91 (1H, d, J=1.6 Hz), 9.23 (1H, brs). LC-MS: MS Calculated 720.2, MS Found 721.3 [M+H]$^+$.

[Example A8] Preparation of N-(6-((5-bromo-2-((5-ethyl-2-methoxy-4-(4-(4-methylpiperazin-1-yl)piperidin-1-yl)phenyl)amino)pyrimidin-4-yl)amino)quinoxalin-5-yl)methanesulfonamide

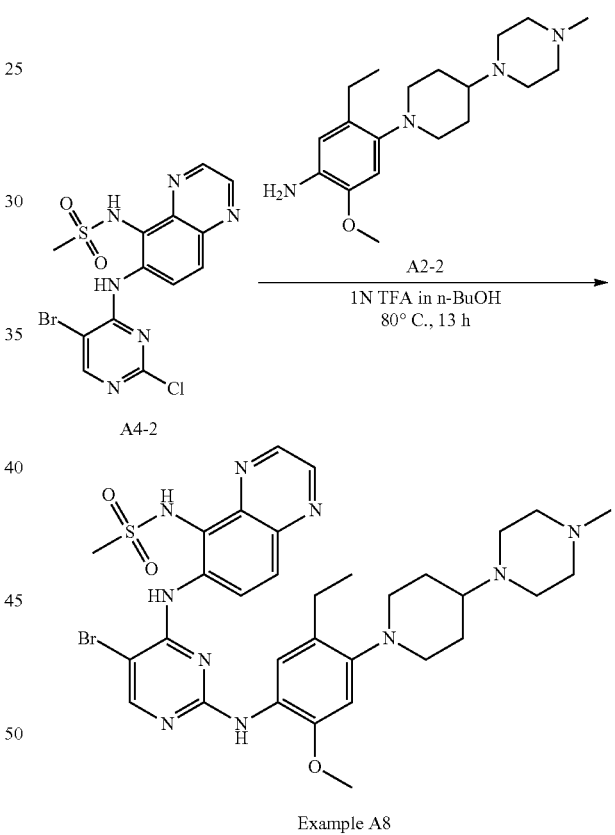

Example A8

A mixture of compound A4-2 (100 mg, 0.233 mmol) and compound A2-2 (77 mg, 0.23 mmol) in 1M TFA/n-butanol (4.0 mL) was stirred at 80° C. for 13 h. The reaction mixture was concentrated under reduced pressure to afford a residue which was purified by prep-HPLC to afford Example A8 as a yellow solid.

$^1$H NMR (400 MHz, DMSO-$d_6$) δ 0.75-0.90 (3H, m), 1.49-1.60 (2H, m), 1.82-1.86 (2H, m), 2.15 (3H, s), 2.30-2.45 (7H, m), 2.55-2.75 (6H, m), 2.95-3.08 (5H, m), 3.76 (3H, s), 6.77 (1H, s), 7.38 (1H, s), 7.86 (1H, d, J=8.8 Hz), 8.17 (1H, s), 8.22 (1H, s), 8.28 (1H, s), 8.56-8.70 (1H, m), 8.87 (1H, s), 8.92 (1H, d, J=1.6 Hz), 8.99 (1H, d, J=2.0 Hz).

[Example A9] Preparation of N-(6-((2-((5-ethyl-2-methoxy-4-(4-(4-methylpiperazin-1-yl)piperidin-1-yl)phenyl)amino)-5-fluoropyrimidin-4-yl)amino)quinoxalin-5-yl)methanesulfonamide (Step 1) Preparation of N6-(2-chloro-5-fluoropyrimidin-4-yl)quinoxaline-5,6-diamine (A9-1)

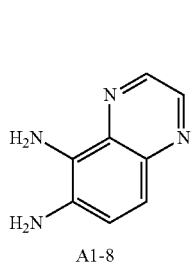

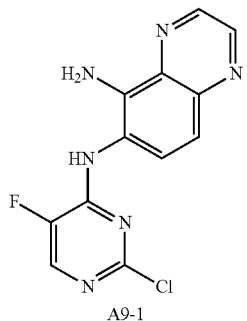

To a solution of A1-8 (300 mg, 1.87 mmol) and 2,4-dichloro-5-fluoropyrimidine (312 mg, 1.87 mmol) in n-butanol (8 mL) was added DIEA (484 mg, 3.75 mmol) at 20° C. The mixture was stirred at 20° C. for 16 h under N₂. The solvent was removed under reduced pressure, and the crude product was triturated with MeCN (15 mL) at 20° C. for 10 min to afford compound A9-1 as a brown solid.

¹H NMR (400 MHz, DMSO-d₆) δ 6.12 (2H, brs), 7.24 (1H, d, J=8.8 Hz), 7.56 (1H, d, J=8.8 Hz), 8.24 (1H, d, J=3.2 Hz), 8.79 (1H, d, J=1.2 Hz), 8.90 (1H, d, J=1.2 Hz), 9.64 (1H, s).

(Step 2) Preparation of N-(6-((2-chloro-5-fluoropyrimidin-4-yl)amino)quinoxalin-5-yl) methanesulfonamide (A9-2)

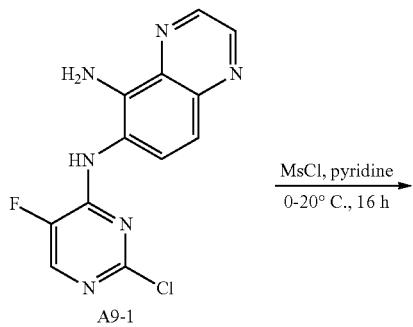

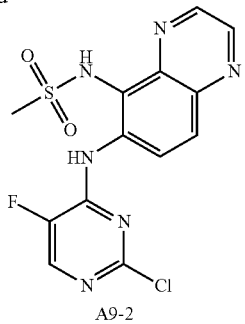

To a solution of compound A9-1 (126 mg, 0.434 mmol) in pyridine (5 mL) was added MsCl (174 mg, 1.52 mmol) at 0° C. The mixture was stirred at 20° C. for 16 hr. The resulting mixture was diluted with H₂O (30 mL) and extracted with EtOAc (50 mL×2). The combined organic layer was washed with brine (50 mL), dried over Na₂SO₄, filtered and concentrated under pressure to afford compound A9-2 as a yellow solid.

¹H NMR (400 MHz, DMSO-d₆) δ 3.07 (3H, s), 8.12 (1H, d, J=9.6 Hz), 8.43 (1H, d, J=9.2 Hz), 8.47 (1H, d, J=3.2 Hz), 8.98 (1H, s), 9.03 (1H, s), 9.72 (2H, brs).

(Step 3) Preparation of N-(6-((2-((5-ethyl-2-methoxy-4-(4-(4-methylpiperazin-1-yl)piperidin-1-yl)phenyl)amino)-5-fluoropyrimidin-4-yl)amino)quinoxalin-5-yl)methanesulfonamide (Example A9)

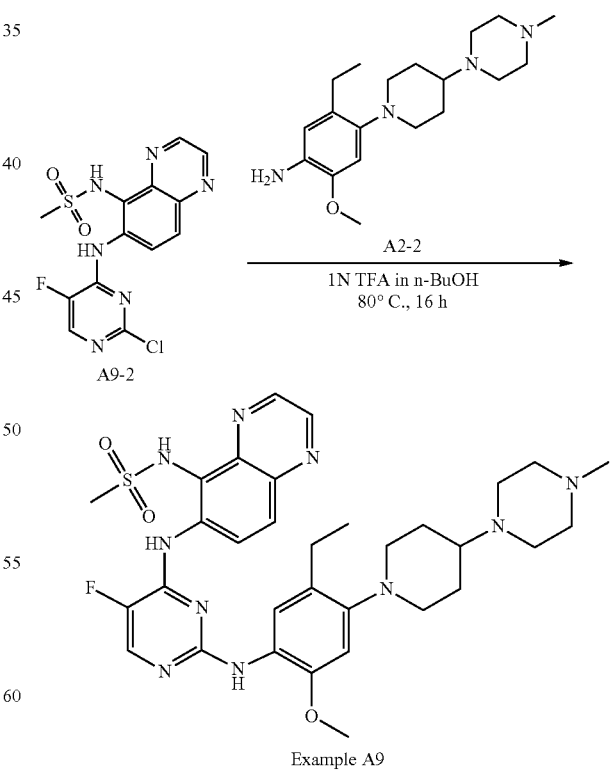

To the mixture of compound A9-2 (120 mg) and A2-2 (141 mg, 0.423 mmol) in n-butanol (5 mL) was added TFA (570 mg, 5.00 mmol) at 25° C. The mixture was stirred at 80° C. for 16 h, and then the solvent was removed under reduced pressure. The residue was diluted with H$_2$O (20 mL) and extracted with EtOAc (50 mL×3). The combined organic layer was washed with brine (100 mL), dried over Na$_2$SO$_4$, filtered and concentrated to give a residue that was purified by prep-HPLC to afford Example A9 as a yellow solid.

$^1$H NMR (400 MHz, CDCl$_3$) δ 0.92 (3H, t, J=7.6 Hz), 1.69-1.71 (2H, m), 1.93-1.95 (2H, m), 2.31-2.33 (5H, m), 2.50-2.68 (11H, m), 2.93 (3H, s), 3.07 (2H, d, J=11.2 Hz), 3.85 (3H, s), 6.65 (1H, s), 7.36 (1H, s), 7.99 (1H, s), 8.07-8.09 (2H, m), 8.84 (1H, s), 8.89-8.94 (2H, m), 9.05 (1H, s).

LC-MS: MS Calculated 664.3, MS Found 665.3 [M+H]$^+$.

[Example A10] Preparation of N-(6-((5-bromo-2-((5-ethyl-2-methoxy-4-(4-(4-methylpiperazin-1-yl) piperidin-1-yl)phenyl)amino)pyrimidin-4-yl)amino) quinoxalin-5-yl)-N-methylmethane sulfonamide (Step 1) Preparation of N-(6-((5-bromo-2-chloropyrimidin-4-yl)amino)quinoxalin-5-yl)-N-methylmethanesulfonamide (A10-1)

(Step 2) Preparation of N-(6-((5-bromo-2-((5-ethyl-2-methoxy-4-(4-(4-methylpiperazin-1-yl)piperidin-1-yl)phenyl)amino)pyrimidin-4-yl)amino)quinoxalin-5-yl)-N-methylmethane sulfonamide (Example A10)

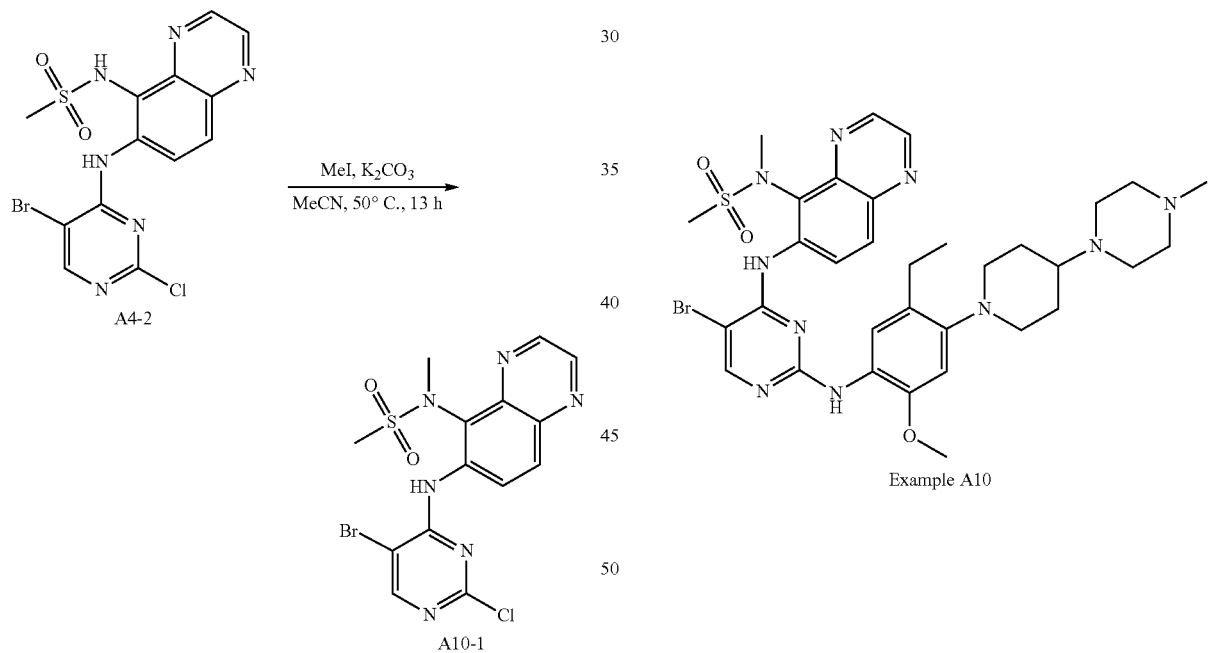

To a solution of compound A4-2 (500 mg, 1.16 mmol) in MeCN (4.0 mL) were added CH$_3$I (248 mg, 1.75 mmol) and K$_2$CO$_3$ (241 mg, 1.75 mmol). The resulting mixture was stirred at 50° C. for 13 h, then poured into water (50 mL) and extracted with EtOAc (50 mL×3). The combined organic layer was washed with brine (50 mL), dried over anhydrous Na$_2$SO$_4$ and concentrated under reduced pressure to afford a residue that was purified by silica gel chromatography to afford compound A10-1 as a white solid.

$^1$H NMR (400 MHz, DMSO-d$_6$) δ 3.18 (3H, s), 3.40 (3H, s), 8.25 (1H, d, J=9.2 Hz), 8.54 (1H, d, J=9.6 Hz), 8.66 (1H, s), 8.78-8.96 (2H, m), 9.12 (1H, s).

A mixture of compound A10-1 (61 mg, 0.14 mmol) and compound A2-2 (46 mg, 0.14 mmol) in 1M TFA/n-butanol (4.0 mL) was stirred at 80° C. for 13 h. The reaction mixture was then concentrated under reduced pressure to afford a residue that was purified by prep-HPLC to afford Example A10 as a yellow solid.

$^1$H NMR (400 MHz, DMSO-d$_6$) δ 0.75-0.94 (3H, m), 1.52-1.63 (2H, m), 1.84-1.87 (2H, m), 2.16 (3H, s), 2.25-2.48 (9H, m), 2.51-2.62 (5H, m), 2.62-2.78 (2H, m), 2.95-3.12 (2H, m), 3.22 (3H, s), 3.75 (3H, s), 6.80 (1H, s), 7.34 (1H, s), 7.90 (1H, d, J=8.4 Hz), 8.23 (1H, s), 8.30 (1H, s), 8.39 (1H, s), 8.57 (1H, s), 8.80 (1H, s), 8.92 (1H, s), 8.96 (1H, s). LC-MS: MS Calculated 738.2, MS Found 739.1 [M+H]$^+$.

[Example A11] Preparation of N-(6-((5-chloro-2-((5-ethyl-2-methoxy-4-(4-(4-methylpiperazin-1-yl)piperidin-1-yl)phenyl)amino)pyrimidin-4-yl)(methyl)amino)quinoxalin-5-yl)methanesulfonamide (Step 1) Preparation of N-(quinoxalin-6-yl)acetamide (A11-1)

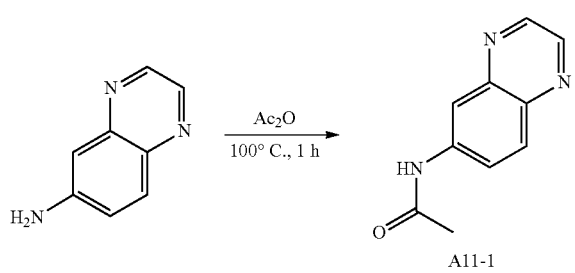

A mixture of quinoxalin-6-amine (14.0 g, 96.0 mmol) in Ac₂O (131 g, 1.28 mol) was stirred at 100° C. for 1 h. The reaction mixture was concentrated under reduced pressure to afford a residue. It was poured into DCM (100 mL) and filtered. The resulting cake was dried under reduced pressure to afford compound A1-1 as a yellow solid.

$^1$H NMR (400 MHz, DMSO-$d_6$) δ 2.14 (3H, s), 7.80-7.92 (1H, m), 8.02-8.16 (1H, m), 8.49 (1H, d, J=2.0 Hz), 8.79 (1H, d, J=1.6 Hz), 8.85 (1H, d, J=1.6 Hz), 10.48 (1H, s).

(Step 2) Preparation of N-methyl-N-(quinoxalin-6-yl)acetamide (A11-2)

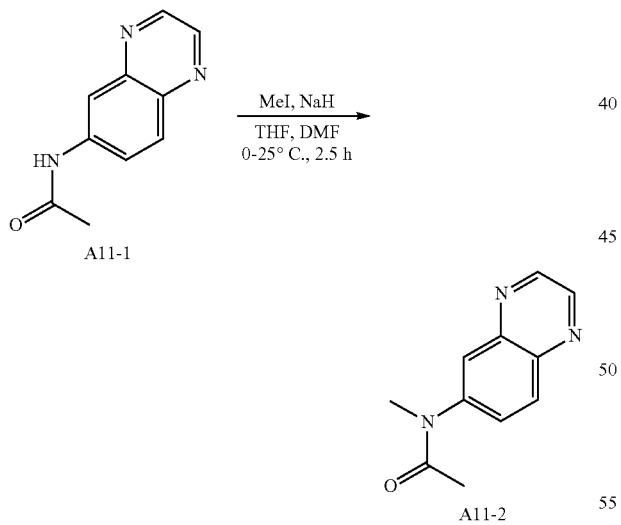

To a solution of compound A11-1 (14.0 g, 74.8 mmol) in THF (200 mL) and DMF (10 mL) was added NaH (5.98 g, 150 mmol, 60% in mineral oil) at 0° C. The resulting mixture was stirred at 0° C. for 20 min., and then MeI (12.7 g, 89.7 mmol) was added. After stirring at 25° C. for 2 h, the reaction mixture was poured into water (80 mL) and extracted with EtOAc (80 mL×3). The combined organic layer was washed with 50% aq. NaCl (80 mL×3), dried over anhydrous Na₂SO₄ and concentrated under reduced pressure to afford compound A11-2 as a yellow solid.

$^1$H NMR (400 MHz, CDCl₃) δ 2.02 (3H, s), 3.42 (3H, s), 7.65 (1H, d, J=8.0 Hz), 7.94 (1H, d, J=2.4 Hz), 8.18 (1H, d, J=8.8 Hz), 8.89 (2H, s).

(Step 3) Preparation of N-methyl-5-nitroquinoxalin-6-amine (A11-3)

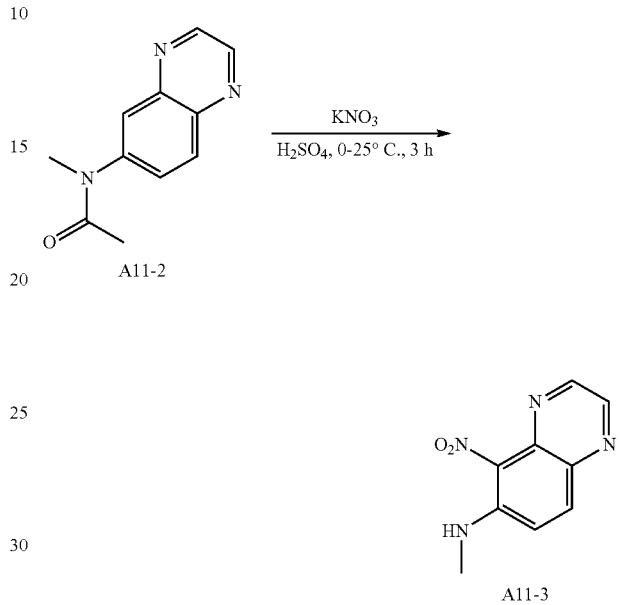

To a mixture of compound A11-2 (3.60 g, 17.9 mmol) in con. H₂SO₄ (10 mL) was added KNO₃ (1.81 g, 17.89 mmol). The resulting mixture was stirred at 0° C. for 1 h and then at 25° C. for 2 h. The reaction mixture was then poured into ice water (100 mL) and basified with sat. aq. NaHCO₃ to pH=7-8, then extracted with EtOAc (100 mL×3). The combined organic layer was washed with brine (100 mL), dried over anhydrous Na₂SO₄ and concentrated under reduced pressure to afford a residue. The crude product was triturated with THF (20 mL) to afford compound A11-3 as a yellow solid.

$^1$H NMR (400 MHz, DMSO-$d_6$) δ 2.98 (3H, d, J=8.8 Hz), 7.34-7.48 (1H, m), 7.58 (1H, d, J=9.6 Hz), 8.05 (1H, d, J=9.6 Hz), 8.66 (1H, d, J=1.6 Hz), 8.79 (1H, d, J=2.0 Hz).

(Step 4) Preparation of N-(2,5-dichloropyrimidin-4-yl)-N-methyl-5-nitroquinoxalin-6-amine (A11-4)

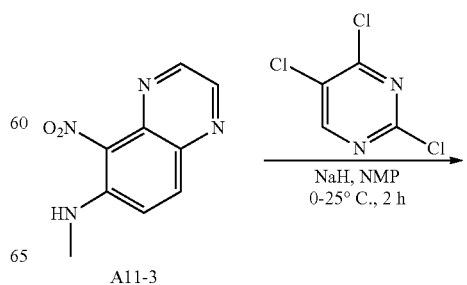

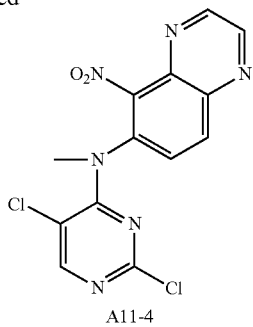

A11-4

To a mixture of compound A11-3 (620 mg, 3.04 mmol) and 2,4,5-trichloropyrimidine (668 mg, 3.64 mmol) in NMP (4.0 mL) was added NaH (364 mg, 9.11 mmol, 60% in mineral oil) at 0° C. The resulting mixture was stirred at 25° C. for 2 h, then poured into 50% aq. NaCl (30 mL) and extracted with EtOAc (30 mL×3). The combined organic layer was dried over anhydrous Na₂SO₄ and concentrated under reduced pressure to afford a residue. The residue was purified by flash NH-silica gel chromatography to afford compound A11-4 as a yellow solid.

(Step 5) Preparation of N6-(2,5-dichloropyrimidin-4-yl)-N6-methylquinoxaline-5,6-diamine (A11-5)

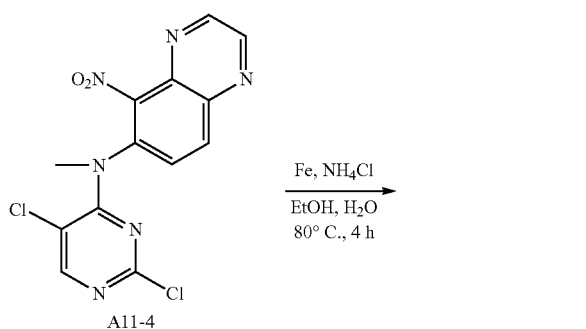

To a mixture of compound A11-4 (510 mg, 1.45 mmol) in EtOH (3.0 mL) and H₂O (1.0 mL) was added Fe powder (324 mg, 5.81 mmol) and NH₄Cl (622 mg, 11.6 mmol). The resulting mixture was stirred at 80° C. for 4 h, then poured into water (30 mL) and extracted with EtOAc (30 mL×3). The combined organic layer was washed with brine (30 mL), dried over anhydrous Na₂SO₄ and concentrated under reduced pressure to afford a residue. The residue was purified by flash NH-silica gel chromatography (PE/EtOAc=2/1) to afford compound A11-5 as a yellow solid.

¹H NMR (400 MHz, DMSO-d₆) δ 3.39 (3H, s), 6.12 (2H, s), 7.23 (1H, d, J=8.8 Hz), 7.54 (1H, d, J=8.8 Hz), 8.25-8.52 (1H, m), 8.71-8.82 (2H, m), 8.90-9.03 (1H, m).

(Step 6) Preparation of N-(6-((2,5-dichloropyrimidin-4-yl)(methyl)amino)quinoxalin-5-yl)methane sulfonamide (A11-6)

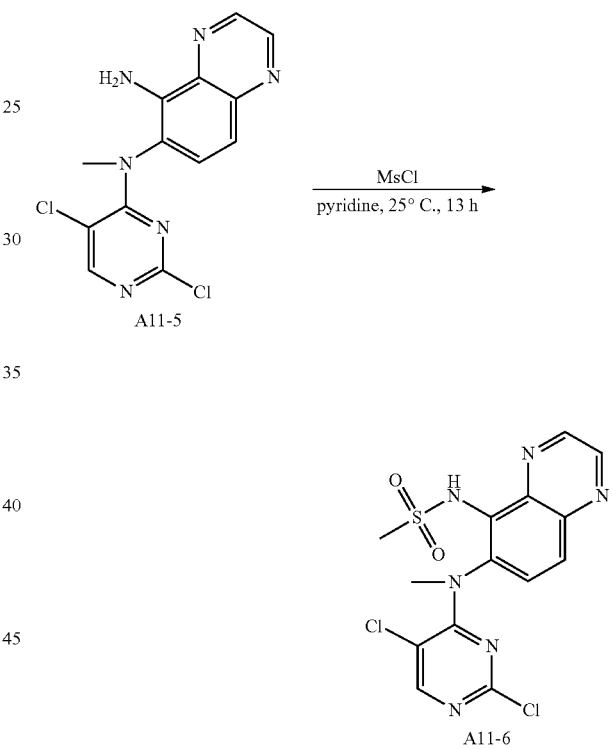

To a solution of compound A11-5 (180 mg, 0.560 mmol) in pyridine (3.0 mL) was added MsCl (449 mg, 3.92 mmol), and then the mixture was stirred at 25° C. for 13 h. The reaction mixture was poured into water (30 mL), acidified with 1M aq. HCl to pH=6-7, and extracted with EtOAc (30 mL×3). The combined organic layer was washed with brine (30 mL), dried over anhydrous Na₂SO₄ and concentrated under reduced pressure to afford a residue. The residue was purified by flash NH-silica gel chromatography (PE/EtOAc=1/2) to afford the compound A11-6 as a yellow solid.

¹H NMR (400 MHz, DMSO-d₆) δ 3.25 (3H, s), 3.48 (3H, s), 7.82-7.95 (1H, m), 8.01-8.15 (1H, m), 8.20-8.35 (1H, m), 9.00-9.15 (2H, m), 9.53 (1H, s).

(Step 7) Preparation of N-(6-((5-chloro-2-((5-ethyl-2-methoxy-4-(4-(4-methylpiperazin-1-yl) piperidin-1-yl)phenyl)amino)pyrimidin-4-yl)(methyl)amino) quinoxalin-5-yl)methanesulfonamide (Example A11)

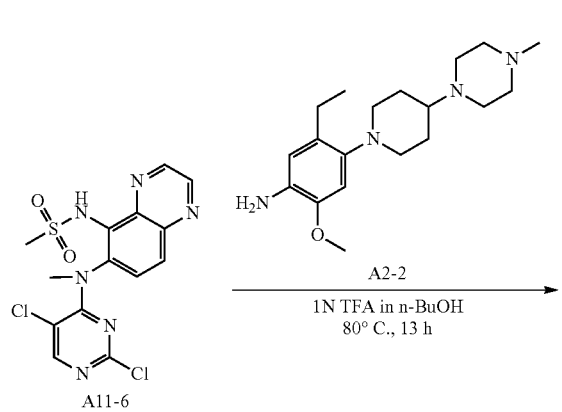

A mixture of compound A11-6 (70 mg, 0.18 mmol) and compound A2-2 (70 mg, 0.21 mmol) in TFA/n-butanol (1M, 4.0 mL) was stirred at 80° C. for 13 h. The reaction mixture was concentrated under reduced pressure to afford a residue which was purified by prep-HPLC to afford Example A11 as a yellow solid.

$^1$H NMR (400 MHz, DMSO-$d_6$) δ 1.18-1.32 (3H, m), 1.47 (2H, s), 1.77 (2H, s), 2.19 (3H, s), 2.24-2.48 (9H, m), 2.54-2.87 (6H, m), 3.22 (3H, s), 3.47 (3H, s), 3.82 (3H, s), 6.68 (1H, s), 7.05-7.52 (1H, m), 7.72-7.80 (2H, m), 7.89-8.10 (1H, m), 8.10-8.25 (1H, m), 9.01-9.03 (2H, m), 9.34 (1H, s).

LC-MS: MS Calculated 694.3, MS Found 695.4 [M+H]$^+$.

[Example A12] Preparation of N-(6-((2-((5-ethyl-2-methoxy-4-(4-(4-methylpiperazin-1-yl)piperidin-1-yl)phenyl)amino)-5-(trifluoromethyl)pyrimidin-4-yl) amino)quinoxalin-5-yl)methanesulfonamide (Step 1) Preparation of 5-nitroquinoxalin-6-amine (A12-2)

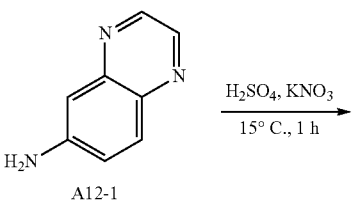

To a stirred solution of quinoxalin-6-amine (A12-1, 5.00 g, 34.4 mmol) in con. H$_2$SO$_4$ (50 mL) was added KNO$_3$ (3.48 g, 34.4 mmol) portion wise at 0° C. The reaction mixture was stirred at 15° C. for 1 h. The reaction mixture was then diluted with ice water (300 mL) and, adjusted to pH=8 with sat. aq. NaHCO$_3$. The mixture was filtered, and the resulting solids were washed with EtOAc (300 mL). The filtrate was washed with brine (200 mL), dried over Na$_2$SO$_4$, filtered and concentrated under reduced pressure to give a residue that was purified by reverse column chromatography to afford compound A12-2 as a brown solid.

$^1$H NMR (400 MHz, DMSO-$d_6$) δ 7.35 (2H, brs), 7.44 (1H, d, J=9.2 Hz), 7.92 (1H, d, J=9.2 Hz), 8.64 (1H, d, J=2.0 Hz), 8.77 (1H, d, J=2.0 Hz).

(Step 2) Preparation of N-(2-chloro-5-(trifluoromethyl)pyrimidin-4-yl)-5-nitroquinoxalin-6-amine (A12-3)

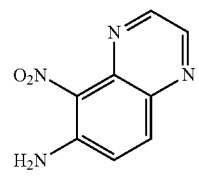

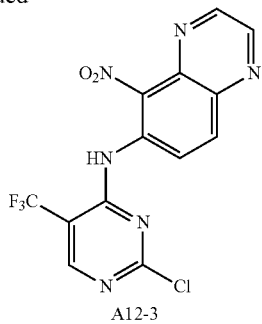

A12-3

To a stirred solution of compound A12-2 (340 mg, 1.79 mmol) in NMP (20 mL) was added NaH (215 mg, 5.36 mmol, 60% in mineral oil) at 0° C. for 10 min. To the mixture was then added 2,4-dichloro-5-(trifluoromethyl)pyrimidine (466 mg, 2.15 mmol). The resulting mixture was stirred at 0° C. for 2 h, then quenched with ice water (20 mL) and extracted with EtOAc (20 mL×4). The combined organic layer was washed with brine (100 mL), dried over Na$_2$SO$_4$, filtered and concentrated under reduced pressure to give a residue. The residue was purified by flash silica gel chromatography to afford compound A12-3 as a yellow solid.

$^1$H NMR (400 MHz, DMSO-d$_6$) δ 8.16 (1H, d, J=9.2 Hz), 8.36 (1H, d, J=9.2 Hz), 8.84 (1H, s), 9.06 (1H, d, J=2.0 Hz), 9.09 (1H, d, J=2.0 Hz), 11.29 (1H, brs).

(Step 3) Preparation of N6-(2-chloro-5-(trifluoromethyl)pyrimidin-4-yl)quinoxaline-5,6-diamine (A12-4)

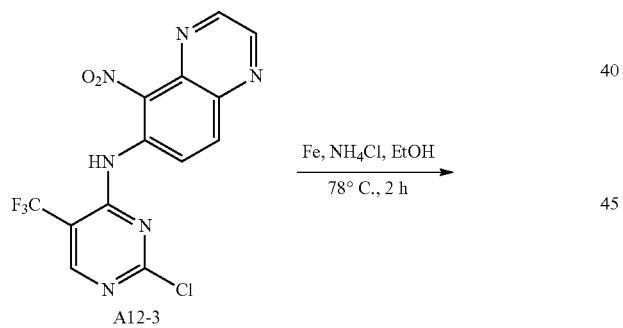

To a solution of compound A12-3 (200 mg, 0.540 mmol) in EtOH (15 mL) and H$_2$O (5.0 mL) was added Fe powder (121 mg, 2.16 mmol) and NH$_4$Cl (231 mg, 4.32 mmol). The mixture was stirred under N$_2$ at 78° C. for 2 h, then filtered to remove solids. The remaining filtered cake was washed with MeOH (10 mL×3), and the filtrate was concentrated under reduced pressure to give a residue. The residue was dissolved in EtOAc (50 mL), then washed with H$_2$O (20 mL×3), brine (20 mL). The organic phase was dried over Na$_2$SO$_4$, filtered and concentrated under reduced pressure to afford compound A12-4 as a yellow solid.

$^1$H NMR (400 MHz, DMSO-d$_6$) δ 5.99 (2H, brs), 7.25 (1H, d, J=8.4 Hz), 7.66 (1H, d, J=8.8 Hz), 8.55-8.94 (3H, m), 10.08 (1H, brs).

(Step 4) Preparation of N-(6-((2-chloro-5-(trifluoromethyl)pyrimidin-4-yl)amino)quinoxalin-5-yl)methanesulfonamide (A12-5)

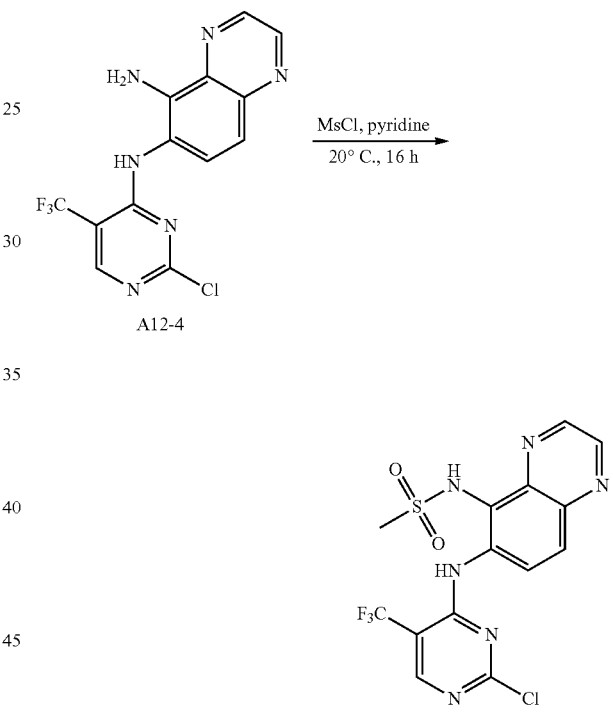

A solution of compound A12-4 (252 mg, 0.740 mmol) in pyridine (10 mL) was cooled to 0° C. before the dropwise addition of MsCl (254 mg, 2.22 mmol). The resulting solution was allowed to warm to 20° C., and then stirred for 16 h. The mixture was then diluted with ice water (5 mL), adjusted to pH=5 with 1 M aq. HCl, then extracted with EtOAc (100 mL×3). The combined organic layer was washed with brine (200 mL), dried over Na$_2$SO$_4$, filtered and concentrated under reduced pressure to give a residue that was purified by reverse phase column chromatography to afford compound A12-5 as a yellow solid.

$^1$H NMR (400 MHz, DMSO-d$_6$) δ 3.08 (3H, s), 8.05 (1H, d, J=8.8 Hz), 8.42 (1H, d, J=9.2 Hz), 8.85 (1H, s), 8.94 (1H, d, J=1.6 Hz), 9.00 (1H, d, J=1.6 Hz), 9.89 (2H, brs).

(Step 5) Preparation of N-(6-((2-((5-ethyl-2-methoxy-4-(4-(4-methylpiperazin-1-yl)piperidin-1-yl)phenyl)amino)-5-(trifluoromethyl)pyrimidin-4-yl)amino)quinoxalin-5-yl)methanesulfonamide (Example A12)

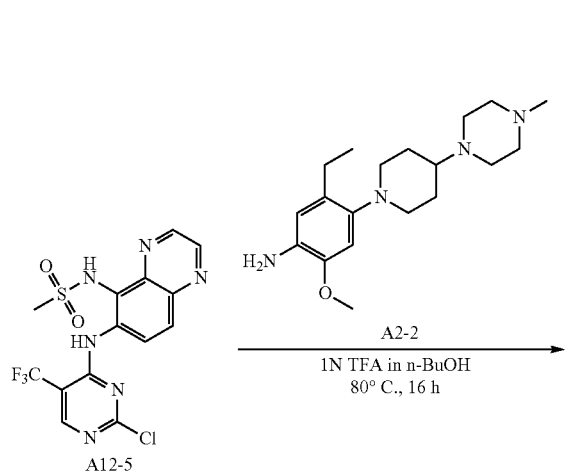

[Example A13] N-(6-((5-chloro-2-((5-methyl-2-(methylamino)-4-(4-(4-methylpiperazin-1-yl) piperidin-1-yl)phenyl)amino)pyrimidin-4-yl)amino)quinoxalin-5-yl)methanesulfonamide (Step 1) Preparation of 4-bromo-5-fluoro-N-methyl-2-nitroaniline (A13-1)

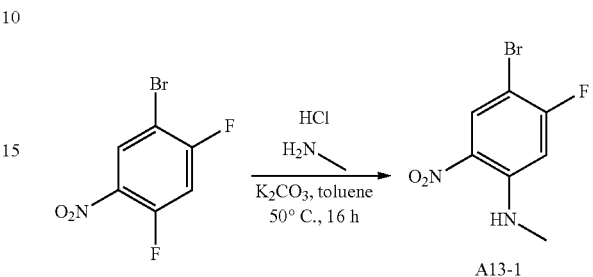

To a stirred solution of 1-bromo-2,4-difluoro-5-nitrobenzene (5.00 g, 21.0 mmol) and MeNH$_2$—HCl (1.56 g, 23.1 mmol) in toluene (50 mL) was added K$_2$CO$_3$ (6.39 g, 46.2 mmol). The mixture was stirred at 50° C. for 16 h, then concentrated under reduced pressure to give a residue. The residue was diluted with water (50 mL) and extracted with EtOAc (50 mL×3). The combined organic layer was washed with brine (100 mL), dried over Na$_2$SO$_4$, filtered and concentrated under reduced pressure to give a residue. The residue was purified by trituration from PE (20 mL). The mixture was filtered, and the cake was dried under reduced pressure to afford compound A13-1 as a yellow solid.

$^1$H NMR (400 MHz, CDCl$_3$) δ 3.14 (3H, d, J=4.8 Hz), 6.59 (1H, d, J=10.8 Hz), 8.12 (1H, brs), 8.42 (1H, d, J=7.2 Hz).

(Step 2) Preparation of tert-butyl (4-bromo-5-fluoro-2-nitrophenyl)(methyl)carbamate (A13-2)

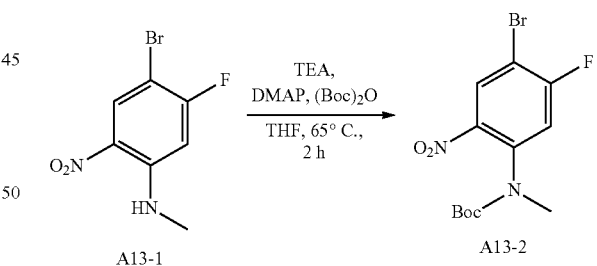

To a stirred solution of compound A13-1 (2.01 g, 8.07 mmol) and Boc$_2$O (2.64 g, 12.1 mmol) in THF (20 mL) was added DMAP (99 mg, 0.81 mmol). The resulting mixture was stirred at 65° C. for 2 h, then concentrated under reduced pressure to give a residue. The residue was diluted with water (10 mL) and extracted with EtOAc (10 mL×3). The combined organic layer was washed with brine (20 mL), dried over Na$_2$SO$_4$, filtered and concentrated under reduced pressure to give a residue. The residue was purified by flash silica gel column chromatography to afford compound A13-2 as yellow oil.

$^1$H NMR (400 MHz, CDCl$_3$) δ 1.34 (9H, s), 3.31 (3H, s), 7.13 (1H, d, J=8.4 Hz), 8.21 (1H, d, J=6.8 Hz).

To a solution of TFA (1.00 g, 8.77 mmol) in n-butanol (8.0 mL) were added compound A12-5 (40 mg, 0.96 mmol) and compound A2-2 (38 mg, 0.12 mmol). The resulting mixture was stirred under N$_2$ at 80° C. for 16 h, then concentrated under reduced pressure to give a residue. The residue was purified by prep-HPLC to afford Example A12 as a brown solid.

$^1$H NMR (400 MHz, CDCl$_3$) δ 0.84 (3H, s), 1.92-2.01 (2H, m), 2.13-2.20 (2H, m), 2.36-2.42 (2H, m), 2.52-2.82 (10H, m), 2.89-2.91 (4H, m), 3.00 (3H, s), 3.20-3.23 (2H, m), 3.88 (3H, s), 6.62 (1H, s), 7.57-7.59 (1H, m), 7.79 (1H, s), 7.95 (1H, d, J=9.2 Hz), 8.04 (1H, brs), 8.32 (1H, s), 8.62 (1H, d, J=9.6 Hz), 8.83-8.90 (2H, m), 10.04 (1H, brs).

LC-MS: MS Calculated 714.3, MS Found 715.2 [M+H]$^+$.

(Step 3) Preparation of tert-butyl (4-bromo-5-(4-(4-methylpiperazin-1-yl)piperidin-1-yl)-2-nitrophenyl)(methyl)carbamate (A13-3)

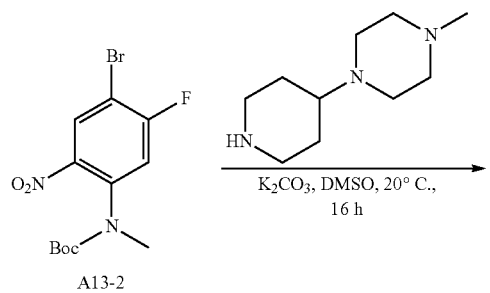

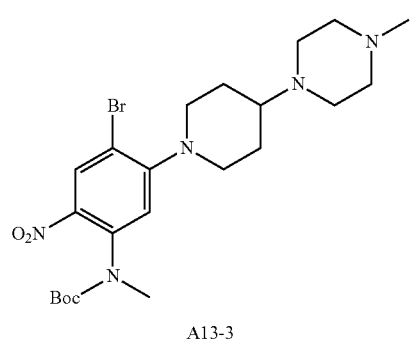

To a stirred solution of compound A13-2 (2.31 g, 6.62 mmol) in DMSO (30 mL) were added K₂CO₃ (1.37 g, 9.92 mmol) and 1-methyl-4-(piperidin-4-yl)piperazine (1.33 g, 7.28 mmol). The mixture was stirred at 20° C. for 16 h, then diluted with water (150 mL). The resulting suspension was filtered and the remaining cake was washed with water (30 mL×3). The collected solid was purified by reverse-phase column chromatography to afford compound A13-3 as a yellow solid.

$^1$H NMR (400 MHz, CDCl$_3$) δ 1.31 (9H, s), 1.75-1.79 (2H, m), 1.97-2.02 (2H, m), 2.31 (3H, s), 2.50-2.80 (11H, m), 3.29 (3H, s), 3.58-3.62 (2H, m), 6.80 (1H, s), 8.18 (1H, s).

(Step 4) Preparation of tert-butyl methyl(4-methyl-5-(4-(4-methylpiperazin-1-yl)piperidin-1-yl)-2-nitrophenyl)carbamate (A13-4)

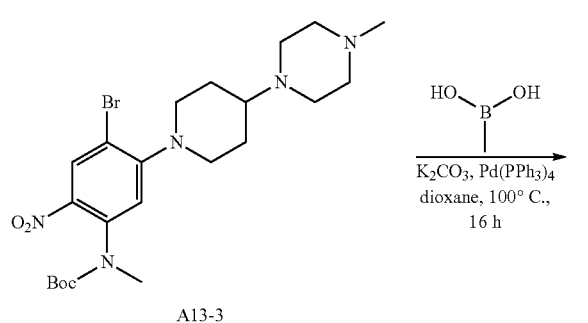

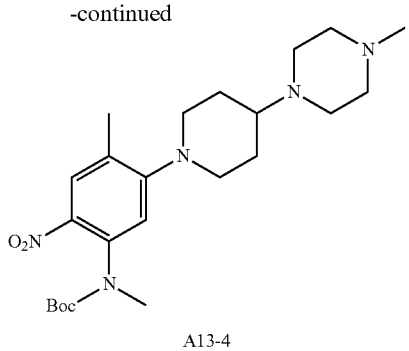

To a mixture of compound A13-3 (1.00 g, 1.95 mmol) and methylboronic acid (700 mg, 11.7 mmol) in dioxane (30 mL) were added K₂CO₃ (809 mg, 5.85 mmol) and Pd(PPh$_3$)$_4$ (225 mg, 0.195 mmol). The reaction mixture was stirred at 100° C. for 16 h, then concentrated under reduced pressure to give a residue that was extracted by EtOAc (50 mL×3) and water (50 mL). The combined organic layer was washed with brine (100 mL), dried over Na$_2$SO$_4$, filtered and concentrated under reduced pressure to give a residue which was purified by reverse-phase column chromatography to afford compound A13-4 as yellow oil.

$^1$H NMR (400 MHz, CDCl$_3$) δ 1.31 (9H, s), 1.69-1.72 (2H, m), 1.98-2.01 (2H, m), 2.34 (3H, s), 2.48-2.75 (11H, m), 3.25 (3H, s), 3.27 (3H, s), 3.30-3.35 (2H, m), 6.75 (1H, s), 7.79 (1H, s).

(Step 5) Preparation of tert-butyl (2-amino-4-methyl-5-(4-(4-methylpiperazin-1-yl)piperidin-1-yl)phenyl)(methyl)carbamate (A13-5)

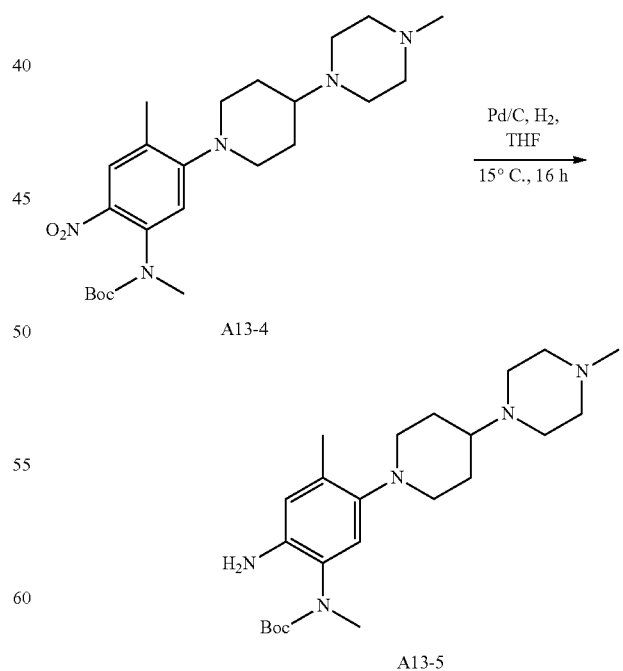

To a solution of compound A13-4 (800 mg, 1.79 mmol) in THF (10 mL) was added Pd/C (80 mg, 10 mol %). The suspension was degassed under vacuum and purged with H$_2$ several times. The mixture was stirred under H$_2$ (15 psi) at 15° C. for 16 h, and then filtered to remove solids. The solids were further washed with MeOH (10 mL×3), and the filtrate was concentrated under reduced pressure. The remaining residue was purified by reverse-phase column chromatography to afford compound A13-5 as a brown solid.

$^1$H NMR (400 MHz, CDCl$_3$) δ 1.35-1.53 (9H, m), 1.65-1.70 (2H, m), 1.89-1.95 (2H, m), 2.20 (3H, s), 2.28-2.35 (4H, m), 2.45-2.75 (10H, m), 3.03-3.08 (2H, m), 3.13 (3H, s), 3.46 (2H, brs), 6.58 (1H, s), 6.67 (1H, s).

(Step 6) Preparation of N-(6-((5-chloro-2-((5-methyl-2-(methylamino)-4-(4-(4-methylpiperazin-1-yl)piperidin-1-yl)phenyl)amino)pyrimidin-4-yl)amino)quinoxalin-5-yl)methanesulfonamide. (Example A13)

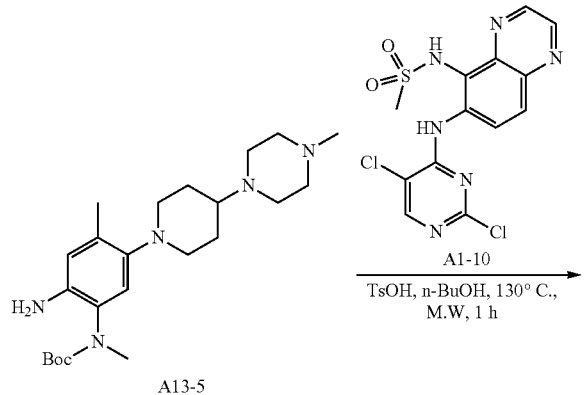

A mixture of compound A13-5 (100 mg, 0.239 mmol), compound A1-10 (92 mg, 0.24 mmol) and TsOH (62 mg, 0.36 mmol) in n-butanol (2 mL) was stirred at 130° C. for 1 h under microwave irradiation. The reaction mixture was then concentrated under reduced pressure to give a residue which was purified by prep-HPLC to afford Example A13 as a red solid.

$^1$H NMR (400 MHz, DMSO-d$_6$) δ 1.73-1.76 (2H, m), 1.95-2.00 (2H, m), 2.17 (3H, s), 2.34 (3H, s), 2.38-2.41 (1H, m), 2.53-2.75 (10H, m), 2.79 (3H, s), 2.91 (3H, s), 3.22-3.27 (2H, m), 3.91 (1H, brs), 6.32 (1H, s), 6.44 (1H, s), 7.04 (1H, s), 7.90 (1H, brs), 8.12 (1H, s), 8.78-8.81 (1H, m), 8.83-8.87 (2H, m), 9.13 (1H, s).

[Example A14] Preparation of N-(6-((5-bromo-2-((2-(dimethylamino)-5-methyl-4-(4-(4-methyl piperazin-1-yl)piperidin-1-yl)phenyl)amino)pyrimidin-4-yl)amino)quinoxalin-5-yl) methanesulfonamide To a mixture of compound A4-2 (19 mg, 0.045 mmol) and compound A14-1 (30 mg, 0.090 mmol) in n-butanol (2.0 mL) was added TsOH (12 mg, 0.067 mmol). The reaction mixture was stirred at 130° C. for 2 h under microwave irradiation, then concentrated under reduced pressure to afford a residue. The residue was dissolved in MeOH (3 mL) and basified with TEA to pH=7-8, then concentrated under reduced pressure. The remaining residue was purified by reverse column chromatography and further purified by prep-HPLC to afford Example A14 as a yellow solid.

$^1$H NMR (400 MHz, CDCl$_3$) δ 1.65-1.71 (2H, m), 1.89-1.95 (2H, m), 1.99-2.06 (3H, m), 2.31 (3H, s), 2.49-2.73 (17H, m), 2.95 (3H, s), 3.09-3.14 (2H, m), 6.84 (1H, s), 7.88 (1H, s), 8.03-8.10 (2H, m), 8.25 (1H, s), 8.83-8.86 (2H, m), 8.88 (1H, d, J=1.6 Hz).

[Example A15] Preparation of N-(6-((5-chloro-2-((2-methoxy-4-(4-(4-methyl-4,7-diazaspiro[2.5]octan-7-yl)piperidin-1-yl)phenyl)amino)pyrimidin-4-yl)amino)quinoxalin-5-yl)methanesulfonamide (Step 1) Preparation of tert-butyl 7-(1-((benzyloxy)carbonyl)piperidin-4-yl)-4,7-diazaspiro[2.5] octane-4-carboxylate compound (A15-2)

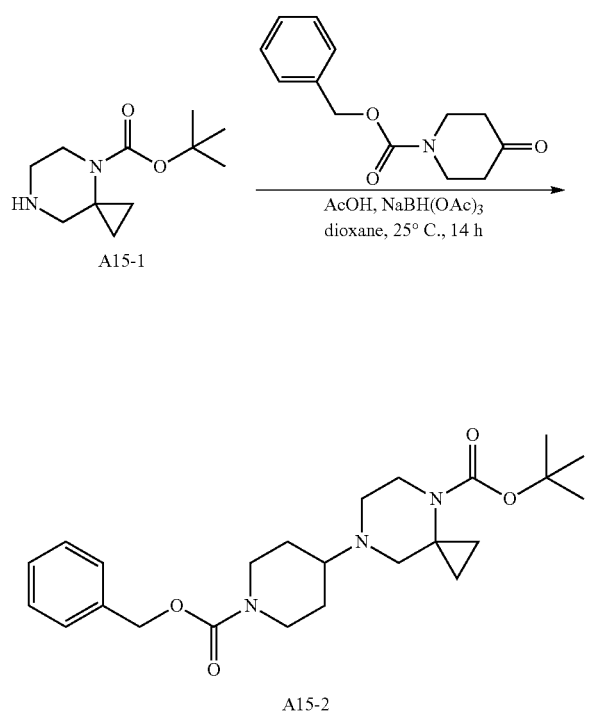

To a mixture of tert-butyl 4,7-diazaspiro[2.5]octane-4-carboxylate (A15-1) (1.40 g, 6.59 mmol) and benzyl 4-oxopiperidine-1-carboxylate (1.69 g, 7.25 mmol) in dioxane (15 mL) was added AcOH (396 mg, 6.59 mmol) at 25° C. The resulting mixture was stirred at 25° C. for 1 h, then NaBH(OAc)$_3$ (4.19 g, 19.8 mmol) was added and the mixture was stirred at 25° C. for additional 13 h. The reaction mixture was then poured into water (50 mL) and extracted with EtOAc (50 mL×3). The combined organic layer was washed with brine (50 mL), dried over anhydrous Na$_2$SO$_4$ and concentrated under reduced pressure. The remaining residue was purified by Combi Flash to afford the desired product (A15-2) which was further purified by reverse column chromatography to afford compound A15-2 as a white solid.

$^1$H NMR (400 MHz, DMSO-d$_6$) δ 0.61-0.75 (2H, m), 0.78-0.92 (2H, m), 1.21-1.32 (2H, m), 1.38 (9H, s), 1.65-1.76 (2H, m), 2.21-2.33 (3H, m), 2.38-2.48 (2H, m), 2.80 (2H, brs), 3.30-3.37 (2H, m), 3.90-4.02 (2H, m), 5.05 (2H, s), 7.25-7.46 (5H, m).

(Step 2) Preparation of benzyl 4-(4,7-diazaspiro[2.5]octan-7-yl)piperidine-1-carboxylate (A15-3)

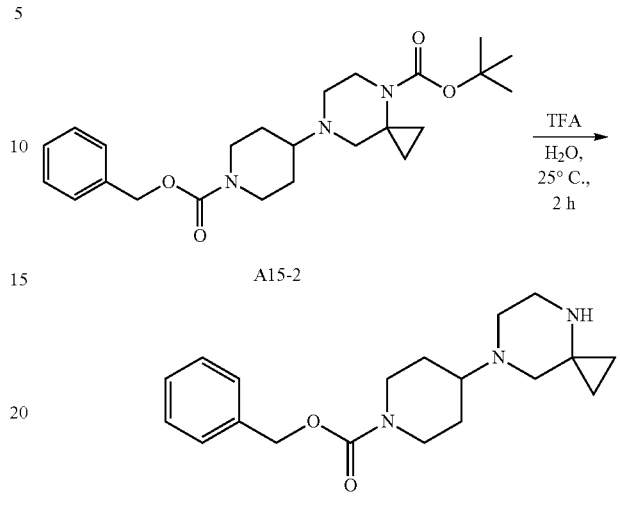

A mixture of compound A15-2 (1.00 g, 2.33 mmol) in TFA (9 mL) and H$_2$O (1 mL) was stirred at 25° C. for 2 h, then basified with 1 M NaOH aq. to pH=8. The resulting mixture was poured into water (50 mL) and extracted with EtOAc (50 mL×3). The combined organic layer was washed with brine (50 mL), dried over anhydrous Na$_2$SO$_4$ and concentrated under reduced pressure to afford compound A15-3 as colorless oil.

$^1$H NMR (400 MHz, DMSO-d$_6$) δ 0.23-0.34 (2H, m), 0.35-0.48 (2H, m), 1.21-1.32 (2H, m), 1.65-1.76 (2H, m), 2.16-2.34 (3H, m), 2.36-2.48 (2H, m), 2.65-2.91 (4H, m), 3.84-4.02 (2H, m), 5.05 (2H, s), 7.25-7.46 (5H, m).

(Step 3) Preparation of benzyl 4-(4-methyl-4,7-diazaspiro[2.5]octan-7-yl)piperidine-1-carboxylate (A15-4)

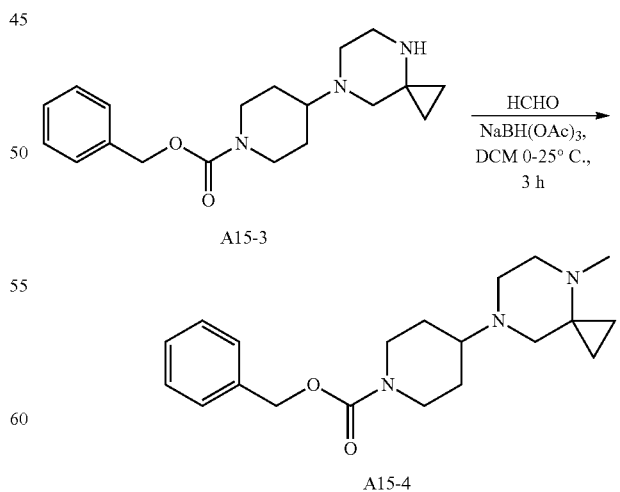

To a mixture of compound A15-3 (760 mg, 2.31 mmol) in DCM (8 mL) was added HCHO (281 mg, 3.46 mmol, 37% in H$_2$O) and NaBH(OAc)$_3$ (636 mg, 3.00 mmol) at 0° C. The mixture was then stirred at 25° C. for 3 h. The reaction was monitored by LC-MS. The mixture was poured into sat. NaHCO₃ aq. (50 mL) and extracted with DCM (50 mL×3). The combined organic layer was washed with brine (50 mL), dried over anhydrous Na₂SO₄ and concentrated under reduced pressure to afford compound A15-4 as colorless oil.

¹H NMR (400 MHz, DMSO-d₆) δ 0.21-0.34 (2H, m), 0.46-0.58 (2H, m), 1.21-1.32 (2H, m), 1.72-1.86 (2H, m), 2.14 (3H, s), 2.18-2.34 (3H, m), 2.36-2.48 (2H, m), 2.65-2.91 (4H, m), 3.91-4.02 (2H, m), 5.05 (2H, s), 7.32-7.46 (5H, m).

(Step 4) Preparation of 4-methyl-7-(piperidin-4-yl)-4,7-diazaspiro[2.5]octane (A15-5)

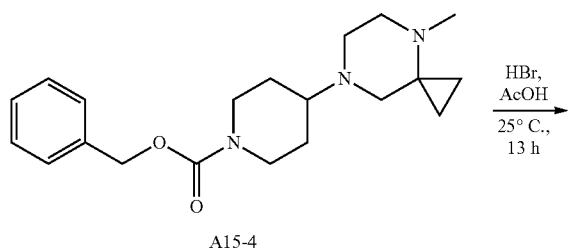

A15-4

To a mixture of compound A15-4 (507 mg, 1.48 mmol) in AcOH (3 mL) was added HBr (4.47 g, 22.1 mmol, 3 mL, 40% in AcOH) at 25° C., and the mixture was stirred at 25° C. for 13 h. The reaction was monitored by LC-MS. The reaction mixture was concentrated under reduced pressure to afford crude compound A15-5 (300 mg) as a brown solid.

(Step 5) Preparation of 7-(1-(3-methoxy-4-nitrophenyl)piperidin-4-yl)-4-methyl-4,7-diazaspiro[2.5]octane (A15-6)

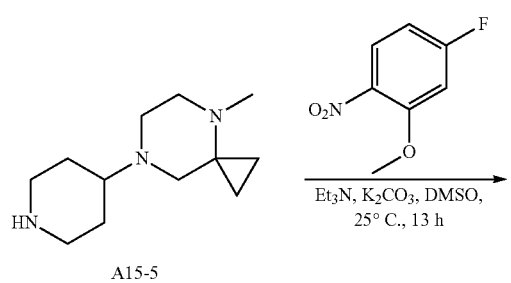

A15-5

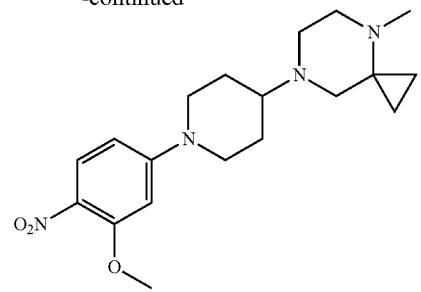

A15-6

To a solution of 4-fluoro-2-methoxy-1-nitrobenzene (223 mg, 1.30 mmol) in DMSO (5 mL) were added compound A15-5 (299 mg, 1.43 mmol), TEA (1.32 g, 13.00 mmol) and K₂CO₃ (270 mg, 1.95 mmol) at 25° C., and then the mixture was stirred at 25° C. for 13 h. The reaction was monitored by LC-MS. The reaction mixture was poured into water (30 mL) and extracted with EtOAc (30 mL×3). The combined organic layer was washed with 50% NaCl aq. (30 mL), dried over anhydrous Na₂SO₄ and concentrated under reduced pressure. The residue was purified by Combi Flash to afford compound A15-6 as a yellow solid.

¹H NMR (400 MHz, CDCl₃) δ 0.41-0.53 (2H, m), 0.81-0.93 (2H, m), 1.65-1.75 (2H, m), 1.95-2.05 (2H, m), 2.33 (3H, s), 2.40-2.55 (3H, m), 2.63-2.75 (2H, m), 2.90-3.06 (4H, m), 3.91-4.05 (5H, m), 6.29 (1H, d, J=2.4 Hz), 6.40 (1H, dd, J=9.6, 2.4 Hz), 7.97 (1H, d, J=9.2 Hz).

(Step 6) Preparation of 2-methoxy-4-(4-(4-methyl-4,7-diazaspiro[2.5]octan-7-yl)piperidin-1-yl)aniline (A15-7)

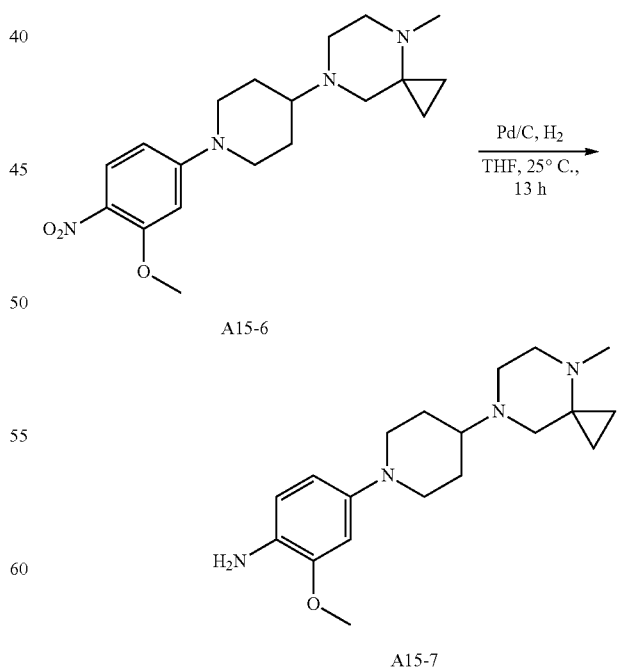

To a solution of compound A15-6 (200 mg, 0.555 mmol) in THF (3 mL) was added Pd/C (20 mg, 10 mol %) under N₂.

The suspension was degassed under vacuum and purged with H₂ several times. The mixture was stirred under H₂ (15 psi) at 25° C. for 13 h. The reaction was monitored by LC-MS. The mixture was filtered and the filtrate was concentrated under reduced pressure to afford compound A15-7 as a white solid.

¹H NMR (400 MHz, CDCl₃) δ 0.41-0.55 (2H, m), 0.71-0.85 (2H, m), 1.71-1.85 (2H, m), 1.95-2.05 (2H, m), 2.33 (3H, s), 2.40-2.55 (2H, m), 2.63-2.65 (2H, m), 2.67-2.81 (2H, m), 2.85-3.04 (3H, m), 3.51-3.65 (2H, m), 3.84 (3H, s), 6.41 (1H, dd, J=8.8, 2.8 Hz), 6.52 (1H, d, J=2.4 Hz), 6.63 (1H, d, J=8.8 Hz).

(Step 7) Preparation of N-(6-((5-chloro-2-((2-methoxy-4-(4-(4-methyl-4,7-diazaspiro[2.5]octan-7-yl)piperidin-1-yl)phenyl)amino)pyrimidin-4-yl)amino)quinoxalin-5-yl)methanesulfonamide (Example A15)

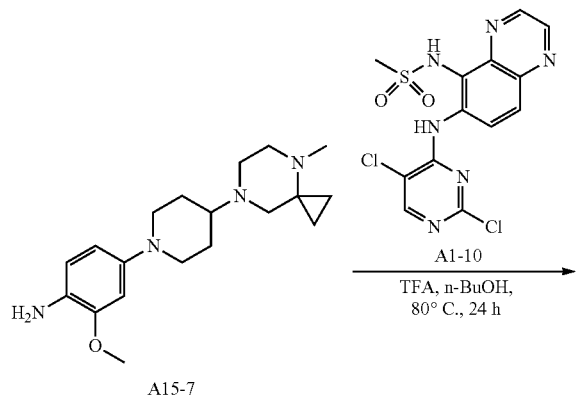

A15-7

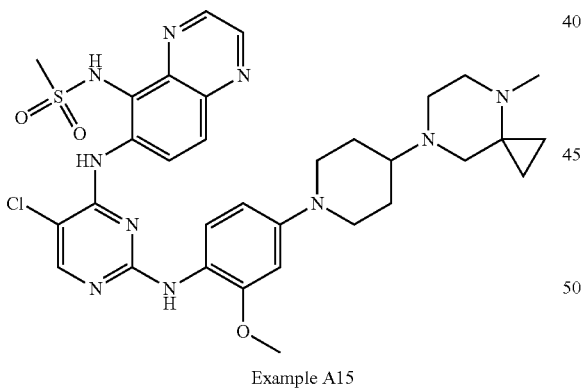

Example A15

To a mixture of compound A1-10 (117 mg, 0.304 mmol) and compound A15-7 (100 mg, 0.304 mmol) in n-butanol (4 mL) was added TFA (456 mg, 4.00 mmol) at 15° C., and then the mixture was stirred at 80° C. for 24 h. The reaction was monitored by LC-MS. The reaction mixture was concentrated under reduced pressure to be purified by prep-HPLC to afford Example A15 as an off-white solid.

¹H NMR (400 MHz, CDCl₃) δ 0.42-0.61 (2H, m), 0.85-0.97 (2H, m), 1.71-1.85 (2H, m), 1.98-2.15 (2H, m), 2.37 (3H, s), 2.45-2.63 (3H, m), 2.65-2.76 (2H, m), 2.78-2.88 (2H, m), 2.94 (3H, s), 2.9-3.15 (2H, m), 3.58-3.72 (2H, m), 3.86 (3H, s), 6.42 (1H, dd, J=8.8, 2.0 Hz), 6.53 (1H, d, J=2.0 Hz), 7.32 (1H, s), 7.96 (1H, d, J=8.8 Hz), 8.09 (1H, d, J=9.6 Hz), 8.15 (1H, s), 8.76-8.75 (3H, m), 9.20 (1H, s).

LC-MS: MS Calculated 678.3, MS Found 679.3 [M+H]⁺.

[Example A16] Preparation of N-(6-((5-chloro-2-((2-(dimethylamino)-5-methyl-4-(4-(4-methyl piperazin-1-yl)piperidin-1-yl)phenyl)amino)pyrimidin-4-yl)amino)quinoxalin-5-yl)methane sulfonamide (Step 1) Preparation of 4-bromo-5-fluoro-N,N-dimethyl-2-nitroaniline (A16-2)

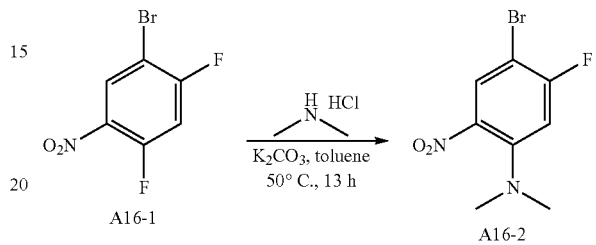

To a solution of 1-bromo-2,4-difluoro-5-nitrobenzene A16-1 (10.0 g, 42.0 mmol) in toluene (150 mL) were added K₂CO₃ (11.6 g, 84.0 mmol) and dimethyl amine hydrochloride (3.43 g, 42.0 mmol). The mixture was stirred at 50° C. for 13 h. The reaction was monitored by LC-MS. The reaction mixture was concentrated under reduced pressure to afford a residue that was poured into water (50 mL) and extracted with EtOAc (50 mL×3). The combined organic layer was washed with brine (50 mL), dried over anhydrous Na₂SO₄ and concentrated under reduced pressure to afford compound A16-2 as yellow oil. ¹H NMR (400 MHz, CDCl₃) δ 2.91 (6H, s), 6.75 (1H, d, J=11.2 Hz), 8.04 (1H, d, J=7.2 Hz).

(Step 2) Preparation of 4-bromo-N,N-dimethyl-5-(4-(4-methylpiperazin-1-yl)piperidin-1-yl)-2-nitroaniline (A16-3)

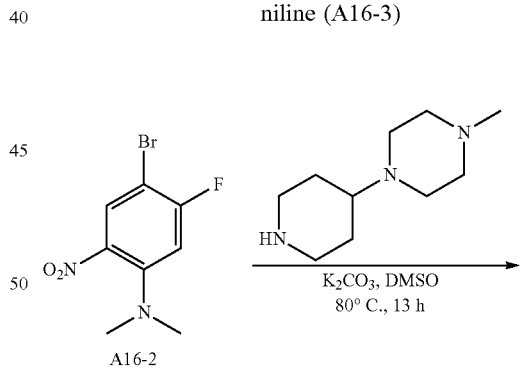

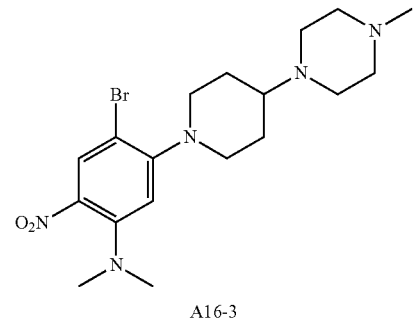

A16-3

To a solution of compound A16-2 (11.0 g, 41.8 mmol) in DMSO (100 mL) were added K₂CO₃ (8.67 g, 62.7 mmol) and 1-methyl-4-(piperidin-4-yl)piperazine (10.1 g, 46.0 mmol). The mixture was stirred at 80° C. for 13 h. The reaction was monitored by LC-MS. The reaction mixture was poured into water (50 mL) and extracted with EtOAc (50 mL×3). The combined organic layer was washed with 50% aq. NaCl (50 mL×3), dried over anhydrous Na₂SO₄ and concentrated under reduced pressure to afford a residue which was purified by Combi Flash to afford compound A16-3 as a yellow solid.

¹H NMR (400 MHz, CDCl₃) δ 1.72-1.83 (2H, m), 1.92-1.99 (2H, m), 2.31 (3H, s), 2.35-2.45 (2H, m), 2.46-2.58 (3H, m), 2.62-2.77 (6H, m), 2.88 (6H, s), 3.53-3.62 (2H, m), 6.44 (1H, s), 8.10 (1H, s).

(Step 3) Preparation of N, N, 4-trimethyl-5-(4-(4-methylpiperazin-1-yl)piperidin-1-yl)-2-nitroaniline (A16-4)

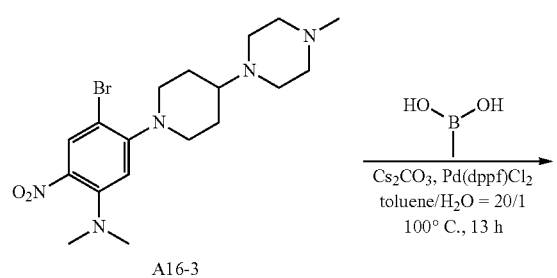

To a mixture of compound A16-3 (6.00 g, 14.1 mmol) and methylboronic acid (1.01 g, 16.9 mmol) in toluene (60 mL) and H₂O (3 mL) were added Cs₂CO₃ (9.17 g, 28.2 mmol) and Pd(dppf)Cl₂ (1.03 g, 1.41 mmol). It was stirred at 100° C. for 13 h. The reaction was monitored by LC-MS. It was concentrated under reduced pressure to afford a residue (6.20 g). 2 g of the residue was purified by prep-HPLC and concentrated under reduced pressure to afford compound A16-4 as a yellow solid.

¹H NMR (400 MHz, CDCl₃) δ 1.64-1.75 (2H, m), 1.94-2.01 (2H, m), 2.19 (3H, s), 2.31 (3H, s), 2.35-2.75 (11H, m), 2.88 (6H, s), 3.28-3.36 (2H, m), 6.44 (1H, s), 7.74 (1H, s).

(Step 4) Preparation of N1, N1, 4-trimethyl-5-(4-(4-methylpiperazin-1-yl)piperidin-1-yl)benzene-1,2-diamine (A16-5)

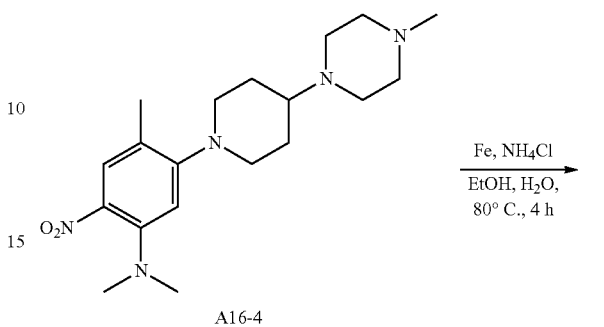

To a mixture of compound A16-4 (450 mg, 1.24 mmol) in EtOH (10 mL) and H₂O (3 mL) were added Fe powder (278 mg, 4.98 mmol) and NH₄Cl (533 mg, 9.96 mmol). It was stirred at 80° C. for 4 h. The reaction was monitored by TLC. The mixture was filtered and the filtrate was concentrated under reduced pressure to afford compound A16-5 as a brown solid.

¹H NMR (400 MHz, CDCl₃) δ 1.73-1.85 (2H, m), 2.00-2.11 (2H, m), 2.16 (3H, s), 2.57-2.72 (12H, m), 2.95-3.25 (10H, m), 6.57 (1H, s), 6.74 (1H, s).

(Step 5) Preparation of N-(6-((5-chloro-2-((2-(dimethylamino)-5-methyl-4-(4-(4-methylpiperazin-1-yl)piperidin-1-yl)phenyl)amino)pyrimidin-4-yl)amino)quinoxalin-5-yl)methanesulfonamide (Example A16)

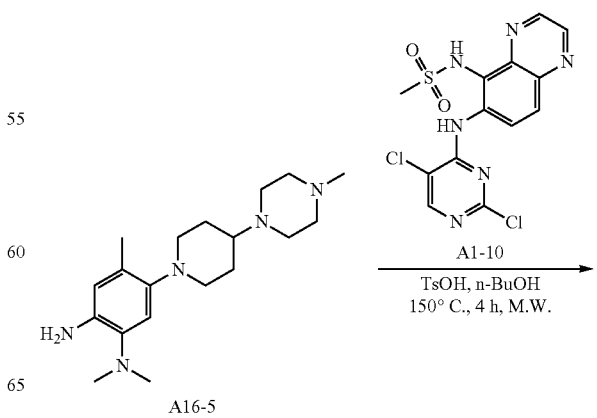

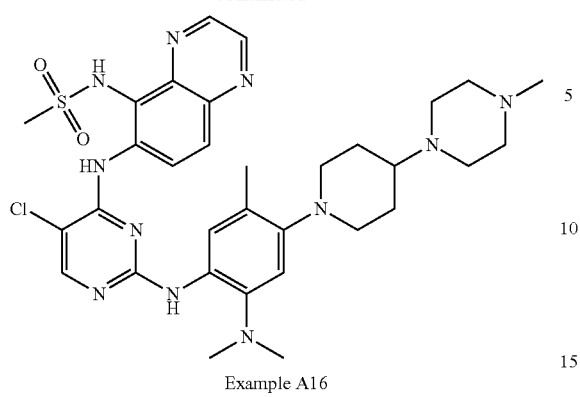

Example A16

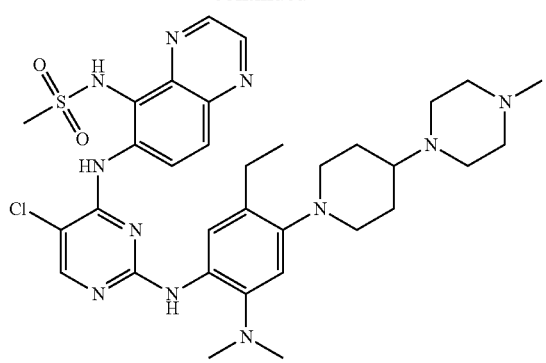

Example A17

To a mixture of compound A16-5 (200 mg, 0.600 mmol) and compound A1-10 (116 mg, 0.300 mmol) in n-butanol (3 mL) was added TsOH (78 mg, 0.45 mmol). The reaction mixture was stirred at 150° C. for 4 h under microwave irradiation. The reaction was monitored by LC-MS. The reaction mixture was concentrated under reduced pressure to afford a residue that was purified by prep-HPLC to afford Example A16 as a yellow solid.

$^1$H NMR (400 MHz, CDCl$_3$) δ 1.66-1.71 (2H, m), 1.90-1.95 (2H, m), 2.07 (3H, s), 3.31 (3H, s), 2.50-2.70 (17H, m), 2.94 (3H, s), 3.10-3.14 (2H, m), 6.85 (1H, s), 7.94 (1H, s), 8.03-8.07 (2H, m), 8.15 (1H, s), 8.22 (1H, d, J=2.0 Hz), 8.85 (1H, d, J=2.0 Hz), 8.89 (1H, d, J=9.2 Hz).

LC-MS: MS Calculated 679.3, MS Found: 680.2 [M+H]$^+$.

[Example A17] Preparation of N-(6-((5-chloro-2-((2-(dimethylamino)-5-ethyl-4-(4-(4-methyl piperazin-1-yl)piperidin-1-yl)phenyl)amino)pyrimidin-4-yl)amino)quinoxalin-5-yl)methane sulfonamide To a mixture of compound A17-1 (200 mg, 0.580 mmol) and compound A1-10 (111 mg, 0.290 mmol) in n-butanol (5.0 mL) was added TsOH (75 mg, 0.43 mmol). The reaction mixture was stirred at 150° C. for 2 h under microwave. The reaction was monitored by LC-MS. The mixture was concentrated under reduced pressure to afford a residue that was purified by prep-HPLC to afford Example A17 as a yellow solid.

$^1$H NMR (400 MHz, CDCl$_3$) δ 0.71-0.78 (3H, m), 1.64-1.71 (2H, m), 1.89-1.95 (2H, m), 2.37 (3H, s), 2.39-2.48 (4H, m), 2.62-2.75 (15H, m), 2.95 (3H, s), 3.02-3.07 (2H, m), 6.88 (1H, s), 7.92 (1H, s), 8.05 (1H, s), 8.09 (1H, d, J=9.6 Hz), 8.15 (1H, s), 8.80 (1H, d, J=9.6 Hz), 8.85 (1H, d, J=1.6 Hz), 8.91 (1H, d, J=1.6 Hz), 9.20 (1H, s).

LC-MS: MS Calculated 693.3, MS Found: 694.2 [M+H]$^+$.

[Example A18] Preparation of N-(6-((2-((5-ethyl-2-methoxy-4-(4-(4-methylpiperazin-1-yl)piperidin-1-yl)phenyl)amino)-5-fluoropyrimidin-4-yl)amino)quinoxalin-5-yl)methanesulfonamide

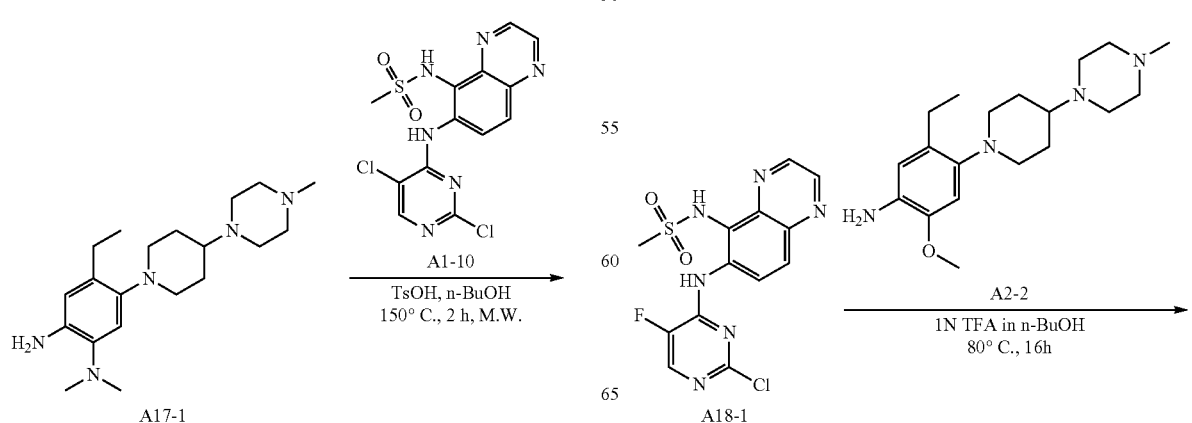

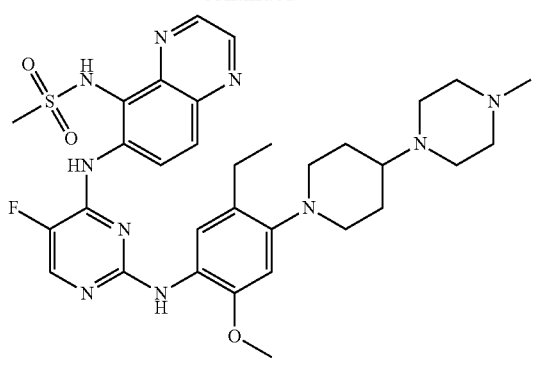

Example A18

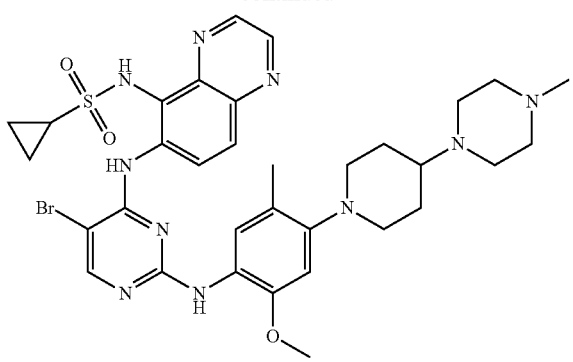

Example A19

To a mixture of compound A18-1 (120 mg, crude) and compound A2-2 (141 mg, 0.423 mmol) in n-butanol (5 mL) was added TFA (570 mg, 5.00 mmol) at 25° C. The mixture was stirred at 80° C. for 16 h. The reaction was monitored by LC-MS. The solvent was removed under reduced pressure and the residue was extracted by EtOAc (50 mL×3) and H$_2$O (20 mL). The combined organic layer was washed with brine (100 mL), drive over Na$_2$SO$_4$, filtered and concentrated to give a residue which was purified by prep-HPLC to afford Example A18 as a yellow solid.

$^1$H NMR (400 MHz, CDCl$_3$) δ 0.92 (3H, t, J=7.6 Hz), 1.69-1.71 (2H, m), 1.93-1.95 (2H, m), 2.31-2.33 (5H, m), 2.50-2.68 (11H, m), 2.93 (3H, s), 3.07 (2H, d, J=11.2 Hz), 3.85 (3H, s), 6.65 (1H, s), 7.36 (1H, s), 7.99 (1H, s), 8.07-8.09 (2H, m), 8.84 (1H, s), 8.89-8.94 (2H, m), 9.05 (1H, s).

LC-MS: MS Calculated 664.3, MS Found 665.3 [M+H]$^+$.

[Example A19] Preparation of N-(6-((5-bromo-2-((2-methoxy-5-methyl-4-(4-(4-methylpiperazin-1-yl)piperidin-1-yl)phenyl)amino)pyrimidin-4-yl)amino)quinoxalin-5-yl)cyclopropanesulfonamide A mixture of compound A19-1 (70 mg, 0.15 mmol) and A1-5 (59 mg, 0.18 mmol) in TFA/n-butanol (1N, 3.0 mL) was stirred at 80° C. for 36 h. The reaction was monitored by LC-MS. The reaction mixture was concentrated under reduced pressure to afford a residue that was purified by prep-HPLC to afford Example A19 as a yellow solid.

$^1$H NMR (400 MHz, CDCl$_3$) δ 0.63-0.70 (2H, m), 1.01-1.06 (2H, m), δ 1.68-1.71 (3H, m), 1.91-1.97 (2H, m), 1.99 (3H, s), 2.35-2.41 (4H, m), 2.45-2.85 (10H, m), 3.09-3.17 (2H, m), 3.84 (3H, s), 6.59 (1H, s), 7.38 (1H, s), 7.85 (1H, s), 8.05 (1H, d, J=9.2 Hz), 8.24 (1H, s), 8.75 (1H, d, J=9.6 Hz), 8.83 (1H, d, J=1.6 Hz), 8.89 (1H, d, J=1.6 Hz), 9.13 (1H, s).

[Example A20] Preparation of N-(6-((2-((2-methoxy-5-methyl-4-(4-(4-methylpiperazin-1-yl)piperidin-1-yl)phenyl)amino)-5-(trifluoromethyl)pyrimidin-4-yl)amino)quinoxalin-5-yl)methane sulfonamide

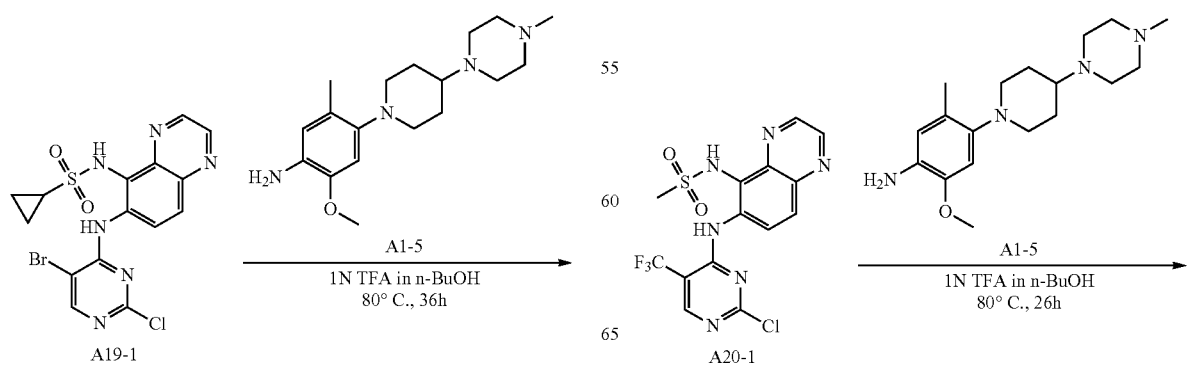

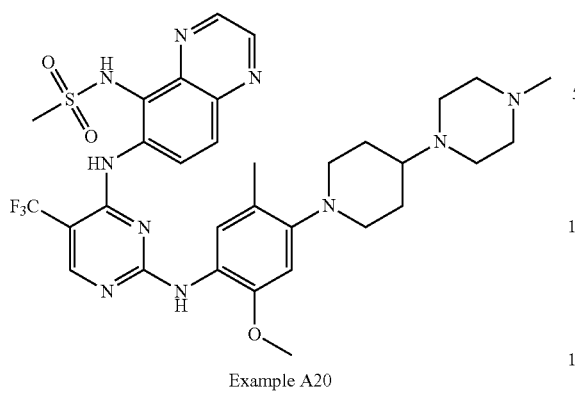

Example A20

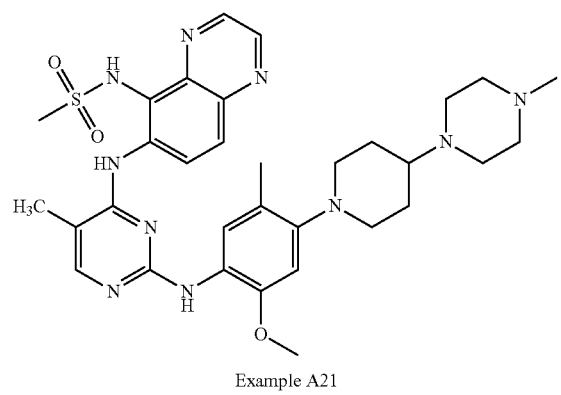

Example A21

To a mixture of compound A20-1 (100 mg, 0.239 mmol) and compound A1-5 (76 mg, 0.24 mmol) in n-butanol (4 mL) was added TFA (456 mg, 4.00 mmol), then it was stirred at 80° C. for 26 h. The reaction was monitored by LC-MS. The reaction mixture was concentrated under reduced pressure to be purified by prep-HPLC to afford Example A20 as a yellow solid.

$^1$H NMR (400 MHz, DMSO-$d_6$) δ 1.54-1.68 (2H, m), 1.82-1.95 (2H, m), 2.10 (3H, s), 2.17 (3H, s), 2.28-2.41 (6H, m), 2.55-2.62 (3H, m), 2.65-2.75 (2H, m), 3.04 (3H, s), 3.10-3.23 (2H, m), 3.75 (3H, s), 6.80 (1H, s), 7.28 (1H, s), 7.69 (1H, d, J=9.6 Hz), 8.38-8.50 (3H, m), 8.78-8.91 (2H, m), 8.95-9.01 (1H, m). LC-MS: MS Calculated 700.3, MS Found 701.5 [M+H]$^+$.

[Example A21] Preparation of N-(6-((2-((2-methoxy-5-methyl-4-(4-(4-methylpiperazin-1-yl)piperidin-1-yl)phenyl)amino)-5-methylpyrimidin-4-yl)amino)quinoxalin-5-yl)methane sulfonamide To a mixture of compound A21-1 (100 mg, 0.274 mmol) and compound A1-5 (87 mg, 0.27 mmol) in n-butanol (4 mL) was added TFA (456 mg, 4.00 mmol), then it was stirred at 80° C. for 26 h. The reaction was monitored by LC-MS. The reaction mixture was concentrated under reduced pressure to be purified by prep-HPLC to afford Example A21 as a yellow solid.

$^1$H NMR (400 MHz, DMSO-$d_6$) δ 1.51-1.62 (2H, m), 1.78-1.92 (2H, m), 2.00 (3H, s), 2.11-2.22 (7H, m), 2.23-2.45 (7H, m), 2.54-2.64 (3H, m), 2.97-3.12 (5H, m), 3.78 (3H, s), 6.69 (1H, s), 7.60-7.71 (2H, m), 7.93 (1H, d, J=9.6 Hz), 8.00 (1H, s), 8.51 (1H, s), 8.80 (1H, d, J=9.2 Hz), 8.89 (1H, d, J=2.0 Hz), 8.98 (1H, d, J=2.0 Hz). LC-MS: MS Calculated 646.3, MS Found 647.3 [M+H]$^+$.

[Example A22] Preparation of N-(6-((5-fluoro-2-((2-methoxy-5-methyl-4-(4-(4-methylpiperazin-1-yl)piperidin-1-yl)phenyl)amino)pyrimidin-4-yl)amino)quinoxalin-5-yl)methanesulfonamide

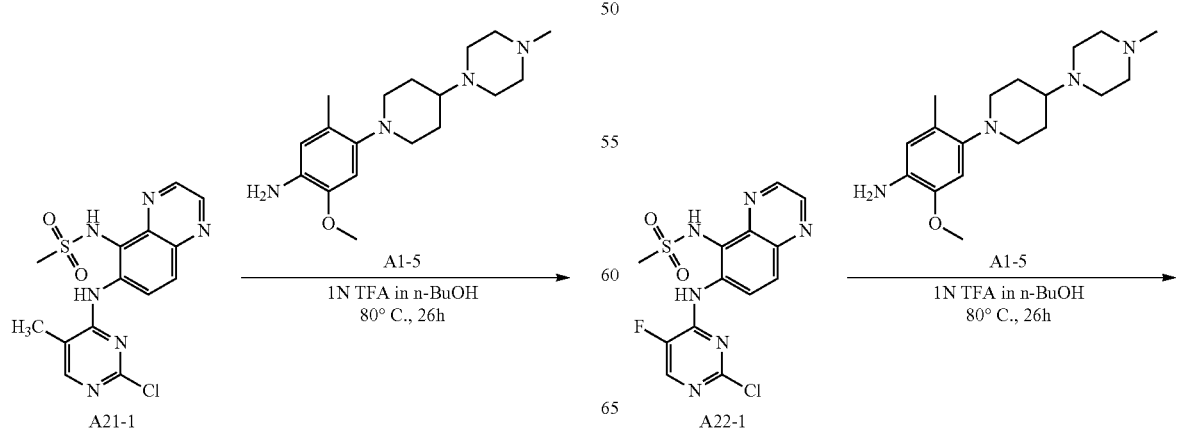

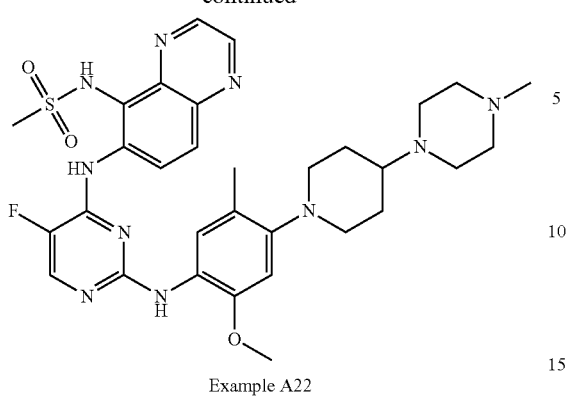

Example A22

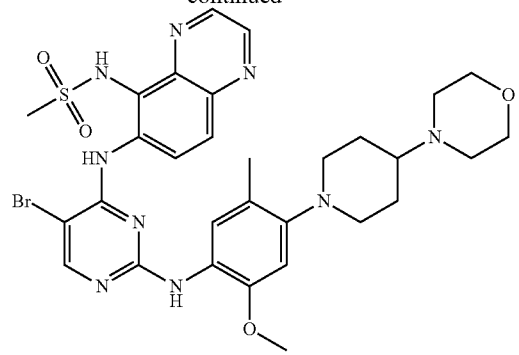

Example A23

To a mixture of compound A22-1 (70 mg, 0.19 mmol) and compound A1-5 (60 mg, 0.19 mmol) in n-butanol (4 mL) was added TFA (456 mg, 4.00 mmol), then it was stirred at 80° C. for 26 h. The reaction was monitored by LC-MS. The reaction mixture was concentrated under reduced pressure to be purified by prep-HPLC to afford Example A22 as a brown solid.

$^1$H NMR (400 MHz, DMSO-$d_6$) δ 1.54-1.65 (2H, m), 1.78-1.91 (2H, m), 2.03 (3H, s), 2.31 (3H, s), 2.53-2.75 (11H, m), 2.97-3.11 (5H, m), 3.77 (3H, s), 6.70 (1H, s), 7.52 (1H, s), 7.88-8.02 (2H, m), 8.21 (1H, d, J=2.4 Hz), 8.71 (1H, d, J=9.2 Hz), 8.88 (1H, s), 8.93 (1H, s), 9.00 (1H, s).

LC-MS: MS Calculated 650.3, MS Found 651.6 [M+H]$^+$.

[Example A23] Preparation of N-(6-((5-bromo-2-((2-methoxy-5-methyl-4-(4-morpholinopiperidin-1-yl)phenyl)amino)pyrimidin-4-yl)amino)quinoxalin-5-yl)methanesulfonamide A mixture of compound A23-1 (40 mg, 0.13 mmol) and compound A4-2 (56 mg, 0.13 mmol) in TFA/n-butanol (1N, 3.0 mL) was stirred at 80° C. for 13 h. The reaction was monitored by LC-MS. The reaction mixture was concentrated under reduced pressure to be purified by prep-HPLC to afford Example A23 as a yellow solid.

$^1$H NMR (400 MHz, CDCl$_3$) δ 1.66-1.71 (2H, m), 1.92-1.96 (2H, m), 2.02 (3H, s), 2.27-2.33 (1H, m), 2.58-2.64 (6H, m), 2.95 (3H, s), 3.11-3.17 (2H, m), 3.75-3.79 (4H, m), 3.85 (3H, s), 6.60 (1H, s), 7.38 (1H, s), 7.85 (1H, s), 8.07 (1H, d, J=9.6 Hz), 8.25 (1H, s), 8.80 (1H, d, J=9.2 Hz), 8.84 (1H, d, J=2.0 Hz), 8.89 (1H, d, J=2.0 Hz), 9.13 (1H, s).

[Example A24] Preparation of N-(6-((5-bromo-2-((2-methoxy-5-methyl-4-(4-(4-methylpiperazin-1-yl)piperidin-1-yl)phenyl)amino)pyrimidin-4-yl)amino)quinoxalin-5-yl)ethanesulfonamide

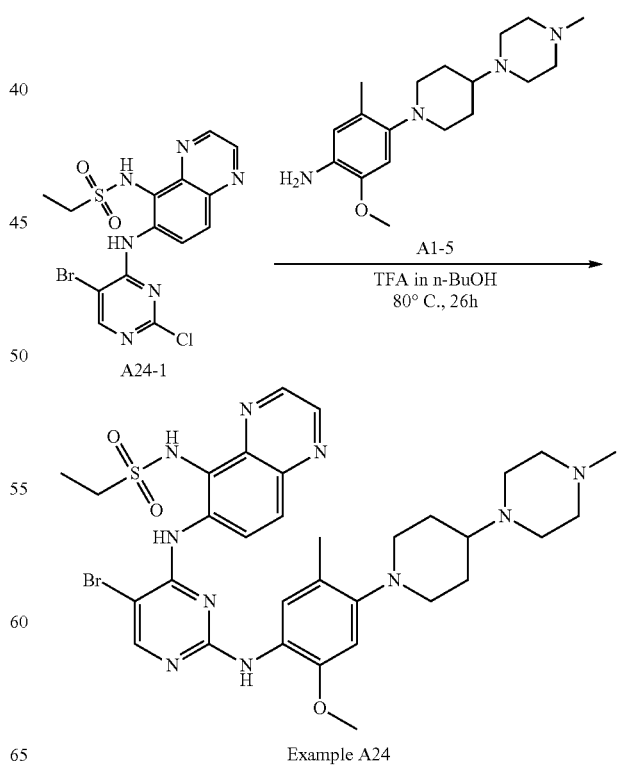

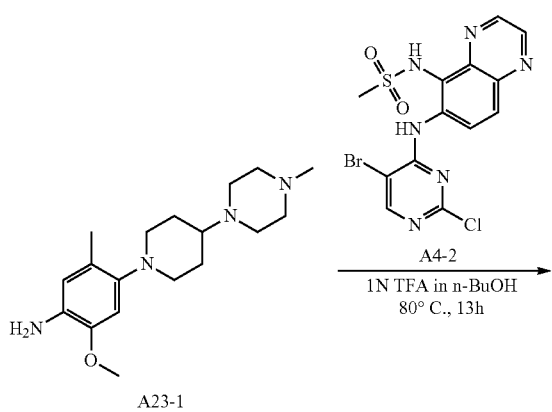

To a mixture of compound A24-1 (173 mg, 0.390 mmol) and compound A1-5 (124 mg, 0.390 mmol) in n-butanol (4 mL) was added TFA (526 mg, 4.61 mmol) at 25° C., and then the mixture was stirred at 80° C. for 26 h. The reaction was monitored by LC-Mass. The reaction mixture was concentrated under reduced pressure to be purified by prep-HPLC to afford Example A24 as a yellow solid.

$^1$H NMR (400 MHz, CDCl$_3$) δ 1.43 (3H, d, J=7.6 Hz), 1.67-1.69 (2H, m), 1.85-1.98 (2H, m), 1.99 (3H, s), 2.30-2.43 (4H, m), 2.51-2.72 (10H, m), 3.01-3.16 (4H, m), 3.84 (3H, s), 6.59 (1H, s) 7.38 (1H, s), 7.83 (1H, s), 8.06 (1H, d, J=9.6 Hz), 8.25 (1H, s), 8.73 (1H, d, J=9.6 Hz), 8.83 (1H, d, J=2.0 Hz), 8.90 (1H, d, J=1.6 Hz), 9.21 (1H, s).

[Example A25] Preparation of N-(6-((5-chloro-2-((2-methoxy-5-methyl-4-(4-(4-methylpiperazin-1-yl) piperidin-1-yl)phenyl)amino)pyrimidin-4-yl)amino) quinoxalin-5-yl)ethanesulfonamide

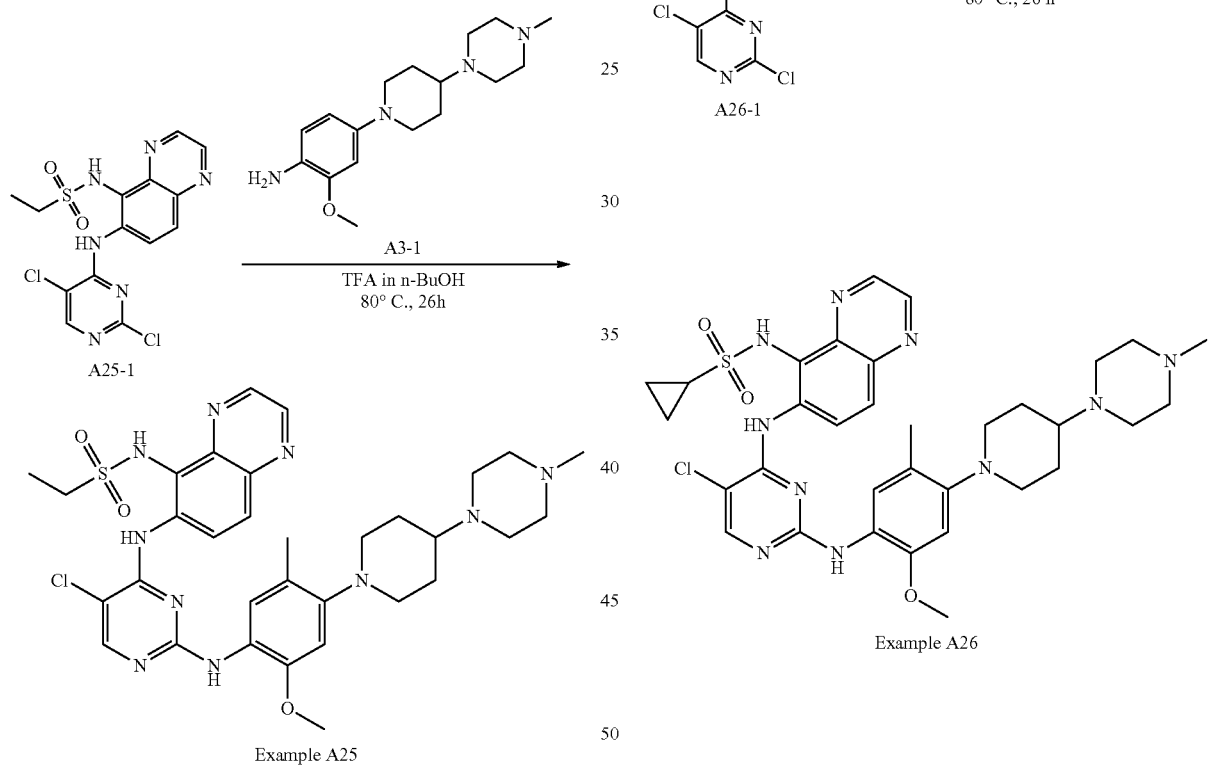

Example A25

[Example A26] Preparation of N-(6-((5-chloro-2-((2-methoxy-5-methyl-4-(4-(4-methylpiperazin-1-yl) piperidin-1-yl)phenyl)amino)pyrimidin-4-yl)amino) quinoxalin-5-yl)cyclopropanesulfonamide

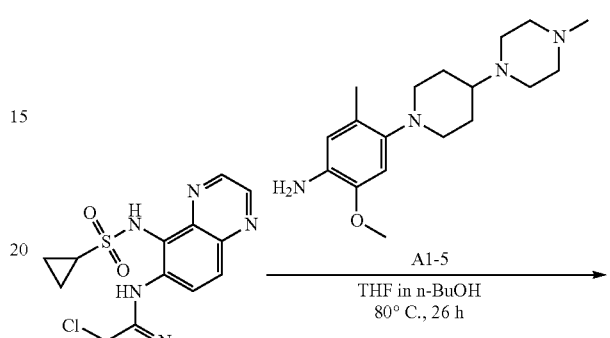

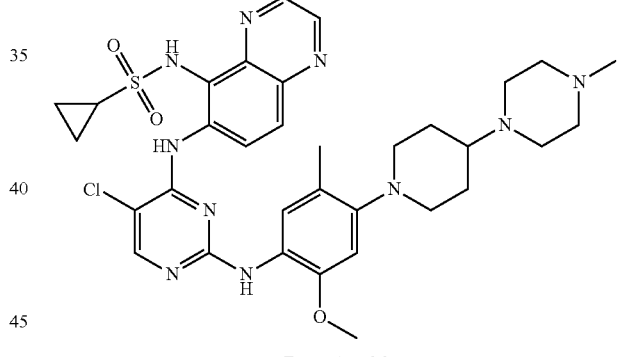

Example A26

To a mixture of compound A25-1 (80 mg, 0.200 mmol) and compound A3-1 (64 mg, 0.20 mmol) in n-butanol (4 mL) was added TFA (456 mg, 4.00 mmol) at 25° C. and the mixture was stirred at 80° C. for 26 h. The reaction was monitored by LC-MS. The mixture was filtered and the filtrate was concentrated under reduced pressure to be purified by prep-HPLC to afford Example A25 as a yellow solid.

$^1$H NMR (400 MHz, CDCl$_3$) δ 1.41 (3H, t, J=7.2 Hz), 1.65-1.76 (2H, m), 1.80-1.96 (2H, m), 2.01 (3H, s), 2.35-2.42 (4H, m), 2.43-2.74 (10H, m), 3.00-3.21 (4H, m), 3.84 (3H, s), 6.59 (1H, s), 7.39 (1H, s), 7.86 (1H, s), 8.06 (1H, d, J=9.2 Hz), 8.16 (1H, s), 8.78 (1H, d, J=9.6 Hz), 8.79-8.85 (1H, m), 8.86-8.92 (1H, m), 9.31 (1H, s). LC-MS: MS Calculated 680.3, MS Found: 681.3 [M+H]$^+$.

To a mixture of compound A26-1 (100 mg, 0.243 mmol) and compound A1-5 (77 mg, 0.24 mmol) in n-butanol (4 mL) was added TFA (760 mg, 6.67 mmol) at 25° C. and the mixture was stirred at 80° C. for 26 h. The reaction was monitored by LC-MS. The reaction mixture was concentrated under reduced pressure. The residue was purified by prep-HPLC to afford Example A26 as a yellow solid.

$^1$H NMR (400 MHz, DMSO-d$_6$) δ 0.64-0.75 (4H, m), 1.49-1.62 (2H, m), 1.76-1.91 (2H, m), 1.99 (3H, s), 2.16 (3H, s), 2.21-2.41 (6H, m), 2.52-2.71 (6H, m), 2.95-3.14 (2H, m), 3.75 (3H, s), 6.70 (1H, s), 7.39 (1H, s), 7.88 (1H, d, J=8.8 Hz), 8.14 (1H, s), 8.20 (1H, s), 8.58-8.74 (1H, m), 8.86-8.93 (1H, m), 8.95-9.07 (2H, m). LC-MS: MS Calculated 692.3, MS Found 693.4 [M+H]$^+$.

133

[Example A27] Preparation of N-(6-((5-bromo-2-((5-fluoro-2-methoxy-4-(4-(4-methylpiperazin-1-yl)piperidin-1-yl)phenyl)amino)pyrimidin-4-yl)amino)quinoxalin-5-yl)methanesulfonamide

134

[Example A28] Preparation of N-(6-((5-bromo-2-((5-ethyl-2-methoxy-4-(4-morpholinopiperidin-1-yl)phenyl)amino)pyrimidin-4-yl)amino)quinoxalin-5-yl)methanesulfonamide

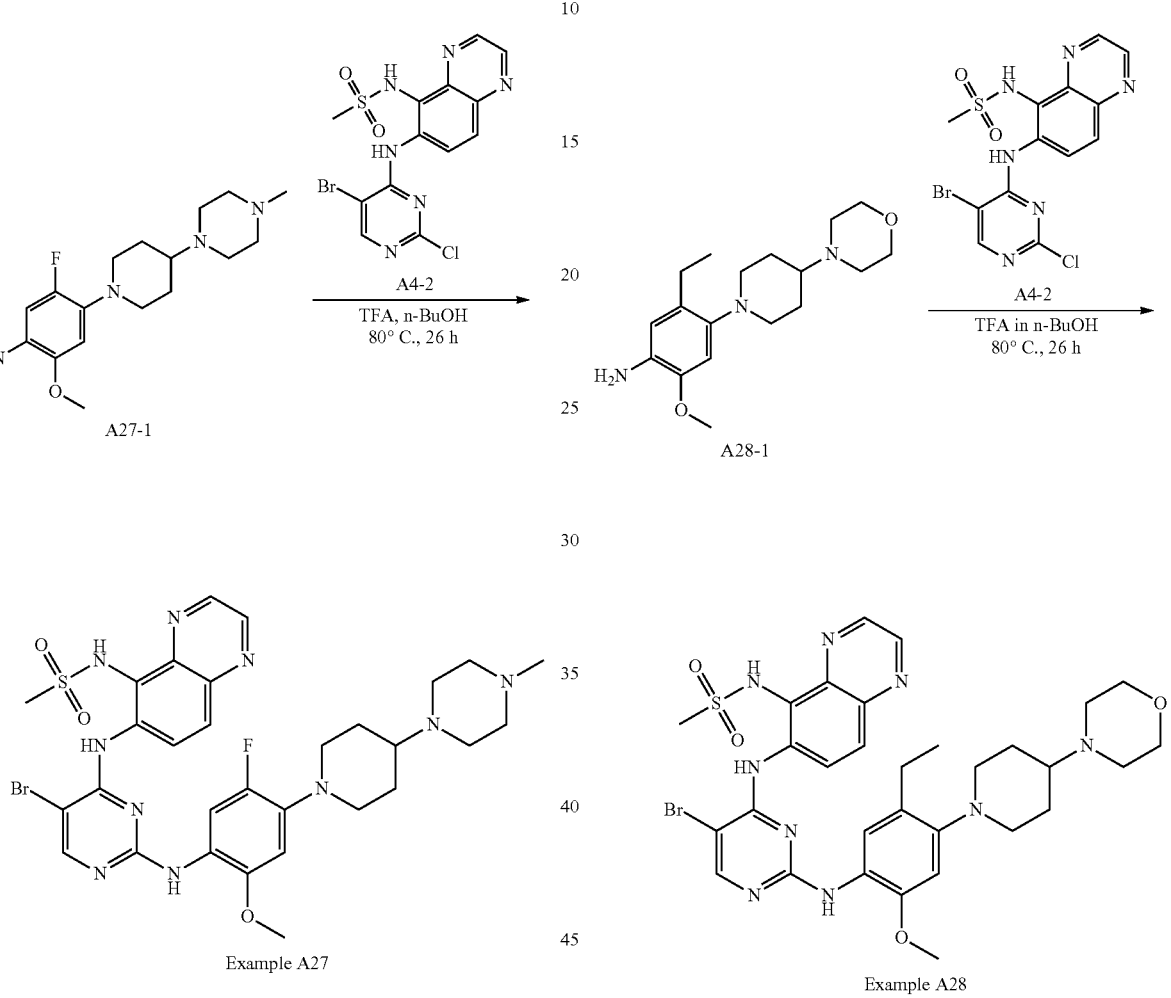

To a mixture of compound A27-1 (250 mg, 0.580 mmol) and compound A4-2 (187 mg, 0.580 mmol) in n-butanol (4 mL) was added TFA (585 mg, 5.13 mmol) at 25° C. and the mixture was stirred at 80° C. for 26 h. The reaction was monitored by LC-MS. The reaction mixture was concentrated under reduced pressure and the remaining residue was purified by prep-HPLC to afford Example A27 as a yellow solid.

$^1$H NMR (400 MHz, CDCl$_3$) δ 1.68-1.74 (2H, m), 1.83-1.86 (2H, m), 2.30-2.43 (4H, m), 2.45-2.63 (10H, m), 2.94 (3H, s), 3.35-3.38 (2H, m), 3.81 (3H, s), 6.46 (1H, d, J=8.0 Hz), 7.44 (1H, s), 7.96 (1H, d, J=14.4 Hz), 8.17 (1H, d, J=8.2 Hz), 8.25 (1H, s), 8.72 (1H, d, J=9.6 Hz), 8.78-8.85 (1H, m), 8.87-8.95 (1H, m), 9.19 (1H, s). LC-MS: MS Calculated 714.2, MS Found 715.1 [M+H]$^+$.

To a mixture of compound A4-2 (100 mg, 0.233 mmol) and compound A28-1 (74 mg, 0.23 mmol) in n-butanol (4 mL) was added TFA (456 mg, 4.00 mmol) at 25° C. and the mixture was stirred at 80° C. for 26 h. The reaction was monitored by LC-MS. The reaction mixture was concentrated under reduced pressure and the residue was purified by HPLC to afford Example A28 as a yellow solid.

$^1$H NMR (400 MHz, DMSO-d$_6$) δ 0.76-0.88 (3H, m), 1.51-1.62 (2H, m), 1.83-1.94 (2H, m), 2.19-2.30 (1H, m), 2.32-2.45 (6H, m), 2.64-2.74 (2H, m), 2.95-3.05 (5H, m), 3.55-3.64 (4H, m), 3.76 (3H, s), 6.78 (1H, s), 7.38 (1H, s), 7.87 (1H, d, J=9.6 Hz), 8.22 (1H, s), 8.28 (1H, s), 8.55-8.71 (1H, m), 8.92 (1H, d, J=2.0 Hz), 8.99 (1H, d, J=2.0 Hz), 9.75-10.01 (1H, s).

[Example A29] Preparation of N-(6-((5-chloro-2-((5-ethyl-2-methoxy-4-(4-morpholinopiperidin-1-yl)phenyl)amino)pyrimidin-4-yl)amino)quinoxalin-5-yl)methanesulfonamide

[Example A30] Preparation of N-(6-((5-chloro-2-((2-methoxy-5-methyl-4-(4-(pyrrolidin-1-yl) piperidin-1-yl)phenyl)amino)pyrimidin-4-yl)amino)quinoxalin-5-yl)methanesulfonamide

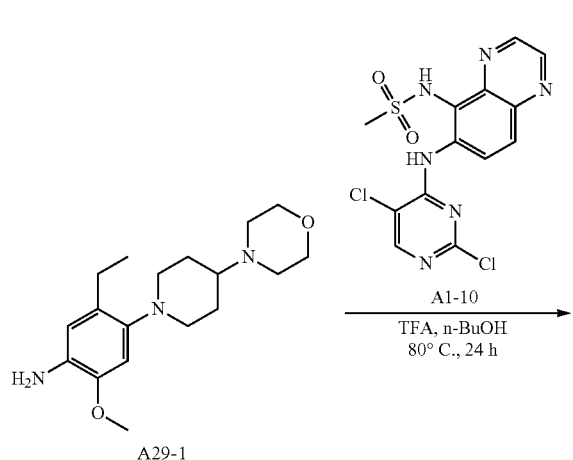

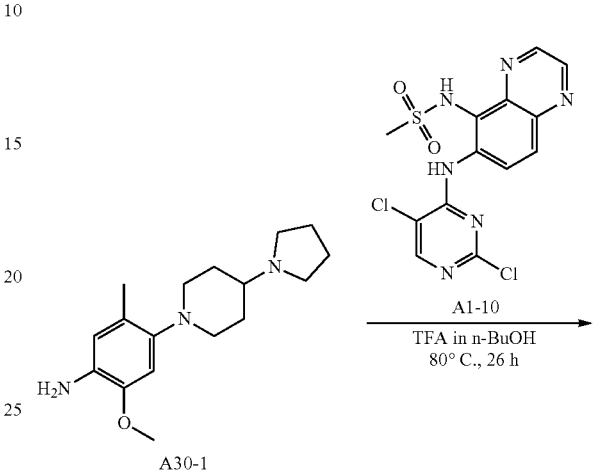

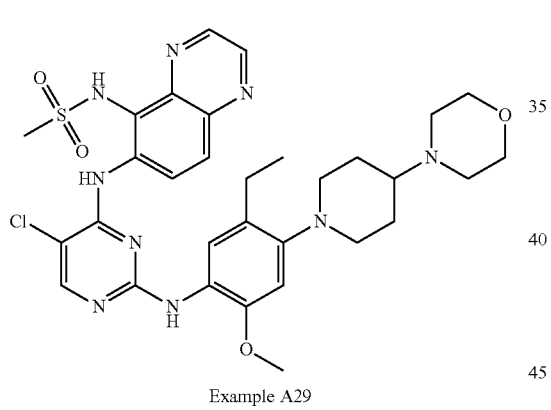

Example A29

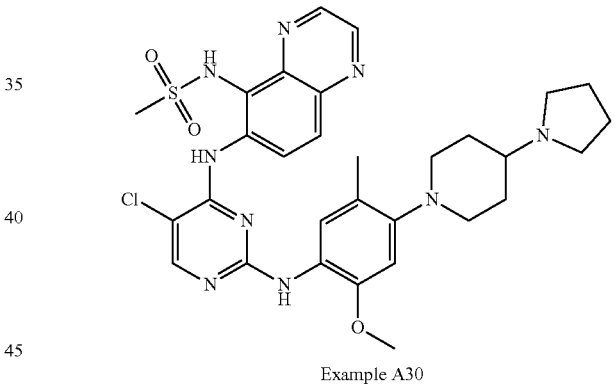

Example A30

To a mixture of compound A29-1 (100 mg, 0.313 mmol) and A1-10 (120 mg, 0.313 mmol) in n-butanol (8 mL) was added TFA (999 mg, 8.77 mmol) at 25° C. and the mixture was stirred at 80° C. for 24 h. The reaction was monitored by LC-Mass. The reaction mixture was concentrated under reduced pressure and the concentrated residue was purified by prep-HPLC to afford Example A29 as a yellow solid.

$^1$H NMR (400 MHz, CDCl$_3$) δ 0.73-0.86 (3H, m), 1.65-1.79 (2H, m), 1.94-2.00 (2H, m), 2.04-2.48 (3H, m), 2.65-2.73 (6H, m), 2.95 (3H, s), 3.05-3.12 (2H, m), 3.79-3.83 (4H, m), 3.85 (3H, s), 6.64 (1H, s), 7.41 (1H, s), 7.92 (1H, s), 8.07 (1H, d, J=9.6 Hz), 8.18 (1H, s), 8.77 (1H, d, J=9.6 Hz), 8.84 (1H, d, J=1.6 Hz), 8.91 (1H, d, J=2.0 Hz), 9.20 (1H, s).

LC-MS: MS Calculated 667.2, MS Found 668.2 [M+H]$^+$.

To a mixture of compound A1-10 (100 mg, 0.260 mmol) and compound A30-1 (75.1 mg, 0.260 mmol) in n-butanol (4 mL) was added TFA (456 mg, 4.00 mmol) at 25° C. and the mixture was stirred at 80° C. for 26 h. The reaction was monitored by LC-MS. The reaction mixture was concentrated under reduced pressure and the concentrated residue was purified by prep-HPLC to afford Example A30 as a yellow solid.

$^1$H NMR (400 MHz, DMSO-d$_6$) δ 1.54-1.64 (2H, m), 1.67-1.74 (4H, m), 1.89-1.99 (2H, m), 2.03 (3H, s), 2.14-2.22 (1H, m), 2.55-2.68 (6H, m), 2.98-3.10 (5H, m), 3.76 (3H, s), 6.72 (1H, s), 7.40 (1H, s), 7.86 (1H, d, J=9.2 Hz), 8.17 (1H, s), 8.21 (1H, s), 8.71 (1H, d, J=9.2 Hz), 8.90 (1H, d, J=2.0 Hz), 8.95-9.07 (2H, m). LC-MS: MS Calculated 637.2, MS Found 638.5 [M+H]$^+$.

[Example A31] Preparation of N-(6-((5-chloro-2-((2-methoxy-5-methyl-4-(4-morpholinopiperidin-1-yl)phenyl)amino)pyrimidin-4-yl)amino)quinoxalin-5-yl)methanesulfonamide

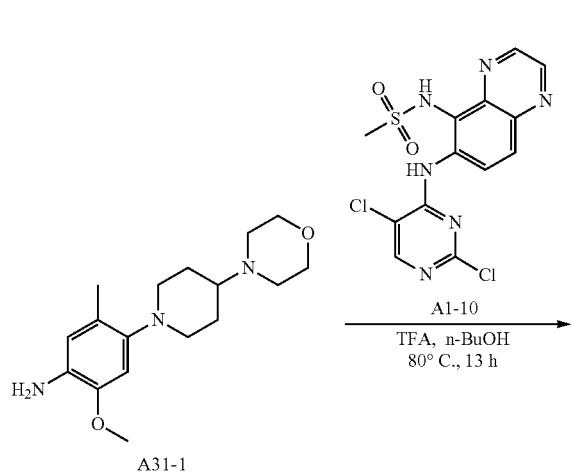

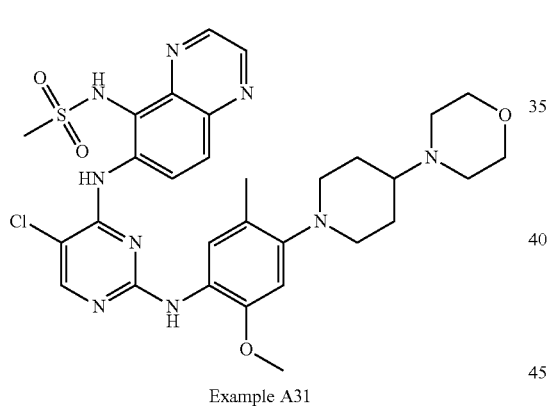

Example A31

To a mixture of compound A31-1 (100 mg, 0.327 mmol) and compound A1-10 (126 mg, 0.327 mmol) in n-butanol (5 mL) was added TFA (746 mg, 6.55 mmol) at 25° C. and the mixture was stirred at 80° C. for 13 h. The reaction was monitored by LC-MS. The reaction mixture was concentrated under reduced pressure and the concentrated residue was purified by prep-HPLC to afford Example A31 as a yellow solid.

$^1$H NMR (400 MHz, CDCl$_3$) δ 1.64-1.74 (2H, m), 1.90-1.98 (2H, m), 2.06 (3H, s), 2.25-2.35 (1H, m), 2.57-2.67 (6H, m), 2.95 (3H, s), 3.11-3.18 (2H, m), 3.74-3.80 (4H, m), 3.85 (3H, s), 6.61 (1H, s), 7.39 (1H, s), 7.89 (1H, s), 8.08 (1H, d, J=9.6 Hz), 8.17 (1H, s), 8.83-8.87 (2H, m), 8.90 (1H, d, J=1.6 Hz), 9.22 (1H, s). LC-MS: MS Calculated 653.2, MS Found: 654.2 [M+H]$^+$.

[Example A32] Preparation of N-(6-((5-fluoro-2-((2-methoxy-4-(4-(4-methylpiperazin-1-yl)piperidin-1-yl)-5-propylphenyl)amino)pyrimidin-4-yl)amino)quinoxalin-5-yl)methanesulfonamide

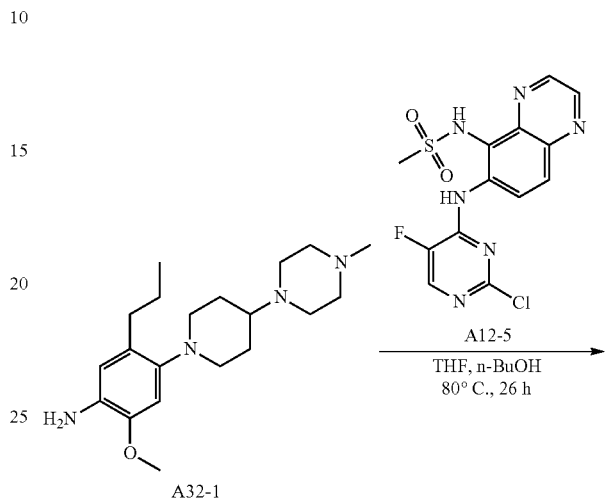

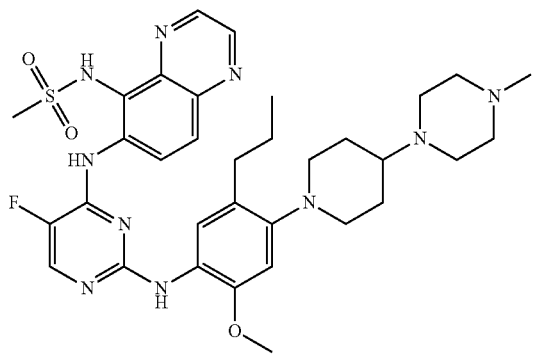

Example A32

To a mixture of compound A12-5 (100 mg, 0.271 mmol) and compound A32-1 (94 mg, 0.27 mmol) in n-butanol (4 mL) was added TFA (456 mg, 4.00 mmol) at 25° C., and then the mixture was stirred at 80° C. for 26 h. The reaction was monitored by LC-MS. The reaction mixture was concentrated under reduced pressure to be purified by prep-HPLC to afford Example A32 as a yellow solid.

$^1$H NMR (400 MHz, CDCl$_3$) δ 0.68 (3H, t, J=7.2 Hz), 1.25-1.38 (2H, m), 1.61-1.74 (2H, m), 1.89-2.01 (2H, m), 2.20-2.43 (6H, m), 2.45-2.75 (10H, m), 2.93 (3H, s), 3.00-3.12 (2H, m), 3.85 (3H, s), 6.65 (1H, s), 7.38 (1H, s), 7.97 (1H, s), 8.05-8.15 (2H, m), 8.84 (1H, d, J=1.6 Hz), 8.88-8.98 (2H, m), 9.07 (1H, d, J=2.0 Hz). LC-MS: MS Calculated 678.3, MS Found 679.7 [M+H]$^+$.

139

[Example A33] Preparation of N-(6-((5-bromo-2-((5-ethyl-2-methoxy-4-(4-(pyrrolidin-1-yl)piperidin-1-yl)phenyl)amino)pyrimidin-4-yl)amino)quinoxalin-5-yl)methanesulfonamide

140

[Example A34] Preparation of N-(6-((5-chloro-2-((5-ethyl-2-methoxy-4-(4-(pyrrolidin-1-yl)piperidin-1-yl)phenyl)amino)pyrimidin-4-yl)amino)quinoxalin-5-yl)methanesulfonamide

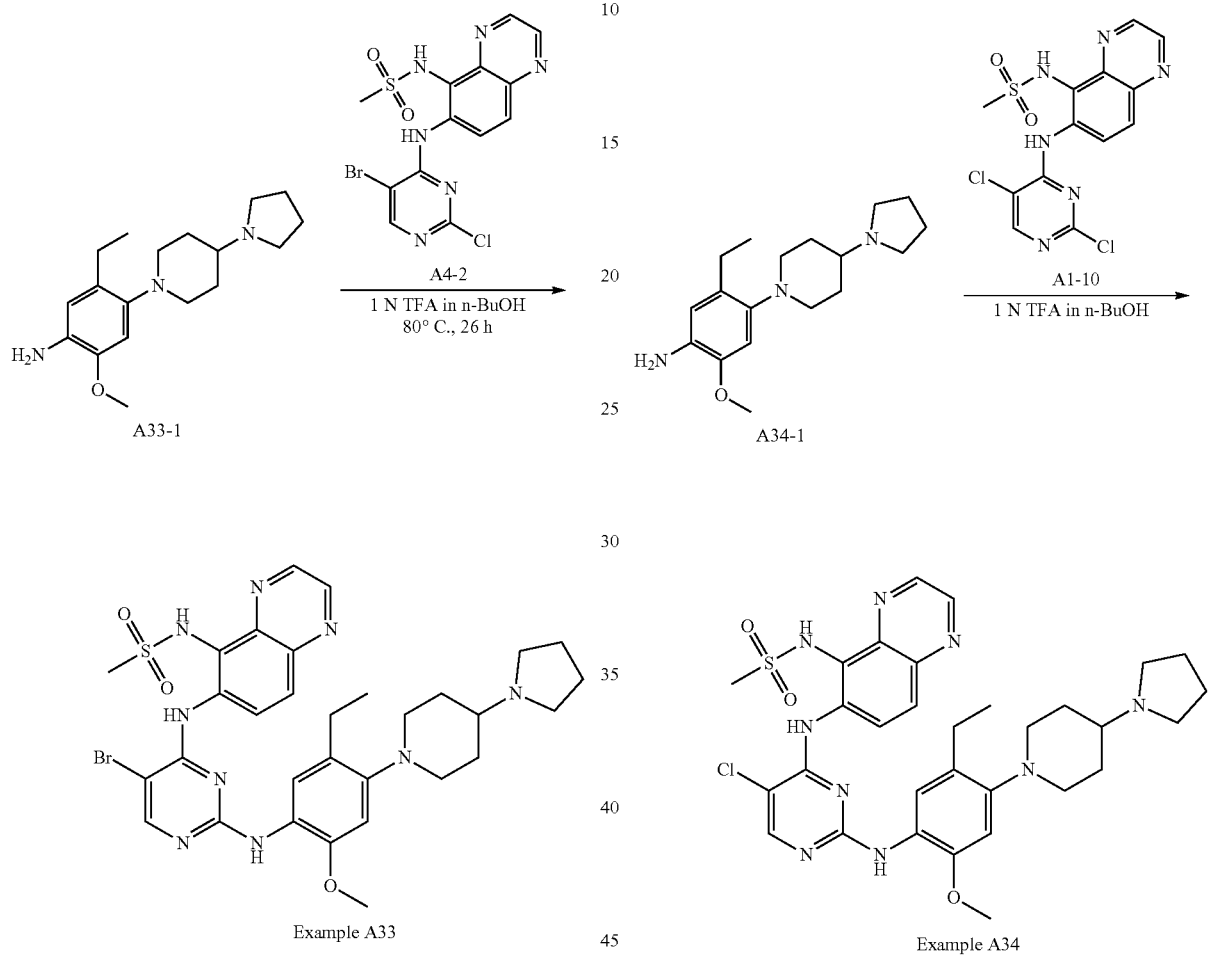

To a mixture of compound A33-1 (100 mg) and compound A4-2 (142 mg, 0.329 mmol) in n-butanol (4 mL) was added TFA (456 mg, 4.00 mmol) at 25° C., and then the mixture was stirred at 80° C. for 26 h. The reaction was monitored by LC-MS. The reaction mixture was concentrated under reduced pressure and the concentrated residue was purified by prep-HPLC to afford Example A33 as a yellow solid.

1H NMR (400 MHz, CDCl$_3$) δ 0.60-0.72 (3H, m), 1.60-1.68 (2H, m), 1.70-1.80 (4H, m), 1.87-1.95 (2H, m), 1.96-2.08 (1H, m), 2.28-2.40 (2H, m), 2.45-2.65 (6H, m), 2.87 (3H, s), 2.90-3.00 (2H, m), 3.77 (3H, s), 6.57 (1H, s), 7.32 (1H, s), 7.81 (1H, s), 7.98 (1H, d, J=9.6 Hz), 8.19 (1H, s), 8.65 (1H, d, J=9.6 Hz), 8.76 (1H, d, J=1.6 Hz), 8.83 (1H, d, J=2.0 Hz), 9.04 (1H, s).

LC-MS: MS Calculated 695.2, MS Found 696.1 [M+H]$^+$.

To a mixture of compound A34-1 (100 mg, 0.329 mmol) and compound A1-10 (126 mg, 0.329 mmol) in n-butanol (4 mL) was added TFA (456 mg, 4.00 mmol). The mixture was stirred at 80° C. for 26 h. The reaction was monitored by LC-MS. The reaction mixture was concentrated under reduced pressure and the concentrated residue was purified by prep-HPLC to afford Example A34 as a yellow solid.

1H NMR (400 MHz, CDCl$_3$) δ 0.75-0.85 (3H, m), 1.70-1.77 (2H, m), 1.81-1.91 (4H, m), 1.95-2.05 (2H, m), 2.08-2.20 (1H, m), 2.41-2.50 (2H, m), 2.59-2.76 (6H, m), 2.96 (3H, s), 3.00-3.12 (2H, m), 3.87 (3H, s), 6.67 (1H, s), 7.42 (1H, s), 7.93 (1H, s), 8.09 (1H, d, J=9.6 Hz), 8.19 (1H, s), 8.79 (1H, d, J=9.2 Hz), 8.86 (1H, d, J=2.0 Hz), 8.92 (1H, d, J=2.0 Hz), 9.21 (1H, s).

LC-MS: MS Calculated 651.3, MS Found 652.2 [M+H]$^+$.

[Example A35] Preparation of N-(6-((5-chloro-2-((4-((3R,4S)-3-fluoro-4-(4-methylpiperazin-1-yl)piperidin-1-yl)-2-methoxyphenyl)amino)pyrimidin-4-yl)amino)quinoxalin-5-yl)methane sulfonamide

[Example A36] Preparation of N-(6-((5-chloro-2-((4-(4-((3S,4R)-3-fluoro-1-methylpiperidin-4-yl)piperazin-1-yl)-2-methoxyphenyl)amino)pyrimidin-4-yl)amino)quinoxalin-5-yl)methane sulfonamide

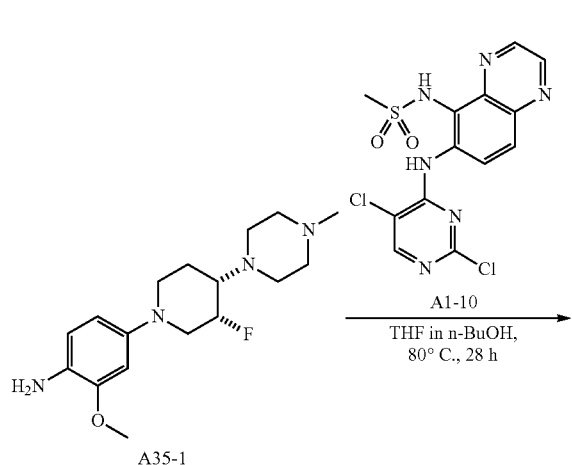

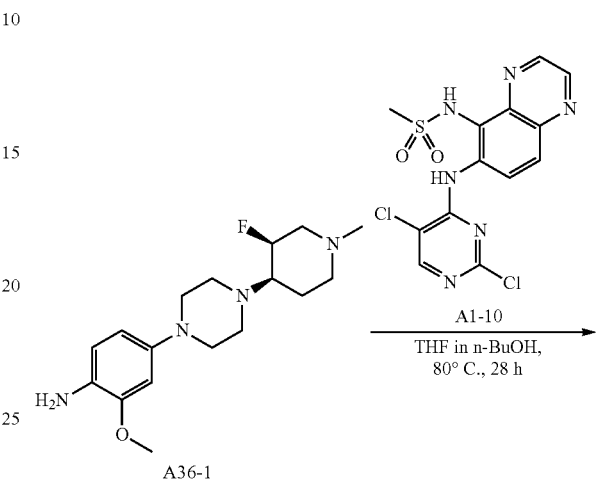

A mixture of compound A35-1 (140 mg, 0.434 mmol), compound A1-10 (167 mg, 0.434 mmol) and TFA (445 mg, 3.90 mmol) in n-butanol (3 mL) was stirred at 80° C. for 28 h. The reaction was monitored by LC-MS. The reaction mixture was concentrated under reduced pressure and the residue was purified by prep-HPLC to afford Example A35 as a yellow solid.

$^1$H NMR (400 MHz, CDCl$_3$) δ 1.76-1.83 (1H, m), 2.10-2.14 (1H, m), 2.24 (3H, s), 2.35-2.54 (5H, m), 2.72-2.82 (6H, m), 2.87 (3H, s), 3.61-3.64 (1H, m), 3.70-3.85 (4H, m), 4.99-5.13 (1H, m), 6.33 (1H, dd, J=8.4, 2.4 Hz), 6.48 (1H, d, J=2.4 Hz), 7.24 (1H, s), 7.86 (1H, d, J=8.8 Hz), 8.02 (1H, d, J=9.6 Hz), 8.08 (1H, s), 8.77 (1H, d, J=2.0 Hz), 8.79 (1H, d, J=9.6 Hz), 8.82 (1H, d, J=2.0 Hz), 9.12 (1H, s). LC-MS: MS Calculated 670.2, MS Found 671.1 [M+H]$^+$.

To a mixture of compound A36-1 (100 mg, 0.310 mmol) and compound A1-10 (119 mg, 0.310 mmol) in n-butanol (3 mL) was added TFA (445 mg, 3.90 mmol) and the mixture was stirred at 80° C. for 28 h. The reaction was monitored by LC-MS. The reaction mixture was concentrated under reduced pressure and the residue was purified by prep-HPLC to afford Example A36 as a yellow solid.

$^1$H NMR (400 MHz, CDCl$_3$) 1.65-1.71 (1H, m), 1.96-2.03 (3H, m), 2.10-2.37 (4H, m), 2.71-2.83 (4H, m), 2.86 (3H, s), 2.90-3.04 (1H, m), 3.06-3.12 (5H, m), 3.78 (3H, s), 4.76-5.01 (1H, m), 6.35 (1H, d, J=9.2 Hz), 6.46 (1H, d, J=2.4 Hz), 7.23 (1H, s), 7.90 (1H, d, J=8.80 Hz), 8.02 (1H, d, J=9.6 Hz), 8.08 (1H, s), 8.76 (1H, d, J=1.6 Hz), 8.79 (1H, d, J=9.6 Hz), 8.82 (1H, d, J=1.6 Hz), 9.12 (1H, s).

LC-MS: MS Calculated 670.2, MS Found 671.2 [M+H]$^+$.

[Example A37] Preparation of N-(6-((5-chloro-2-((4-(4-(4-(2,2-difluoroethyl)piperazin-1-yl)piperidin-1-yl)-2-methoxyphenyl)amino)pyrimidin-4-yl)amino)quinoxalin-5-yl)methane sulfonamide

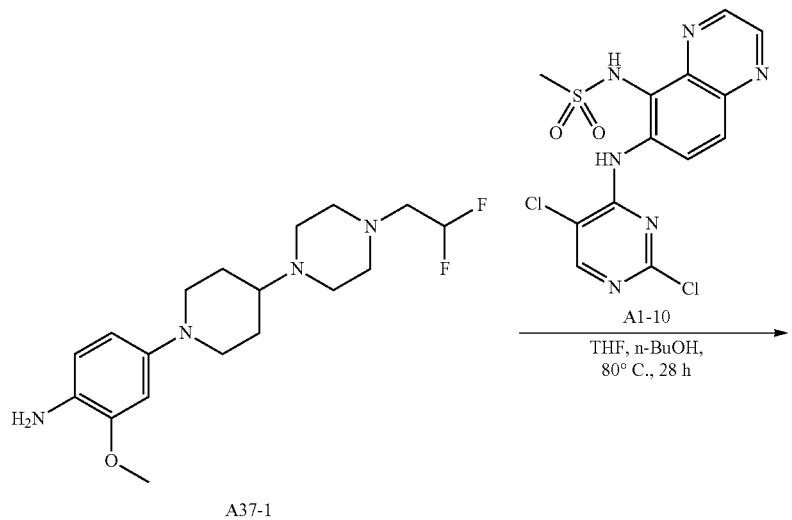

A37-1

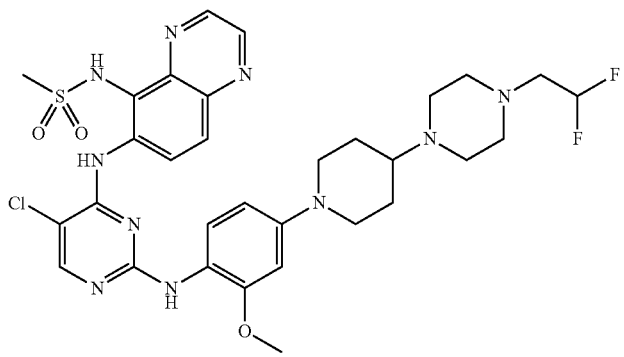

Example A37

To a mixture of compound A37-1 (100 mg, 0.282 mmol) and compound A1-10 (130 mg, 0.339 mmol) in n-butanol (5 mL) was added TFA (444 mg, 3.90 mmol) and the mixture was stirred at 80° C. for 28 h. The reaction was monitored by LC-MS. The reaction mixture was concentrated under reduced pressure and the residue was purified by prep-HPLC to afford Example A37 as a yellow solid.

$^1$H NMR (400 MHz, CDCl$_3$) δ 1.61-1.75 (2H, m), 1.77-1.92 (2H, m), 2.21-2.24 (1H, m), 2.46-2.76 (12H, m), 2.87 (3H, s), 3.50-3.70 (2H, m), 3.79 (3H, s), 5.63-6.01 (1H, m), 6.35 (1H, dd, J=8.8, 2.4 Hz), 6.47 (1H, d, J=2.4 Hz), 7.23 (1H, s), 7.89 (1H, d, J=8.8 Hz), 8.02 (1H, d, J=9.2 Hz), 8.08 (1H, s), 8.76-8.77 (1H, m), 8.80 (1H, d, J=9.6 Hz), 8.82 (1H, d, J=2.0 Hz), 9.13 (1H, s).

LC-MS: MS Calculated 702.2, MS Found 703.2 [M+H]$^+$.

[Example A38] Preparation of N-(6-((5-chloro-2-((5-ethyl-2-methoxy-4-(4-(4-methylpiperazin-1-yl)piperidin-1-yl)phenyl)amino)pyrimidin-4-yl)amino)quinoxalin-5-yl)-N-methylmethanesulfonamide

[Example A39] Preparation of N-(6-((5-bromo-2-((5-ethyl-2-methoxy-4-(4-morpholinopiperidin-1-yl)phenyl)amino)pyrimidin-4-yl)amino)quinoxalin-5-yl)-N-methylmethanesulfonamide

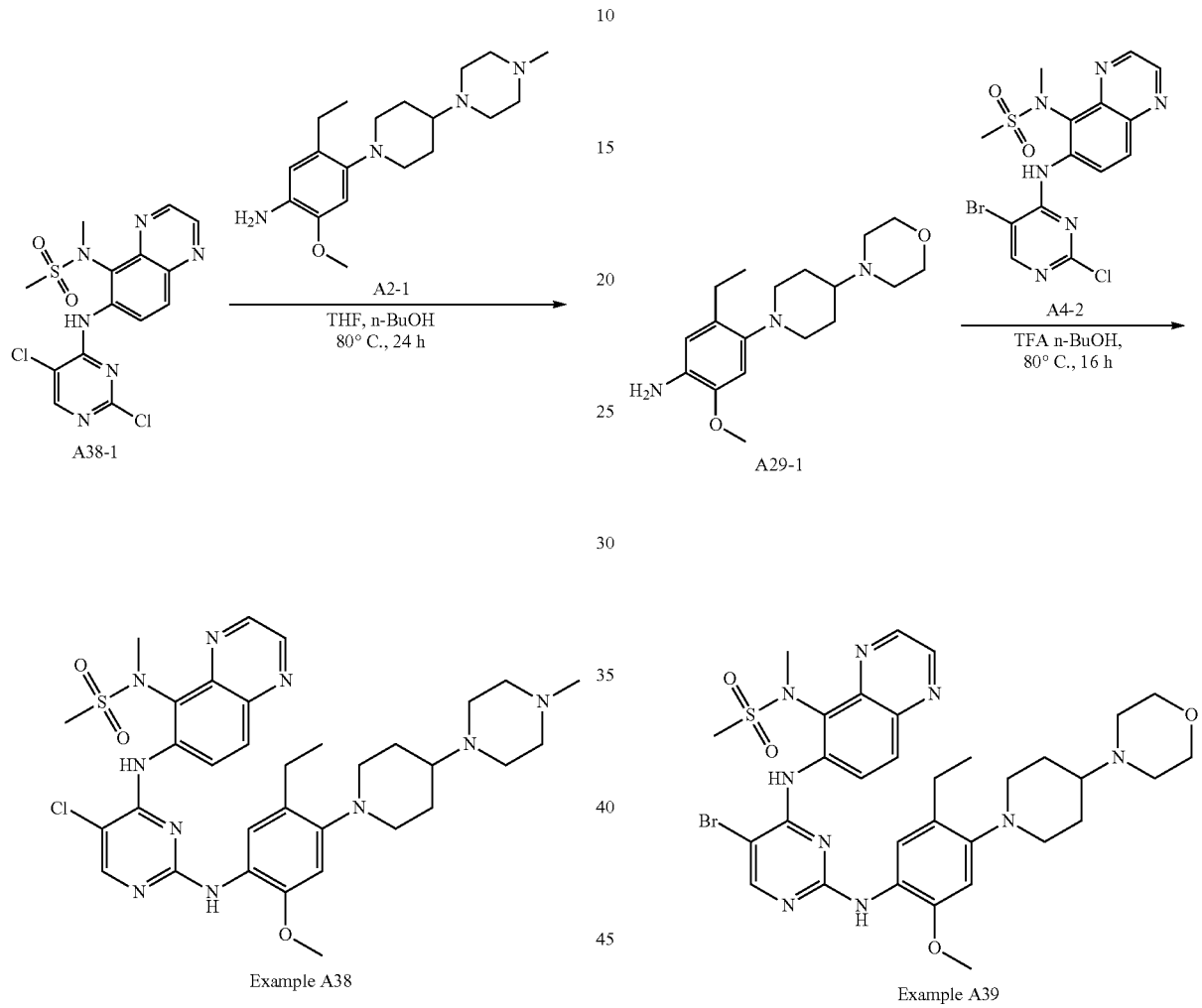

To a mixture of compound A38-1 (120 mg, 0.300 mmol) in n-butanol (5 mL) were added compound A2-2 (100 mg, 0.300 mmol) and TFA (582 mg, 5.11 mmol) at 25° C., and then the mixture was stirred at 80° C. for 24 h. The reaction mixture was concentrated under reduced pressure and the residue was purified by prep-HPLC to afford Example A38 as an off-white solid.

$^1$H NMR (400 MHz, CDCl$_3$) δ 0.86-0.99 (3H, t, J=7.2 Hz), 1.63-1.85 (2H, m), 1.86-2.07 (2H, m), 2.40 (3H, s), 2.43-2.90 (13H, m), 3.05-3.15 (2H, m), 3.18 (3H, s), 3.50 (3H, s), 3.87 (3H, s), 6.67 (1H, s), 7.39 (1H, s), 8.00 (1H, s), 8.10 (1H, d, J=9.6 Hz), 8.19 (1H, s), 8.77-8.87 (3H, m), 9.01 (1H, d, J=9.2 Hz). LC-MS: MS Calculated 694.3, MS Found 695.3 [M+H]$^+$.

To a mixture of compound A29-1 (86 mg, 0.27 mol) and compound A4-2 (100 mg, 0.23 mmol) in n-butanol (4 mL) was added TFA (456 mg, 4.00 mmol). It was stirred at 80° C. for 16 h. The reaction mixture was concentrated under reduced pressure and the residue was purified by prep-HPLC to afford Example A39 as a yellow solid.

$^1$H NMR (400 MHz, CDCl$_3$) δ 0.91 (3H, t, J=6.8 Hz), 1.60-1.79 (4H, m), 1.98-2.02 (2H, m), 2.45-2.73 (9H, m), 3.08-3.15 (2H, m), 3.19 (3H, s), 3.50 (3H, s), 3.75-3.85 (2H, m), 3.87 (3H, s), 6.67 (1H, s), 7.39 (1H, s), 7.98 (1H, s), 8.08 (1H, d, J=9.2 Hz), 8.27 (1H, s), 8.81-8.84 (3H, m), 8.99 (1H, d, J=9.2 Hz). LC-MS: MS Calculated 725.2, MS Found 726.2 [M+H]$^+$.

[Example A40] Preparation of N-(6-((5-chloro-2-((5-ethyl-2-methoxy-4-(4-morpholinopiperidin-1-yl)phenyl)amino)pyrimidin-4-yl)amino)quinoxalin-5-yl)-N-methylmethanesulfonamide

[Example A41] Preparation of N-(6-((5-chloro-2-((2-methoxy-4-(4-morpholinopiperidin-1-yl)-5-propylphenyl)amino)pyrimidin-4-yl)amino)quinoxalin-5-yl)-N-methylmethanesulfonamide

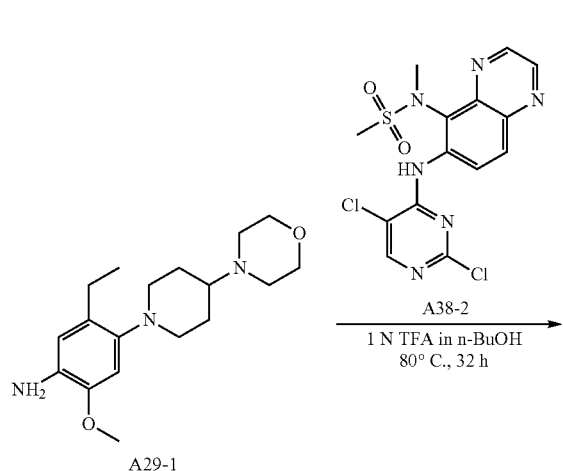

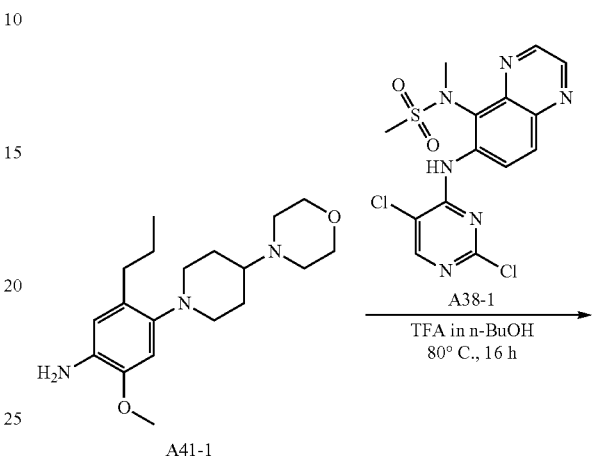

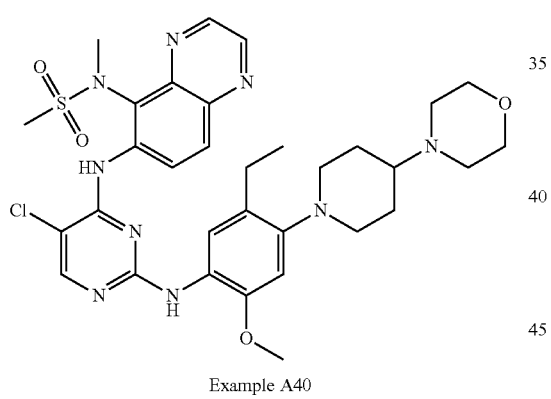

Example A40

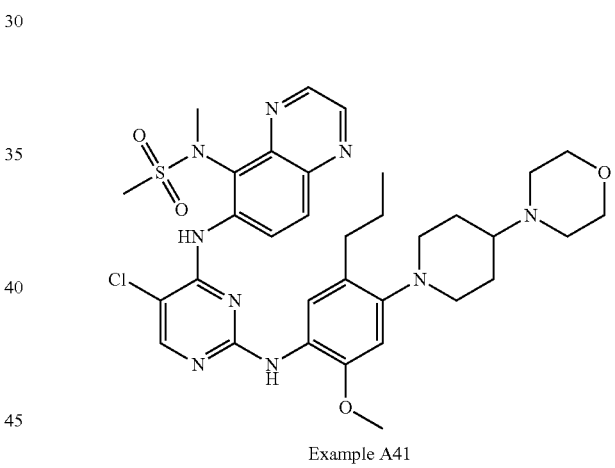

Example A41

To a mixture of compound A29-1 (100 mg, 0.250 mmol) and compound A38-1 (96 mg, 0.30 mmol) in n-butanol (6 mL) was added TFA (684 mg, 6.00 mmol) at 15° C., and then the mixture was stirred at 80° C. for 32 h. The reaction mixture was concentrated under reduced pressure and purified by prep-HPLC to afford Example A40 as a yellow solid.

$^1$H NMR (400 MHz, DMSO-d$_6$) δ 0.92 (3H, t, J=7.2 Hz), 1.51-1.65 (2H, m), 1.81-1.92 (2H, m), 2.21-2.35 (1H, m), 2.41-2.49 (6H, m), 2.65-2.75 (2H, m), 2.95-3.05 (2H, m), 3.22 (3H, s), 3.36 (3H, s), 3.55-3.64 (4H, m), 3.76 (3H, s), 6.79 (1H, s), 7.37 (1H, s), 7.92 (1H, d, J=9.2 Hz), 8.24 (1H, s), 8.35 (1H, s), 8.61 (1H, s), 8.74-8.85 (1H, m), 8.92 (1H, d, J=2.0 Hz), 8.97 (1H, d, J=1.6 Hz).
LC-MS: MS Calculated 681.3, MS Found 682.2 [M+H]$^+$.

To a mixture of compound A41-1 (120 mg, 0.301 mmol) and compound A38-1 (120 mg, 0.361 mmol) in n-butanol (5 mL) was added TFA (547 mg, 4.80 mmol) at 20° C. The mixture was stirred at 80° C. for 16 h. The mixture was filtered and the filtrate was concentrated under reduced pressure. The concentrated residue was purified by prep-HPLC to afford Example A41 as a yellow solid.

$^1$H NMR (400 MHz, CDCl$_3$) δ 0.70 (3H, t, J=6.8 Hz), 1.21-1.35 (2H, m), 1.43-1.62 (2H, m), 1.80-1.95 (2H, m), 2.20-2.30 (1H, m), 2.33-2.42 (2H, m), 2.51-2.57 (4H, m), 2.62-2.79 (2H, m), 2.93-3.06 (2H, m), 3.22 (3H, s), 3.36 (3H, s), 3.55-3.62 (4H, m), 3.76 (3H, s), 6.80 (1H, s), 7.38 (1H, s), 7.92 (1H, d, J=9.2 Hz), 8.24 (1H, s), 8.32 (1H, s), 8.61 (1H, s), 8.71-8.85 (1H, m), 8.89-8.94 (1H, m), 8.95-9.00 (1H, m). LC-MS: MS Calculated 695.3, MS Found 696.3 [M+H]$^+$.

149

[Example A42] Preparation of N-(6-((5-chloro-2-((2-methoxy-5-propyl-4-(4-(pyrrolidin-1-yl)piperidin-1-yl)phenyl)amino)pyrimidin-4-yl)amino)quinoxalin-5-yl)-N-methylmethanesulfonamide

150

[Example A43] Preparation of N-(6-((5-chloro-2-((5-ethyl-2-methoxy-4-(4-(pyrrolidin-1-yl)piperidin-1-yl)phenyl)amino)pyrimidin-4-yl)amino)quinoxalin-5-yl)-N-methylmethanesulfonamide

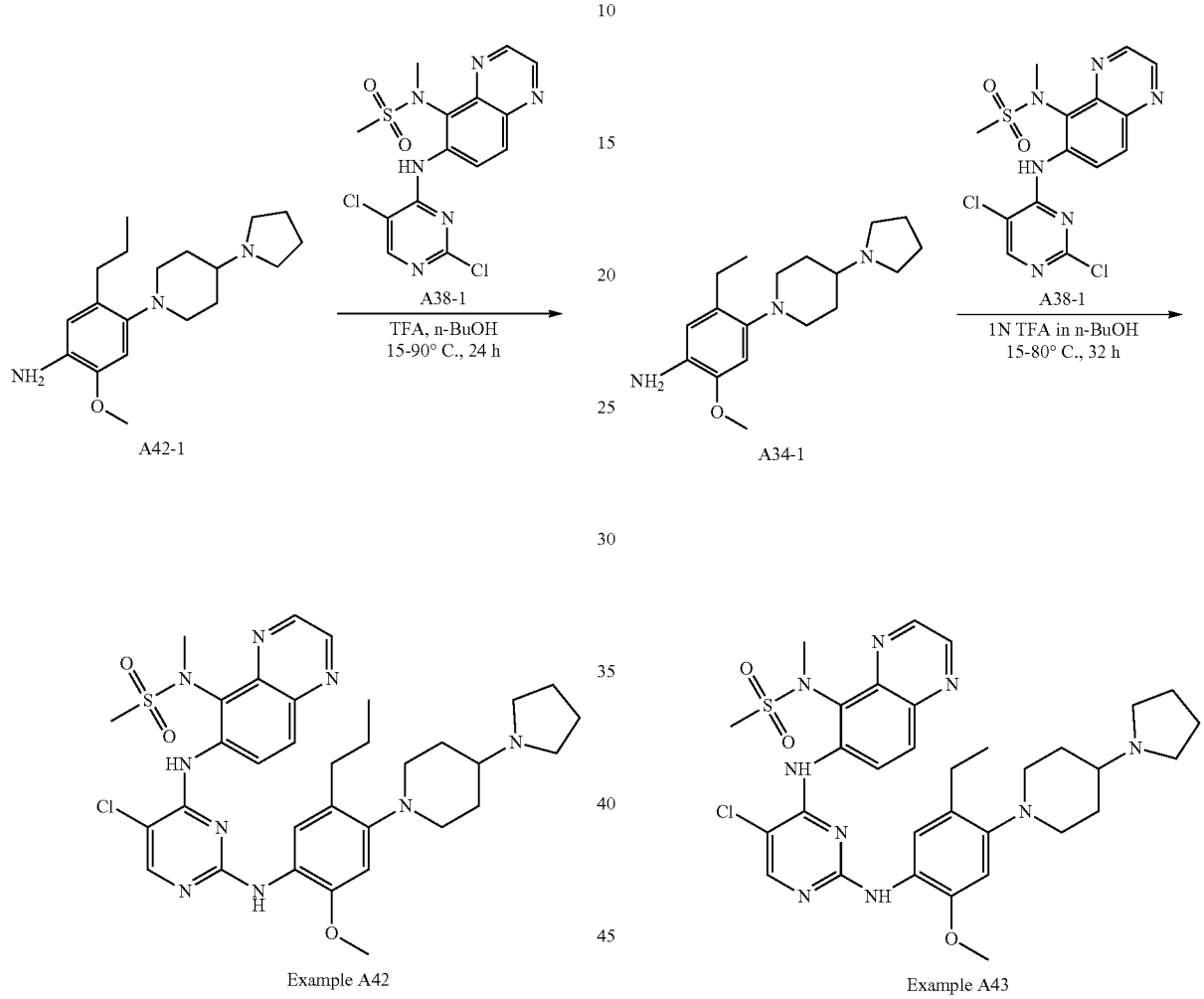

To a mixture of compound A38-1 (100 mg, 0.250 mmol) and compound A42-1 (95 mg, 0.30 mmol) in n-butanol (6 mL) was added TFA (684 mg, 6.00 mmol) at 15° C., and then the mixture was stirred at 90° C. for 24 h. The reaction mixture was concentrated under reduced pressure and the residue was purified by prep-HPLC to afford Example A42 as a yellow solid.

$^1$H NMR (400 MHz, CDCl$_3$) δ 0.65 (3H, t, J=6.8 Hz), 1.21-1.42 (3H, m), 1.71-1.81 (5H, m), 2.01-2.15 (3H, m), 2.31-2.42 (1H, m), 2.49-2.60 (1H, m), 2.68-2.81 (6H, m), 3.01-3.12 (2H, m), 3.18 (3H, s), 3.50 (3H, s), 3.87 (3H, s), 6.68 (1H, s), 7.41 (1H, s), 7.98 (1H, s), 8.10 (1H, d, J=9.6 Hz), 8.19 (1H, s), 8.75-8.90 (3H, s), 8.97 (1H, d, J=9.6 Hz).

LC-MS: MS Calculated 679.3, MS Found 680.2 [M+H]$^+$.

To a mixture of compound A38-1 (100 mg, 0.250 mmol) and compound A34-1 (91 mg, 0.30 mmol) in n-butanol (6 mL) was added TFA (684 mg, 6.00 mmol) at 15° C., and then the mixture was stirred at 80° C. for 32 h. The reaction mixture was concentrated under reduced pressure and the residue was purified by prep-HPLC to afford Example A43 as a yellow solid.

$^1$H NMR (400 MHz, DMSO-d$_6$) δ 0.93 (3H, t, J=7.2 Hz), 1.51-1.62 (2H, m), 1.65-1.76 (4H, m), 1.91-2.03 (2H, m), 2.05-2.14 (1H, m), 2.31-2.48 (2H, m), 2.58-2.65 (4H, m), 2.68-2.75 (2H, m), 2.94-3.04 (2H, m), 3.22 (3H, s), 3.36 (3H, s), 3.76 (3H, s), 6.80 (1H, s), 7.37 (1H, s), 7.92 (1H, d, J=9.2 Hz), 8.24 (1H, s), 8.36 (1H, s), 8.61 (1H, s), 8.75-8.87 (1H, m), 8.92 (1H, d, J=1.6 Hz), 8.97 (1H, d, J=2.0 Hz).

LC-MS: MS Calculated 665.3, MS Found 666.2 [M+H]$^+$.

[Example A44] Preparation of N-(6-((2-((4-([1,4'-bipiperidin]-1'-yl)-5-ethyl-2-methoxyphenyl)amino)-5-bromopyrimidin-4-yl)amino)quinoxalin-5-yl)-N-methylmethanesulfonamide

[Example A45] Preparation of N-(6-((5-chloro-2-((5-ethyl-2-methoxy-4-(4-(5-methyl-2,5-diazabicyclo[2.2.2]octan-2-yl)piperidin-1-yl)phenyl)amino)pyrimidin-4-yl)amino)quinoxalin-5-yl)methanesulfonamide

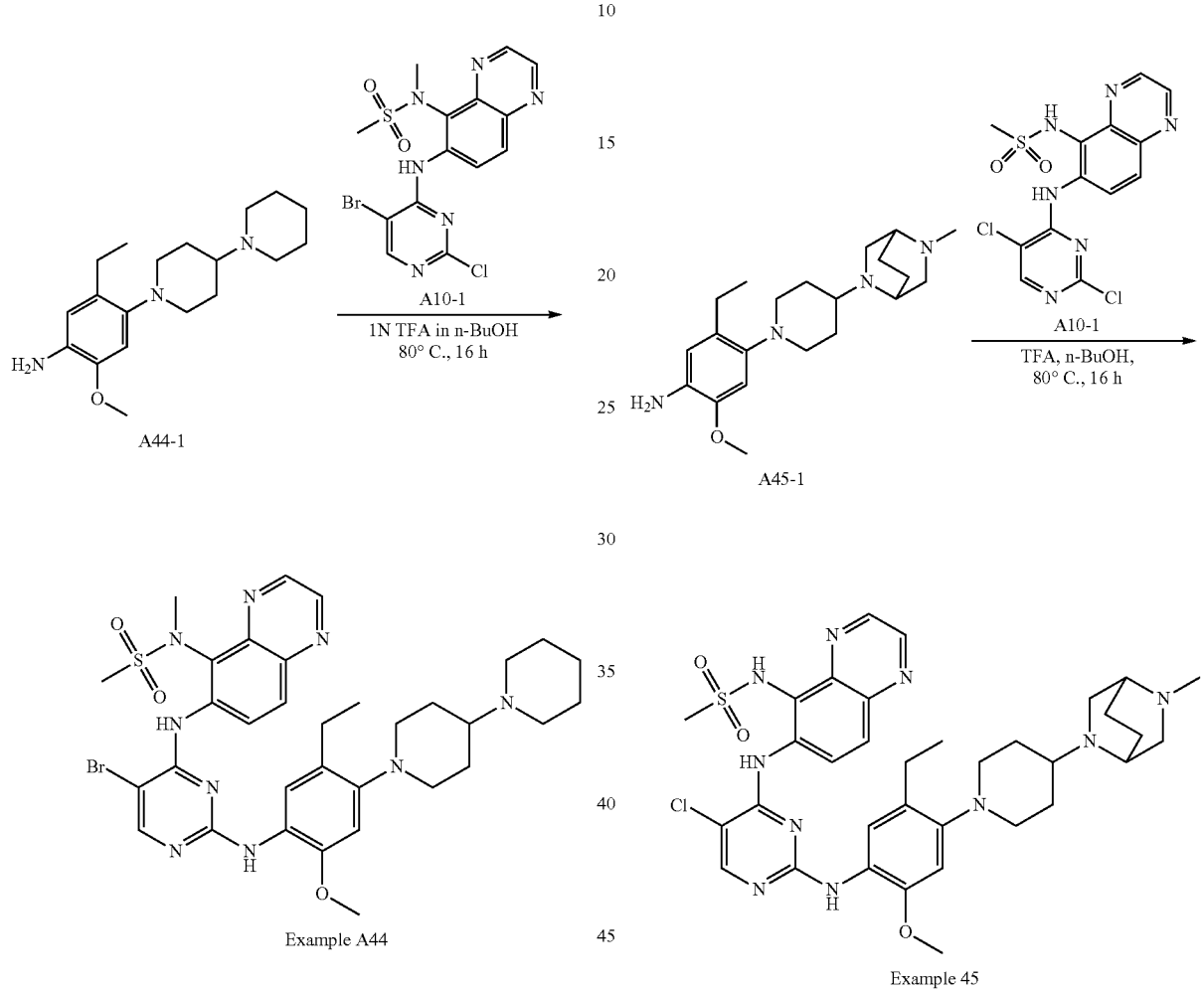

To a mixture of compound A10-1 (350 mg, 0.788 mmol) and compound A44-1 (300 mg, 0.946 mmol) in n-butanol (10 mL) was added TFA (1.14 g, 10 mmol), and then the mixture was stirred at 80° C. for 16 h. The mixture was filtered and the filtrate was concentrated under reduced pressure. The residue was poured into DCM (100 mL) and washed with NH₄OH (20 mL). The organic layer was concentrated under reduce pressure to be purified by Combi Flash to give Example A44 as white solid.

$^1$H NMR (400 MHz, CDCl$_3$) δ 0.93 (3H, t, J=7.2 Hz), 1.47-1.52 (2H, m), 1.65-1.84 (6H, m), 1.85-2.04 (2H, m), 2.35-2.78 (9H, m), 3.08-3.17 (2H, m), 3.20 (3H, s), 3.51 (3H, s), 3.88 (3H, s), 6.68 (1H, s), 7.39 (1H, s), 7.99 (1H, s), 8.10 (1H, d, J=9.6 Hz), 8.29 (1H, s), 8.80-8.88 (3H, m), 9.01 (1H, d, J=9.2 Hz). LC-MS: MS Calculated 723.2, MS Found 724.2 [M+H]$^+$.

To a mixture of compound A45-1 (110 mg, 0.307 mmol) and compound A1-10 (99 mg, 0.26 mmol) in n-butanol (4 mL) was added TFA (456 mg, 4.00 mmol), and then the mixture was stirred at 80° C. for 16 h. The reaction mixture was concentrated under reduced pressure and the residue was purified by prep-HPLC to afford Example 45 as a yellow solid.

$^1$H NMR (400 MHz, CD$_3$OD) δ 0.50-1.00 (3H, m), 2.00-2.60 (11H, m), 3.02 (3H, s), 3.12 (3H, s), 3.22-3.27 (1H, m), 3.37-3.45 (2H, m), 3.79-4.15 (9H, m), 4.23-4.30 (1H, m), 7.08 (1H, s), 7.40 (1H, s), 8.04 (1H, d, J=9.2 Hz), 8.17-8.42 (2H, m), 9.00 (1H, d, J=1.6 Hz), 9.04 (1H, d, J=2.0 Hz).

LC-MS: MS Calculated 706.3, MS Found 707.2 [M+H]$^+$.

153

[Example A46] Preparation of N-(6-((5-bromo-2-((5-ethyl-2-methoxy-4-(4-(5-methyl-2,5-diazabicyclo[2.2.2]octan-2-yl)piperidin-1-yl)phenyl)amino)pyrimidin-4-yl)amino)quinoxalin-5-yl)methanesulfonamide

154

[Example A47] Preparation of N-(6-((5-chloro-2-((5-ethyl-2-methoxy-4-(4-(5-methyl-2,5-diazabicyclo[2.2.2]octan-2-yl)piperidin-1-yl)phenyl)amino)pyrimidin-4-yl)amino)quinoxalin-5-yl)-N-methylmethanesulfonamide

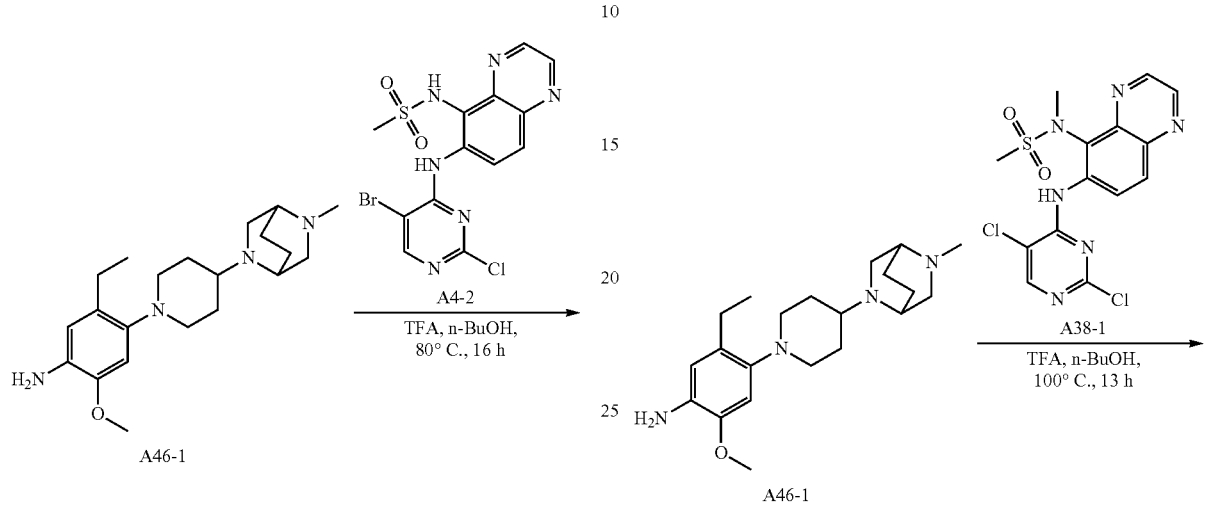

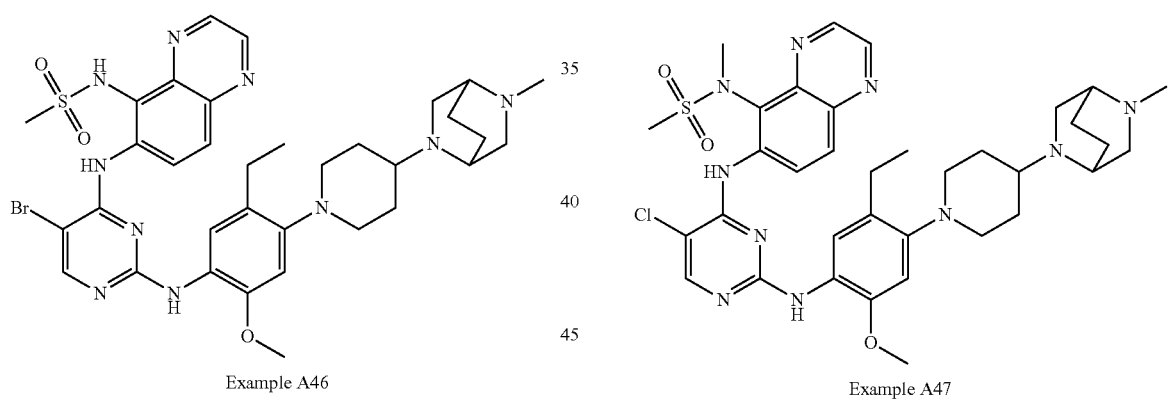

To a mixture of compound A46-1 (110 mg, 0.307 mmol) and compound A4-2 (110 mg, 0.256 mmol) in n-butanol (4 mL) was added TFA (456 mg, 4.00 mmol), and then the mixture was stirred at 80° C. for 16 h. The reaction mixture was concentrated under reduced pressure and the residue was purified by prep-HPLC to afford Example A46 as a yellow solid.

$^1$H NMR (400 MHz, CD$_3$OD) δ 0.50-1.00 (3H, m), 2.00-2.52 (11H, m), 3.02 (3H, s), 3.04-3.08 (1H, m), 3.12 (3H, s), 3.25-3.31 (2H, m), 3.79-4.15 (9H, m), 4.07-4.15 (1H, m), 6.95 (1H, s), 7.32 (1H, s), 7.92-8.07 (1H, m), 8.15-8.53 (2H, m), 8.99 (1H, d, J=2.0 Hz), 9.03 (1H, d, J=2.0 Hz).

To a mixture of compound A46-1 (110 mg, 0.307 mmol) and compound A38-1 (102 mg, 0.256 mmol) in n-butanol (4 mL) was added TFA (456 mg, 4.00 mmol), and then the mixture was stirred at 100° C. for 13 h. The reaction mixture was concentrated under reduced pressure and the residue was poured into DCM (10 mL) and washed with NH$_4$OH (10 mL×5). The organic layer was concentrated under reduced pressure and the residue was purified by Combi Flash to afford Example A47 as a yellow solid.

$^1$H NMR (400 MHz, CDCl$_3$) δ 0.85 (3H, t, J=7.2 Hz), 1.60-2.08 (8H, m), 2.27-2.47 (5H, m), 2.50-2.67 (4H, m), 2.70-2.84 (2H, m), 2.85-3.05 (4H, m), 3.06-3.20 (4H, m), 3.42 (3H, s), 3.79 (3H, s), 6.61 (1H, s), 7.31 (1H, s), 7.91 (1H, s), 8.02 (1H, d, J=9.6 Hz), 8.11 (1H, s), 8.65-8.80 (3H, m), 8.93 (1H, d, J=9.6 Hz). LC-MS: MS Calculated 720.3, MS Found 721.6 [M+H]$^+$.

[Example A48] Preparation of N-(6-((5-bromo-2-((5-ethyl-2-methoxy-4-(4-(5-methyl-2,5-diazabicyclo[2.2.2]octan-2-yl)piperidin-1-yl)phenyl)amino)pyrimidin-4-yl)amino)quinoxalin-5-yl)-N-methylmethanesulfonamide

[Example A49] Preparation of N-(6-((5-bromo-2-((5-ethyl-2-methoxy-4-(4-(1-methylpiperidin-4-yl)piperazin-1-yl)phenyl)amino)pyrimidin-4-yl)amino)quinoxalin-5-yl)-N-methylmethane sulfonamide

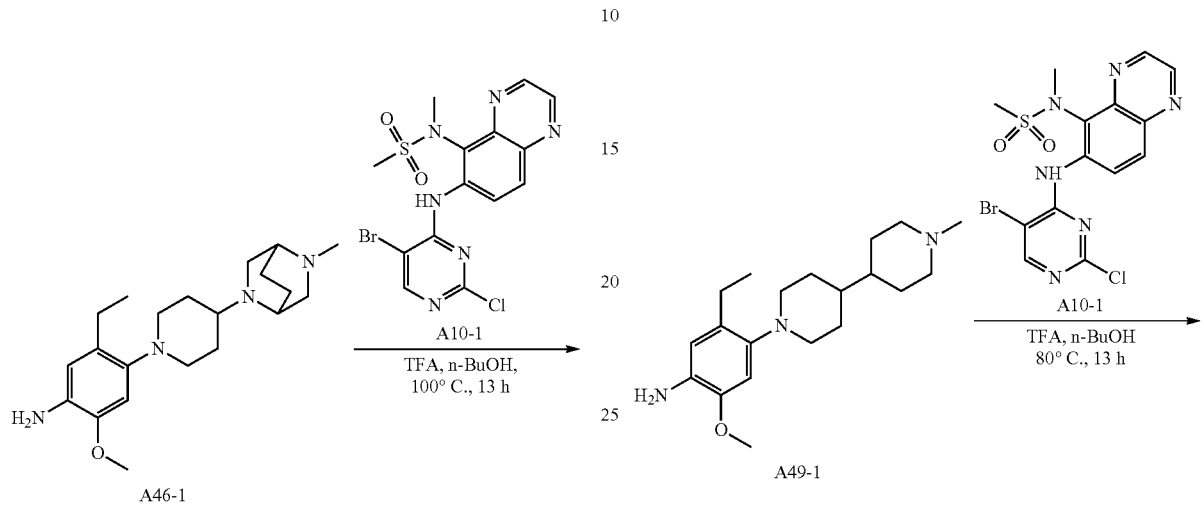

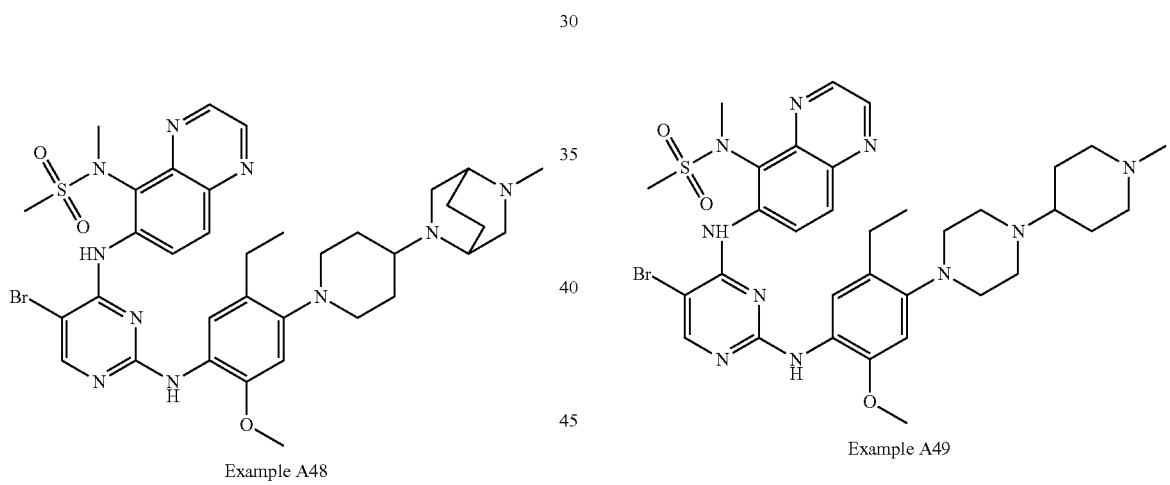

To a mixture of compound A46-1 (110 mg, 0.307 mmol) and A10-1 (113 mg, 0.256 mmol) in n-butanol (4 mL) was added TFA (456 mg, 4.00 mmol), and then the mixture was stirred at 100° C. for 13 h. The reaction mixture was concentrated under reduced pressure and the residue was poured into DCM (10 mL) and washed with NH₄OH (10 mL×5). The organic layer was concentrated under reduced pressure and the residue was purified by Combi Flash to afford Example 48 as a yellow solid.

¹H NMR (400 MHz, CDCl₃) δ 0.82-0.97 (3H, m), 1.60-1.77 (5H, m), 1.90-2.02 (3H, m), 2.42-3.13 (15H, m), 3.17-3.26 (4H, m), 3.49 (3H, s), 3.86 (3H, s), 6.67 (1H, s), 7.38 (1H, s), 7.97 (1H, s), 8.08 (1H, d, J=9.2 Hz), 8.27 (1H, s), 8.77-8.84 (3H, m), 8.98 (1H, d, J=9.2 Hz).

To a mixture of compound 49-1 (150 mg, 0.451 mmol) and compound A10-1 (182 mg, 0.410 mmol) in n-butanol (4 mL) was added TFA (514 mg, 4.51 mmol) at 25° C., and then the mixture was stirred at 80° C. for 13 h. The reaction mixture was concentrated under reduced pressure. The residue was purified by prep-HPLC to afford Example A49 as a light yellow solid.

¹H NMR (400 MHz, DMSO-d₆) δ 0.45-0.95 (3H, m), 2.07-2.21 (2H, m), 2.24-2.35 (2H, m), 2.38-2.44 (2H, m), 2.51 (3H, s), 2.54-2.64 (1H, s), 2.73-2.75 (2H, m), 2.97-3.13 (4H, m), 3.19 (3H, s), 3.21-3.23 (2H, m), 3.34 (3H, s), 3.57-3.62 (4H, m), 3.80 (3H, s), 6.72 (1H, s), 7.37 (1H, s), 8.01 (1H, d, J=9.2 Hz), 8.44 (1H, s), 8.55 (1H, br s), 8.99 (1H, d, J=1.6 Hz), 9.02 (1H, d, J=1.6 Hz), 9.08 (1H, br s), 9.19 (1H, br s), 10.73 (1H, s), 11.31 (1H, s).

[Example B1] Preparation of N-(6-((5-bromo-2-((4-(4-(dimethylamino)piperidin-1-yl)-2-methoxy-5-methylphenyl)amino)pyrimidin-4-yl)amino)quinoxalin-5-yl)methanesulfonamide

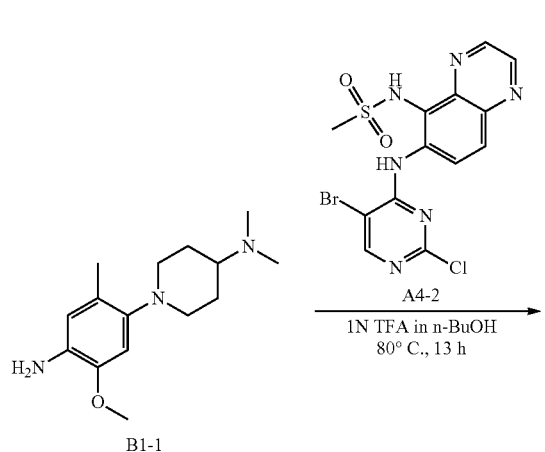

[Example B2] Preparation of N-(6-((5-bromo-2-((4-(4-(dimethylamino)piperidin-1-yl)-5-ethyl-2-methoxyphenyl)amino)pyrimidin-4-yl)amino)quinoxalin-5-yl)methanesulfonamide

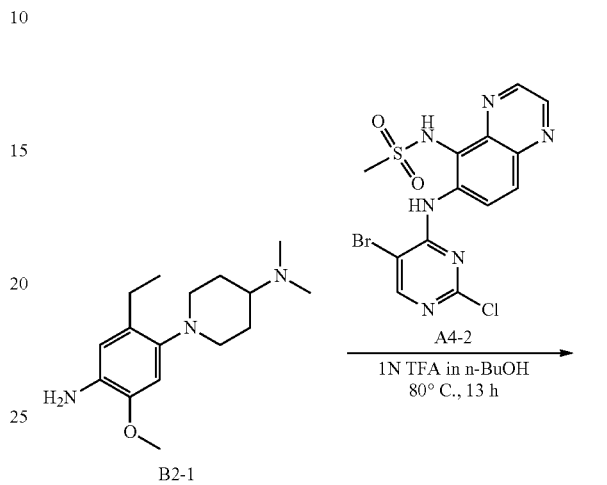

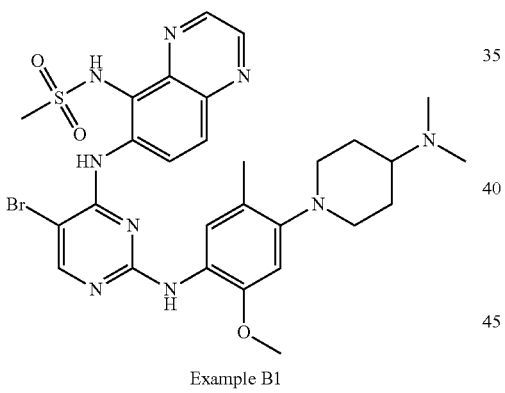

Example B1

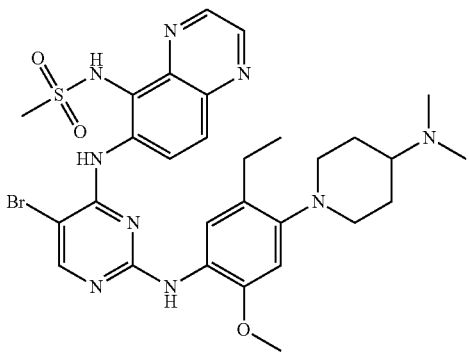

Example B2

A mixture of compound B1-1 (110 mg, 4.19 mmol) and compound A4-2 (150 mg, 3.49 mmol) in TFA/n-butanol (1N, 4.0 mL) was stirred at 80° C. for 13 h. The reaction was monitored by LC-MS. It was concentrated under reduced pressure and the residue was purified by prep-HPLC to afford Example B1 as a brown solid.

$^1$H NMR (400 MHz, DMSO-$d_6$) δ 1.70-1.84 (2H, m), 1.95-2.05 (5H, m), 2.48-2.52 (7H, s), 2.61-2.72 (2H, m), 2.95 (3H, s), 3.10-3.22 (2H, m), 3.85 (3H, s), 6.59 (1H, s), 7.39 (1H, s), 7.86 (1H, s), 8.07 (1H, d, J=9.2 Hz), 8.25 (1H, s), 8.65-8.95 (3H, m), 9.14 (1H, s).

LC-MS: MS Calculated 655.2, MS Found 656.0 [M+H]$^+$.

A mixture of compound A4-2 (150 mg, 0.349 mmol) and compound B2-1 (116 mg, 0.419 mmol) in TFA/n-butanol (1N, 4.0 mL) was stirred at 80° C. for 13 h. The reaction was monitored by LC-MS. The resulting mixture was filtered, and the filtrate was concentrated under reduced pressure. The remaining residue was purified by prep-HPLC to afford Example B2 as a yellow solid.

$^1$H NMR (400 MHz, CDCl$_3$) δ 0.72-0.76 (3H, m), 1.68-1.88 (2H, m), 1.93-2.15 (2H, m), 2.28-2.45 (2H, m), 2.53-2.75 (8H, m), 2.82-3.01 (4H, m), 3.07-3.22 (2H, m), 3.83 (3H, s), 6.60 (1H, s), 7.44 (1H, s), 7.90 (1H, s), 8.04 (1H, d, J=9.6 Hz), 8.24 (1H, s), 8.56 (1H, s), 8.68 (1H, d, J=9.2 Hz), 8.80-8.98 (2H, m), 9.12 (1H, s).

[Example B3] Preparation of N-(6-((5-bromo-2-((4-(4-(dimethylamino)piperidin-1-yl)-2-methoxy phenyl)amino)pyrimidin-4-yl)amino)quinoxalin-5-yl)methanesulfonamide

[Example B4] Preparation of N-(6-((5-chloro-2-((4-(4-(dimethylamino)piperidin-1-yl)-2-methoxy-5-methylphenyl)amino)pyrimidin-4-yl)amino)quinoxalin-5-yl)methanesulfonamide

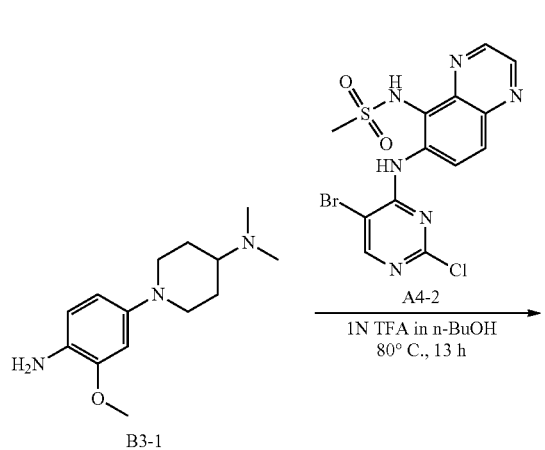

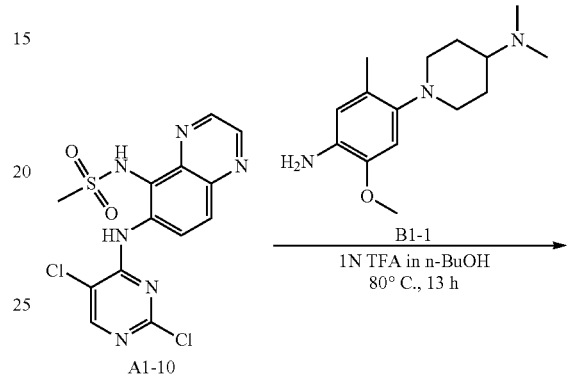

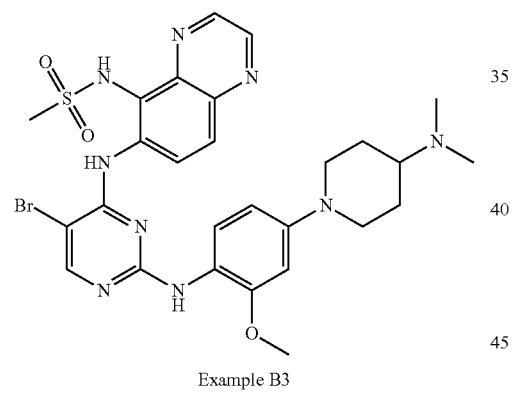

Example B3

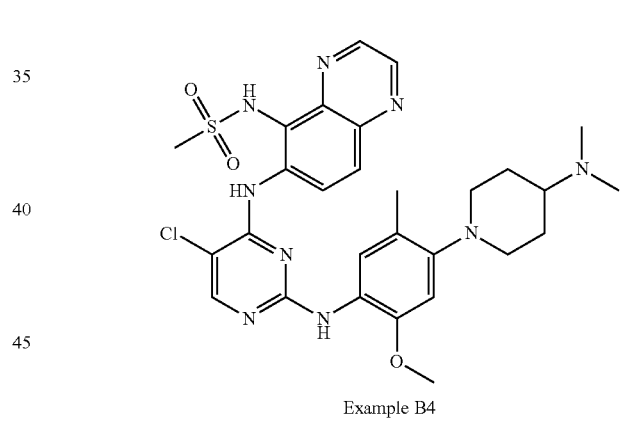

Example B4

A mixture of compound A4-2 (200 mg, 0.465 mmol) and compound B3-1 (139 mg, 0.559 mmol) in TFA/n-butanol (1N, 4.0 mL) was stirred at 80° C. for 13 h. The reaction was monitored by LC-MS. The mixture was filtered and the filtrate was concentrated under reduced pressure. The remaining residue was purified by prep-HPLC to afford Example B3 as an off-white solid.

$^1$H NMR (400 MHz, DMSO-$d_6$) δ 1.43-1.58 (2H, m), 1.82-1.93 (2H, m), 2.20-2.34 (7H, m), 2.60-2.75 (2H, m), 3.01 (3H, s), 3.72-3.85 (5H, m), 6.41-6.58 (1H, m), 6.60-6.73 (1H, m), 7.32 (1H, d, J=8.4 Hz), 7.86 (1H, d, J=9.2 Hz), 8.21-8.34 (2H, m), 8.65-8.78 (1H, m), 8.80-8.93 (2H, m), 8.95-9.06 (1H, m).

A mixture of compound B1-1 (130 mg, 3.37 mmol) and compound A1-10 (106 mg, 4.04 mmol) in TFA/n-butanol (1N, 4.0 mL) was stirred at 80° C. for 13 h. The reaction was monitored by LC-MS. It was concentrated under reduced pressure to provide a residue that was purified by prep-HPLC to afford Example B4 as a yellow solid.

$^1$H NMR (400 MHz, CDCl$_3$) δ 1.69-1.72 (2H, m), 1.99-2.09 (5H, m), 2.43-2.46 (7H, m), 2.58-2.68 (2H, m), 2.95 (3H, s), 3.09-3.20 (2H, m), 3.85 (3H, s), 6.60 (1H, s), 7.39 (1H, s), 7.88 (1H, s), 8.15-8.14 (1H, m), 8.17 (1H, s), 8.78-8.95 (3H, m), 9.22 (1H, s).

LC-MS: MS Calculated 611.2, MS Found 612.5 [M+H]$^+$.

161

[Example B5] Preparation of N-(6-((5-chloro-2-((4-(4-(dimethylamino)piperidin-1-yl)-5-ethyl-2-methoxyphenyl)amino)pyrimidin-4-yl)amino)quinoxalin-5-yl)methanesulfonamide

162

[Example B6] Preparation of N-(6-((5-bromo-2-((2-(dimethylamino)-4-(4-(dimethylamino)piperidin-1-yl)-5-methylphenyl)amino)pyrimidin-4-yl)amino)quinoxalin-5-yl)methanesulfonamide

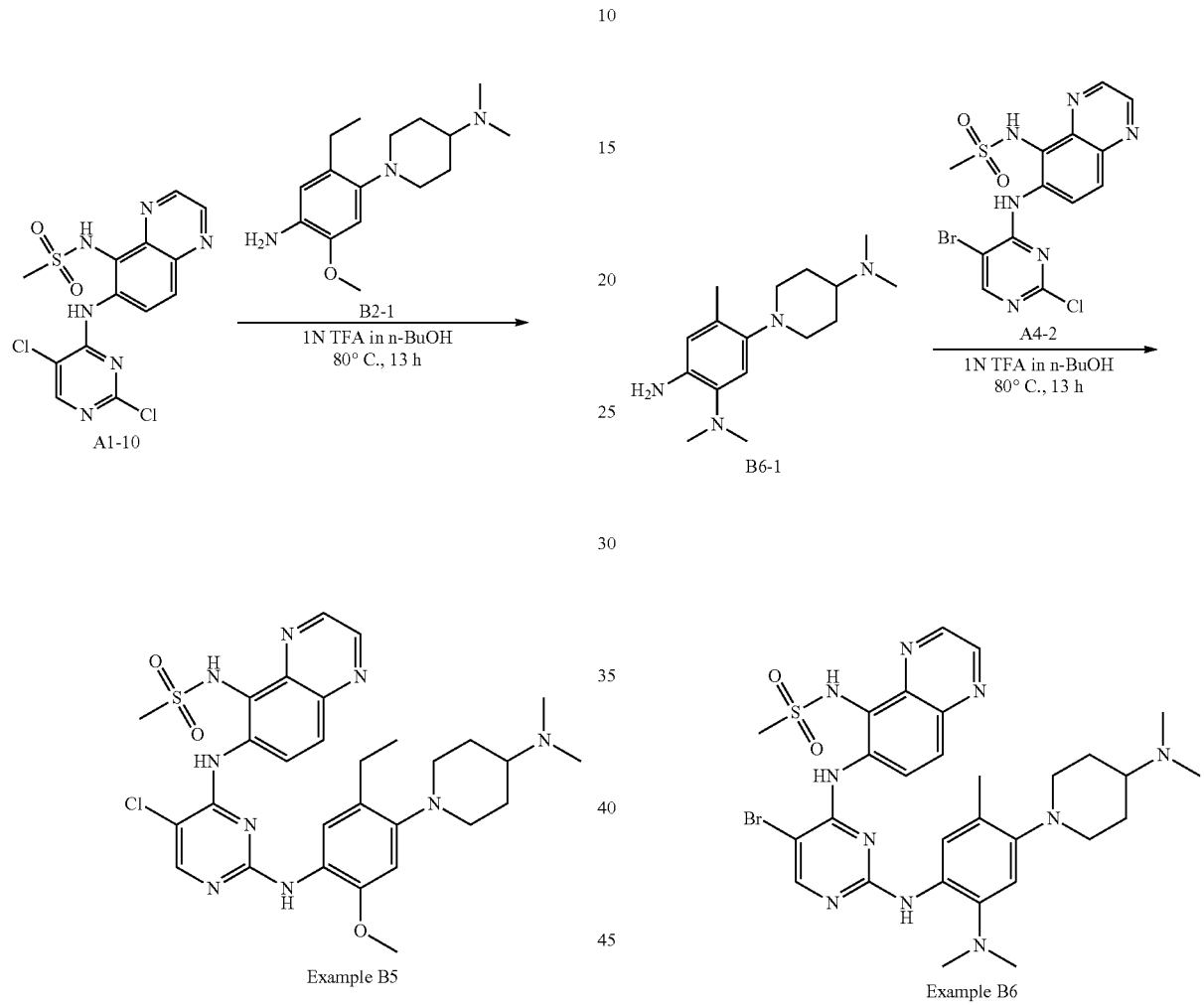

A mixture of compound A1-10 (150 mg, 0.389 mmol) and compound B2-1 (130 mg, 0.467 mmol) in TFA/n-butanol (1N, 4.0 mL) was stirred at 80° C. for 13 h. The reaction was monitored by LC-MS. The mixture was filtered and the filtrate was concentrated under reduced pressure to be purified by prep-HPLC to afford Example B5 as a brown solid.

$^1$H NMR (400 MHz, CD$_3$OD) δ 0.65-0.85 (3H, m), 1.72-1.84 (2H, m), 2.05-2.18 (2H, m), 2.35-2.45 (2H, m), 2.50-2.68 (7H, m), 2.70-2.80 (2H, m), 2.95 (3H, s), 3.08-3.21 (2H, m), 3.85 (3H, s), 6.63 (1H, s), 7.42 (1H, s), 7.93 (1H, s), 8.06 (1H, d, J=9.6 Hz), 8.17 (1H, s), 8.58 (1H, s), 8.75 (1H, d, J=9.6 Hz), 8.82-8.95 (2H, m), 9.21 (1H, s). LC-MS: MS Calculated 625.2, MS Found 626.3 [M+H]$^+$.

A mixture of compound A4-2 (100 mg, 0.233 mmol) and compound B6-1 (77 mg, 0.28 mmol) in TFA/n-butanol (1M, 4.0 mL) was stirred at 80° C. for 13 h. The reaction was monitored by LC-MS. The mixture was filtered and the filtrate was concentrated under reduced pressure. The remaining residue was purified by prep-HPLC to afford Example B6 as a yellow solid.

$^1$H NMR (400 MHz, CDCl$_3$) δ 1.58-1.71 (2H, m), 1.82-1.95 (2H, m), 2.03 (3H, s), 2.22-2.32 (1H, m), 2.34 (6H, s), 2.61-2.75 (8H, m), 2.96 (3H, s), 3.06-3.18 (2H, m), 6.85 (1H, s), 7.87 (1H, s), 8.06 (1H, s), 8.11 (1H, d, J=9.2 Hz), 8.26 (1H, s), 8.78-8.84 (2H, m), 8.86-8.95 (1H, m), 9.15 (1H, s).

163

[Example B7] Preparation of N-(6-((5-bromo-2-((4-(4-(dimethylamino)piperidin-1-yl)-2-methoxy-5-methylphenyl)amino)pyrimidin-4-yl)amino)quinoxalin-5-yl)-N-methylmethanesulfonamide

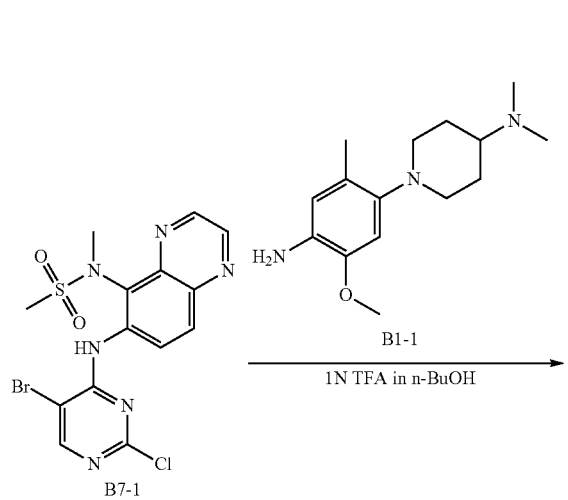

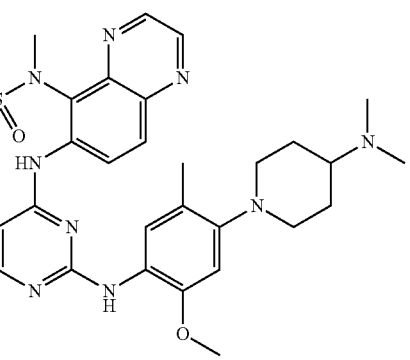

Example B7

To a solution of TFA/n-butanol (1N, 2 mL) were added compound B7-1 (100 mg, 0.225 mmol) and B1-1 (71 mg, 0.27 mmol). The mixture was stirred under $N_2$ at 80° C. for 16 h. The reaction was monitored by LC-MS. The reaction mixture was concentrated under reduced pressure to give a residue that was purified by prep-HPLC to afford Example B7 as a yellow solid.

$^1$H NMR (400 MHz, CDCl$_3$) δ 1.70-1.81 (2H, m), 1.96-2.04 (2H, m), 2.18 (3H, s), 2.47 (7H, s), 2.66-2.68 (2H, m), 3.15-3.23 (5H, m), 3.51 (3H, s), 3.87 (3H, s), 6.64 (1H, s), 7.37 (1H, s), 7.97 (1H, s), 8.10 (1H, d, J=9.2 Hz), 8.27 (1H, s), 8.83 (3H, s), 9.10 (1H, d, J=9.2 Hz).

164

[Example B8] Preparation of N-(6-((2-((4-(1-acetylpiperidin-4-yl)-2-methoxyphenyl)amino)-5-chloropyrimidin-4-yl)amino)quinoxalin-5-yl)methanesulfonamide

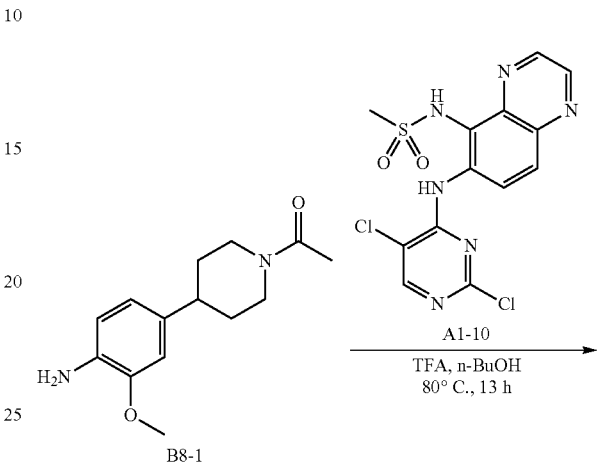

Example B8

To a mixture of compound B8-1 (200 mg, 0.805 mmol) and compound A1-10 (207 mg, 0.537 mmol) in n-butanol (4 mL) was added TFA (456 mg, 4.00 mmol) and the mixture was stirred at 80° C. for 13 h. The reaction was monitored by LC-MS and the reaction mixture was concentrated under reduced pressure. The residue was purified by prep-HPLC to afford Example B8 as a yellow solid.

$^1$H NMR (400 MHz, CDCl$_3$) δ 1.60-1.70 (2H, m), 1.82-1.95 (2H, m), 2.15 (3H, s), 2.56-2.76 (2H, m), 2.94 (3H, s), 3.11-3.22 (1H, m), 3.88 (3H, s), 3.91-4.00 (1H, m), 4.67-4.86 (1H, m), 6.67 (1H, d, J=8.4, 1.6 Hz), 6.79 (1H, d, J=1.6 Hz), 7.51 (1H, s), 8.07-8.15 (2H, m), 8.18 (1H, s), 8.82 (1H, d, J=9.6 Hz), 8.84 (1H, d, J=2.0 Hz), 8.91 (1H, d, J=1.6 Hz), 9.24 (1H, s).

LC-MS: MS Calculated 596.2, MS Found 597.2 [M+H]$^+$.

165

[Example B9] Preparation of N-(6-((2-((4-(4-(dimethylamino)piperidin-1-yl)-2-methoxy-5-methylphenyl)amino)-5-(trifluoromethyl)pyrimidin-4-yl)amino)quinoxalin-5-yl) methane sulfonamide

166

[Example B10] Preparation of N-(6-((5-bromo-2-((2-methoxy-5-methyl-4-morpholinophenyl) amino)pyrimidin-4-yl)amino)quinoxalin-5-yl)methanesulfonamide

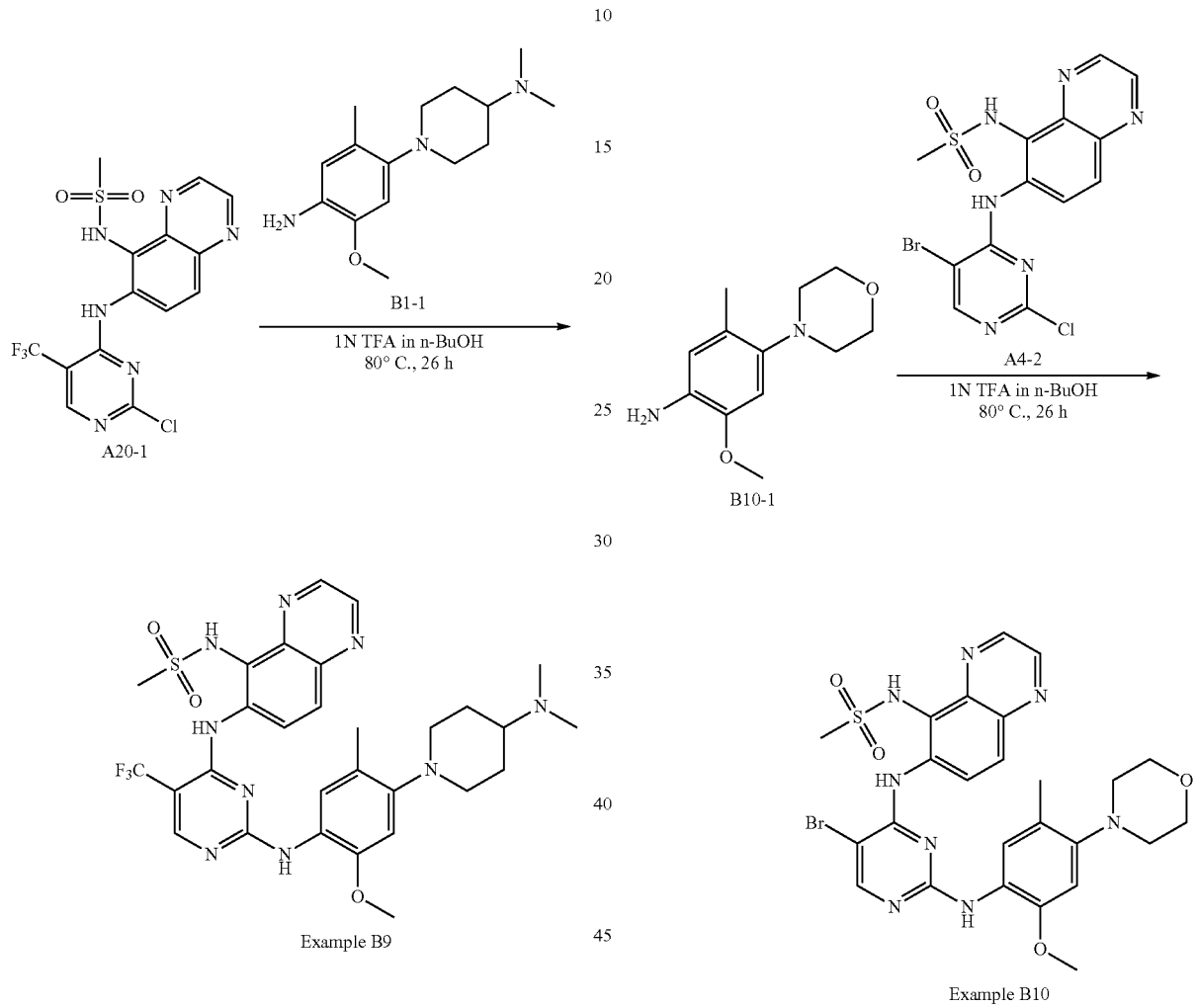

To a mixture of A20-1 (100 mg, 0.239 mmol) and B1-1 (63 mg, 0.24 mmol) in n-butanol (4 mL) was added TFA (456 mg, 4.00 mmol), then it was stirred at 80° C. for 26 h. The reaction was monitored by LC-MS. The reaction mixture was concentrated under reduced pressure to afford a residue. It was purified by prep-HPLC (0.225% FA as additive), most of MeCN was removed under reduced pressure and the remaining solvent was removed by lyophilization to afford Example B9 as a yellow solid.

$^1$H NMR (400 MHz, DMSO-$d_6$) δ 1.56-1.68 (2H, m), 1.85-1.97 (2H, m), 2.10 (3H, s), 2.26-2.39 (7H, m), 2.64-2.77 (2H, m), 3.04 (3H, s), 3.10-3.23 (2H, m), 3.75 (3H, s), 6.80 (1H, s), 7.29 (1H, s), 7.69 (1H, d, J=9.6 Hz), 8.35-8.50 (3H, m), 8.78-8.91 (2H, m), 8.95-9.04 (1H, m).

LC-MS: MS Calculated 645.3, MS Found 646.5 [M+H]$^+$.

To a mixture of compound A4-2 (100 mg, 0.233 mmol) and compound B10-1 (52 mg, 0.23 mmol) in n-butanol (4 mL) was added TFA (456 mg, 4.00 mmol) and it was stirred at 80° C. for 26 h. The reaction was monitored by LC-MS. The reaction mixture was concentrated under reduced pressure to afford a residue that was purified by HPLC to afford Example B10 as a yellow solid.

$^1$H NMR (400 MHz, DMSO-$d_6$) δ 2.03 (3H, s), 2.81-2.93 (4H, m), 3.02 (3H, s), 3.71-3.84 (7H, m), 6.75 (1H, s), 7.38 (1H, s), 7.91 (1H, d, J=9.2 Hz), 8.23 (1H, s), 8.29 (1H, s), 8.62-8.75 (1H, m), 8.80-8.89 (1H, m), 8.93 (1H, d, J=1.6 Hz), 8.99 (1H, d, J=1.6 Hz), 9.92 (1H, s).

LC-MS: MS Calculated 614.1, MS Found 615.0 [M+H]$^+$.

[Example B11] Preparation of N-(6-((5-bromo-2-((2-methoxy-5-methyl-4-(piperidin-4-yl)phenyl)amino)pyrimidin-4-yl)amino)quinoxalin-5-yl)methanesulfonamide

[Example B12] Preparation of N-(6-((5-chloro-2-((4-(4-(dimethylamino)piperidin-1-yl)-2-methoxy-5-propylphenyl)amino)pyrimidin-4-yl)amino)quinoxalin-5-yl)methanesulfonamide

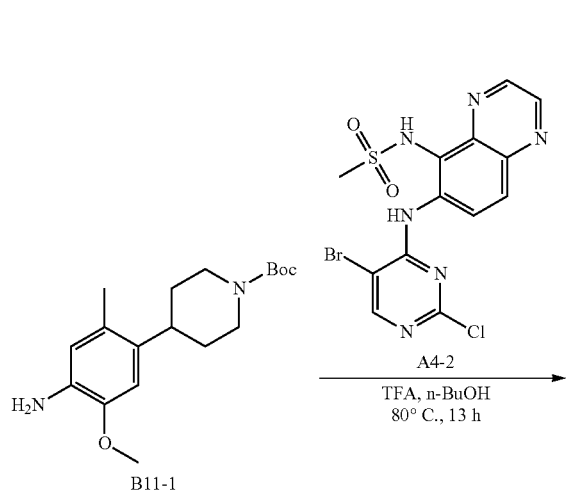

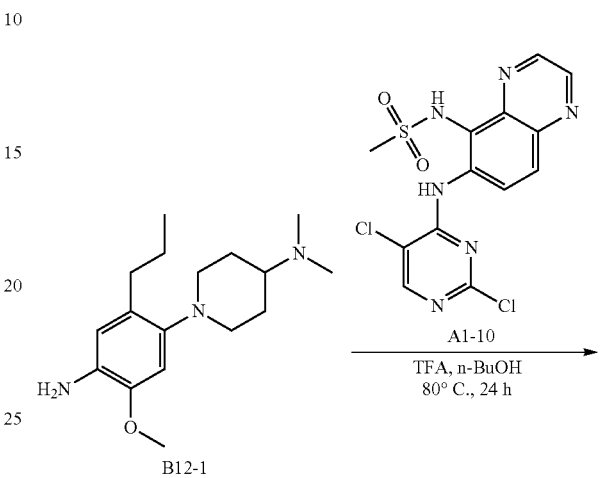

To a mixture of compound B11-1 (125 mg, 0.391 mmol) and compound A4-2 (140 mg, 0.326 mmol) in n-butanol (5 mL) was added TFA (631 mg, 5.54 mmol) at 25° C. and the mixture was stirred at 80° C. for 13 h. The reaction was monitored by LC-MS. The reaction mixture was purified by reverse phase column chromatography, and it was further purified by prep-HPLC to afford Example B11 as a yellow solid.

$^1$H NMR (400 MHz, DMSO-$d_6$) δ 1.64-1.74 (4H, m), 2.11 (3H, s), 2.73-2.84 (3H, m), 2.97 (3H, s), 3.09-3.23 (2H, m), 3.78 (3H, s), 6.80 (1H, s), 7.49 (1H, s), 7.56 (1H, d, J=9.2 Hz), 8.10 (1H, s), 8.23 (1H, s), 8.72 (1H, d, J=9.6 Hz), 8.76 (1H, d, J=2.0 Hz), 8.84 (1H, d, J=2.0 Hz), 9.47 (1H, s).

To a mixture of compound B12-1 (100 mg, 0.343 mmol) and A1-10 (132 mg, 0.343 mmol) in n-butanol (8 mL) was added TFA (1.02 g, 8.92 mmol) at 25° C. and the mixture was stirred at 80° C. for 24 h. The reaction was monitored by LC-MS. The reaction mixture was concentrated under reduced pressure. The remaining residue was purified by prep-HPLC to afford Example B12 as a yellow solid.

$^1$H NMR (400 MHz, CDCl$_3$) δ 0.57-0.66 (3H, m), 1.18-1.28 (2H, m), 1.60-1.71 (2H, m), 1.88-1.95 (2H, m), 2.16-2.29 (1H, m), 2.35 (6H, s), 2.36-2.42 (2H, m), 2.62-2.69 (2H, m), 2.94 (3H, s), 3.02-3.08 (2H, m), 3.85 (3H, s), 6.66 (1H, s), 7.41 (1H, s), 7.90 (1H, s), 8.06 (1H, d, J=9.6 Hz), 8.18 (1H, s), 8.78 (1H, d, J=9.6 Hz), 8.84 (1H, d, J=1.6 Hz), 8.90 (1H, d, J=1.6 Hz), 9.21 (1H, s).

LC-MS: MS Calculated 639.2, MS Found 640.2 [M+H]$^+$.

[Example B13] Preparation of N-(6-((5-bromo-2-((4-(4-(dimethylamino)piperidin-1-yl)-2-methoxy-5-propylphenyl)amino)pyrimidin-4-yl)amino)quinoxalin-5-yl)methanesulfonamide

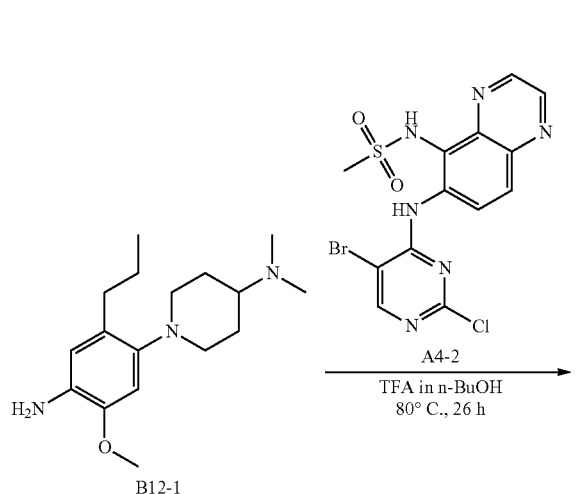

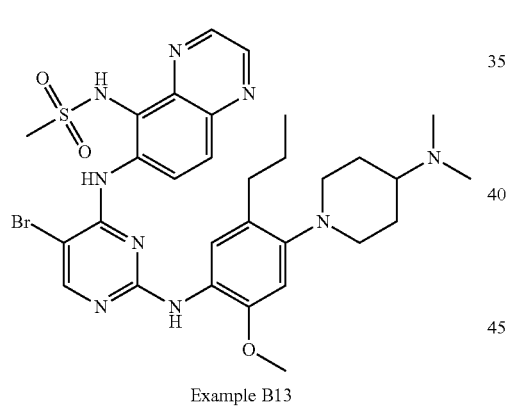

Example B13

To a mixture of compound A4-2 (100 mg, 0.233 mmol) and compound B12-1 (68 mg, 0.23 mmol) in n-butanol (4.00 mL) was added TFA (456 mg, 4.00 mmol) at 25° C. and the mixture was stirred at 80° C. for 26 h. The reaction was monitored by LC-MS. The reaction mixture was concentrated under reduced pressure and the residue was purified by prep-HPLC to afford Example B13 as a yellow solid.

$^1$H NMR (400 MHz, DMSO-$d_6$) δ 0.55-0.70 (3H, m), 1.21-1.35 (2H, m), 1.55-1.66 (2H, m), 1.89-2.01 (2H, m), 2.31-2.44 (9H, m), 2.65-2.75 (2H, m), 2.95-3.06 (5H, m), 3.76 (3H, s), 6.78 (1H, s), 7.40 (1H, s), 7.87 (1H, d, J=9.2 Hz), 8.19 (1H, s), 8.29 (1H, s), 8.55-8.71 (1H, m), 8.88 (1H, s), 8.93 (1H, d, J=1.6 Hz), 9.00 (1H, d, J=1.6 Hz).

[Example B14] Preparation of N-(6-((5-bromo-2-((4-(4-(dimethylamino)piperidin-1-yl)-5-ethyl-2-methoxyphenyl)amino)pyrimidin-4-yl)amino)quinoxalin-5-yl)-N-methylmethanesulfonamide

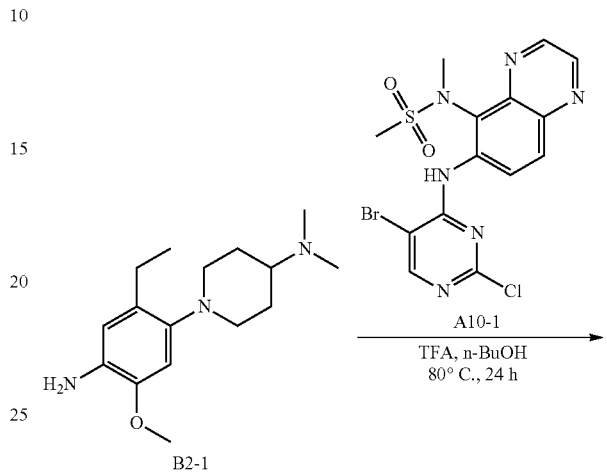

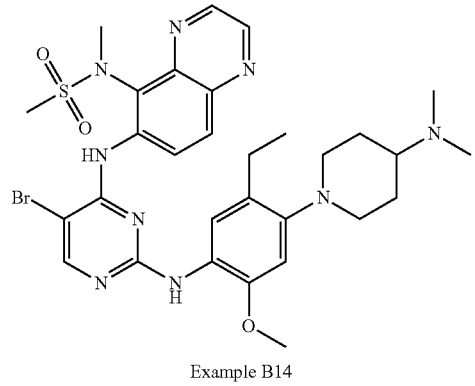

Example B14

To a mixture of compound B2-1 (65 mg, 0.23 mmol) and compound A10-1 (104 mg, 0.234 mmol) in n-butanol (5 mL) at 25° C., was added TFA (614 mg, 5.39 mmol). The resulting mixture was stirred at 80° C. for 24 h. The reaction was monitored by LC-MS. The reaction mixture was concentrated under reduced pressure and the residue was purified by prep-HPLC and normal phase column purification to afford Example B14 as a yellow solid.

$^1$H NMR (400 MHz, CDCl$_3$) δ 0.87-0.94 (3H, m), 1.75-1.82 (2H, m), 2.03-2.09 (2H, m), 2.49-2.56 (7H, m), 2.57-2.64 (2H, m), 2.67-2.74 (2H, m), 3.09-3.16 (2H, m), 3.19 (3H, s), 3.50 (3H, s), 3.87 (3H, s), 6.66 (1H, s), 7.39 (1H, s), 7.99 (1H, s), 8.09 (1H, d, J=9.2 Hz), 8.28 (1H, s), 8.81 (1H, s), 8.82-8.85 (2H, m), 8.98 (1H, d, J=9.6 Hz).

[Example B15] Preparation of N-(6-((5-chloro-2-((2-methoxy-4-(piperidin-4-yl)phenyl) amino)pyrimidin-4-yl)amino)quinoxalin-5-yl)methanesulfonamide

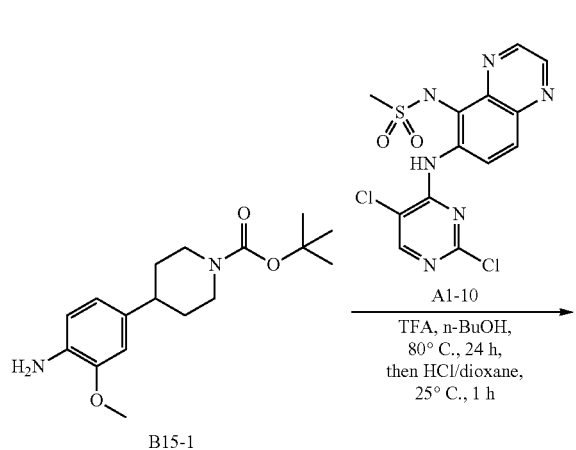

[Example B16] Preparation of N-(6-((5-chloro-2-((2-methoxy-4-(piperazin-1-yl)phenyl)amino)pyrimidin-4-yl)amino)quinoxalin-5-yl)methanesulfonamide

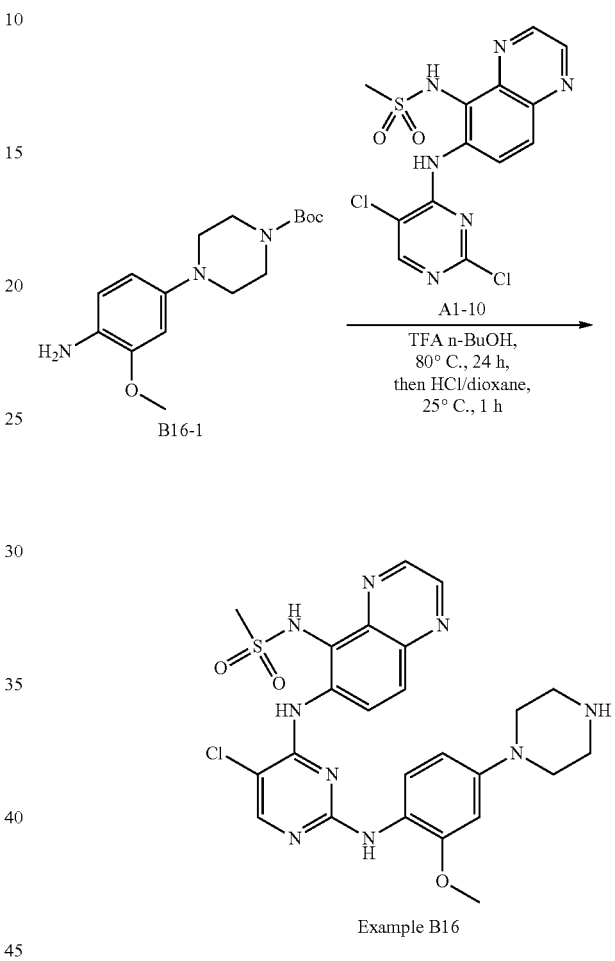

To a mixture of compound B15-1 (65 mg, 0.21 mmol) in n-butanol (5 mL) were added A1-10 (82 mg, 0.21 mmol) and TFA (629 mg, 5.52 mmol) at 25° C. and the mixture was stirred at 80° C. for 24 h. The reaction was monitored by LC-MS. The mixture was concentrated under reduced pressure. To this residue, 4 M HCl/dioxane (3 mL) was added and the mixture was stirred at 25° C. for 1 h. The reaction mixture was then concentrated under reduced pressure and the resulting residue was purified by prep-HPLC to afford Example B15 as a yellow solid.

$^1$H NMR (400 MHz, CDCl$_3$) δ 1.58-1.71 (2H, m), 1.79-1.87 (2H, m), 2.54-2.63 (1H, m), 2.70-2.80 (2H, m), 2.95 (3H, s), 3.17-3.24 (2H, m), 3.88 (3H, s), 6.70 (1H, d, J=8.0 Hz), 6.76 (1H, d, J=1.6 Hz), 7.51 (1H, s), 8.05-8.14 (2H, m), 8.18 (1H, s), 8.81-8.86 (2H, m), 8.91 (1H, d, J=2.0 Hz), 9.25 (1H, s). LC-MS: MS Calculated 554.2, MS Found 555.1 [M+H]$^+$.

To a mixture of compound B16-1 (65 mg, 0.21 mmol) in n-butanol (5 mL) were added A1-10 (81.5 mg, 0.211 mmol) and TFA (627 mg, 5.50 mmol) at 25° C. and the mixture was stirred at 80° C. for 24 h. The mixture was concentrated under reduced pressure. To this residue was added 4 M HCl/dioxane (3 mL), the mixture was stirred at 25° C. for 1 h. The reaction was monitored by LC-MS. The reaction mixture was concentrated under reduced pressure and the residue was purified by prep-HPLC to afford Example B16 as a yellow solid.

$^1$H NMR (400 MHz, CDCl$_3$) δ 2.94 (3H, s), 3.05-3.12 (8H, m), 3.87 (3H, s), 6.43 (1H, dd, J=8.8, 2.0 Hz), 6.54 (1H, d, J=2.8 Hz), 7.32 (1H, s), 7.99 (1H, d, J=8.8 Hz), 8.10 (1H, d, J=9.6 Hz), 8.16 (1H, s), 8.84 (1H, d, J=2.0 Hz), 8.87 (1H, d, J=9.2 Hz), 8.90 (1H, d, J=2.0 Hz), 9.21 (1H, s).

LC-MS: MS Calculated 555.2, MS Found 556.0 [M+H]$^+$.

[Example B17] Preparation of N-(6-((5-fluoro-2-((2-methoxy-4-(piperidin-4-yl)phenyl)amino)pyrimidin-4-yl)amino)quinoxalin-5-yl)methanesulfonamide

[Example B18] Preparation of N-(6-((5-bromo-2-((2-methoxy-4-(piperidin-4-yl)phenyl)amino)pyrimidin-4-yl)amino)quinoxalin-5-yl)methanesulfonamide

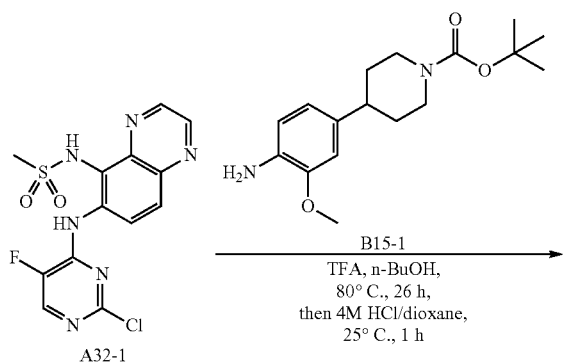

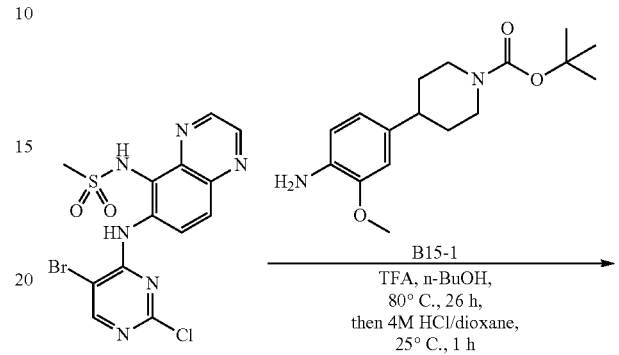

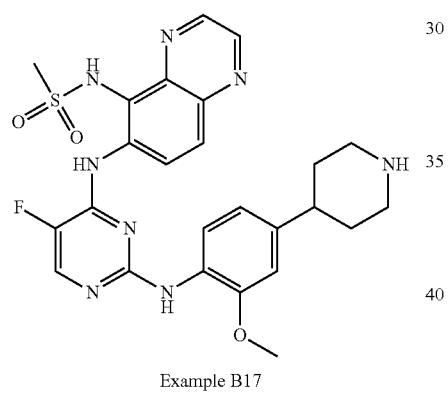

Example B17

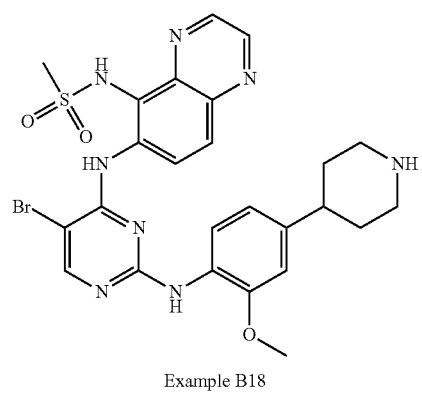

Example B18

To a mixture of compound A32-1 (100 mg, 0.271 mmol) and compound B15-1 (83 mg, 0.27 mmol) in n-butanol (4 mL) was added TFA (456 mg, 4.00 mmol) at 25° C. and the mixture was stirred at 80° C. for 26 h. The reaction mixture was concentrated under reduced pressure and 4 N HCl/dioxane (5 mL) was added to this residue for a complete reaction and then the mixture was stirred at 25° C. for 1 h. The reaction was monitored by LC-MS. The reaction mixture was concentrated under reduced pressure and the concentrated residue was purified by prep-HPLC to afford Example B17 as a yellow solid.

$^1$H NMR (400 MHz, CDCl$_3$) δ 1.62-1.74 (2H, m), 1.81-1.92 (2H, m), 2.55-2.65 (1H, m), 2.72-2.85 (2H, m), 2.94 (3H, s), 3.18-3.29 (2H, m), 3.89 (3H, s), 6.71-6.83 (2H, m), 7.48 (1H, s), 8.05-8.21 (3H, m), 8.85 (1H, d, J=1.6 Hz), 8.90 (1H, d, J=2.0 Hz), 8.96 (1H, d, J=9.6 Hz), 9.10 (1H, s).

LC-MS: MS Calculated 538.2, MS Found 539.4 [M+H]$^+$.

To a mixture of compound A4-2 (100 mg, 0.233 mmol) and compound B15-1 (71 mg, 0.23 mmol) in n-butanol (4 mL) was added TFA (456 mg, 4.00 mmol) at 25° C. and the mixture was stirred at 80° C. for 26 h. The reaction mixture was concentrated under reduced pressure. To the residue was added 4 M HCl/dioxane (5 mL) and then the mixture was stirred at 25° C. for 1 h. The reaction was monitored by LC-MS. The reaction mixture was concentrated under reduced pressure and the residue was purified by prep-HPLC to afford Example B18 as a yellow solid.

$^1$H NMR (400 MHz, CDCl$_3$) δ 1.68-1.70 (2H, m), 1.78-1.92 (2H, m), 2.51-2.60 (1H, m), 2.68-2.80 (2H, m), 2.95 (3H, s), 3.16-3.28 (2H, m), 3.87 (3H, s), 6.68 (1H, d, J=8.0 Hz), 6.75 (1H, d, J=1.6 Hz), 7.52 (1H, s), 8.05 (1H, d, J=8.4 Hz), 8.10 (1H, d, J=9.6 Hz), 8.26 (1H, s), 8.80 (1H, d, J=9.6 Hz), 8.85 (1H, d, J=2.0 Hz), 8.91 (1H, d, J=2.0 Hz), 9.17 (1H, s).

[Example B19] Preparation of N-(6-((5-bromo-2-((4-(4-(dimethylamino)piperidin-1-yl)-5-ethyl-2-methoxyphenyl)amino)pyrimidin-4-yl)(methyl)amino)quinoxalin-5-yl)-N-methylmethane sulfonamide

[Example B20] Preparation of N-(6-((5-cyclopropyl-2-((2-methoxy-4-(piperidin-4-yl)phenyl)amino)pyrimidin-4-yl)amino)quinoxalin-5-yl)methanesulfonamide

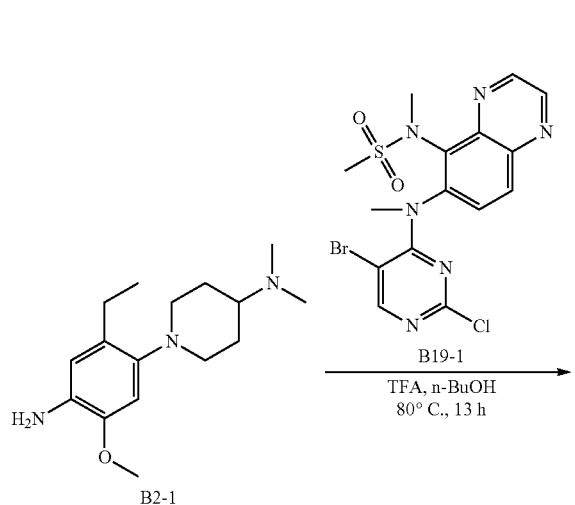

Example B19

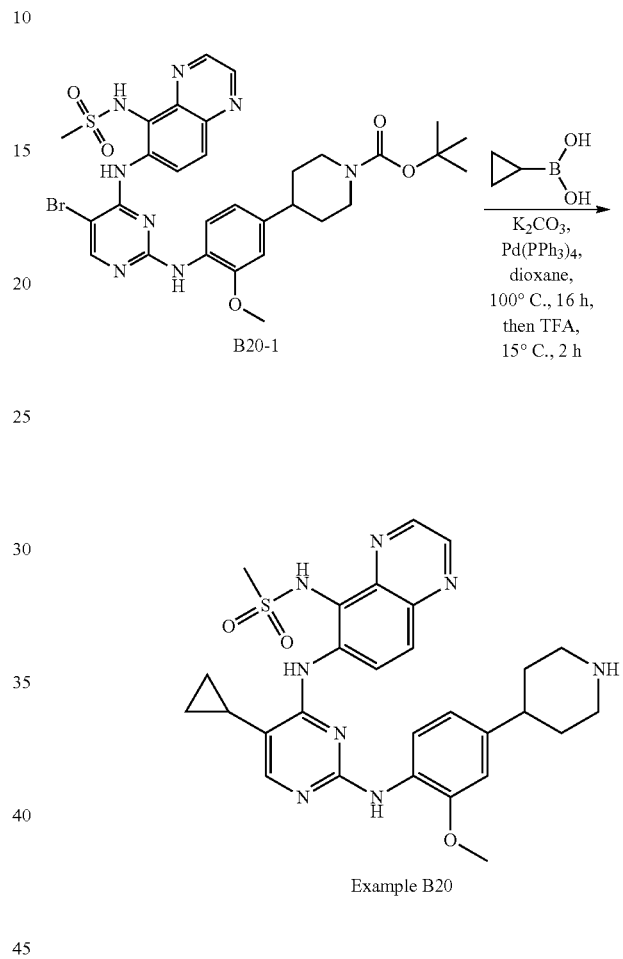

Example B20

To a mixture of compound B2-1 (50 mg, 0.18 mmol) and compound B19-1 (70 mg, 0.15 mmol) in n-butanol (2 mL) was added TFA (228 mg, 2.00 mmol) and the mixture was stirred at 80° C. for 13 h. The reaction was monitored by LC-MS. The mixture was filtered and the filtrate was concentrated under reduced pressure. The residue was purified by prep-HPLC to afford Example B19 as a yellow solid.

$^1$H NMR (400 MHz, CDCl$_3$) δ 1.20 (3H, t, J=7.2 Hz), 1.90-1.99 (2H, m), 2.20-2.29 (2H, m), 2.55-2.65 (2H, m), 2.76-2.86 (8H, m), 3.13-3.22 (6H, m), 3.28 (3H, s), 3.75 (3H, s), 3.89 (3H, s), 6.64 (1H, s), 7.61 (1H, s), 7.74 (1H, d, J=9.2 Hz), 8.01-8.19 (2H, m), 8.35 (1H, s), 8.82-8.92 (2H, m).

To a mixture of compound B20-1 (250 mg), cyclopropylboronic acid (184 mg, 2.14 mmol) and K$_2$CO$_3$ (148 mg, 1.07 mmol) in dioxane (5 mL) was added Pd(PPh$_3$)$_4$ (41 mg, 0.036 mmol, 10 mol %). The mixture was then stirred at 100° C. for 16 h under N$_2$ atmosphere, To this mixture was added TFA (5 mL) and the mixture was stirred at 15° C. for 2 h. The reaction was monitored by LC-MS. The mixture was filtered and the filtrate was concentrated under reduced pressure. The remaining residue was purified by prep-HPLC to afford Example B20 as a yellow solid.

$^1$H NMR (400 MHz, CDCl$_3$) δ 0.65-0.72 (2H, m), 1.10-1.18 (2H, m), 1.69-1.76 (1H, m), 1.96-2.24 (4H, m), 2.65-2.79 (1H, m), 2.94 (3H, s), 2.97-3.08 (2H, m), 3.52-3.63 (2H, m), 3.88 (3H, s), 6.68-6.72 (1H, m), 6.74-6.78 (1H, m), 7.97-8.00 (1H, m), 8.00-8.11 (3H, m), 8.80-8.83 (1H, m), 8.85-8.89 (1H, m), 8.96 (1H, d, J=9.6 Hz), 9.32 (1H, s). LC-MS: MS Calculated 560.2, MS Found 561.2 [M+H]$^+$.

[Example B21] Preparation of N-(6-((5-chloro-2-((5-fluoro-2-methoxy-4-(piperidin-4-yl)phenyl)amino)pyrimidin-4-yl)amino)quinoxalin-5-yl)methanesulfonamide

[Example B22] Preparation of N-(6-((5-chloro-2-((2-isopropoxy-4-(piperidin-4-yl)phenyl)amino)pyrimidin-4-yl)amino)103quinoxaline-5-yl)methanesulfonamide

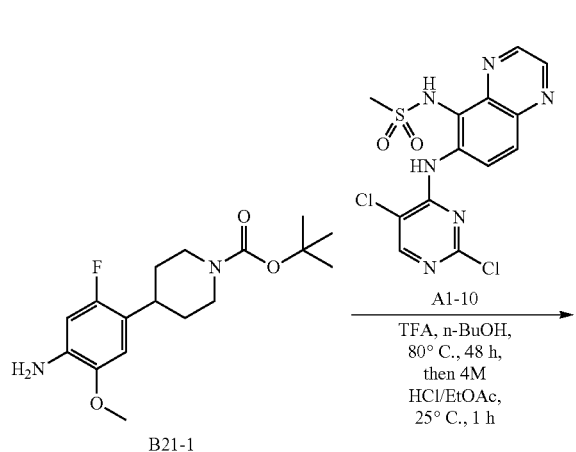

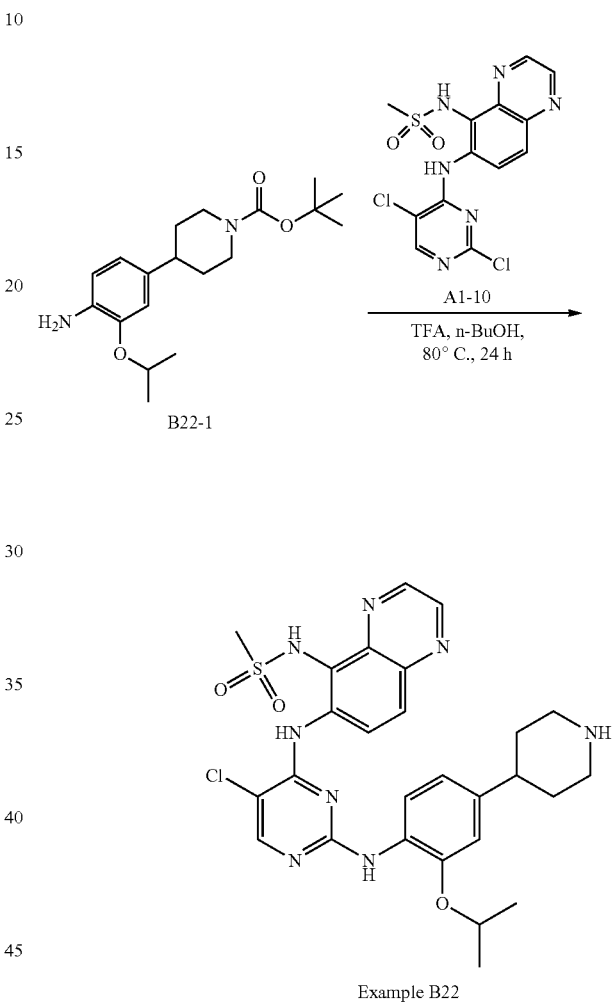

To a mixture of compound B21-1 (150 mg, 0.462 mmol) and compound A1-10 (178 mg, 0.462 mmol) in n-butanol (5 mL) was added TFA (632 mg, 5.55 mmol). The resulting mixture was stirred at 80° C. for 48 h. To the above mixture was added 4 M HCl/EtOAc (3 mL), and the mixture was stirred at 25° C. for 1 h. The reaction was monitored by LC-MS. The reaction mixture was concentrated under reduced pressure to be purified by prep-HPLC to provide Example B21 as a yellow solid.

$^1$H NMR (400 MHz, CDCl$_3$) δ 1.73-1.97 (4H, m), 2.86-2.96 (5H, m), 3.98-3.06 (1H, m), 3.33-3.49 (2H, m), 3.84-3.88 (3H, s), 6.68 (1H, d, J=6.4 Hz), 7.61 (1H, s), 8.02 (1H, d, J=12.8 Hz), 8.16-8.22 (2H, m), 8.72 (1H, d, J=9.2 Hz), 8.85 (1H, d, J=2.0 Hz), 8.93 (1H, d, J=2.0 Hz), 9.29 (1H, s).

LC-MS: MS Calculated 572.2, MS Found 573.2 [M+H]$^+$.

To a mixture of compound B22-1 (150 mg, 0.448 mmol) and compound A1-10 (172 mg, 0.448 mmol) in n-butanol (5 mL) was added TFA (664 mg, 5.83 mmol) at 25° C. and the mixture was stirred at 80° C. for 24 h. The reaction was monitored by LC-MS. The reaction mixture was concentrated under reduced pressure to be purified by prep-HPLC to afford Example B22 as a yellow solid.

$^1$H NMR (400 MHz, DMSO-d$_6$) δ 1.24 (6H, d, J=6.0 Hz), 1.70-1.89 (4H, m), 2.69-2.79 (1H, m), 2.84-2.92 (2H, m), 2.99 (3H, s), 3.22-3.34 (2H, m), 4.54-4.65 (1H, m), 6.65 (1H, d, J=8.0 Hz), 6.89 (1H, s), 7.74 (1H, d, J=8.4 Hz), 7.85 (1H, d, J=9.2 Hz), 8.01 (1H, s), 8.23 (1H, s), 8.38 (1H, s), 8.71 (1H, d, J=9.2 Hz), 8.88 (1H, d, J=1.2 Hz), 8.95 (1H, d, J=1.2 Hz), 9.21 (1H, s).

LC-MS: MS Calculated 582.2, MS Found: 583.3 [M+H]$^+$.

[Example B23] Preparation of N-(6-((5-chloro-2-((2-methoxy-4-(1-methylpiperidin-4-yl)phenyl)amino)pyrimidin-4-yl)amino)quinoxalin-5-yl)methanesulfonamide

[Example B24] Preparation of N-(6-((5-bromo-2-((4-(4-(dimethylamino)piperidin-1-yl)-2-methoxy-5-propylphenyl)amino)pyrimidin-4-yl)amino)quinoxalin-5-yl)-N-methylmethanesulfonamide

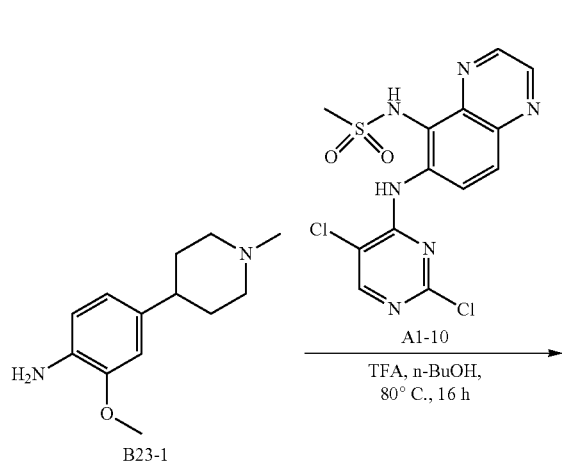

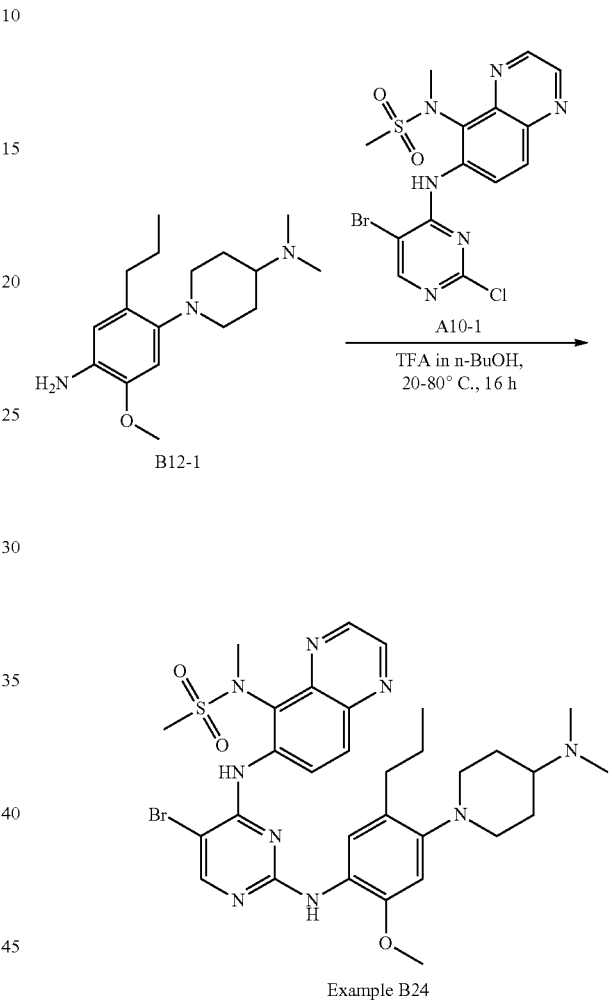

To a mixture of compound B23-1 (180 mg, 0.817 mmol) and compound A1-10 (210 mg, 0.545 mmol) in n-butanol (4 mL) was added TFA (462 mg, 4.05 mmol) at 15° C. The resulting mixture was stirred at 80° C. for 16 h. The reaction was monitored by LC-MS. The reaction mixture was filtered and the filtrate was concentrated under reduced pressure to be purified by prep-HPLC to afford Example B23 as a yellow solid.

$^1$H NMR (400 MHz, CDCl$_3$) δ 1.88-1.98 (2H, m), 2.12-2.29 (2H, m), 2.46-2.73 (6H, m), 2.94 (3H, s), 3.22-3.46 (2H, m), 3.88 (3H, s), 6.67 (1H, d, J=8.0 Hz), 6.77 (1H, s), 7.52 (1H, s), 8.03-8.13 (2H, m), 8.17 (1H, s), 8.79 (1H, d, J=9.2 Hz), 8.85 (1H, d, J=1.2 Hz), 8.91 (1H, d, J=1.2 Hz), 9.24 (1H, s).

LC-MS: MS Calculated 568.2, MS Found: 569.2 [M+H]$^+$.

To a mixture of compound A10-1 (100 mg, 0.225 mmol) and compound B12-1 (79 mg, 0.27 mmol) in n-butanol (4 mL) was added TFA (456.09 mg, 4 mmol) at 20° C., and then the mixture was stirred at 80° C. for 16 h. The mixture was concentrated under reduced pressure and the residue was purified by prep-HPLC to afford Example B24 as a yellow solid.

$^1$H NMR (400 MHz, DMSO-d$_6$) δ 0.55-0.85 (3H, m), 1.24-1.39 (2H, m), 1.46-1.58 (2H, m), 1.83-1.93 (2H, m), 2.17-2.25 (7H, m), 2.32-2.43 (2H, m), 2.65-2.76 (2H, m), 2.93-3.05 (2H, m), 3.22 (3H, s), 3.42-3.51 (3H, m), 3.75 (3H, s), 6.80 (1H, s), 7.36 (1H, s), 7.90 (1H, d, J=9.2 Hz), 8.30 (1H, s), 8.35 (1H, s), 8.56 (1H, s), 8.70-8.87 (1H, m), 8.90-8.94 (1H, m), 8.95-9.01 (1H, m).

[Example B25] Preparation of N-(6-((5-chloro-2-((5-ethyl-4-(5-isopropyl-2,5-diazabicyclo[2.2.2]octan-2-yl)-2-methoxyphenyl)amino)pyrimidin-4-yl)amino) quinoxaline-5-yl)methanesulfonamide

[Example B26] Preparation of N-(6-((5-chloro-2-((5-ethyl-4-(6-isopropyl-2,6-diazaspiro[3.3]heptan-2-yl)-2-methoxyphenyl)amino)pyrimidin-4-yl)amino)quinoxalin-5-yl)methanesulfonamide

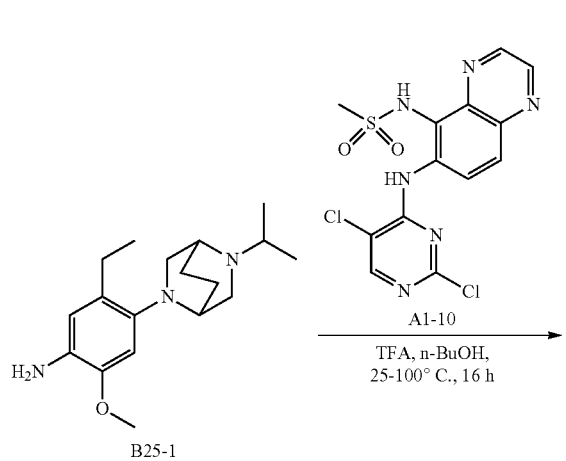

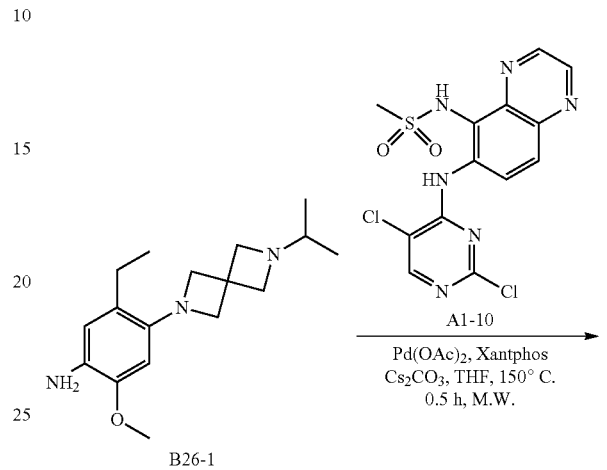

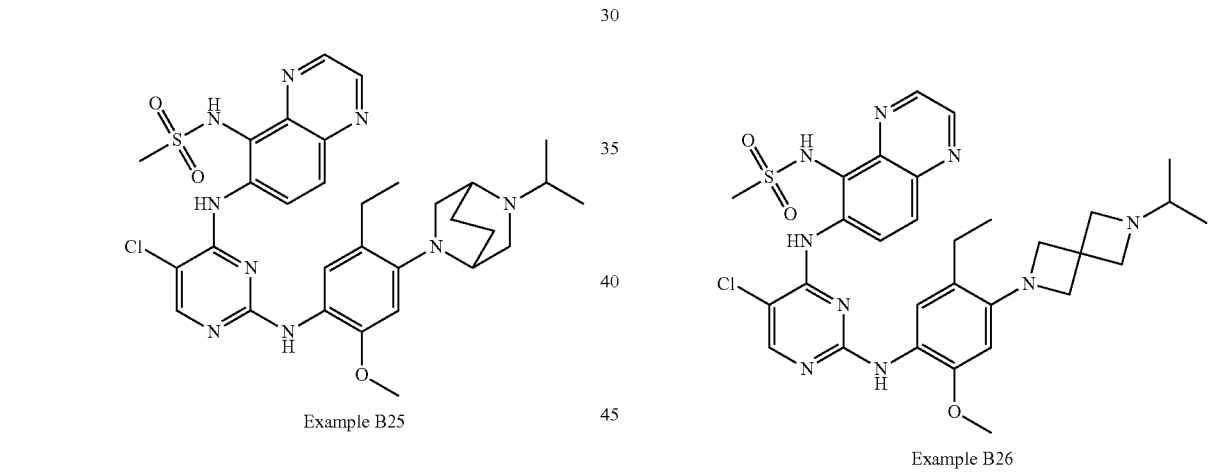

To a mixture of compound B25-1 (100 mg, 0.329 mmol) and compound A1-10 (106 mg, 0.275 mmol) in n-butanol (4 mL) was added TFA (456 mg, 4.00 mmol) at 25° C., and the mixture was stirred at 100° C. for 16 h. The mixture was concentrated under reduced pressure and the residue was purified by prep-HPLC to afford Example B25 as a yellow solid.

$^1$H NMR (400 MHz, DMSO-$d_6$) δ 0.69-0.92 (3H, m), 1.03-1.25 (6H, m), 1.63-1.80 (2H, m), 2.04-2.14 (2H, m), 2.31-2.58 (3H, m), 2.72-2.91 (2H, m), 2.93 (3H, s), 3.01-3.10 (1H, m), 3.13-3.27 (2H, m), 3.54-3.75 (1H, m), 3.86 (3H, s), 6.67-6.87 (1H, m), 7.29-7.38 (1H, m), 7.78-7.90 (1H, m), 8.04 (1H, d, J=9.6 Hz), 8.16 (1H, s), 8.80 (1H, d, J=9.2 Hz), 8.83 (1H, d, J=1.6 Hz), 8.86-8.89 (1H, m), 9.18 (1H, s). LC-MS: MS Calculated 651.3, MS Found 652.1 [M+H]$^+$.

To a mixture of compound B26-1 (100 mg, 0.346 mmol) and compound A1-10 (133 mg, 0.346 mmol) in THF (3 mL) were added Xantphos (40 mg, 20 mol %), Pd(Oac)$_2$ (8 mg, 10 mol %) and Cs$_2$CO$_3$ (338 mg, 1.04 mmol) at 25° C., and then the mixture was stirred at 150° C. for 30 min under microwave irradiation. The mixture was concentrated under reduced pressure to be purified by prep-HPLC to afford Example B26 as a yellow solid.

$^1$H NMR (400 MHz, CDCl$_3$) δ 0.84-0.95 (3H, m), 0.96 (6H, d, J=6.4 Hz), 2.25-2.41 (3H, m), 2.93 (3H, s), 3.38 (4H, s), 3.83 (3H, s), 3.95 (4H, s), 6.06 (1H, s), 7.18 (1H, s), 7.67 (1H, s), 8.01 (1H, d, J=9.2 Hz), 8.14 (1H, s), 8.71-8.82 (2H, m), 8.87 (1H, d, J=1.6 Hz), 9.15 (1H, s). LC-MS: MS Calculated 637.2, MS Found 638.2 [M+H]$^+$.

[Example B27] Preparation of N-(6-((5-chloro-2-((5-ethyl-4-(6-isopropyl-2,6-diazaspiro[3.3]heptan-2-yl)-2-methoxyphenyl)amino)pyrimidin-4-yl)amino)quinoxalin-5-yl)-N-methylmethanesulfonamide

[Example B28] Preparation of N—N-(6-((5-chloro-2-((5-ethyl-4-(5-isopropyl-2,5-diazabicyclo[2.2.2]octan-2-yl)-2-methoxyphenyl)amino)pyrimidin-4-yl)amino)quinoxalin-5-yl)-N-methylmethanesulfonamide

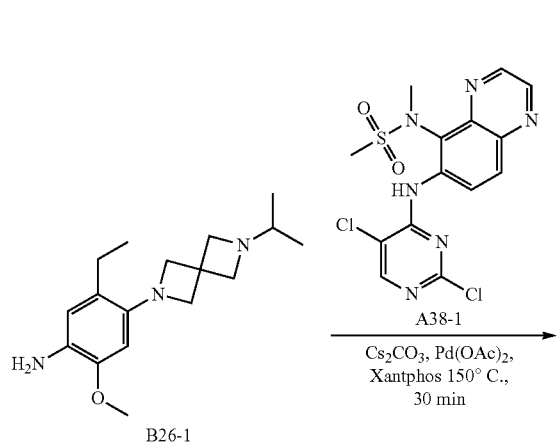

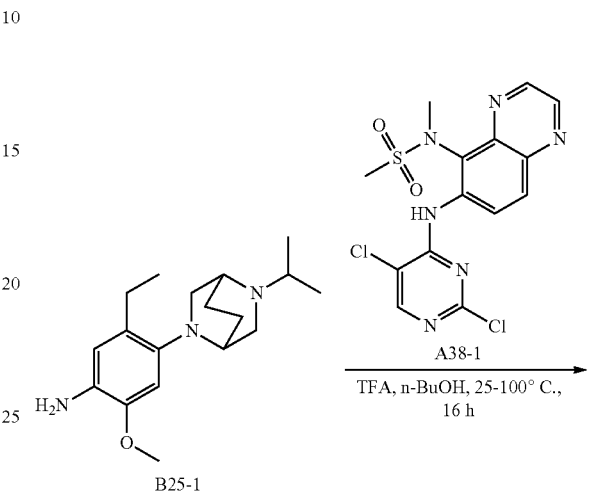

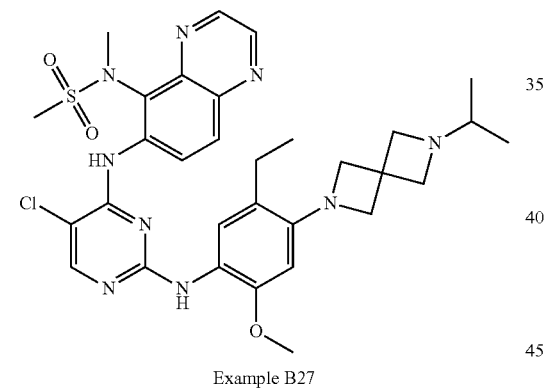

Example B27

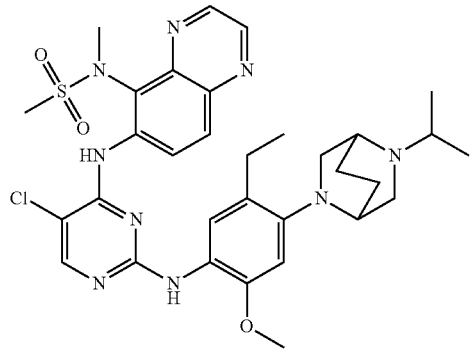

Example B28

A mixture of compound B26-1 (100 mg, 0.34 mmol), compound A38-1 (138 mg, 0.35 mmol), Xantphos (40 mg, 0.07 mmol, 20 mol %), Pd(Oac)$_2$ (8 mg, 0.03 mmol, 10 mol %) and Cs$_2$CO$_3$ (337 mg, 1.04 mmol) in THF (3 mL) was stirred at 150° C. for 30 min under microwave condition. The reaction mixture was concentrated under reduced pressure and the residue was purified by Combi Flash and then prep-HPLC to afford Example B27 as a white solid.

$^1$H NMR (400 MHz, DMSO-d$_6$) δ 0.85 (6H, d, J=6.0 Hz), 0.96 (3H, t, J=7.2 Hz), 2.23-2.29 (1H, m), 2.32-2.38 (2H, m), 3.23 (3H, s), 3.28 (3H, s), 3.59 (4H, s), 3.73 (3H, s), 3.92 (4H, s), 6.16 (1H, s), 7.09 (1H, s), 7.80-7.90 (1H, m), 8.19 (1H, s), 8.34 (1H, s), 8.56 (1H, s), 8.80-8.86 (1H, m), 8.90 (1H, d, J=2.0 Hz), 8.96 (1H, d, J=2.0 Hz). LC-MS: MS Calculated 651.3, MS Found 652.3 [M+H]$^+$.

To a mixture of compound A38-1 (143 mg, 0.357 mmol) and compound B25-1 (130 mg, 0.428 mmol) in n-butanol (4 mL) was added TFA (456 mg, 4.00 mmol) at 25° C., and the mixture was stirred at 100° C. for 16 h. The mixture was concentrated under reduced pressure to be purified by prep-HPLC to afford Example B28 as a black solid.

$^1$H NMR (400 MHz, CD$_3$OD) δ 0.47-1.26 (3H, m), 1.46-1.52 (6H, m), 1.84-1.98 (1H, m), 2.05-2.15 (1H, m), 2.18-2.42 (4H, m), 3.16 (3H, s), 3.43-3.53 (4H, m), 3.57-3.72 (2H, m), 3.79-4.11 (7H, m), 6.86-7.07 (1H, m), 7.27 (1H, s), 7.75-8.53 (3H, m), 8.98 (1H, d, J=1.6 Hz), 9.03 (1H, d, J=2.0 Hz)

LC-MS: MS Calculated 665.3, MS Found 666.2 [M+H]$^+$.

[Example B29] Preparation of N-(6-((5-bromo-2-((5-ethyl-4-(6-isopropyl-2,6-diazaspiro[3.3]heptan-2-yl)-2-methoxyphenyl)amino)pyrimidin-4-yl)amino)quinoxalin-5-yl)-N-methylmethanesulfonamide

[Example B30] Preparation of N-(6-((5-bromo-2-((5-ethyl-4-(5-isopropyl-2,5-diazabicyclo[2.2.2]octan-2-yl)-2-methoxyphenyl)amino)pyrimidin-4-yl)amino)quinoxalin-5-yl)-N-methylmethanesulfonamide

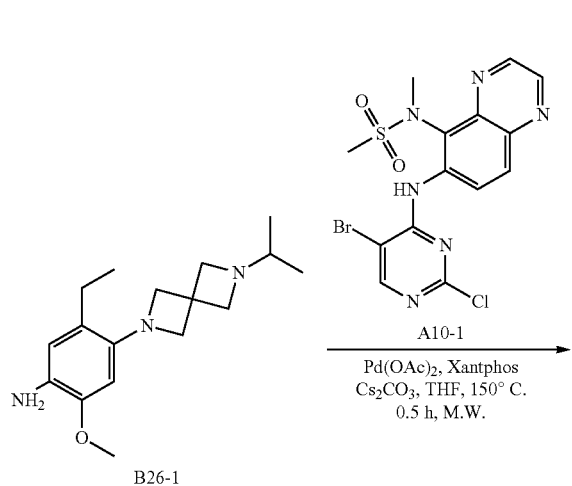
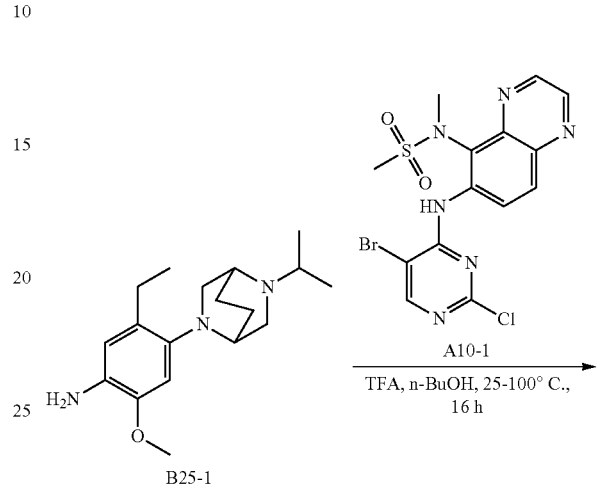

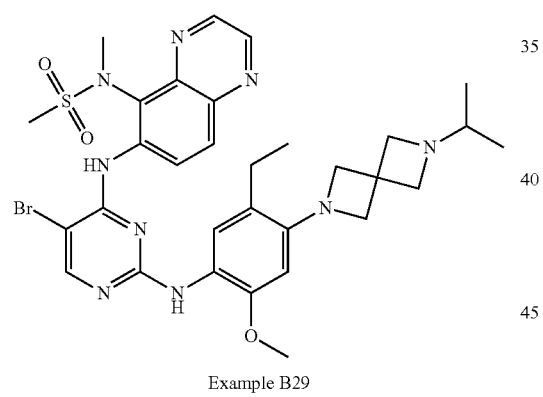

Example B29

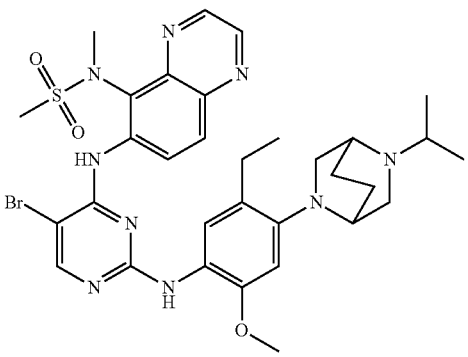

Example B30

To a mixture of compound A10-1 (153 mg, 0.350 mmol) and compound B26-1 (100 mg, 0.350 mmol) in THF (3 mL) were added Xantphos (40 mg, 20 mol %), Pd(Oac)$_2$ (8 mg, 10 mol %) and Cs$_2$CO$_3$ (338 mg, 1.04 mmol) at 25° C., and then the mixture was stirred at 150° C. for 30 min under N$_2$. The reaction mixture was concentrated under reduced pressure and purified by Combi Flash, and then prep-HPLC to afford Example B29 as a yellow solid.

$^1$H NMR (400 MHz, CDCl$_3$) δ 0.91.02 (9H, m), 1.75-2.25 (3H, m), 3.19 (3H, s), 3.44 (4H, s), 3.49 (4H, s), 3.85 (3H, s), 3.98 (4H, s), 6.09 (1H, s), 7.15 (1H, s), 7.72 (1H, s), 8.04 (1H, d, J=9.2 Hz), 8.24 (1H, s), 8.71-8.85 (3H, m), 9.03 (1H, d, J=9.6 Hz).

To a mixture of compound B25-1 (158 mg, 0.357 mmol) and compound A10-1 (130 mg, 0.428 mmol) in n-butanol (4 mL) was added TFA (456 mg, 4.00 mmol) at 25° C., and the mixture was stirred at 100° C. for 16 h. The mixture was concentrated under reduced pressure and purified by prep-HPLC to afford Example B30 as a black solid.

$^1$H NMR (400 MHz, CD$_3$OD) δ 0.56-1.33 (3H, m), 1.47-1.55 (6H, m), 1.83-2.00 (1H, m), 2.03-2.19 (1H, m), 2.23-2.52 (4H, m), 3.19 (3H, s), 3.42-3.58 (4H, m), 3.60-3.75 (2H, m), 3.78-4.12 (7H, m), 6.87-7.13 (1H, m), 7.28 (1H, s), 7.69-8.89 (3H, m), 8.99 (1H, d, J=1.6 Hz), 9.03 (1H, d, J=1.6 Hz)

LC-MS: MS Calculated 709.2, MS Found 710.2 [M+H]$^+$.

[Example B31] Preparation of N-(6-((5-bromo-2-((5-ethyl-4-(1-isopropyl-1,6-diazaspiro[3.3]heptan-6-yl)-2-methoxyphenyl)amino)pyrimidin-4-yl)amino)quinoxalin-5-yl)-N-methylmethanesulfonamide

[Example B32] Preparation of N-(6-((5-bromo-2-((5-ethyl-2-isopropoxy-4-(1-methylpiperidin-4-yl)phenyl)amino)pyrimidin-4-yl)amino)quinoxalin-5-yl)-N-methylmethanesulfonamide (Step 1) Preparation of N-(6-((5-bromo-2-((5-ethyl-2-isopropoxy-4-(piperidin-4-yl)phenyl)amino)pyrimidin-4-yl)amino)quinoxalin-5-yl)-N-methylmethanesulfonamide

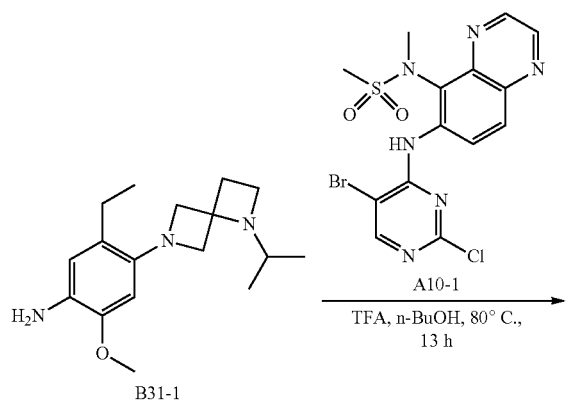

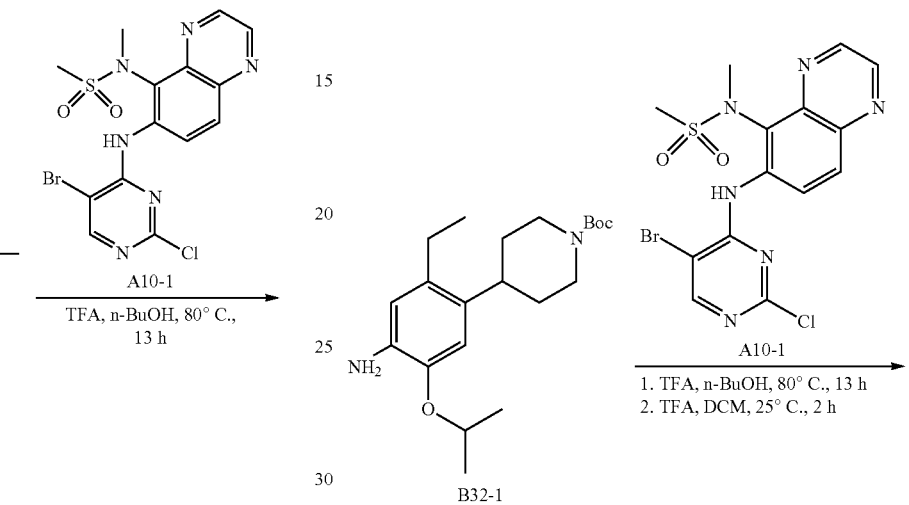

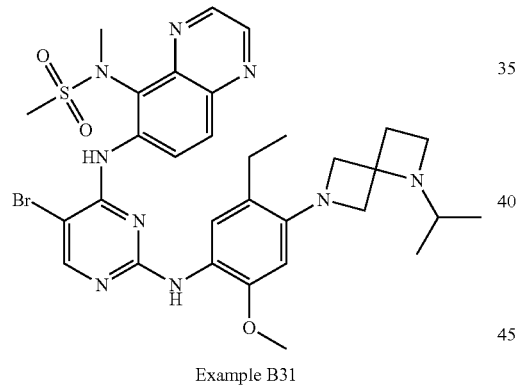

Example B31

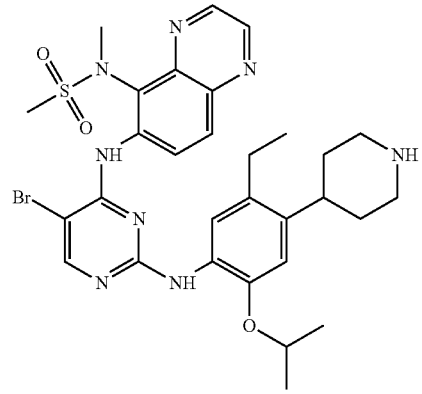

B32-2

To a mixture of compound B31-1 (100 mg, 0.346 mmol) and compound A10-1 (128 mg, 0.288 mmol) in n-butanol (2 mL) was added TFA (326 mg, 2.86 mmol), and then the mixture was stirred at 80° C. for 13 h. The reaction mixture was concentrated under reduced pressure. The residue was basified by NH$_4$OH (pH=7) and was purified by prep-HPLC to afford Example B31 as a yellow solid.

$^1$H NMR (400 MHz, CDCl$_3$) δ 0.98 (3H, t, J=7.2 Hz), 1.10 (6H, d, J=6.0 Hz), 2.33 (2H, t, J=6.4 Hz), 2.41-2.51 (2H, m), 2.76-2.84 (1H, m), 3.15-3.19 (5H, m), 3.48 (3H, s), 3.52 (3H, s) 3.902-3.94 (2H, m), 4.23 (2H, m), 6.10 (1H, s), 7.15 (1H, s), 7.73 (1H, s), 8.04 (1H, d, J=9.6 Hz), 8.23 (1H, s), 8.77 (1H, s), 8.80 (2H, m), 9.04 (1H, d, J=9.6 Hz).

LC-MS: MS Calculated 695.2, MS Found 696.2 [M+H]$^+$.

To a mixture of compound B32-1 (260 mg, 0.717 mmol) and A10-1 (318 mg, 0.717 mmol) in n-butanol (8 mL) was added TFA (981 mg, 8.61 mmol) at 25° C., and then it was stirred at 80° C. for 13 h. The reaction mixture was concentrated under reduced pressure. The residue was dissolved in DCM (4 mL) and was added TFA (1 mL) at 25° C., and then it was stirred at 25° C. for 2 h. The reaction mixture was concentrated under reduced pressure and purified by Combi Flash to afford compound B32-2 as a yellow oil.

$^1$H NMR (400 MHz, CDCl$_3$) δ 0.90-1.00 (3H, m), 1.30-1.34 (6H, m), 1.85-1.97 (2H, m), 2.07-2.17 (2H, m), 2.45-2.54 (2H, m), 2.92-2.99 (1H, m), 3.02-3.09 (2H, m), 3.16 (3H, s), 3.49 (3H, s), 3.54-3.62 (2H, m), 4.55-4.62 (1H, m), 6.75 (1H, s), 6.86 (1H, s), 7.68 (1H, s), 7.96 (1H, d, J=9.2 Hz), 8.20 (1H, s), 8.79 (1H, d, J=9.2 Hz), 8.82-8.90 (2H, m), 9.09 (1H, s)

(Step 2) Preparation of N-(6-((5-bromo-2-((5-ethyl-2-isopropoxy-4-(1-methylpiperidin-4-yl)phenyl)amino)pyrimidin-4-yl)amino)quinoxalin-5-yl)-N-methylmethanesulfonamide

[Example C1] Preparation of N-(2-((5-bromo-2-((2-methoxy-5-methyl-4-(4-(4-methylpiperazin-1-yl)piperidin-1-yl)phenyl)amino)pyrimidin-4-yl)amino)-6-methoxyphenyl)methanesulfonamide

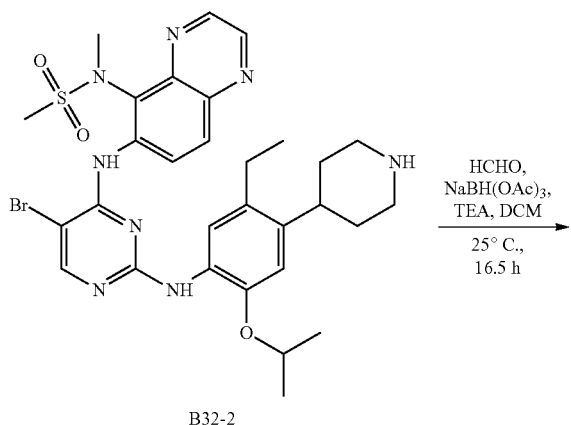

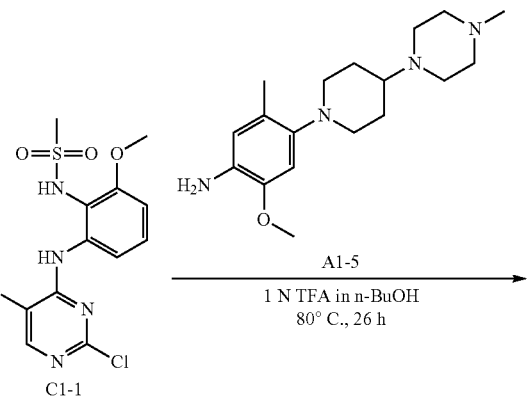

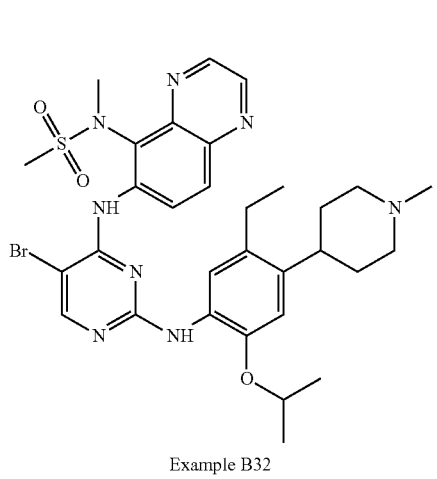

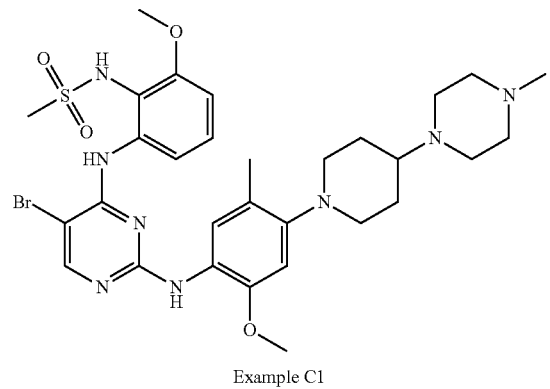

To a mixture of compound B32-2 (180 mg, 0.268 mmol) in DCM (5 mL) was added TEA (54.4 mg, 0.537 mmol) at 25° C., it was stirred at 25° C. for 0.5 h. To a mixture were added HCHO (12.1 mg, 0.403 mmol, 37% purity in H$_2$O) and NaBH(OAc)$_3$ (74.0 mg, 0.349 mmol) at 0° C., and then it was stirred at 25° C. for 16 h. The reaction mixture was concentrated under reduced pressure and purified by prep-HPLC to afford Example B32 as a yellow solid.

$^1$H NMR (400 MHz, CDCl$_3$) δ 0.83-0.97 (3H, m), 1.29-1.40 (6H, m), 1.81-2.05 (2H, m), 2.37-2.52 (2H, m), 2.57-2.71 (2H, m), 2.85 (3H, s), 2.87-3.04 (2H, m), 3.14 (3H, s), 3.49 (3H, s), 3.66 (2H, s), 4.55-4.78 (1H, m), 6.99 (1H, s), 7.52 (1H, br s), 7.95 (1H, d, J=9.6 Hz), 8.13 (1H, s), 8.65 (1H, d, J=8.8 Hz), 8.88-8.95 (2H, m), 9.35 (2H, s), 12.56 (1H, s).

To a mixture of compound C1-1 (100 mg, 0.245 mmol) and compound A1-5 (78 mg, 0.24 mmol) in n-butanol (4.0 mL) was added TFA (456 mg, 4.00 mmol). It was stirred at 80° C. for 26 h which was monitored by LC-MS. The reaction mixture was concentrated under reduced pressure to give a residue that was purified by prep-HPLC to afford Example C1 as a purple solid.

$^1$H NMR (400 MHz, DMSO-d$_6$) δ 1.58-1.71 (2H, m), 1.82-1.95 (2H, m), 2.11 (3H, s), 2.20 (3H, s), 2.25-2.48 (6H, m), 2.53-2.68 (5H, m), 2.97 (3H, s), 3.03-3.15 (2H, m), 3.75 (3H, s), 3.85 (3H, s), 6.69 (1H, s), 7.17 (1H, t, J=8.4 Hz), 7.45 (1H, s), 7.75-7.85 (2H, m), 8.03 (1H, s), 8.19 (1H, s), 8.22 (1H, s), 8.42 (1H, s).

[Example C2] Preparation of N-(2-((5-bromo-2-((2-methoxy-5-methyl-4-(4-(4-methylpiperazin-1-yl)piperidin-1-yl)phenyl)amino)pyrimidin-4-yl)amino)-5-methoxyphenyl)methanesulfonamide

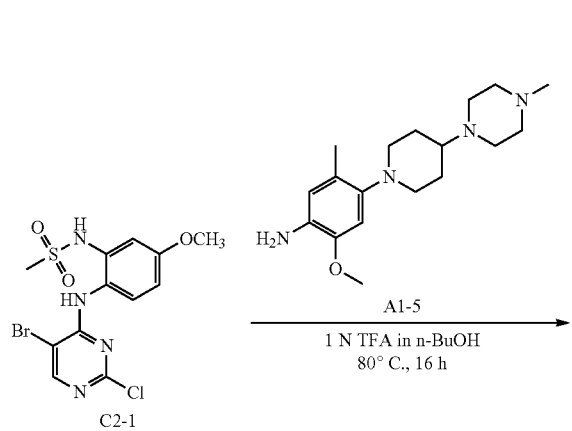

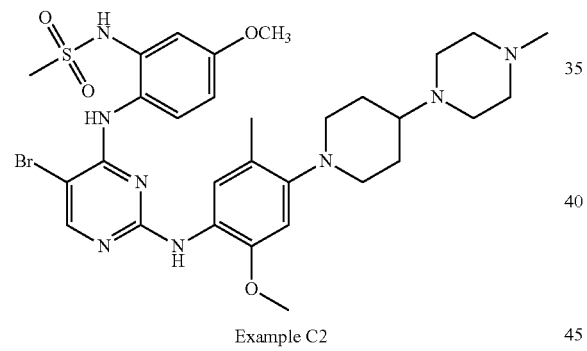

Example C2

[Example C3] Preparation of N-(2-((5-bromo-2-((4-(4-(dimethylamino)piperidin-1-yl)-2-methoxy-5-methylphenyl)amino)pyrimidin-4-yl)amino)-6-methoxyphenyl)methanesulfonamide

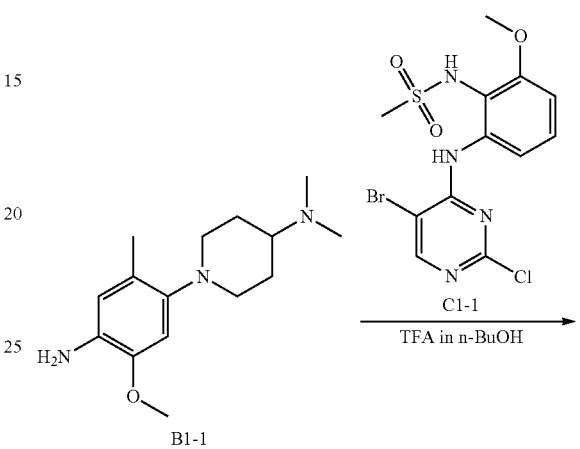

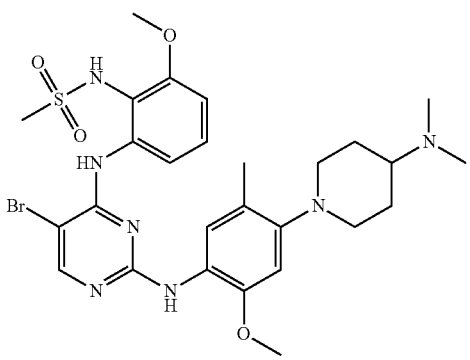

Example C3

To a solution of TFA (650 mg, 5.70 mmol) in n-butanol (5 mL) were added compound C2-1 (100 mg, 0.245 mmol) and compound A1-5 (78 mg, 0.25 mmol). The mixture was stirred at 80° C. for 16 h under $N_2$. The reaction was monitored by LC-MS. The reaction mixture was concentrated under reduced pressure to give a residue that was purified by prep-HPLC to afford Example C2 as a white solid.

$^1$H NMR (400 MHz, CDCl$_3$) δ 1.65-1.70 (2H, m), 1.89-1.93 (2H, m), 1.97 (3H, s), 2.31-2.33 (4H, m), 2.55-2.65 (10H, m), 2.81 (3H, s), 3.05-3.09 (2H, m), 3.81 (3H, s), 3.87 (3H, s), 6.53 (1H, s), 6.80-6.87 (2H, m), 7.21 (1H, s), 7.27-7.35 (2H, m), 7.57 (1H, s), 8.14 (1H, s).

LC-MS: MS Calculated 688.2, MS Found 689.2 [M+H]$^+$.

To a mixture of compound B1-1 (45 mg, 0.17 mmol) and compound C1-1 (70 mg, 0.17 mmol) in n-butanol (3 mL) was added TFA (447 mg, 3.92 mmol) at 25° C. and the mixture was stirred at 80° C. for 26 h. The reaction was monitored by LC-MS. The reaction mixture was concentrated under reduced pressure and purified by prep-HPLC to afford Example C3 as a red solid.

$^1$H NMR (400 MHz, CDCl$_3$) δ 1.72 (2H, m), 1.95-1.98 (2H, m), 2.14 (3H, s), 2.41 (7H, m), 2.61-2.66 (2H, m), 3.00 (3H, s), 3.08-3.20 (2H, m), 3.84 (3H, s), 3.94 (3H, s), 6.60 (1H, s), 6.77 (1H, d, J=8.4 Hz), 7.31-7.36 (2H, m), 7.93 (1H, d, J=7.6 Hz), 7.96 (1H, s), 8.16 (1H, s), 8.58 (1H, s).

[Example C4] Preparation of N-(2-((5-chloro-2-((4-(4-(dimethylamino)piperidin-1-yl)-2-methoxy-5-methylphenyl)amino)pyrimidin-4-yl)amino)-5-methoxyphenyl)methanesulfonamide

[Example C5] Preparation of N-(2-((5-bromo-2-((4-(4-(dimethylamino)piperidin-1-yl)-2-methoxy-5-methylphenyl)amino)pyrimidin-4-yl)amino)-6-methoxyphenyl)-N-methylmethanesulfonamide

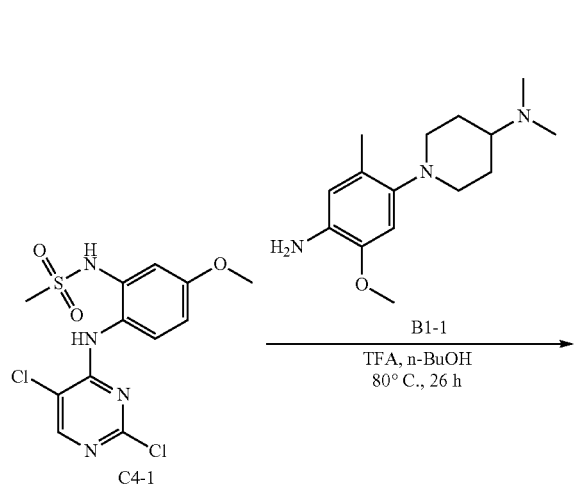

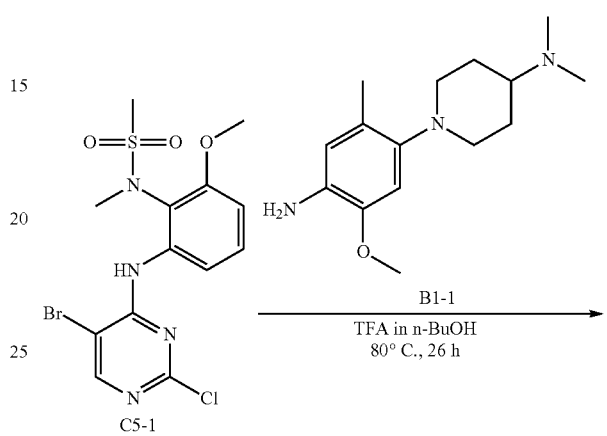

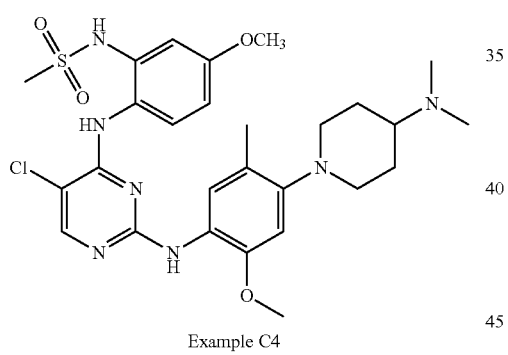

Example C4

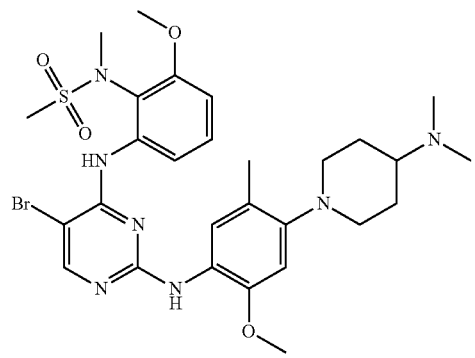

Example C5

To a mixture of compound C4-1 (100 mg, 0.275 mmol) and compound B1-1 (73 mg, 0.28 mmol) in n-butanol (4 mL) was added TFA (456 mg, 4.00 mmol) at 25° C. and the mixture was stirred at 80° C. for 26 h which was monitored by LC-MS. The reaction mixture was concentrated under reduced pressure to be purified by prep-HPLC to afford Example C4 as a white solid.

$^1$H NMR (400 MHz, DMSO-$d_6$) δ 1.51-1.62 (2H, m), 1.81-1.93 (2H, m), 1.99 (3H, s), 2.31 (6H, s), 2.34-2.44 (1H, m), 2.55-2.65 (2H, m), 2.85 (3H, s), 2.98-3.10 (2H, m), 3.75 (3H, s), 3.76 (3H, s), 6.65 (1H, s), 6.67-6.75 (1H, m), 6.96 (1H, d, J=2.8 Hz), 7.49 (1H, s), 7.55-7.70 (2H, m), 8.04 (1H, s), 8.49 (1H, s). LC-MS: MS Calculated 589.2, MS Found 590.4 [M+H]$^+$.

To a mixture of compound C5-1 (100 mg, 0.237 mmol) and compound B1-1 (81 mg, 0.31 mmol) in n-butanol (3 mL) was added TFA (445 mg, 3.90 mmol) and the mixture was stirred at 80° C. for 26 h. The reaction was monitored by LC-MS. The reaction mixture was concentrated under reduced pressure. The remaining residue was purified by prep-HPLC to afford Example C5 as an off-red solid.

$^1$H NMR (400 MHz, CDCl$_3$) δ 1.57-1.75 (2H, m), 1.85-2.00 (2H, m), 2.20 (3H, s), 2.21-2.35 (1H, m), 2.36 (6H, s), 2.61-2.66 (2H, m), 3.02 (3H, s), 3.12-3.15 (2H, m), 3.25 (3H, s), 3.85 (3H, s), 3.93 (3H, s), 6.62 (1H, s), 6.73 (1H, d, J=7.6 Hz), 7.28-7.35 (2H, m), 8.02 (1H, s), 8.09 (1H, d, J=7.6 Hz), 8.17 (1H, s), 8.36 (1H, s).

[Example C6] Preparation of N-(2-((5-chloro-2-((2-methoxy-4-(piperazin-1-yl)phenyl)amino)pyrimidin-4-yl)amino)-6-methoxyphenyl)methanesulfonamide

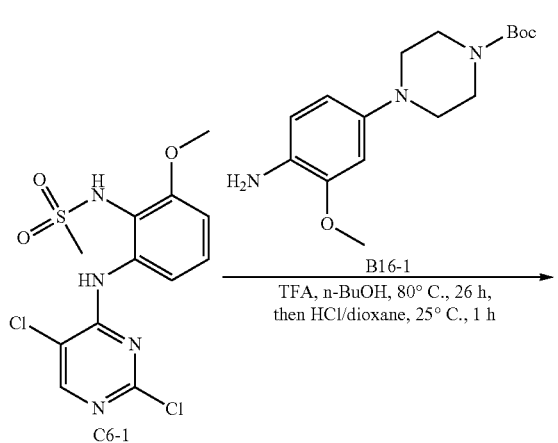

[Example C7] Preparation of N-(2-((5-bromo-2-((5-ethyl-2-methoxy-4-(4-(4-methylpiperazin-1-yl)piperidin-1-yl)phenyl)amino)pyrimidin-4-yl)amino)-6-methoxyphenyl)-N-methylmethane sulfonamide

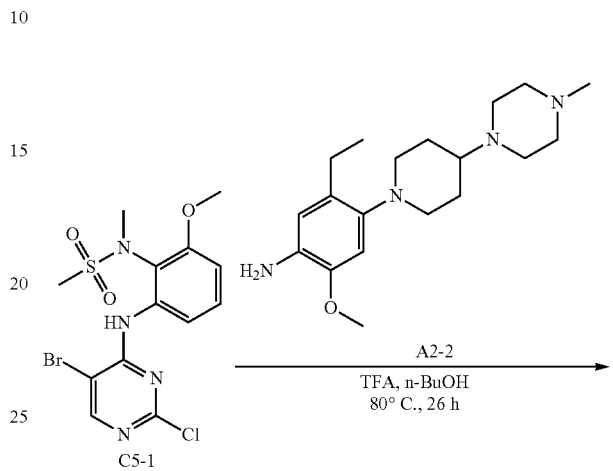

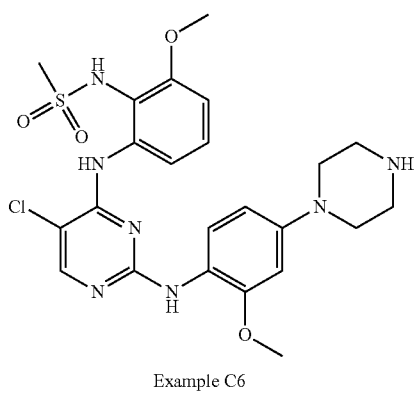

Example C6

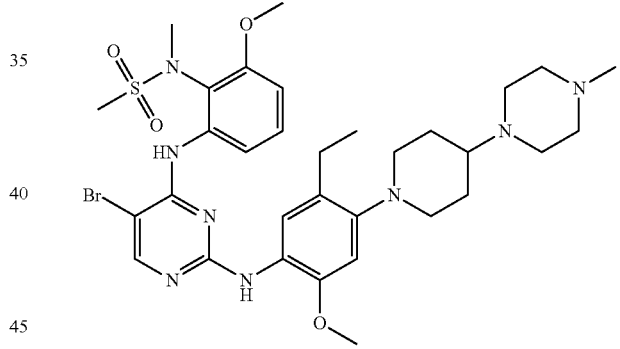

Example C7

To a mixture of compound C6-1 (68 mg, crude) and B16-1 (58 mg, 0.19 mmol) in n-butanol (3 mL) was added TFA (342 mg, 3.00 mmol) and the mixture was stirred at 80° C. for 26 h. To this mixture was added 4 M HCl/dioxane (5 mL) and the mixture was stirred at 25° C. for 1 h. The reaction was monitored by LC-MS. The mixture was concentrated under reduced pressure and the residue was purified by prep-HPLC to afford Example C6 as a white solid.

1H NMR (400 MHz, CDCl$_3$) δ 3.00 (3H, s), 3.06-3.17 (8H, m), 3.88 (3H, s), 3.96 (3H, s), 6.46 (1H, dd, J=9.2, 2.4 Hz), 6.55 (1H, d, J=2.4 Hz), 6.79 (1H, d, J=8.4 Hz), 7.30 (1H, s), 7.35 (1H, t, J=8.8 Hz), 7.97 (1H, d, J=8.8 Hz), 8.05-8.15 (2H, m), 8.66 (1H, s).

LC-MS: MS Calculated 533.2, MS Found 534.4 [M+H]$^+$.

To a mixture of compound C5-1 (103 mg, 0.244 mmol) and A2-2 (81 mg, 0.24 mmol) in n-butanol (4 mL) was added TFA (456 mg, 4.00 mmol) and the mixture was stirred at 80° C. for 26 h. The reaction was monitored by LC-MS. The mixture was filtered and the filtrate was concentrated under reduced pressure to provide a crude residue that was purified by prep-HPLC to afford Example C7 as a white solid.

$^1$H NMR (400 MHz, CDCl$_3$) δ 1.06 (3H, t, J=7.6 Hz), 1.65-1.82 (2H, m), 1.88-2.01 (2H, m), 2.49 (3H, s), 2.50-2.92 (13H, m), 3.02 (3H, s), 3.04-3.14 (2H, m), 3.25 (3H, s), 3.85 (3H, s), 3.93 (3H, s), 6.64 (1H, s), 6.74 (1H, d, J=8.4 Hz), 7.31 (1H, t, J=8.4 Hz), 7.36 (1H, s), 8.00 (1H, d, J=8.0 Hz), 8.05 (1H, s), 8.18 (1H, s), 8.35 (1H, s).

[Example C8] Preparation of N-(5-((5-chloro-2-((2-methoxy-4-(4-(4-methylpiperazin-1-yl)piperidin-1-yl)phenyl)amino)pyrimidin-4-yl)amino)benzo[d]thiazol-4-yl)methanesulfonamide

[Example C9] Preparation of N-(6-((5-chloro-2-((2-methoxy-4-(4-(4-methylpiperazin-1-yl)piperidin-1-yl)phenyl)amino)pyrimidin-4-yl)amino)-2,3-dihydrobenzo[b][1,4]dioxin-5-yl)methanesulfonamide

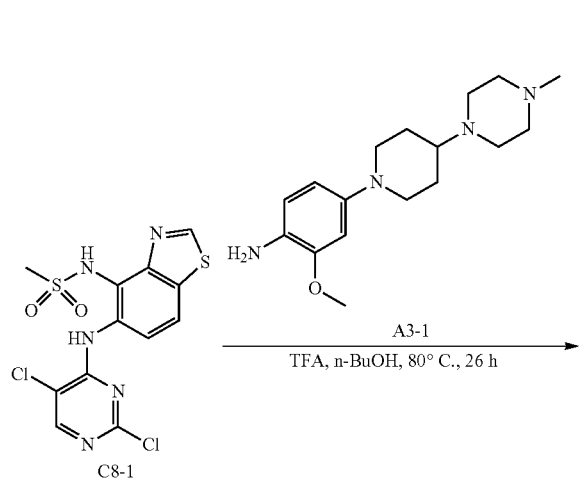

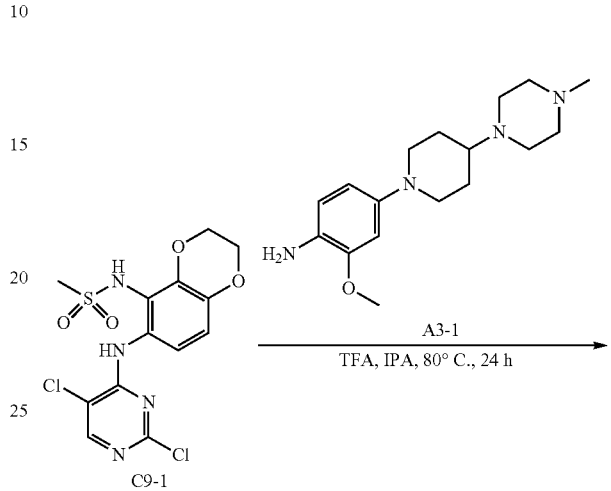

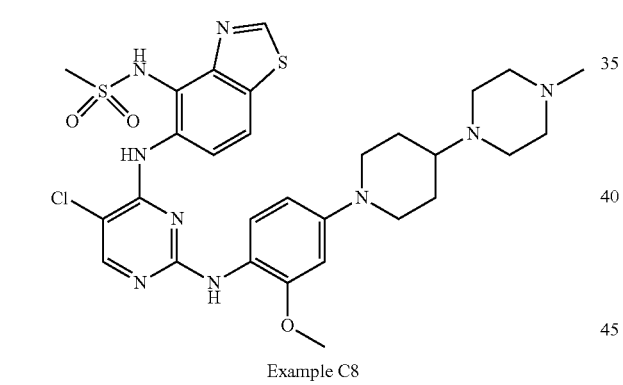

Example C8

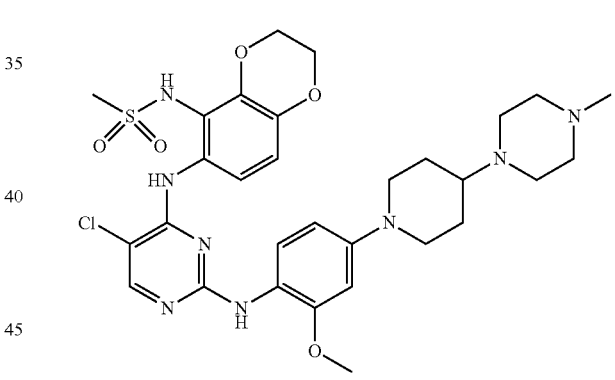

Example C9

To a mixture of compound C8-1 (94 mg, 0.24 mmol) and compound A3-1 (110 mg, 0.361 mmol) in n-butanol (4 mL) was added TFA (456 mg, 4.00 mmol) at 25° C. and the mixture was stirred at 80° C. for 26 h. The reaction was monitored by LC-MS. The reaction mixture was concentrated under reduced pressure and the residue was purified by prep-HPLC to afford Example C8 as an off-white solid.

$^1$H NMR (400 MHz, CDCl$_3$) δ 1.58-1.70 (2H, m), 1.80-1.92 (2H, m), 2.25-2.45 (5H, m), 2.54-2.75 (9H, m), 3.03 (3H, s), 3.52-6.65 (2H, m), 3.81 (3H, s), 6.32 (1H, dd, J=8.8, 2.0 Hz), 6.47 (1H, d, J=2.0 Hz), 7.20-7.25 (1H, m), 7.85-8.03 (2H, m), 8.10 (1H, s), 8.39 (1H, d, J=8.8 Hz), 8.88 (1H, s), 9.03 (1H, s). LC-MS: MS Calculated 657.2, MS Found 658.1 [M+H]$^+$.

To a mixture of compound C9-1 (110 mg, 0.281 mmol) and compound A3-1 (86 mg, 0.28 mmol) in IPA (5 mL) was added TFA (641 mg, 5.62 mmol) and the mixture was stirred at 80° C. for 24 h. The reaction was monitored by LC-MS. The reaction mixture was concentrated under reduced pressure and the residue was purified by prep-HPLC to afford Example C9 as a yellow solid.

$^1$H NMR (400 MHz, CDCl$_3$) δ 1.67-1.77 (2H, m), 1.94-1.97 (2H, m), 2.43 (3H, s), 2.46-2.52 (1H, m), 2.63-2.82 (10H, m), 3.04 (3H, s), 3.57-3.65 (2H, m), 3.84 (3H, s), 4.30-4.39 (4H, m), 6.42 (1H, dd, J=8.8, 2.0 Hz), 6.51 (1H, d, J=2.0 Hz), 6.95 (1H, d, J=9.2 Hz), 7.27 (1H, s), 7.65 (1H, d, J=9.2 Hz), 7.98-8.05 (2H, m), 8.36 (1H, s). LC-MS: MS Calculated 658.3, MS Found 659.2 [M+H]$^+$.

[Example C10] Preparation of N-(2-((5-chloro-2-((2-methoxy-5-methyl-4-(4-(pyrrolidin-1-yl)piperidin-1-yl)phenyl)amino)pyrimidin-4-yl)amino)-6-methoxyphenyl)methanesulfonamide

[Example C11] Preparation of N-(2-((5-chloro-2-((2-methoxy-5-methyl-4-(4-(pyrrolidin-1-yl)piperidin-1-yl)phenyl)amino)pyrimidin-4-yl)amino)-5-methoxyphenyl)methanesulfonamide

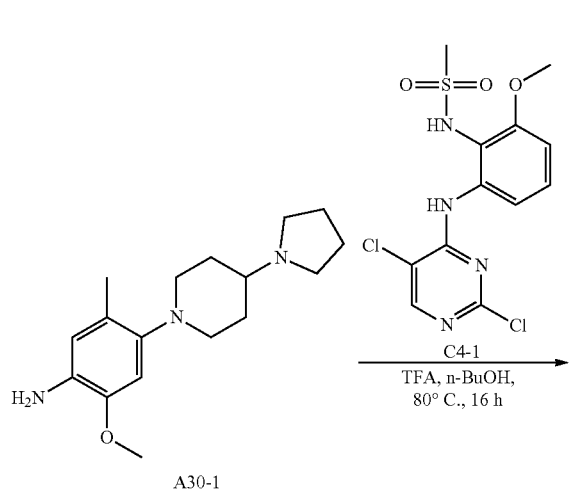

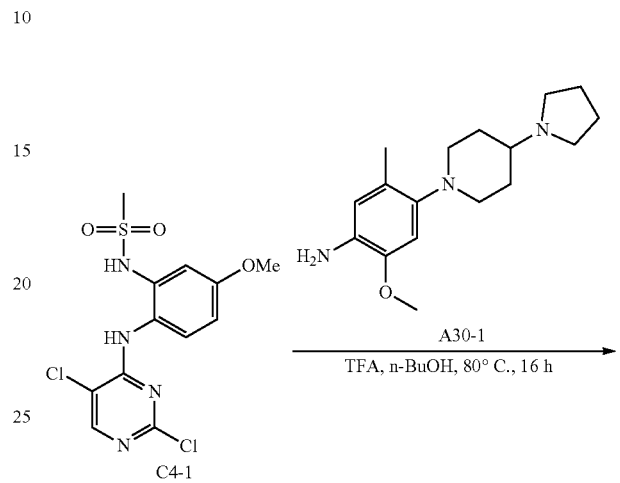

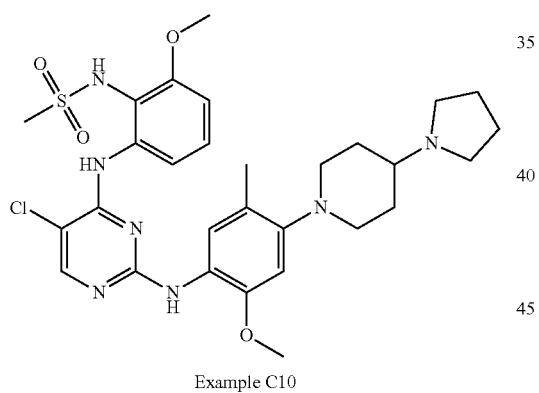

Example C10

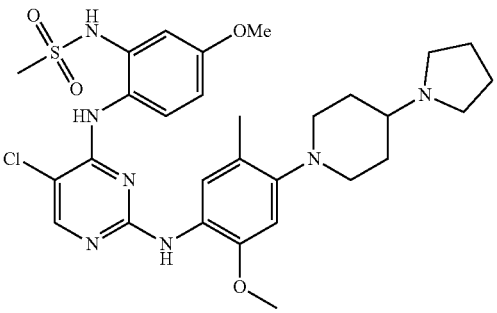

Example C11

To a mixture of compound C4-1 (100 mg, 0.275 mmol) and A30-1 (120 mg, 0.413 mmol) in n-butanol (4 mL) was added TFA (462 mg, 4.05 mmol) at 20° C. under $N_2$ atmosphere and the mixture was stirred at 80° C. for 16 h. The reaction was monitored by LC-MS. The mixture was filtered and the filtrate was concentrated under reduced pressure. The residue was purified by prep-HPLC to afford Example C10 as a yellow solid.

$^1$H NMR (400 MHz, CDCl$_3$) δ 2.04-2.12 (11H, m), 2.55-2.70 (2H, m), 2.86-3.02 (4H, m), 3.03-3.54 (6H, m), 3.82 (3H, s), 3.94 (3H, s), 6.52 (1H, s), 6.77 (1H, d, J=8.4 Hz), 7.31 (1H, t, J=8.4 Hz), 7.36 (1H, s), 7.89 (1H, d, J=8.4 Hz), 7.96 (1H, s), 8.05 (1H, s), 8.67 (1H, s).

LC-MS: MS Calculated 615.2, MS Found 616.2 [M+H]$^+$.

To a mixture of compound C4-1 (100 mg, 0.275 mmol) and A30-1 (120 mg, 0.413 mmol) in n-butanol (4 mL) was added TFA (462 mg, 4.05 mmol) at 15° C. and the mixture was stirred at 80° C. for 16 h. The reaction was monitored by LC-MS. The reaction mixture was filtered and the filtrate was concentrated under reduced pressure. The remaining residue was purified by prep-HPLC to afford Example C11 as a gray solid.

$^1$H NMR (400 MHz, CDCl$_3$) δ 1.62-1.77 (2H, m), 1.83-1.88 (4H, m), 1.91-1.98 (5H, m), 2.10-2.18 (1H, m), 2.52-2.60 (2H, m), 2.65-2.72 (4H, m), 2.81 (3H, s), 2.96-3.01 (2H, m), 3.79 (3H, s), 3.86 (3H, s), 6.50 (1H, s), 6.82 (1H, dd, J=8.8, 2.8 Hz), 7.02 (1H, s), 7.17 (1H, d, J=2.8 Hz), 7.33 (1H, s), 7.36 (1H, d, J=8.8 Hz), 7.60 (1H, s), 8.04 (1H, s).

LC-MS: MS Calculated 615.2, MS Found 616.3 [M+H]$^+$.

[Example C12] Preparation of N-(2-((5-chloro-2-((4-(4-(dimethylamino)piperidin-1-yl)-2-methoxy-5-propylphenyl)amino)pyrimidin-4-yl)amino)-5-methoxyphenyl)methanesulfonamide

[Example C13] Preparation of N-(6-((5-chloro-2-((4-(4-(dimethylamino)piperidin-1-yl)-2-methoxy-5-propylphenyl)amino)pyrimidin-4-yl)amino)-2,3-dihydrobenzo[b][1,4]dioxin-5-yl)methanesulfonamide

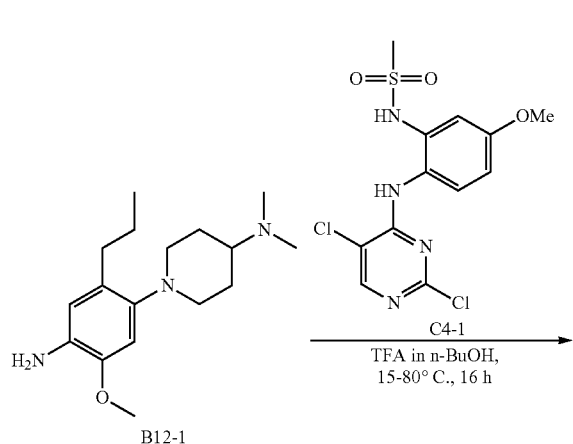

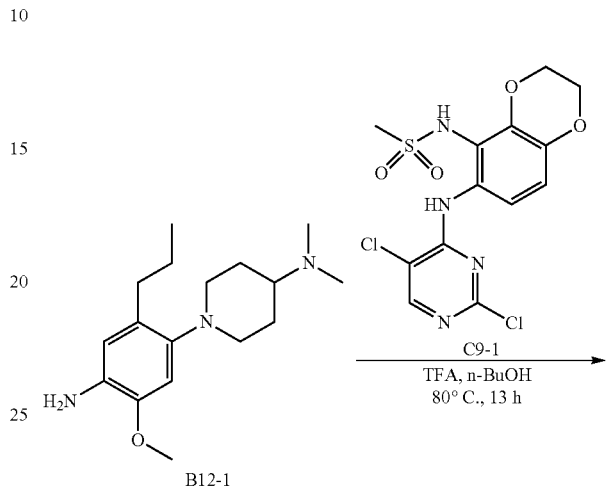

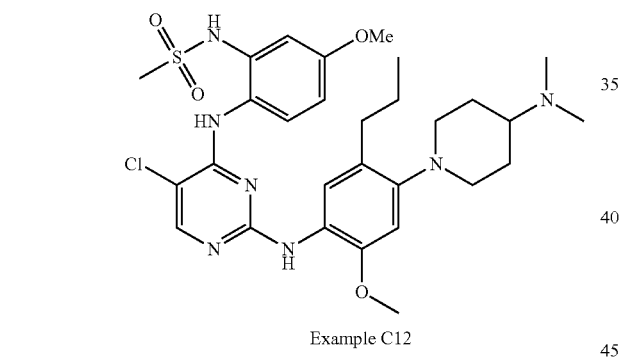

Example C12

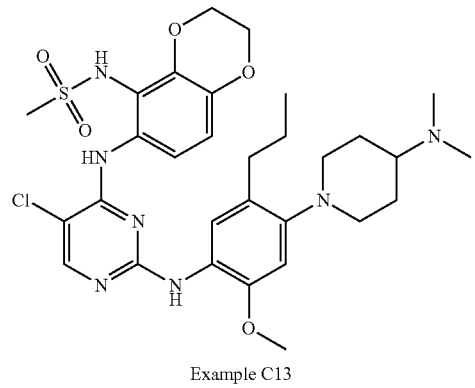

Example C13

To a mixture of compound C4-1 (100 mg, 0.275 mmol) and B12-1 (120 mg, 0.413 mmol) in n-butanol (4 mL) was added TFA (462 mg, 4.05 mmol) at 15° C. and the mixture was stirred at 80° C. for 16 h. The mixture was monitored by LC-MS. The reaction mixture was filtered and the filtrate was concentrated under reduced pressure. The residue was purified by prep-HPLC to afford Example C12 as a gray solid.

$^1$H NMR (400 MHz, CDCl$_3$) δ 0.84 (3H, t, J=7.2 Hz), 1.28-1.40 (2H, m), 1.60-1.68 (2H, m), 1.84-1.93 (2H, m), 2.16-2.25 (2H, m), 2.29-2.32 (1H, m), 2.34 (6H, s), 2.57-2.66 (2H, m), 2.80 (3H, s), 2.95-3.04 (2H, m), 3.80 (3H, s), 3.86 (3H, s), 6.59 (1H, s), 6.81 (1H, dd, J=8.8, 2.8 Hz), 6.86 (1H, s), 7.18 (1H, d, J=2.8 Hz), 7.27-7.35 (2H, m), 7.58-7.68 (1H, m), 8.07 (1H, s).
LC-MS: MS Calculated 617.3, MS Found 618.2 [M+H]$^+$.

To a mixture of compound B12-1 (110 mg, 0.281 mmol) and C9-1 (82 mg, 0.28 mmol) in n-butanol (4 mL) was added TFA (513 mg, 4.50 mmol) at 25° C. and the mixture was stirred at 80° C. for 13 h. The reaction was monitored by LC-MS. The reaction mixture was concentrated under reduced pressure and the residue was purified by prep-HPLC to afford Example C13 as an off-white solid.

$^1$H NMR (400 MHz, CDCl$_3$) δ 0.89 (3H, t, J=7.2 Hz), 1.38-1.50 (2H, m), 1.71-1.83 (2H, m), 1.98-2.08 (2H, m), 2.45-2.50 (2H, m), 2.56 (6H, s), 2.67-2.78 (3H, m), 3.03-3.10 (5H, m), 3.83 (3H, s), 4.27-4.40 (4H, m), 6.62 (1H, s), 6.92 (1H, d, J=9.2 Hz), 7.37 (1H, s), 7.59 (1H, d, J=9.2 Hz), 7.98 (1H, s), 8.04 (1H, s), 8.31 (1H, s). LC-MS: MS Calculated 645.3, MS Found 646.2 [M+H]$^+$.

[Example C14] Preparation of N-(2-((5-chloro-2-((5-ethyl-2-methoxy-4-(4-morpholinopiperidin-1-yl)phenyl)amino)pyrimidin-4-yl)amino)-5-methoxyphenyl) methanesulfonamide

[Example C15] Preparation of N-(6-((5-chloro-2-((5-ethyl-2-methoxy-4-(4-morpholinopiperidin-1-yl)phenyl)amino)pyrimidin-4-yl)amino)-2,3-dihydrobenzo[b][1,4]dioxin-5-yl)methanesulfonamide

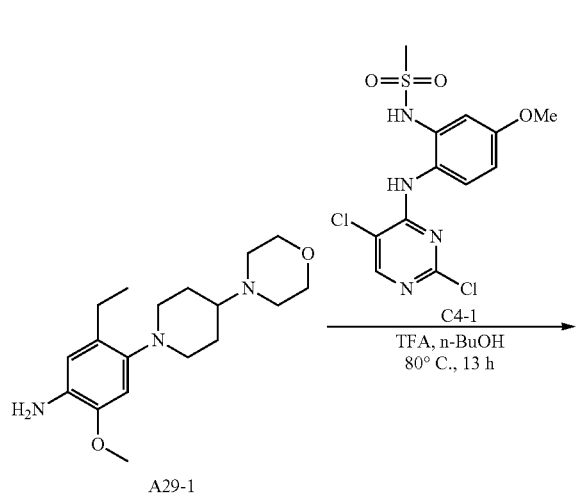

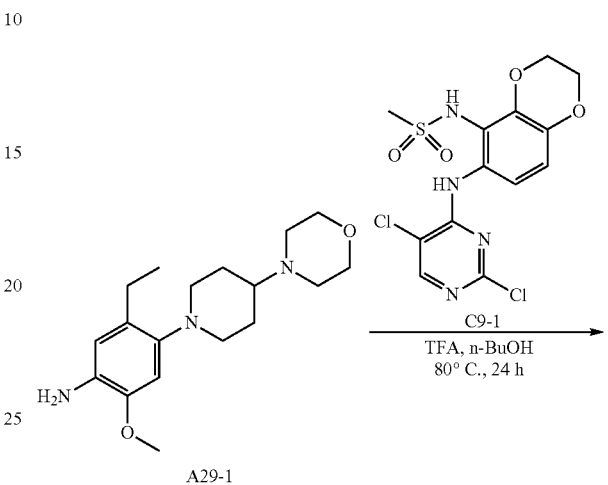

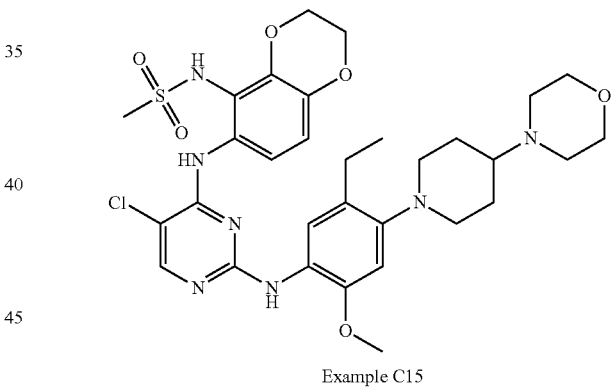

Example C15

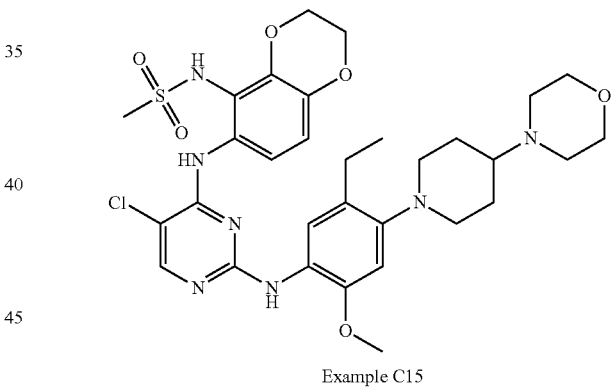

Example C15

To a mixture of compound C4-1 (200 mg, 0.551 mmol) and A29-1 (263 mg, 0.826 mmol) in n-butanol (4 mL) was added TFA (314 mg, 2.75 mmol) and the mixture was stirred at 80° C. for 13 h. The reaction was monitored by LC-MS. The mixture was filtered and the filtrate was concentrated under reduced pressure and the residue was purified by prep-HPLC to afford Example C14 as a yellow solid.

$^1$H NMR (400 MHz, CDCl$_3$) δ 0.89-0.98 (3H, m), 1.70-1.83 (2H, m) 1.99-2.08 (2H, m), 2.33-2.43 (2H, m), 2.56 (1H, s), 2.62-2.71 (2H, m), 2.72-2.88 (7H, m), 3.02-3.08 (2H, m), 3.81 (3H, s), 3.87 (3H, s), 3.90 (4H, s), 6.58 (1H, s), 6.83 (1H, dd, J=8.8, 2.8 Hz), 6.92 (1H, s), 7.20 (1H, d, J=2.8 Hz), 7.32 (1H, d, J=8.8 Hz), 7.39 (1H, s), 7.67 (1H, s), 8.06 (1H, s).
LC-MS: MS Calculated 645.3, MS Found 646.2 [M+H]$^+$.

To a mixture of compound C9-1 (110 mg, 0.281 mmol) and A29-1 (135 mg, 0.422 mmol) in n-butanol (5 mL) was added TFA (641 mg, 5.62 mmol) at 25° C. and the mixture was stirred at 80° C. for 24 h. The reaction was monitored by LC-MS. The reaction mixture was concentrated under reduced pressure and the residue was purified by prep-HPLC to afford Example C15 as a white solid.

$^1$H NMR (400 MHz, CD$_3$CN) δ 0.92-1.08 (3H, m), 1.53-1.64 (2H, m), 1.86-1.91 (2H, m), 2.20-2.27 (1H, m), 2.47-2.58 (6H, m), 2.60-2.70 (2H, m), 2.90-3.09 (5H, m), 3.56-3.66 (4H, m), 3.82 (3H, s), 4.20-4.39 (4H, m), 6.73 (1H, s), 6.87 (1H, d, J=8.8 Hz), 7.25 (1H, s), 7.42 (1H, d, J=8.8 Hz), 7.81 (1H, s), 8.10 (1H, s), 8.21 (1H, s). LC-MS: MS Calculated 673.2, MS Found 674.2 [M+H]$^+$.

[Example C16] Preparation of N-(2-((5-chloro-2-((2-methoxy-5-methyl-4-(4-(4-methylpiperazin-1-yl)piperidin-1-yl)phenyl)amino)pyrimidin-4-yl)amino)-6-methoxyphenyl)ethanesulfonamide

[Example C17] Preparation of N-(2-((5-chloro-2-((2-methoxy-5-methyl-4-(4-(4-methylpiperazin-1-yl)piperidin-1-yl)phenyl)amino)pyrimidin-4-yl)amino)-5-methoxyphenyl)ethanesulfonamide

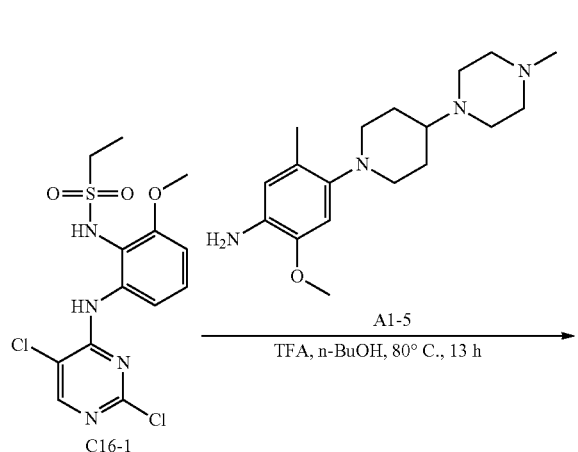

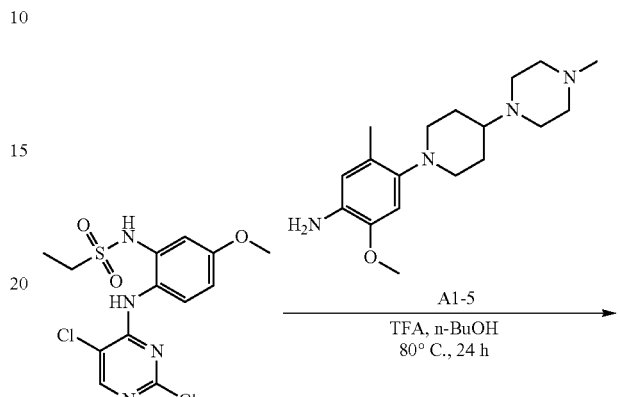

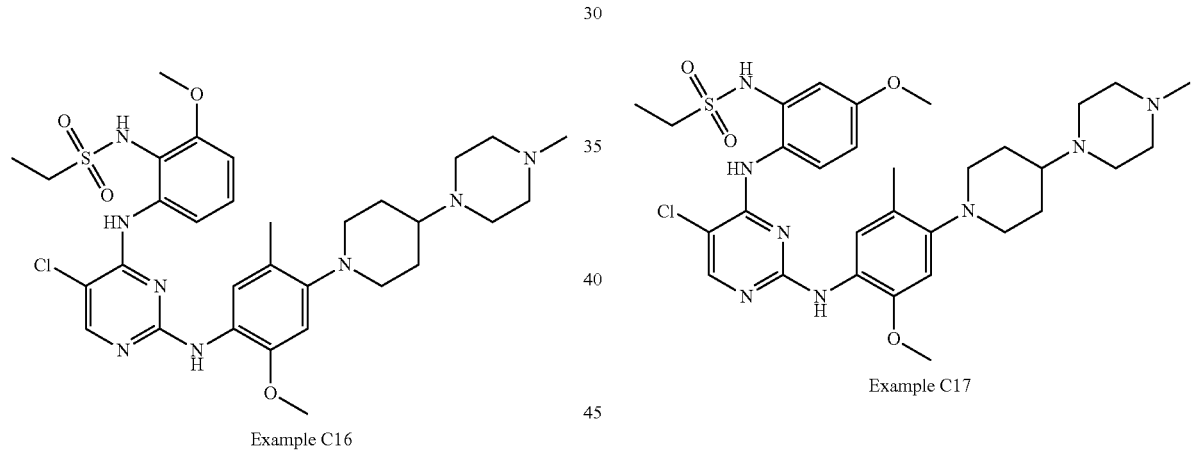

To a mixture of compound C16-1 (140 mg, 0.371 mmol) and A1-5 (118 mg, 0.371 mmol) in n-butanol (5 mL) was added TFA (634 mg, 5.57 mmol) at 25° C. and the mixture was stirred at 80° C. for 13 h. The reaction was monitored by LC-MS. The reaction mixture was concentrated under reduced pressure. The remaining residue was purified by prep-HPLC to afford an Example C16 as an off-white solid.

$^1$H NMR (400 MHz, CDCl$_3$) δ 1.44 (3H, t, J=7.2 Hz), 1.73-1.84 (2H, m), 1.94-2.06 (2H, m), 2.12 (3H, s), 2.55 (3H, s), 2.59-2.66 (3H, m), 2.85-3.05 (8H, m), 3.09-3.17 (4H, m), 3.83 (3H, s), 3.94 (3H, s), 6.56 (1H, s), 6.76 (1H, d, J=7.6 Hz), 7.32 (1H, t, J=8.4 Hz), 7.36 (1H, s), 7.90 (1H, d, J=8.0 Hz), 7.98 (1H, s), 8.08 (1H, s), 8.73 (1H, s). LC-MS: MS Calculated 658.3, MS Found 659.3 [M+H]$^+$.

To a mixture of compound C17-1 (150 mg, 0.398 mmol) and A1-5 (190 mg, 0.596 mmol) in n-butanol (4 mL) was added TFA (456 mg, 4.00 mmol) at 25° C. and the mixture was stirred at 80° C. for 24 h. The reaction was monitored by LC-MS. The reaction mixture was concentrated under reduced pressure. The remaining residue was purified by prep-HPLC to afford Example C17 as an off-white solid.

$^1$H NMR (400 MHz, CDCl$_3$) δ 1.20 (3H, t, J=7.2 Hz), 1.61-1.75 (2H, m), 1.81-1.92 (2H, m), 1.97 (3H, s), 2.25-2.45 (5H, m), 2.55-2.7 (9H, m), 2.90-3.02 (2H, m), 3.05-3.15 (2H, m), 3.81 (3H, s), 3.86 (3H, s), 6.53 (1H, s), 6.82 (1H, dd, J=8.8, 2.8 Hz), 7.02 (1H, s), 7.19 (1H, d, J=2.4 Hz), 7.35 (1H, d, J=8.8 Hz), 7.38 (1H, s), 7.62 (1H, s), 8.05 (1H, s). LC-MS: MS Calculated 658.3, MS Found 659.2 [M+H]$^+$.

[Example C18] Preparation of N-(6-((5-chloro-2-((5-ethyl-2-methoxy-4-(4-morpholinopiperidin-1-yl)phenyl)amino)pyrimidin-4-yl)amino)-2,3-dimethoxyphenyl)methanesulfonamide

[Example C19] Preparation of N-(2-((5-chloro-2-((4-(4-(dimethylamino)piperidin-1-yl)-2-methoxy-5-propylphenyl)amino)pyrimidin-4-yl)amino)-6-methoxyphenyl)methanesulfonamide

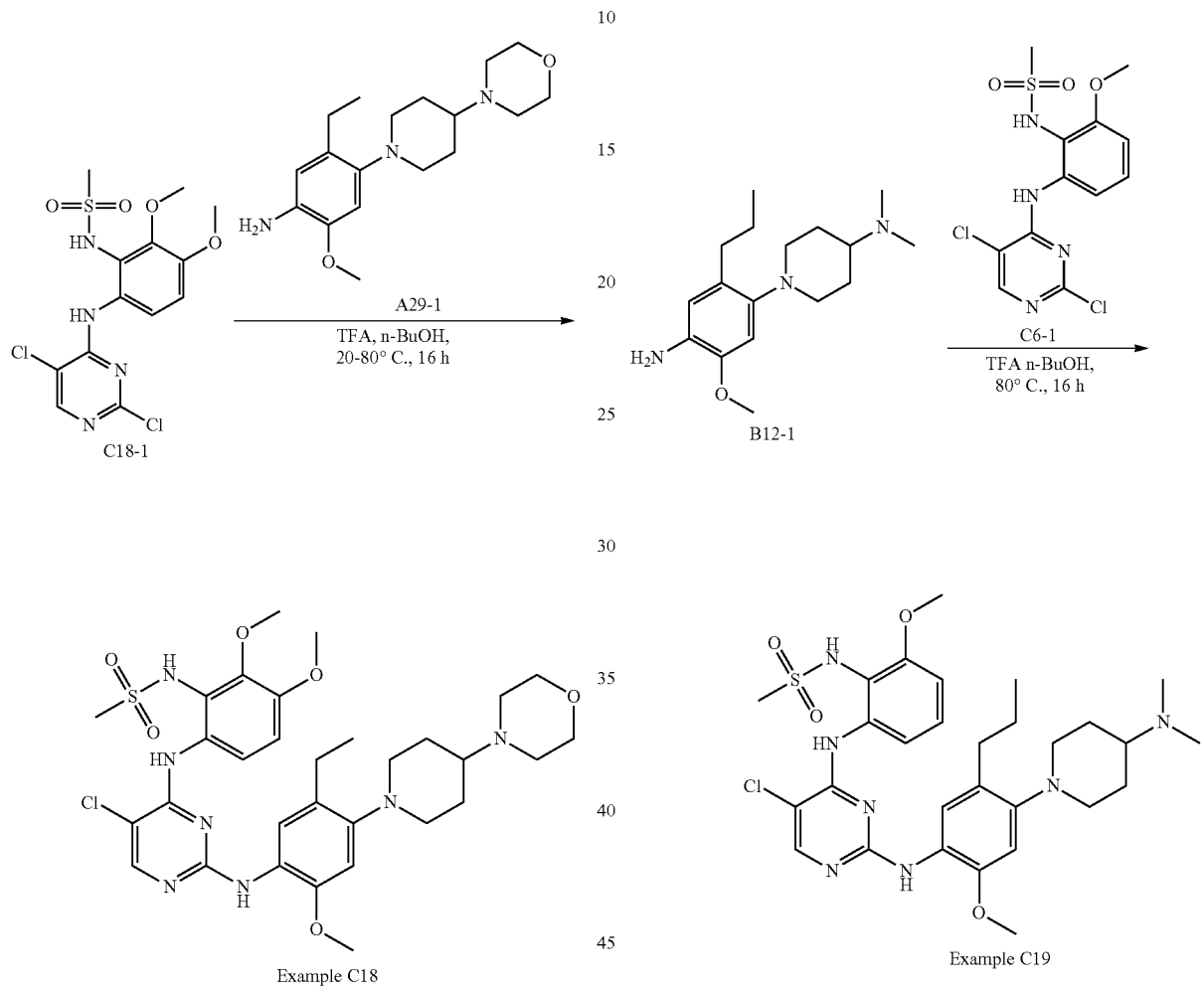

To a mixture of compound C18-1 (100 mg, 0.317 mmol) and A29-1 (152 mg, 0.476 mmol) in n-butanol (4 mL) was added TFA (462 mg, 4.05 mmol) at 20° C. and the mixture was stirred at 80° C. for 16 h. The reaction was monitored by LC-MS. The mixture was filtered and the filtrate was concentrated under reduced pressure and the residue was purified by prep-HPLC to afford Example C18 as a yellow solid.

$^1$H NMR (400 MHz, CDCl$_3$) δ 1.00 (3H, t, J=7.6 Hz), 1.61-1.77 (2H, m), 1.88-2.04 (2H, m), 2.24-2.45 (1H, m), 2.46-2.57 (2H, m), 2.59-2.88 (6H, m), 2.99-3.09 (5H, m), 3.71-3.88 (7H, m), 3.92 (3H, s), 3.99 (3H, s), 6.62 (1H, s), 6.95 (1H, d, J=9.6 Hz), 7.37 (1H, s), 7.71 (1H, d, J=9.2 Hz), 7.97 (1H, s), 8.03 (1H, s), 8.27 (1H, s). LC-MS: MS Calculated 675.3, MS Found 676.2 [M+H]$^+$.

To a mixture of compound B12-1 (87 mg, 0.30 mmol) and compound C6-1 (90 mg, 0.25 mmol) in n-butanol (4 mL) was added TFA (410 mg, 3.60 mmol), and then the mixture was stirred at 80° C. for 16 h. The reaction mixture was concentrated under reduced pressure and the residue was purified by prep-HPLC to afford Example C19 as a white solid.

$^1$H NMR (400 MHz, DMSO) δ 0.86 (3H, t, J=7.2 Hz), 1.41-1.54 (4H, m), 1.84-1.87 (2H, m), 2.15-2.18 (1H, m), 2.22 (6H, s), 2.42-2.47 (2H, m), 2.65-2.70 (2H, m), 2.95-3.01 (5H, m), 3.75 (3H, s), 3.86 (3H, s), 6.77 (1H, s), 6.86 (1H, d, J=7.6 Hz), 7.14 (1H, t, J=8.4 Hz), 7.47 (1H, s), 7.78 (1H, d, J=8.4 Hz), 8.04 (1H, s), 8.13 (1H, s), 8.48 (1H, s), 9.12 (1H, brs).

LC-MS: MS Calculated 617.3, MS Found 618.2 [M+H]$^+$.

[Example C20] Preparation of N-(2-((5-chloro-2-((5-ethyl-2-methoxy-4-(4-morpholinopiperidin-1-yl)phenyl)amino)pyrimidin-4-yl)amino)-6-methoxyphenyl)methanesulfonamide

[Example C21] Preparation of N-(2-((5-bromo-2-((2-methoxy-5-methyl-4-(4-(4-methylpiperazin-1-yl)piperidin-1-yl)phenyl)amino)pyrimidin-4-yl)amino)-6-methoxyphenyl)-N-methylmethanesulfonamide

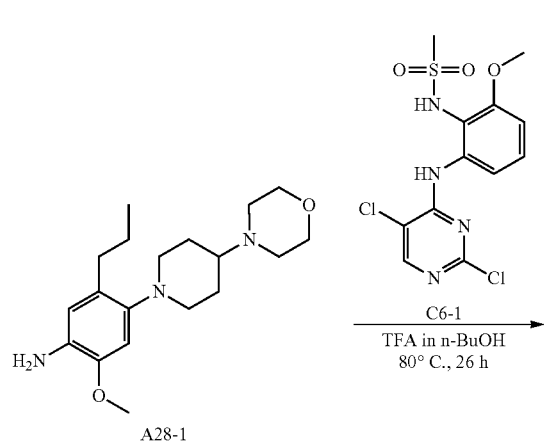

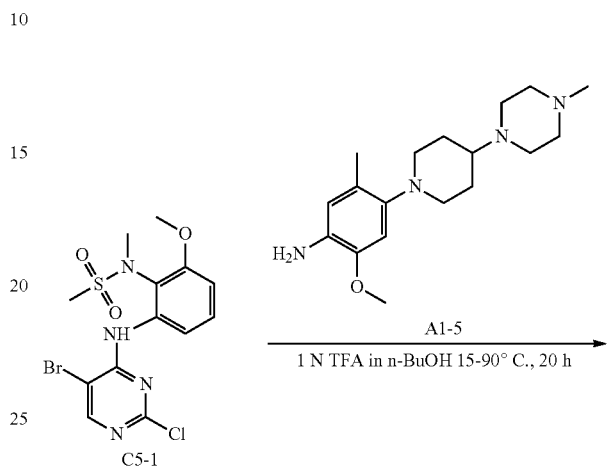

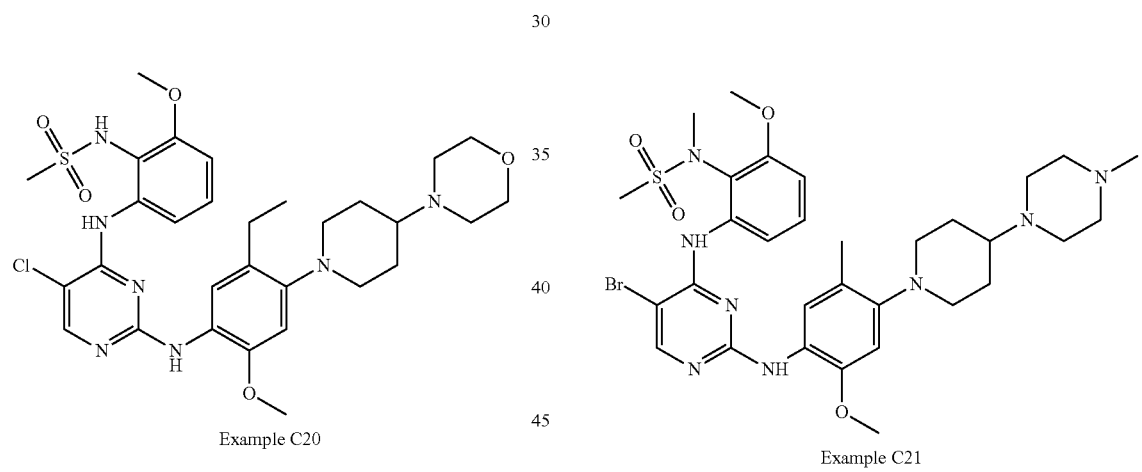

To a mixture compound A28-1 (150 mg, 0.47 mmol) and compound C6-1 (171 mg, 0.47 mmol) in n-butanol (3 mL) was added TFA (456 mg, 4.00 mmol), and then the mixture was stirred at 80° C. for 26 h. The reaction mixture was concentrated under reduced pressure and the residue was purified by prep-HPLC to afford Example C20 as a white solid.

$^1$H NMR (400 MHz, CDCl$_3$) δ 1.05 (3H, t, J=7.2 Hz), 1.64-1.76 (2H, m), 1.91-1.99 (2H, m), 2.28 (1H, s), 2.52-2.71 (8H, m), 2.99 (3H, s), 3.04-3.15 (2H, m), 3.73-3.81 (4H, m), 3.84 (3H, s), 3.94 (3H, s), 6.14 (1H, s), 6.65 (1H, s), 6.76 (1H, d, J=7.6 Hz), 7.32 (1H, t, J=8.0 Hz), 7.36 (1H, s), 7.93 (1H, d, J=8.4 Hz), 8.02 (1H, s), 8.09 (1H, s), 8.65 (1H, s). LC-MS: MS Calculated 645.3, MS Found 646.2 [M+H]$^+$.

To a mixture of compound C5-1 (100 mg, 0.237 mmol) and compound A1-5 (91 mg, 0.28 mmol) in n-butanol (4 mL) was added TFA (456 mg, 4.00 mmol) at 15° C., and then the mixture was stirred at 90° C. for 20 h. The reaction mixture was concentrated under reduced pressure and the residue was purified by prep-HPLC to afford Example C21 as a yellow solid.

$^1$H NMR (400 MHz, CDCl$_3$) δ 1.61-1.75 (2H, m), 1.92-2.08 (2H, m), 2.19 (3H, s), 2.25-2.36 (4H, m), 2.41-2.82 (10H, m), 3.02 (3H, s), 3.11-3.21 (2H, m), 3.25 (3H, s), 3.85 (3H, s), 3.93 (3H, s), 6.61 (1H, s), 6.73 (1H, d, J=7.6 Hz), 7.33-7.42 (2H, m), 8.01 (1H, s), 8.08 (1H, d, J=7.2 Hz), 8.16 (1H, s), 8.36 (1H, s).

[Example C22] Preparation of N-(2-((5-bromo-2-((5-ethyl-2-methoxy-4-(4-(4-methylpiperazin-1-yl)piperidin-1-yl)phenyl)amino)pyrimidin-4-yl)amino)-6-methoxyphenyl)methanesulfonamide

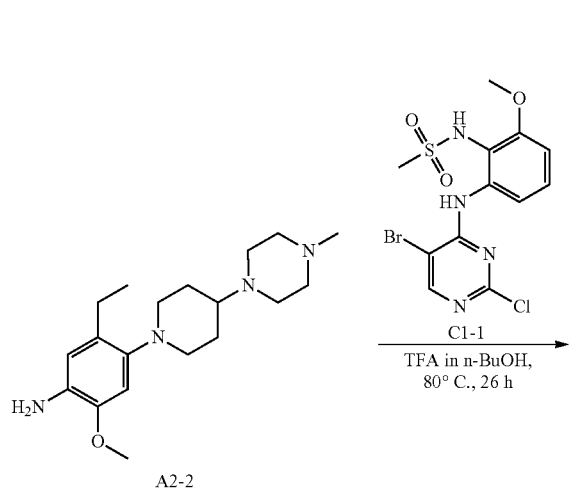

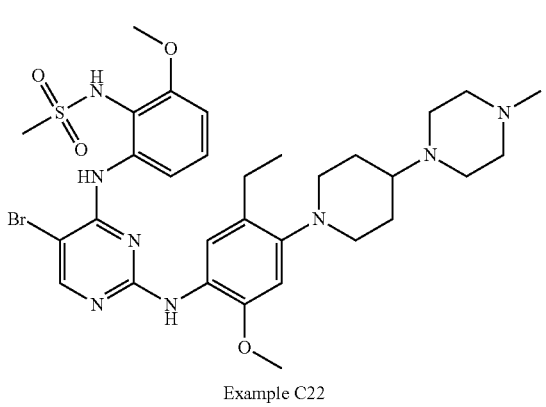

Example C22

To a mixture compound A2-2 (150 mg, 0.451 mmol) and compound C1-1 (184 mg, 0.451 mmol) in n-butanol (3 mL) was added TFA (582 mg, 5.10 mmol), and then the mixture was stirred at 80° C. for 26 h. The reaction mixture was concentrated under reduced pressure and the residue was purified by prep-HPLC to afford Example C22 as a red solid.

$^1$H NMR (400 MHz, CDCl$_3$) δ 1.03 (3H, t, J=7.6 Hz), 1.65-1.76 (2H, m), 1.92-1.97 (2H, m), 2.32 (3H, s), 2.44-2.73 (13H, m), 2.99 (3H, s), 3.03-3.08 (2H, m), 3.84 (3H, s), 3.94 (3H, s), 6.64 (1H, s), 6.76 (1H, d, J=8.4 Hz), 7.32 (1H, t, J=8.4 Hz), 7.35 (1H, s), 7.89 (1H, d, J=8.4 Hz), 7.99 (1H, s), 8.17 (1H, s), 8.57 (1H, s).

[Example C23] Preparation of N-(2-((5-chloro-2-((2-methoxy-4-(4-morpholinopiperidin-1-yl)-5-propylphenyl)amino)pyrimidin-4-yl)amino)-6-methoxyphenyl)methanesulfonamide

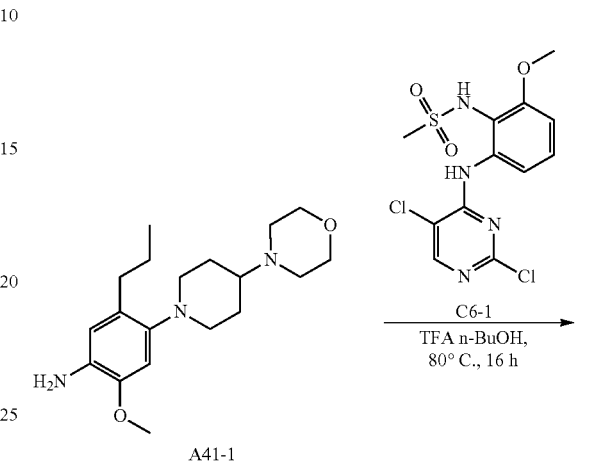

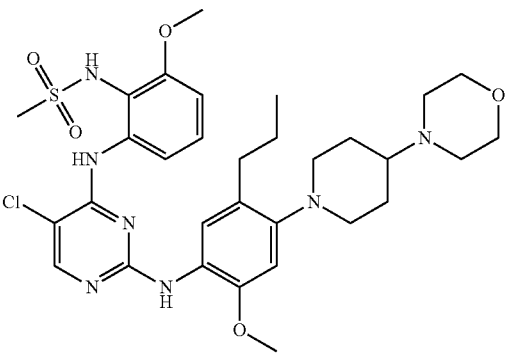

Example C23

To a mixture of compound A41-1 (99 mg, 0.30 mmol) and compound C6-1 (90 mg, 0.25 mmol) in n-butanol (4 mL) was added TFA (456 mg, 4.00 mmol), and then the mixture was stirred at 80° C. for 16 h. The reaction mixture was concentrated under reduced pressure and the residue was purified by prep-HPLC to afford Example C23 as a red solid.

$^1$H NMR (400 MHz, DMSO) δ 0.86 (3H, t, J=7.2 Hz), 1.40-1.59 (4H, m), 1.75-1.89 (2H, m), 2.22-2.33 (2H, m), 2.42-2.49 (2H, m), 2.57-2.71 (3H, m), 2.97-3.00 (5H, m), 3.27-3.32 (2H, m), 3.55-3.62 (4H, m), 3.75 (3H, s), 3.85 (3H, s), 6.77 (1H, s), 6.87 (1H, d, J=7.6 Hz), 7.15 (1H, t, J=8.4 Hz), 7.47 (1H, s), 7.78 (1H, d, J=8.0 Hz), 8.04 (1H, s), 8.13 (1H, s), 8.47 (1H, s), 9.11 (1H, s).

LC-MS: MS Calculated 659.3, MS Found 660.3 [M+H]$^+$.

[Example C24] Preparation of N-(2-((5-chloro-2-((2-methoxy-5-methyl-4-(4-(4-methylpiperazin-1-yl)piperidin-1-yl)phenyl)amino)pyrimidin-4-yl)amino)-6-methoxyphenyl)methanesulfonamide

[Example C25] Preparation of N-(2-((5-bromo-2-((2-methoxy-5-methyl-4-(4-(pyrrolidin-1-yl)piperidin-1-yl)phenyl)amino)pyrimidin-4-yl)amino)-6-methoxyphenyl)methanesulfonamide

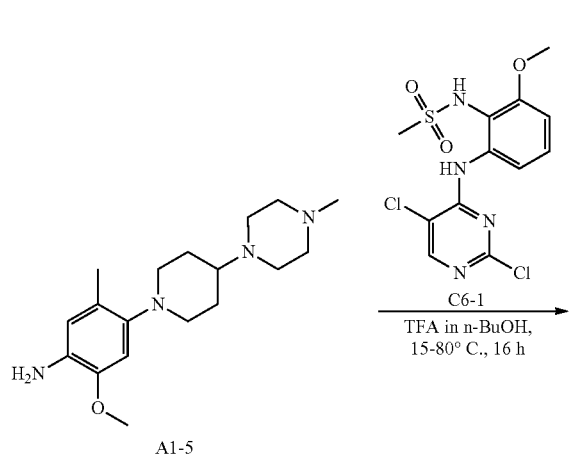

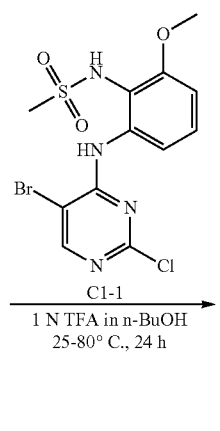

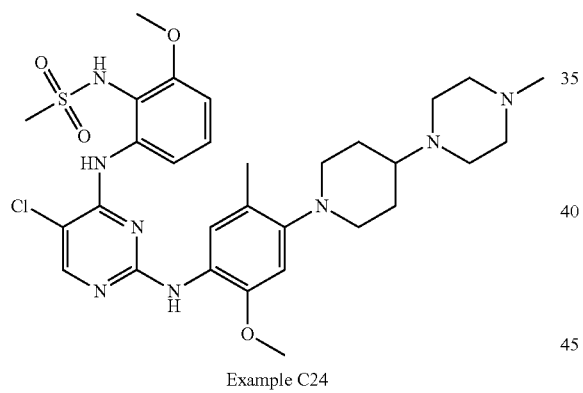

Example C24

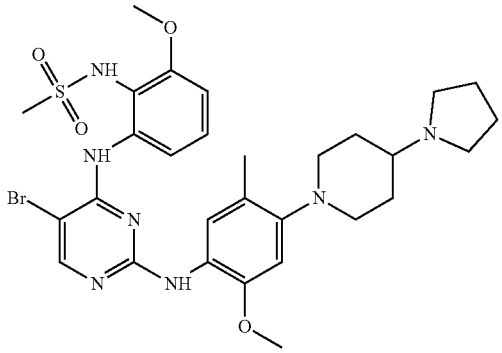

Example C25

To a mixture of compound A1-5 (132 mg, 0.413 mmol) and compound C6-1 (100 mg, 0.275 mmol) in n-butanol (4 mL) was added TFA (462 mg, 4.05 mmol) at 15° C. The mixture was stirred at 80° C. for 16 h. The mixture was filtered and the filtrate was concentrated under reduced pressure. The residue was purified by prep-HPLC to afford Example C24 as a yellow solid.

$^1$H NMR (400 MHz, CDCl$_3$) δ 1.67-1.83 (2H, m), 1.89-2.03 (2H, m), 2.12 (3H, s), 2.52 (3H, s), 2.55-2.66 (3H, m), 2.77-3.16 (13H, m), 3.82 (3H, s), 3.93 (3H, s), 6.55 (1H, s), 6.76 (1H, d, J=8.4 Hz), 7.32 (1H, t, J=8.4 Hz), 7.34 (1H, s), 7.94 (1H, d, J=8.4 Hz), 7.98 (1H, s), 8.06 (1H, s), 8.66 (1H, s).

LC-MS: MS Calculated 644.3, MS Found 645.3 [M+H]$^+$.

To a mixture of compound C1-1 (100 mg, 0.245 mmol) and A30-1 (106 mg, 0.368 mmol) in n-butanol (4 mL) was added TFA (456 mg, 4.00 mmol) at 25° C. and then the mixture was stirred at 80° C. for 24 h. The reaction mixture was concentrated under reduced pressure and the residue was purified by prep-HPLC to afford Example C25 as an off-white solid.

$^1$H NMR (400 MHz, CDCl$_3$) δ 2.01-2.15 (11H, m), 2.55-2.72 (3H, m), 2.99 (3H, s), 3.02-3.24 (6H, m), 3.82 (3H, s), 3.94 (3H, s), 6.53 (1H, s), 8.77 (1H, d, J=8.4 Hz), 7.28-7.41 (2H, m), 7.88 (1H, d, J=8.0 Hz), 7.93 (1H, s), 8.15 (1H, s), 8.60 (1H, s). LC-MS: MS Calculated 659.2, MS Found 660.2 [M+H]$^+$.

215

[Example C26] Preparation of N-(2-((5-chloro-2-((2-methoxy-5-methyl-4-(4-(4-methylpiperazin-1-yl)piperidin-1-yl)phenyl)amino)pyrimidin-4-yl)amino)-5-methoxyphenyl)methanesulfonamide

216

[Example C27] Preparation of N-(6-((5-chloro-2-((2-methoxy-5-methyl-4-(4-(pyrrolidin-1-yl)piperidin-1-yl)phenyl)amino)pyrimidin-4-yl)amino)-2,3-dihydrobenzo[b][1,4]dioxin-5-yl)methanesulfonamide

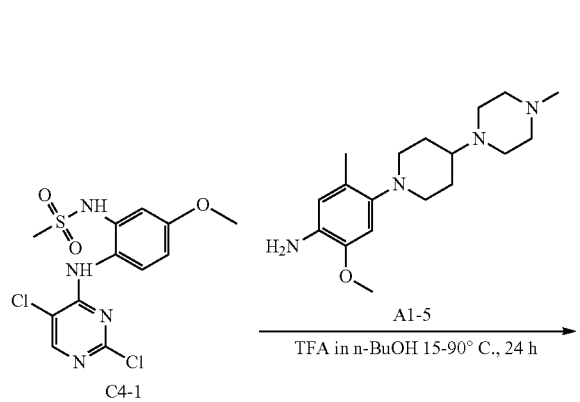

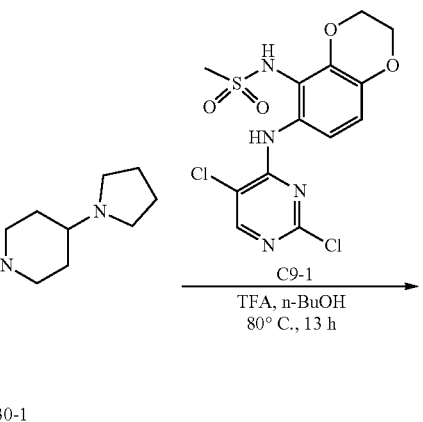

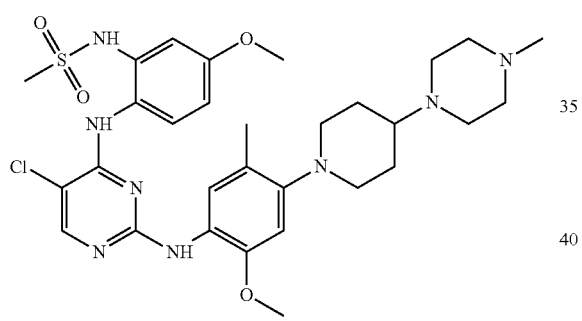

Example C26

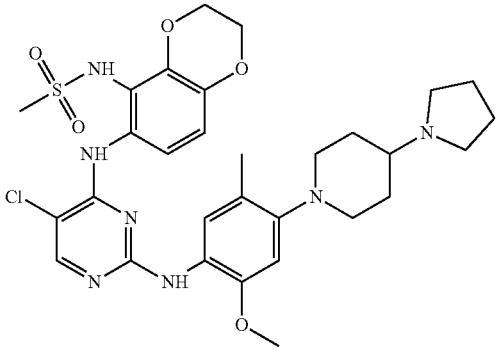

Example C27

To a mixture of compound C4-1 (100 mg, 0.275 mmol) and compound A1-5 (88 mg, 0.28 mmol) in n-butanol (6 mL) was added TFA (684 mg, 6.00 mmol) at 15° C., and then the mixture was stirred at 90° C. for 24 h. The reaction mixture was concentrated under reduced pressure and the residue was purified by prep-HPLC to afford Example C26 as a brown solid.

$^1$H NMR (400 MHz, CDCl$_3$) δ 1.62-1.76 (2H, m), 1.85-2.02 (5H, m), 2.31-2.45 (5H, m), 2.54-2.62 (5H, m), 2.66-2.85 (7H, m), 3.02-3.14 (2H, m), 3.81 (3H, s), 3.87 (3H, s), 6.53 (1H, s), 6.83 (1H, dd, J=8.8, 2.8 Hz), 6.98 (1H, s), 7.20 (1H, d, J=2.4 Hz), 7.31-7.42 (2H, m), 7.60 (1H, s), 8.05 (1H, s).

LC-MS: MS Calculated 644.3, MS Found 645.2 [M+H]$^+$.

To a mixture of compound C9-1 (250 mg, 0.639 mmol) and compound A30-1 (185 mg, 0.639 mmol) in n-butanol (8 mL) was added TFA (1.02 g, 8.95 mmol) at 25° C., and then the mixture was stirred at 80° C. for 13 h. The reaction mixture was concentrated under reduced pressure and the residue was poured into DCM (20 mL) and extracted with NH$_4$OH (20 mL×4). The combined organic layer was washed with brine (10 mL), dried over anhydrous Na$_2$SO$_4$ and concentrated under reduced pressure. The residue was purified by Combi Flash to give Example C27 as a light-yellow solid.

$^1$H NMR (400 MHz, CDCl$_3$) δ 1.66-1.82 (2H, m), 1.83-1.94 (4H, m), 1.96-2.03 (2H, m), 2.12 (3H, s), 2.14-2.31 (1H, m), 2.55-2.83 (6H, m), 3.04 (3H, s), 3.05-3.10 (2H, m), 3.83 (3H, s), 4.26-4.44 (4H, m), 6.57 (1H, s), 6.94 (1H, d, J=8.8 Hz), 7.34 (1H, s), 7.60 (1H, d, J=9.2 Hz), 7.92 (1H, s), 8.03 (1H, s), 8.34 (1H, s). LC-MS: MS Calculated 643.2, MS Found 644.2 [M+H]$^+$.

[Example C28] Preparation of N-(6-((5-bromo-2-((5-ethyl-2-methoxy-4-(4-(4-methylpiperazin-1-yl)piperidin-1-yl)phenyl)amino)pyrimidin-4-yl)amino)-2,3-dihydrobenzo[b][1,4]dioxin-5-yl)-N-methylmethanesulfonamide

[Example C29] Preparation of N-(2-((5-bromo-2-((5-ethyl-2-methoxy-4-(4-(4-methylpiperazin-1-yl)piperidin-1-yl)phenyl)amino)pyrimidin-4-yl)amino)-6-methoxyphenyl)-N-methylmethane sulfonamide

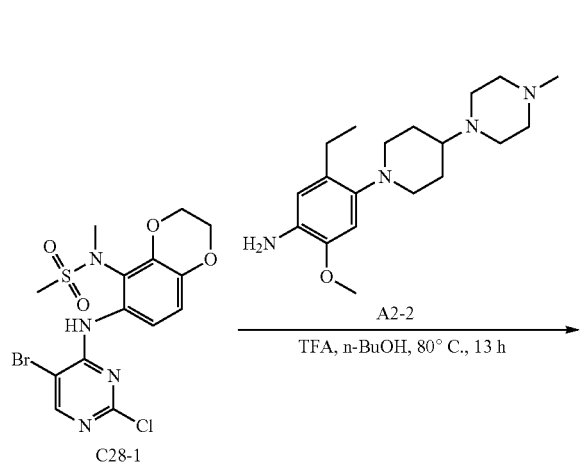

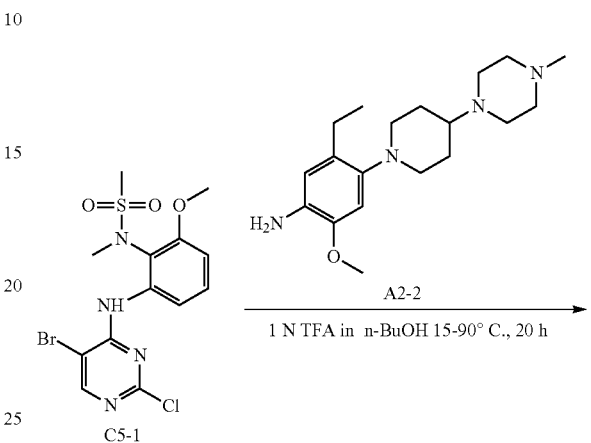

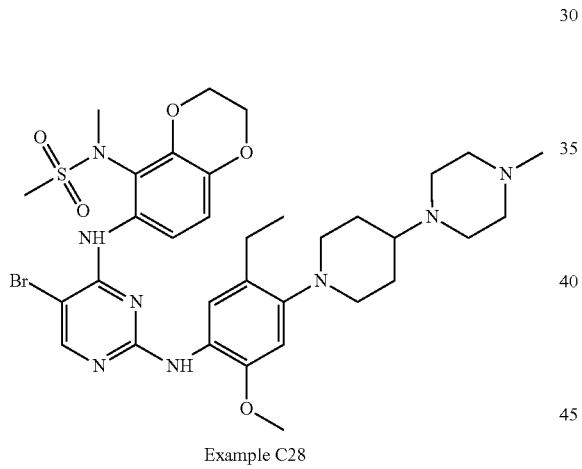

Example C28

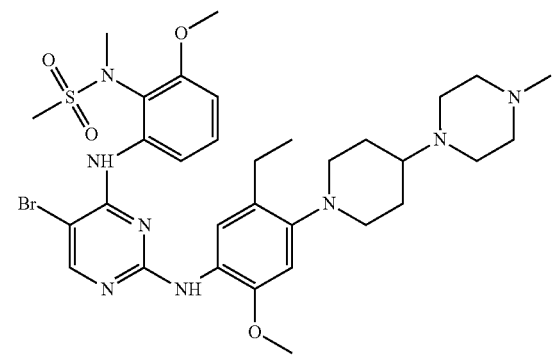

Example C29

To a solution of compound C28-1 (80 mg, 0.18 mmol) in n-butanol (3 mL) was added compound A2-2 (59 mg, 0.18 mmol) and TFA (385 mg, 3.38 mmol,) at 25° C. and the mixture was stirred at 80° C. for 13 h. The reaction mixture was concentrated under reduced pressure and the residue was purified by prep-HPLC to afford Example C28 as a gray solid.

$^1$H NMR (400 MHz, CDCl$_3$) δ 0.95-1.08 (3H, m), 1.69-1.74 (2H, m), 1.91-1.98 (2H, m), 2.34 (4H, s), 2.42-2.77 (12H, m), 2.95-3.16 (5H, m), 3.22 (3H, s), 3.83 (3H, s), 4.29-4.41 (4H, m), 6.63 (1H, s), 6.92 (1H, d, J=9.2 Hz), 7.37 (1H, s), 7.62 (1H, d, J=8.8 Hz), 8.00 (1H, br s), 8.01 (1H, br s), 8.13 (1H, s)

To a mixture of compound C5-1 (100 mg, 0.237 mmol) and compound A2-2 (95 mg, 0.28 mmol) in n-butanol (4 mL) was added TFA (456 mg, 4.00 mmol) at 15° C., and then the mixture was stirred at 90° C. for 20 h. The reaction mixture was concentrated under reduced pressure and the residue was purified by prep-HPLC to afford Example C29 as an off-white solid.

$^1$H NMR (400 MHz, CDCl$_3$) δ 1.05 (3H, t, J=7.6 Hz), 1.65-1.76 (2H, m), 1.88-2.04 (2H, m), 2.27-2.40 (4H, m), 2.41-2.81 (12H, m), 3.02 (3H, s), 3.05-3.15 (2H, m), 3.24 (3H, s), 3.84 (3H, s), 3.93 (3H, s), 6.65 (1H, s), 6.73 (1H, d, J=8.0 Hz), 7.31 (1H, s), 7.35 (1H, t, J=8.4 Hz), 8.00 (1H, d, J=8.4 Hz), 8.03 (1H, s), 8.17 (1H, s), 8.34 (1H, s).

[Example C30] Preparation of N-(6-((5-chloro-2-((5-ethyl-2-methoxy-4-(4-morpholinopiperidin-1-yl)phenyl)amino)pyrimidin-4-yl)amino)-2,3-dihydrobenzo[b][1,4]dioxin-5-yl)-N-methylmethanesulfonamide

[Example C31] Preparation of N-(2-((5-chloro-2-((4-(4-(dimethylamino)piperidin-1-yl)-2-methoxy-5-propylphenyl)amino)pyrimidin-4-yl)amino)-6-methoxyphenyl)-N-methylmethanesulfonamide

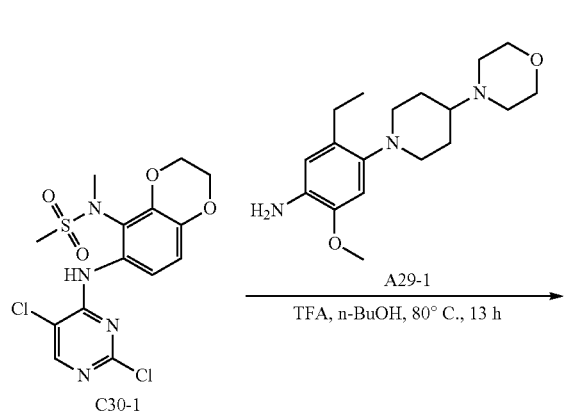

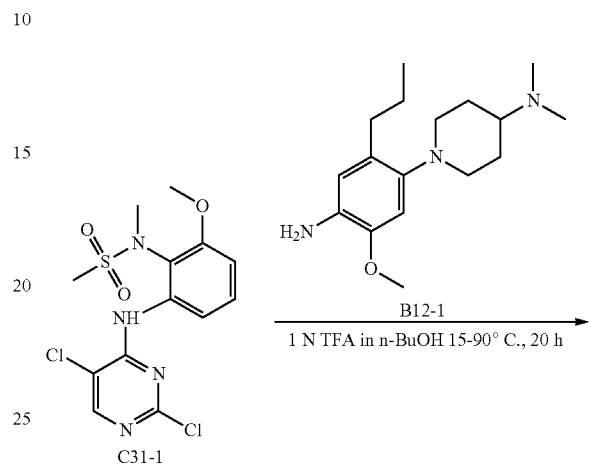

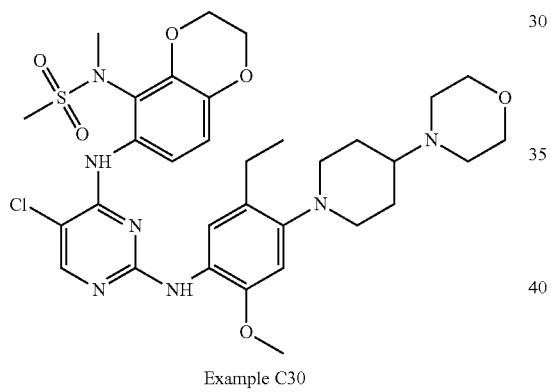

Example C30

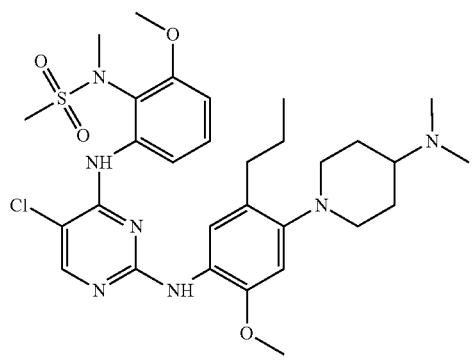

Example C31

To a mixture of compound C30-1 (315 mg, 0.777 mmol) and compound A29-1 (298 mg, 0.932 mmol) in n-butanol (8 mL) was added TFA (1.06 g, 9.33 mmol) at 25° C., and then the mixture was stirred at 80° C. for 13 h. The reaction mixture was concentrated under reduced pressure. The residue was poured into DCM (150 mL) and extracted with NH$_4$OH (50 mL×4). The combined organic layer was washed with brine (50 mL), dried over anhydrous Na$_2$SO$_4$ and concentrated under reduced pressure. The residue was purified by Combi Flash and further purified by prep-HPLC to afford Example C30 as a white solid.

$^1$H NMR (400 MHz, CDCl$_3$) δ 0.99-1.07 (3H, m), 1.66-1.76 (2H, m), 1.90-2.01 (2H, m), 2.23-2.39 (1H, m), 2.46-2.72 (8H, m), 3.02 (3H, s), 3.04-3.13 (2H, m), 3.23 (3H, s), 3.71-3.82 (4H, m), 3.84 (3H, s), 4.31-4.39 (4H, m), 6.64 (1H, s), 6.93 (1H, d, J=8.8 Hz), 7.37 (1H, s), 7.65 (1H, d, J=9.2 Hz), 8.02 (1H, s), 8.03 (1H, s), 8.05 (1H, s). LC-MS: MS Calculated 687, MS Found 688.2 [M+H]$^+$.

To a mixture of compound C31-1 (100 mg, 0.265 mmol) and compound B12-1 (93 mg, 0.32 mmol) in n-butanol (4 mL) was added TFA (456 mg, 4.00 mmol) at 15° C., and then the mixture was stirred at 90° C. for 20 h. The reaction mixture was concentrated under reduced pressure. The residue was purified by prep-HPLC to afford Example C31 as an off-white solid.

$^1$H NMR (400 MHz, DMSO-d$_6$) δ 0.86 (3H, t, J=7.2 Hz), 1.41-1.55 (4H, m), 1.81-1.95 (2H, m), 2.11-2.25 (7H, m), 2.36-2.48 (2H, m), 2.62-2.75 (2H, m), 2.91-3.01 (2H, m), 3.06 (3H, s), 3.11 (3H, s), 3.75 (3H, s), 3.87 (3H, s), 8.77 (1H, s), 6.88 (1H, d, J=8.4 Hz), 7.17 (1H, t, J=8.4 Hz), 7.43 (1H, s), 7.82 (1H, d, J=8.0 Hz), 8.12 (1H, s), 8.13 (1H, s), 8.22 (1H, s). LC-MS: MS Calculated 631.3, MS Found 632.2 [M+H]$^+$.

[Example C32] N-(6-(((5-chloro-2-((5-ethyl-2-methoxy-4-(4-morpholinopiperidin-1-yl)phenyl)amino)pyrimidin-4-yl)amino)-2,3-dimethoxyphenyl)-N-methylmethanesulfonamide

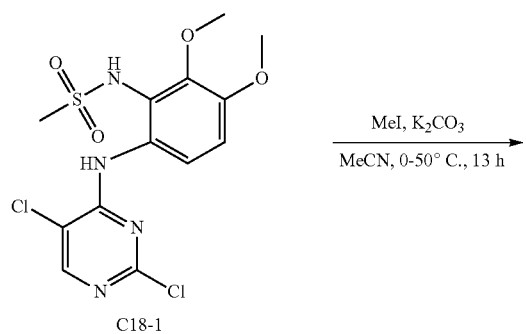

C18-1

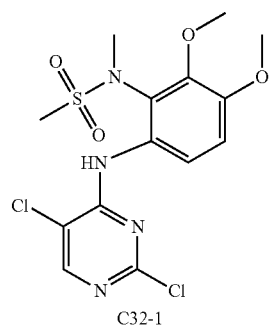

C32-1

To a mixture of C18-1 (580 mg, 1.47 mmol) in MeCN (10 mL) was added K₂CO₃ (245 mg, 1.77 mmol) and MeI (251 mg, 1.77 mmol) at 0° C., it was stirred at 50° C. for 13 h. The reaction mixture was poured into water (10 mL) and extracted with EtOAc (10 mL×3). The combined organic layer was washed with brine (10 mL), dried over anhydrous Na₂SO₄ and concentrated under reduced pressure to afford compound C32-1 as a yellow solid.

$^1$H NMR (400 MHz, CDCl₃) δ 3.01 (3H, s), 3.25 (3H, s), 3.91 (3H, s), 4.04 (3H, s), 7.02 (1H, d, J=9.2 Hz), 7.84 (1H, d, J=9.6 Hz), 8.17 (1H, s), 8.39 (1H, s).

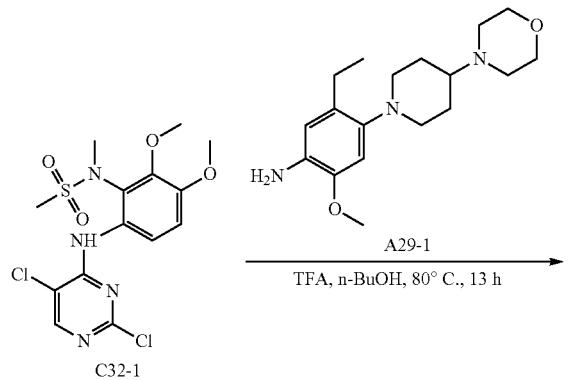

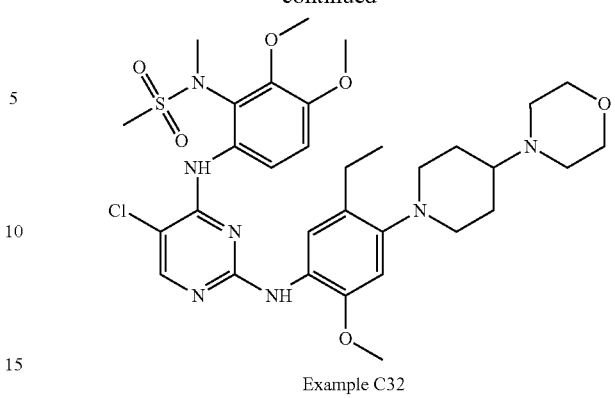

Example C32

To a mixture of compound C32-1 (200 mg, 0.491 mmol) and A29-1 (172 mg, 0.540 mmol) in n-BuOH (5 mL) was added TFA (616 mg, 5.40 mmol) at 20° C., and then the mixture was stirred at 80° C. for 13 h. MeCN was removed under reduced pressure and the remaining solvent was removed by lyophilization to afford Example C32 as a light yellow solid.

$^1$H NMR (400 MHz, CDCl₃) δ 0.98-1.09 (3H, m), 1.65-1.77 (2H, m), 1.87-2.01 (2H, m), 2.23-2.41 (1H, m), 2.47-2.74 (8H, m), 3.04 (3H, s), 3.05-3.17 (2H, m), 3.24 (3H, s), 3.63-3.84 (4H, m), 3.85 (3H, s), 3.92 (3H, s), 4.05 (3H, s), 6.65 (1H, s), 6.99 (1H, d, J=9.2 Hz), 7.38 (1H, s), 7.82 (1H, d, J=9.2 Hz), 7.99 (1H, s), 8.04 (1H, s) 8.05 (1H, s) MS Calcd.: 689.2; MS Found: 690.3 [M+H]⁺.

[Example D1] 5-bromo-N2-(2-methoxy-5-methyl-4-morpholinophenyl)-N4-(5-(methylsulfonyl)quinoxalin-6-yl)pyrimidine-2,4-diamine

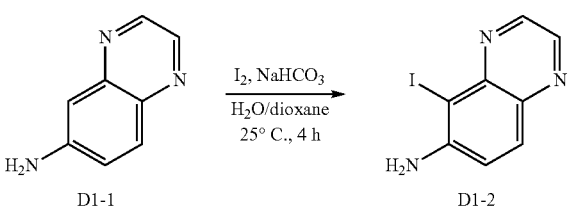 [SMILES: Nc1ccc2nccnc2c1 ; Nc1ccc2nccnc2c1I]

To a mixture of D1-1 (5.00 g, 34.4 mmol) in dioxane (75 mL) and H₂O (25 mL) was added I₂ (21.9 g, 86.1 mmol) and NaHCO₃ (7.23 g, 86.1 mmol) at 25° C., and then the mixture was stirred at 25° C. for 4 h. Then to the mixture was added Na₂SO₃ (11.0 g) at 25° C. and the mixture was stirred at 25° C. for 10 min. The mixture was filtered and the filtrate was concentrated under reduced pressure. The residue was triturated with H₂O (40 mL) at 25° C. for 10 min. The mixture was filtered and the filter cake was concentrated under reduced pressure to afford compound D1-2 as a yellow solid.

$^1$H NMR (400 MHz, DMSO-d₆) δ 6.32 (2H, brs), 7.41 (1H, d, J=8.8 Hz), 7.76 (1H, d, J=8.8 Hz), 8.45-8.60 (1H, m), 8.65-8.80 (1H, m).

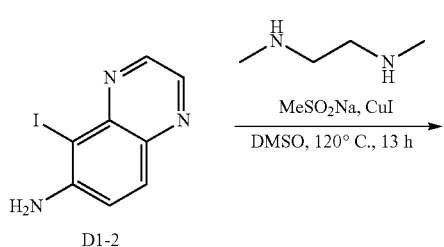

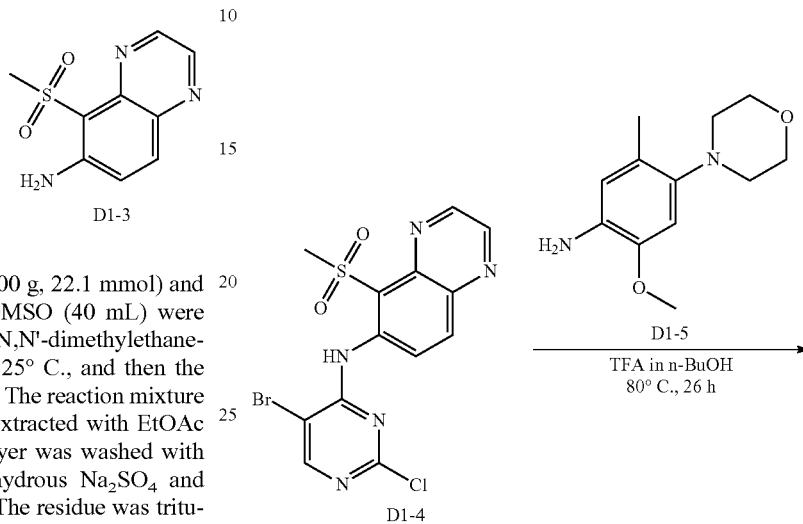

To a mixture of compound D1-2 (6.00 g, 22.1 mmol) and MeSO$_2$Na (2.26 g, 22.1 mmol) in DMSO (40 mL) were added CuI (843 mg, 4.43 mmol) and N,N'-dimethylethane-1,2-diamine (781 mg, 8.85 mmol) at 25° C., and then the mixture was stirred at 120° C. for 13 h. The reaction mixture was poured into water (50 mL) and extracted with EtOAc (50 mL×3). The combined organic layer was washed with 50% NaCl (50 mL), dried over anhydrous Na$_2$SO$_4$ and concentrated under reduced pressure. The residue was triturated with MeCN/H$_2$O (10 mL, 1:1) at 25° C. for 10 min. The precipitated solid was collected by filtration and then dried under reduced pressure to afford compound D1-3 as a yellow solid.

$^1$H NMR (400 MHz, DMSO-d$_6$) δ 3.52 (3H, s), 7.36 (1H, d, J=9.6 Hz), 7.58 (2H, s), 7.91 (1H, d, J=9.2 Hz), 8.60 (1H, d, J=2.0 Hz), 8.76 (1H, d, J=2.0 Hz).

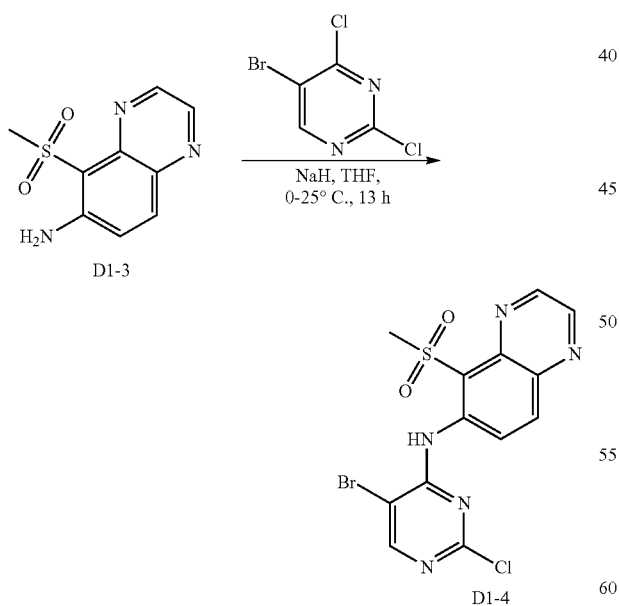

To a mixture of compound D1-3 (500 mg, 2.24 mmol) and 5-bromo-2,4-dichloro-pyrimidine (510 mg, 2.24 mmol) in THF (6 mL) was added NaH (107 mg, 2.69 mmol, 60% purity in mineral oil) at 25° C., and then the mixture was stirred at 25° C. for 13 h. The reaction mixture was added H$_2$O (5 mL) and MeCN (5 mL) triturated for 10 min. The precipitated solid was collected by filtration and then dried under reduced pressure to afford compound D1-4 as a yellow solid.

$^1$H NMR (400 MHz, DMSO-d$_6$) δ 3.77 (3H, s), 8.45 (1H, d, J=9.2 Hz), 8.65-8.70 (2H, m), 8.95-9.04 (1H, m), 9.09-9.15 (1H, m), 10.96 (1H, s).

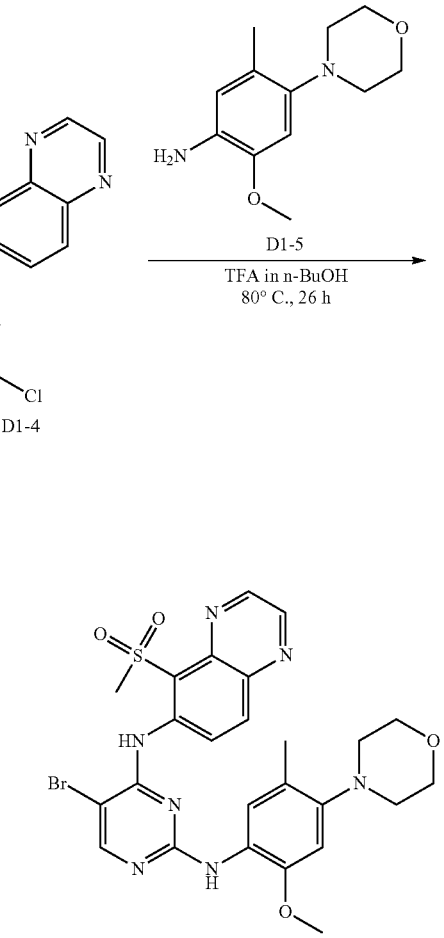

Example D1

To a mixture of compound D1-4 (110 mg, 0.265 mmol) and D1-5 (59.0 mg, 0.265 mmol) in n-BuOH (4.00 mL) was added TFA (2.51 g, 22.0 mmol) at 25° C., and then the mixture was stirred at 80° C. for 26 h. The reaction mixture was concentrated under reduced pressure. The residue was purified by HPLC and most of MeCN was removed under reduced pressure. The remaining solvent was removed by lyophilization to afford Example D1 as a yellow solid.

$^1$H NMR (400 MHz, DMSO-d$_6$) δ 2.09 (3H, s), 2.85-2.97 (5H, m), 3.75-3.89 (9H, m), 6.80 (1H, s), 7.32 (1H, s), 8.01-8.15 (1H, m), 8.36 (1H, s), 8.49 (1H, s), 8.85-9.10 (3H, m), 10.87 (1H, brs). MS Calcd.: 599.1; MS Found: 600.1 [M+H]$^+$.

[Example D3] N-(6-((5-chloro-2-((2-methoxy-4-(piperidin-4-yl)phenyl)amino)pyrimidin-4-yl)amino)quinoxalin-5-yl)acetamide

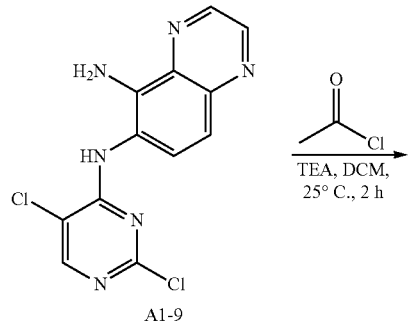

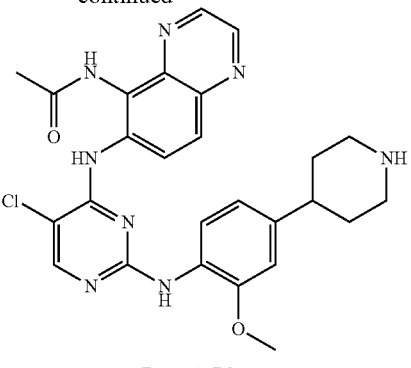

Example D3

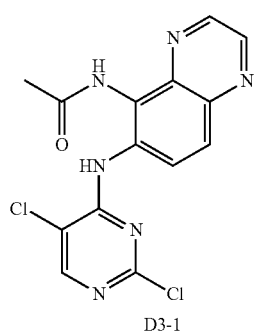

To a mixture of A1-9 (200 mg, 0.651 mmol) and acetyl chloride (77 mg, 0.976 mmol) in DCM (4 mL) was added TEA (131 mg, 1.30 mmol) at 25° C. under N₂ atmosphere, and then the mixture was stirred at 25° C. for 2 h under N₂ atmosphere. The mixture was poured into water (50 mL) and extracted with EtOAc (50 mL×3). The organic layers were washed with brine (50 mL), dried over anhydrous Na₂SO₄, and concentrated under reduced pressure to afford compound D3-1 as a brown solid. The crude product was used in next step without purification.

1H NMR (400 MHz, DMSO-d₆) δ 2.30 (3H, s), 8.08 (1H, d, J=9.2 Hz), 8.23 (1H, d, J=9.2 Hz), 8.50 (1H, s), 9.00-9.08 (2H, m), 9.38 (1H, s).

The mixture of compound D3-1 (127 mg, crude) and D3-2 (111 mg, 0.363 mmol) in n-BuOH (4 mL) was added TFA (497 mg, 4.36 mmol) at 25° C. The mixture was stirred at 80° C. for 26 h. To the mixture was added 4 M HCl/dioxane (5 mL), and then the mixture was stirred at 25° C. for 1 h. The reaction mixture was concentrated under reduced pressure. The residue was purified by prep-HPLC (column: Boston Prime C18 150×30 mm×5 um; mobile phase: [water (0.225% FA)-ACN]; B %: 8%-38%, 9 min), most of MeCN was removed under reduced pressure and the remaining solvent was removed by lyophilization to afford Example D3 as a brown solid.

1H NMR (400 MHz, DMSO-d₆) δ 1.60-1.70 (2H, m), 1.72-1.81 (2H, m), 2.29 (3H, s), 2.63-2.70 (1H, m), 2.73-2.82 (2H, m), 2.92-3.20 (2H, m), 3.80 (3H, s), 6.61 (1H, d, J=8.8 Hz), 6.85 (1H, s), 7.70 (1H, d, J=8.0 Hz), 7.90-7.99 (2H, m), 8.20 (1H, s), 8.38 (1H, s), 8.76 (1H, s), 8.96-9.05 (2H, m), 10.69 (1H, s). MS Calcd.: 518.2; MS Found: 519.5 [M+H]⁺.

[Example D4] methyl (6-((5-chloro-2-((2-methoxy-4-(piperidin-4-yl)phenyl)amino)pyrimidin-4-yl)amino)quinoxalin-5-yl)carbamate

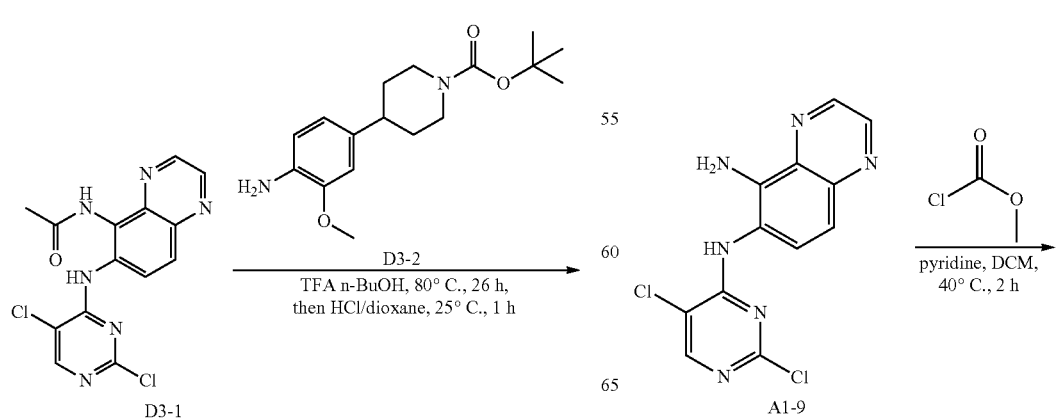

-continued

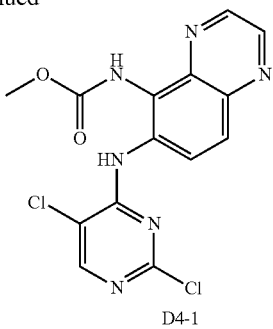

D4-1

The mixture of A1-9 (200 mg, 0.651 mmol) in DCM (4 mL) was added methyl carbonochloridate (540 mg, 5.71 mmol) and pyridine (258 mg, 3.26 mmol), and then the mixture was stirred at 40° C. for 2 h. The reaction mixture was poured into water (50 mL) and extracted with EtOAc (50 mL×3). The combined organic layer was washed with brine (50 mL), dried over anhydrous Na$_2$SO$_4$ and concentrated under reduced pressure to afford compound D4-1 as a brown solid. The crude product was used in next step without further purification.

1H NMR (400 MHz, DMSO-d$_6$) δ 3.70 (3H, s), 8.06 (1H, d, J=9.2 Hz), 8.19 (1H, d, J=9.2 Hz), 8.50 (1H, s), 8.95-9.03 (2H, m), 9.32 (1H, s), 9.75 (1H, s).

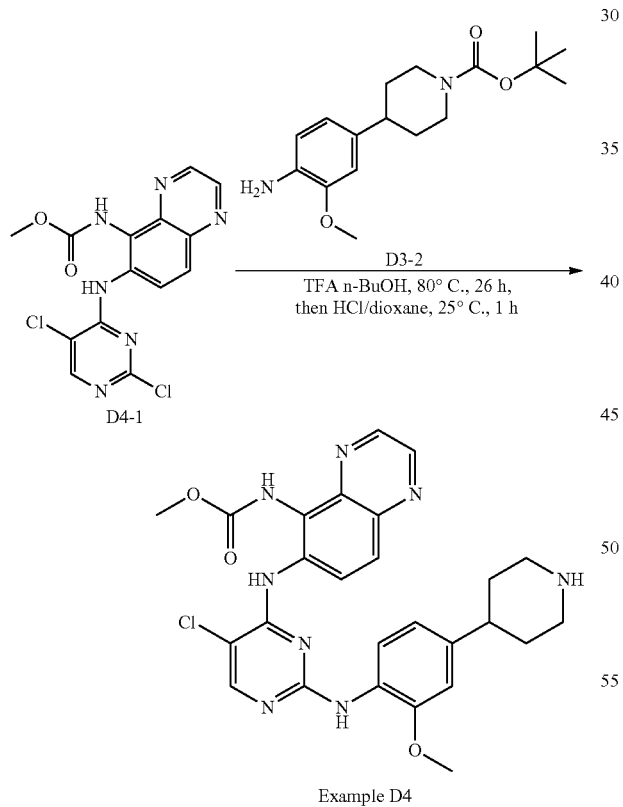

Example D4

The mixture of methyl compound D4-1 (323 mg, crude) and D3-2 (271 mg, 0.884 mmol) in n-BuOH (10 mL) was added TFA (1.21 g, 10.6 mmol). The mixture was stirred at 80° C. for 26 h. To the mixture was added 4M HCl/dioxane (5 mL), and then the mixture was stirred at 25° C. for 1 h. The reaction mixture was concentrated under reduced pressure. The residue was purified by prep-HPLC and most of MeCN was removed under reduced pressure and the remaining solvent was removed by lyophilization to afford Example D4 as a yellow solid.

1H NMR (400 MHz, CD$_3$CN) δ 1.52-1.61 (2H, m), 1.68-1.78 (2H, m), 2.52-2.60 (1H, m), 2.64-2.75 (2H, m), 3.05-3.13 (2H, m), 3.85 (3H, s), 3.86 (3H, s), 6.63 (1H, dd, J=8.4, 2.0 Hz), 6.85 (1H, d, J=2.0 Hz), 7.38 (1H, s), 7.89 (1H, d, J=8.4 Hz), 8.02 (1H, d, J=9.6 Hz), 8.16 (1H, s), 8.42 (1H, d, J=9.2 Hz), 8.86 (1H, d, J=2.0 Hz) 8.93 (2H, m). MS Calcd.: 534.2; MS Found: 535.4 [M+H]$^+$.

[Example D6] N-(6-((2-((4-(azetidin-3-yloxy)-2-methoxyphenyl)amino)-5-chloropyrimidin-4-yl)amino)quinoxalin-5-yl)methanesulfonamide

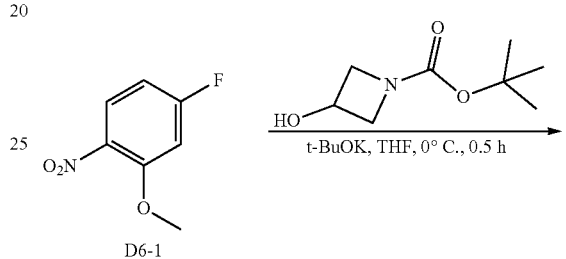

D6-1

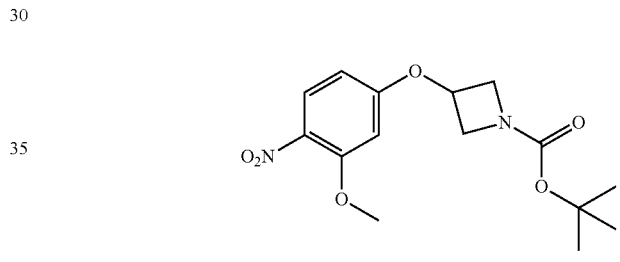

D6-2

To a mixture compound D6-1 (1.00 g, 5.84 mmol) and 3-acetoxy-Boc-2-azetidinone (1.11 g, 6.43 mmol) in THF (5 mL). was added a solution of t-BuOK (655 mg, 5.84 mmol) in THF (10 mL) at 0° C., and then the mixture was stirred at 0° C. for 0.5 h. The reaction mixture was poured into water (15 mL) and extracted with EtOAc (15 mL×3). The combined organic layer was washed with brine (15 mL), dried over anhydrous Na$_2$SO$_4$ and concentrated under reduced pressure to afford compound D6-2 as black oil.

$^1$H NMR (400 MHz, CDCl$_3$) δ 1.46 (9H, s), 3.95 (3H, s), 3.98-4.02 (2H, m), 4.32-4.36 (2H, m), 4.88-5.00 (1H, m), 6.27 (1H, dd, J=9.2, 2.4 Hz), 6.48 (1H, d, J=2.4 Hz), 7.98 (1H, d, J=9.2 Hz).

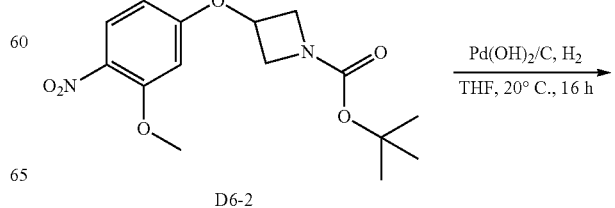

D6-2

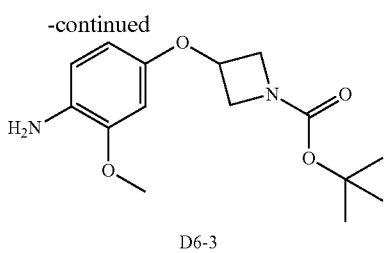

D6-3

To a solution compound D6-2 (1.88 g, 5.80 mmol) in THF (10 mL) was added Pd(OH)$_2$/C (40 mg, 20% purity). The suspension was degassed under vacuum and purged with H$_2$ several times. The mixture was stirred at 20° C. for 16 h under H$_2$ (15 psi) atmosphere. The reaction mixture was concentrated under reduced pressure to afford compound D6-3 as black oil.

$^1$H NMR (400 MHz, CDCl$_3$) δ 1.46 (9H, s), 3.84 (3H, s), 3.97-4.02 (2H, m), 4.22-4.39 (2H, m), 4.66-4.85 (1H, m), 6.11 (1H, dd, J=8.4, 2.4 Hz), 6.40 (1H, d, J=2.4 Hz), 6.62 (1H, d, J=8.4 Hz).

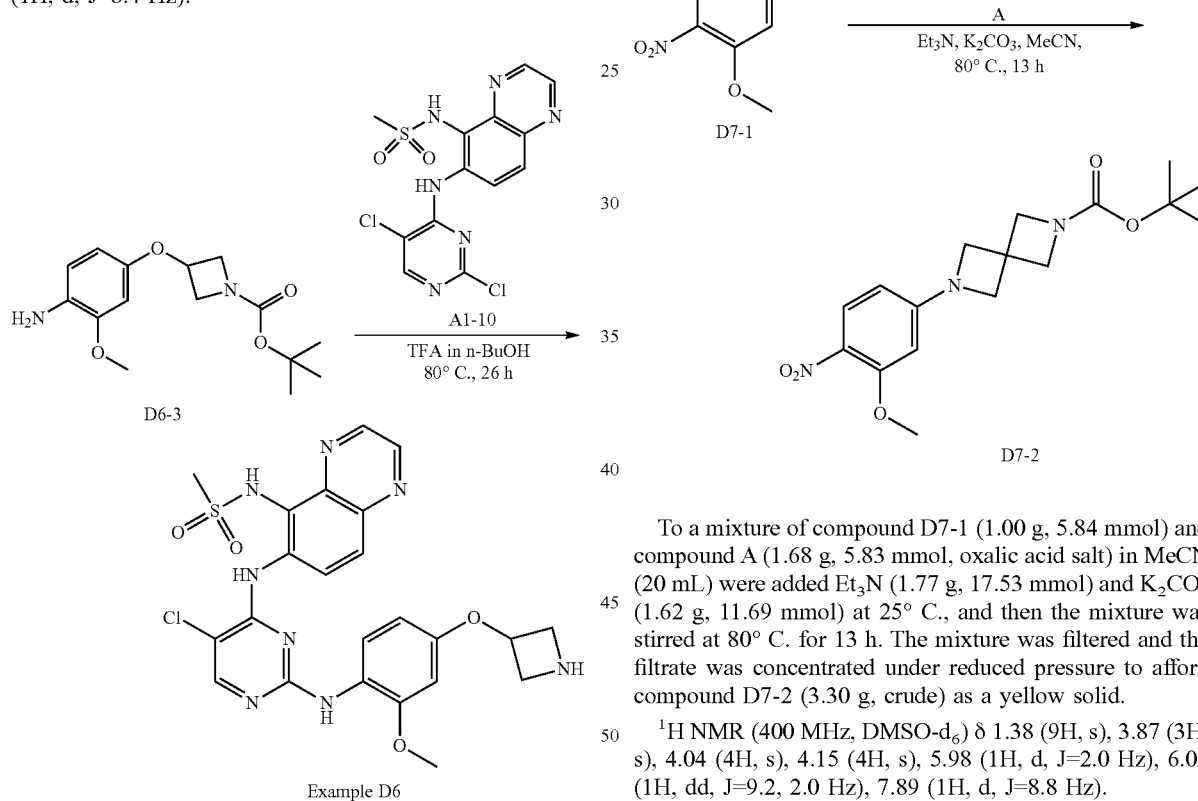

To a mixture compound D6-3 (200 mg, 0.679 mmol) and A1-10 (262 mg, 0.680 mmol) in n-BuOH (3 mL), was added TFA (456 mg, 4.00 mmol), and then the mixture was stirred at 80° C. for 26 h. The mixture was concentrated under reduced pressure. To the residue was added TFA (4 mL), and the mixture was stirred at 20° C. for 2 h. The reaction mixture was concentrated under reduced pressure. The residue was purified by prep-HPLC. Most of MeCN was removed under reduced pressure and the remaining solvent was removed by lyophilization to afford Example D6 as a yellow solid.

$^1$H NMR (400 MHz, DMSO-d$_6$) δ 3.01 (3H, s), 3.57-3.63 (2H, m), 3.76 (3H, s), 3.87-3.95 (2H, m), 4.95-5.06 (1H, m), 6.31 (1H, dd, J=8.8, 2.4 Hz), 6.57 (1H, d, J=2.4 Hz), 7.42 (1H, d, J=8.8 Hz), 7.80 (1H, d, J=9.6 Hz), 8.18 (1H, s), 8.3 (1H, s), 8.74 (1H, d, J=8.8 Hz), 8.87 (1H, d, J=2.4 Hz), 8.94 (1H, d, J=1.2 Hz), 9.08 (1H, s). MS Calcd.: 542.1; MS Found: 543.2 [M+H]$^+$.

[Example D7] N-(6-((5-chloro-2-((2-methoxy-4-(2,6-diazaspiro[3.3]heptan-2-yl)phenyl)amino)pyrimidin-4-yl)amino)quinoxalin-5-yl)methanesulfonamide To a mixture of compound D7-1 (1.00 g, 5.84 mmol) and compound A (1.68 g, 5.83 mmol, oxalic acid salt) in MeCN (20 mL) were added Et$_3$N (1.77 g, 17.53 mmol) and K$_2$CO$_3$ (1.62 g, 11.69 mmol) at 25° C., and then the mixture was stirred at 80° C. for 13 h. The mixture was filtered and the filtrate was concentrated under reduced pressure to afford compound D7-2 (3.30 g, crude) as a yellow solid.

$^1$H NMR (400 MHz, DMSO-d$_6$) δ 1.38 (9H, s), 3.87 (3H, s), 4.04 (4H, s), 4.15 (4H, s), 5.98 (1H, d, J=2.0 Hz), 6.02 (1H, dd, J=9.2, 2.0 Hz), 7.89 (1H, d, J=8.8 Hz).

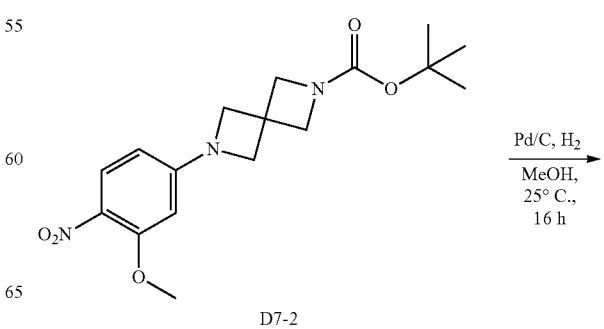

-continued

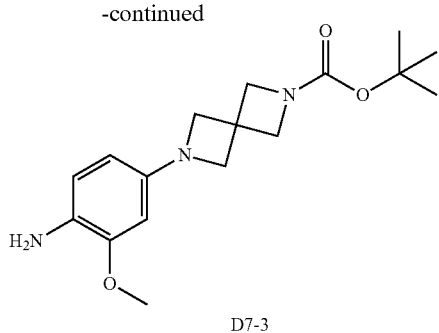

D7-3

To a solution of compound D7-2 (3.30 g, crude) in MeOH (30 mL) was added wet Pd/C (330 mg, 0.944 mmol, 10% purity). The suspension was degassed under vacuum and purged with $H_2$ several times. The mixture was stirred under $H_2$ (15 psi) at 25° C. for 16 h. The mixture was filtered and the filtrate was concentrated under reduced pressure to afford compound D7-3 (2.40 g, yield: 80%) as a black brown solid.

$^1$H NMR (400 MHz, DMSO-$d_6$) δ 1.38 (9H, s), 3.71 (3H, s), 3.76 (4H, s), 3.98 (4H, s), 4.16 (2H, brs), 5.82 (1H, dd, J=8.4, 2.0 Hz), 5.99 (1H, d, J=1.6 Hz), 6.50 (1H, d, J=8.4 Hz).

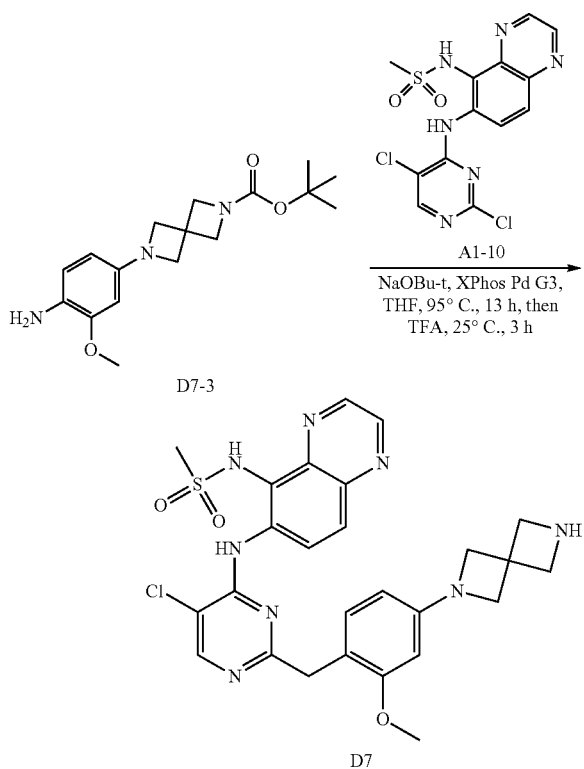

To a mixture of compound D7-3 (170 mg, 0.532 mmol) and A1-10 (205 mg, 0.532 mmol) in THF (15 mL) were added NaOBu-t (153 mg, 1.60 mmol) and XPhos Pd G3 (90 mg, 0.11 mmol, 20 mol %) at 25° C. under $N_2$ atmosphere, and then the mixture was stirred at 95° C. for 13 h under $N_2$ atmosphere. The reaction mixture was concentrated under reduced pressure. To the residue was added TFA (3 mL), and the mixture was stirred at 25° C. for 3 h. The reaction mixture was concentrated under reduced pressure. The residue was purified by prep-HPLC (column: Boston Prime C18 150×30 mm×5 um; mobile phase: [water (0.225% FA)-ACN]; B %: 11%-41%, 9 min), most of MeCN was removed under reduced pressure and the remaining solvent was removed by lyophilization to afford Example D7 (11.5 mg, FA salt, yield: 3%) as a gray solid.

$^1$H NMR (400 MHz, CDCl$_3$) δ 2.94 (3H, s), 3.84 (3H, s), 4.01 (4H, s), 4.17 (4H, s), 5.94 (1H, dd, J=8.8, 2.4 Hz), 6.02 (1H, d, J=2.4 Hz), 7.20 (1H, s), 8.88 (1H, d, J=8.4 Hz), 8.05 (1H, d, J=9.6 Hz), 8.14 (1H, s), 8.81-8.86 (2H, m), 8.90 (1H, d, J=1.6 Hz), 9.12 (1H, s). MS Calcd.: 567.2; MS Found: 568.1 [M+H]$^+$.

EXPERIMENTAL EXAMPLES

<Experimental Example 1> Measurement of an Inhibitory Ability on Wild-Type Ba/F3 EGFR and Ba/F3 EGFR Mutations in Ba/F3 Cell Lines In order to evaluate an inhibitory ability on wild-type Ba/F3 EGFR and Ba/F3 EGFR mutations in Ba/F3 cell lines by the compounds of Formula 1, the experiment was carried out as described below. The results are shown in Table 5.

The measurement of activities on Ba/F3 cells harboring wild-type EGFR and EGFR mutants by the compounds of the present invention were determined utilizing the CELL-TITER-GLO™ system from Promega, as follows. The CELLTITER-GLO™ assay is a method for measuring the ATP present in cells to determine the cell viability. Ba/F3 EGFR wild-type and Ba/F3 EGFR L858R/C797S (L/C), Ba/F3 EGFR L858R/T790M/C797S (L/T/C), Ba/F3 EGFR Del19/T790M (D/T), Ba/F3 EGFR Del19/C797S (D/C), Ba/F3 EGFR Del19/T790M/C797S (D/T/C) mutant cell lines were maintained in RPMI1640, containing 1000 FBS, 1% penicillin-streptomycin, 1 ag/mL puromycin. Cells were grown in a humidified incubator at 37° C. with 50 CO$_2$.

The analysis of an EGFR inhibitory activity by the compounds was carried out in accordance with the analysis reaction recipe below.

2500 cells/90 μL were seeded in 96 well cell culture plate, and after 24 hours, treated with the compounds represented by Formula 1 in concentrations of 0, 0.3, 0.9, 2.7, 8.2, 24.7, 74.1, 222.2, 666.7, 2000 (nM). After the reaction of 72 hours, the plate was incubated for 30 minutes at ambient temperature, and then, was further treated with 100 μL of the CELLTITER-GLO™ reagent and was shaken for 10 minutes at ambient temperature. Finally, measurement of the luminescence values were obtained using the SPECTRA-MAX™ iD3 (Molecular Devices), and the IC$_{50}$ values of the compound were analyzed using the GraphPad Prism program (version 9.0.2, GraphPad Software, Inc.). The inhibitory activity of the compound was confirmed, and the results are summarized in Table 4.

TABLE 5

Measurement of an inhibitory ability on wild-type Ba/F3 EGFR and Ba/F3 EGFR mutations in Ba/F3 cell lines

| | Ba/F3 EGFR mutant cell (IC$_{50}$, nM) | | | | | |
|---|---|---|---|---|---|---|
| Example | WT$^a$ | L/C$^b$ | L/T/C$^c$ | D/T$^d$ | D/C$^e$ | D/T/C$^f$ |
| A1 | 312 | 33 | 17 | 7 | 17 | 6 |
| A2 | 381 | 26 | 9 | 4 | 12 | 4 |
| A3 | N/T* | N/T | 97.6 | N/T | N/T | 48 |
| A4 | 249 | 34 | 6 | 3 | 12 | 1 |

TABLE 5-continued

Measurement of an inhibitory ability on wild-type Ba/F3 EGFR and Ba/F3 EGFR mutations in Ba/F3 cell lines

| Example | Ba/F3 EGFR mutant cell (IC$_{50}$, nM) | | | | | |
|---|---|---|---|---|---|---|
| | WT[a] | L/C[b] | L/T/C[c] | D/T[d] | D/C[e] | D/T/C[f] |
| A5 | 938 | 244 | 69 | N/T | 76 | 23 |
| A6 | 498 | 29 | 12 | 5 | 14 | 4 |
| A7 | 602 | 246 | 169 | N/T | 96 | 36 |
| A8 | 919 | 147 | 18 | N/T | 38 | 6 |
| A9 | 524 | 106 | 80 | N/T | 15 | 62 |
| A10 | 400 | 37 | 9 | 5 | 16 | 4 |
| A11 | N/T | N/T | N/T | N/T | N/T | N/T |
| A12 | N/T | N/T | N/T | N/T | N/T | N/T |
| A13 | >2000 | 646 | 338 | N/T | 265 | 109 |
| A14 | N/T | N/T | N/T | N/T | N/T | N/T |
| A15 | 811 | 423 | 473 | 156 | 295 | 211 |
| A16 | N/T | N/T | N/T | N/T | N/T | N/T |
| A17 | N/T | N/T | N/T | N/T | N/T | N/T |
| A19 | 395 | 80 | 43 | 6 | 66 | 24 |
| A20 | >2000 | >2000 | >2000 | N/T | >2000 | 1595 |
| A21 | 460 | 52 | 103 | 24 | 23 | 58 |
| A22 | 521 | 189 | 369 | N/T | 73 | 189 |
| A23 | 416 | 114 | 49 | 41 | 51 | 16 |
| A24 | 397 | 114 | 13 | 10 | 49 | 74 |
| A25 | 373 | 112 | 34 | 18 | 46 | 134 |
| A26 | 1285 | 163 | 107 | N/T | 72 | 79 |
| A27 | 183 | 184 | 65 | 27 | 101 | 192 |
| A28 | 318 | 101 | 17 | 10 | 36 | 51 |
| A29 | 200 | 79 | 25 | 13 | 27 | 69 |
| A30 | 266 | 83 | 23 | 31 | 28 | 100 |
| A31 | 223 | 79 | 43 | 39 | 50 | 131 |
| A32 | 603 | 51 | 229 | 27 | 11 | 91 |
| A33 | >2000 | 57 | 18 | 8 | 4 | 6 |
| A34 | >2000 | 16 | 13 | 5 | 1 | 4 |
| A35 | 576 | 335 | 659 | 219 | 145 | 272 |
| A36 | 657 | 267 | 485 | 73 | 111 | 241 |
| A37 | 734 | 451 | 640 | 174 | 126 | 205 |
| A38 | 347 | 18 | 33 | 5 | 0.052 | 5 |
| A39 | 779 | 61 | 35 | 4 | 8 | 8 |
| A40 | 845 | 50 | 94 | 10 | 10 | 12 |
| A41 | >2000 | 210 | 258 | 44 | 8 | 28 |
| A42 | 1862 | 80 | 117 | 33 | 2 | 7 |
| A43 | 507 | 28 | 35 | 8 | 6 | 5 |
| A44 | >2000 | 94 | 38 | 12 | 6 | 10 |
| A45 | 734 | 103 | 71 | 9 | 10 | 7 |
| A46 | 739 | 113 | 43 | 7 | 12 | 8 |
| A47 | 730 | 125 | 64 | 17 | 7 | 25 |
| A48 | 601 | 112 | 28 | 9 | 6 | 17 |
| A49 | 243 | 15 | 64 | 4 | 10 | 4 |
| B1 | 302 | 64 | 28 | 8 | 38 | 7 |
| B2 | 2103 | 195 | 13 | N/T | 28 | 7 |
| B3 | 725 | 325 | 86 | N/T | 147 | 30 |
| B4 | 10 | 14 | 9 | N/T | 9 | 4 |
| B5 | 1861 | 223 | 36 | N/T | 30 | 14 |
| B6 | N/T | N/T | N/T | N/T | N/T | N/T |
| B7 | 595 | 98 | 33 | 21 | 34 | 8 |
| B8 | 729 | 554 | 861 | 424 | 320 | 292 |
| B9 | >2000 | >2000 | >2000 | N/T | >2000 | >2000 |
| B10 | 858 | 678 | 584 | N/T | 537 | 252 |
| B11 | 1266 | 781 | 264 | 443 | 583 | 725 |
| B12 | 431 | 87 | 36 | 19 | 29 | 104 |
| B13 | 468 | 114 | 22 | 13 | 41 | 60 |
| B14 | 427 | 41 | 23 | 3 | 6 | 8 |
| B15 | >2000 | 1542 | 2139 | 1312 | 581 | 746 |
| B16 | 1895 | 778 | 823 | 402 | 361 | 741 |
| B17 | >2000 | >2000 | >2000 | 9015 | 1252 | >2000 |
| B18 | >2000 | 1024 | 1441 | 598 | 725 | 818 |
| B19 | 1413 | 182 | 82 | 20 | 36 | 25 |
| B20 | >2000 | 1135 | 1848 | 1807 | 697 | 758 |
| B21 | 1731 | 500 | 693 | 469 | 342 | 448 |
| B22 | >2000 | >2000 | >2000 | 3794 | 2610 | >2000 |
| B23 | 868 | 302 | 354 | 154 | 100 | 112 |
| B24 | 908 | 185 | 65 | 23 | 17 | 20 |
| B25 | 829 | 93 | 83 | 26 | 16 | 22 |
| B26 | 528 | 59 | 61 | 38 | 42 | 9 |
| B27 | 359 | 35 | 40 | 25 | 18 | 5 |
| B28 | 332 | 26 | 50 | 23 | 14 | 5 |
| B29 | 317 | 27 | 68 | 9 | 14 | 2 |
| B30 | 233 | 23 | 71 | 7 | 11 | 2 |
| B31 | 482 | 43 | 43 | 8 | 15 | 6 |
| B32 | 851 | 200 | 83 | 154 | 172 | 29 |
| C1 | 408 | 63 | 12 | 6 | 18 | 13 |
| C2 | 385 | 32 | 18 | 3 | 13 | 9 |
| C3 | 288 | 113 | 23 | 17 | 60 | 92 |
| C4 | 263 | 91 | 38 | 30 | 31 | 132 |
| C5 | 545 | 91 | 94 | 17 | 19 | 34 |
| C6 | 626 | 305 | 596 | 268 | 106 | 222 |
| C7 | 534 | 52 | 24 | 6 | 10 | 10 |
| C8 | 804 | 316 | 308 | 94 | 210 | 170 |
| C9 | 755 | 345 | 356 | 152 | 281 | 260 |
| C10 | 404 | 61 | 45 | 6 | 9 | 9 |
| C11 | 458 | 45 | 39 | 5 | 6 | 9 |
| C12 | 731 | 28 | 29 | 8 | 6 | 9 |
| C13 | 769 | 61 | 52 | 20 | 23 | 27 |
| C14 | 415 | 22 | 21 | 2 | 4 | 4 |
| C15 | 638 | 44 | 30 | 8 | 13 | 14 |
| C16 | 486 | 51 | 34 | 6 | 9 | 10 |
| C17 | 655 | 52 | 40 | 7 | 9 | 14 |
| C18 | 835 | 215 | 194 | 39 | 55 | 54 |
| C19 | 668 | 30 | 54 | 9 | 12 | 7 |
| C20 | 1164 | 87 | 148 | 21 | 22 | 21 |
| C21 | 660 | 61 | 49 | 18 | 10 | 13 |
| C22 | 738 | 36 | 25 | 4 | 5 | 2 |
| C23 | 1677 | 72 | 137 | 30 | 14 | 10 |
| C24 | 605 | 41 | 83 | 14 | 6 | 7 |
| C25 | 707 | 55 | 44 | 6 | 18 | 6 |
| C26 | 421 | 35 | 54 | 8 | 7 | 5 |
| C27 | 565 | 43 | 48 | 16 | 10 | 15 |
| C28 | 699 | 68 | 13 | 10 | 7 | 10 |
| C29 | 669 | 76 | 21 | 7 | 5 | 5 |
| C30 | 664 | 38 | 35 | 10 | 6 | 13 |
| C31 | 698 | 89 | 68 | 22 | 10 | 20 |
| C32 | 1917 | 82 | 191 | 176 | 79 | 46 |
| D1 | >2000 | 1122 | 536 | 477 | 1012 | 959 |
| D2 | 1430 | 771 | 330 | 342 | 462 | 710 |
| D3 | >2000 | 1029 | 1177 | 678 | 378 | 717 |
| D4 | >2000 | 1567 | >2000 | 694 | 746 | 870 |
| D5 | 1716 | 680 | 1323 | 466 | 595 | 699 |
| D6 | >2000 | 1125 | 1076 | 800 | 706 | 592 |
| D7 | >2000 | >2000 | >2000 | >2000 | 2689 | >2000 |

In Table 5 above,
*N/T refers to Not Tested.
[a]WT refers to Ba/F3 EGFR Wild-type
[b]L/C refers to Ba/F3 EGFR L858R/C797S mutants
c[c]L/T/C refers to Ba/F3 EGFR L858R/T790M/C797S mutants
[d]D/T refers to Ba/F3 EGFR Del19/T790M mutants
[e]D/C refers to Ba/F3 EGFR Del19/C797S mutants
[f]D/T/C refers to Ba/F3 EGFR Del19/T790M/C797S mutants As indicated in Table 5 above, it was confirmed that the example compounds according to the present invention showed very high inhibitory activities on various EGFR mutations including EGFR L858R/T790M/C797S and EGFR Del19/T790M/C797S.

In addition, the example compounds according to the present invention show relatively weak inhibitory activity on wild-type EGFR in a Ba/F3 cell line leading to high selectivity over EGFR mutations including EGFR L858R/T790M/C797S and EGFR Del19/T790M/C797S.

<Experimental Example 2> In Vivo Anti-Tumor Efficacy of the Compound of Formula 1 on the Subcutaneous Ba/F3 EGFR L858R/T790M/C797S and Ba/F3 EGFR Del19/T790M/C797S Murine Pro-B Cell Tumor Models of Female BALB/c Nude Mice or NOD-SCID Mice To evaluate an in vivo inhibitory ability on tumor growth of Ba/F3 cells with EGFR L858R/T790M/C797S(L/T/C) and Del19/T790M/C797S(D/T/C) mutations by the compounds of Formula 1, Experimental Example 2 was carried out as described below.

The Ba/F3 EGFR L/T/C and D/T/C cells were maintained in vitro as a suspension culture in RPMI1640 medium supplemented with 10% fetal bovine serum, 100 U/mL penicillin and 100 µg/mL streptomycin at 37° C. with 5% $CO_2$. Each mouse was inoculated subcutaneously at the right flank with Ba/F3 EGFR L/T/C and D/T/C cells ($0.5×10^6$) in 0.1 mL of PBS supplemented with BD Matrigel (1:1) for tumor development. The tumor cells were routinely subcultured twice weekly. The cells growing in an exponential growth phase were harvested and counted for tumor inoculation. Each mouse was inoculated subcutaneously at the right flank with Ba/F3 EGFR L/T/C and D/T/C cells ($0.5×10^6$) in 0.1 mL of PBS supplemented with BD Matrigel (1:1) for tumor development. The animals were randomized and started treatment when the average tumor volume reached >160 $mm^3$ for the efficacy study. The inhibitory ability on tumor growth evaluation study consisted of five sets (Set A, B, C, D, and E). The experimental design of the five sets of the study were summarized in Table 6.

using the formula: $V=0.5a×b^2$ where a and b were the long and short diameters of the tumor, respectively.

Tumor Growth Inhibition was calculated for each group using the formula: TGI (%)=[1−(Ti−T0)/(Vi−V0)]×100; where Ti was the average tumor volume of a treatment group on a given day, T0 was the average tumor volume of the treatment group on the first day of treatment, Vi was the average tumor volume of the vehicle control group on the same day with Ti, and V0 was the average tumor volume of the vehicle group on the first day of treatment.

Tumor volume was measured at study termination. The T/C value (in percent) was an indication of antitumor effectiveness, T and C were the mean tumor volume of the treated and control groups, respectively, on a given day.

A one-way ANOVA was performed to compare the tumor volume, comparisons between all groups were carried out with Games-Howell or Dunnett's test. In addition, independent-sample t-test was also calculated to compare different groups as supplemental reference. All data were analyzed using SPSS 17.0. $p<0.05$ was considered to be statistically significant.

The results of this Experimental Example are shown in FIGS. 1A-5B.

Figure 1B:
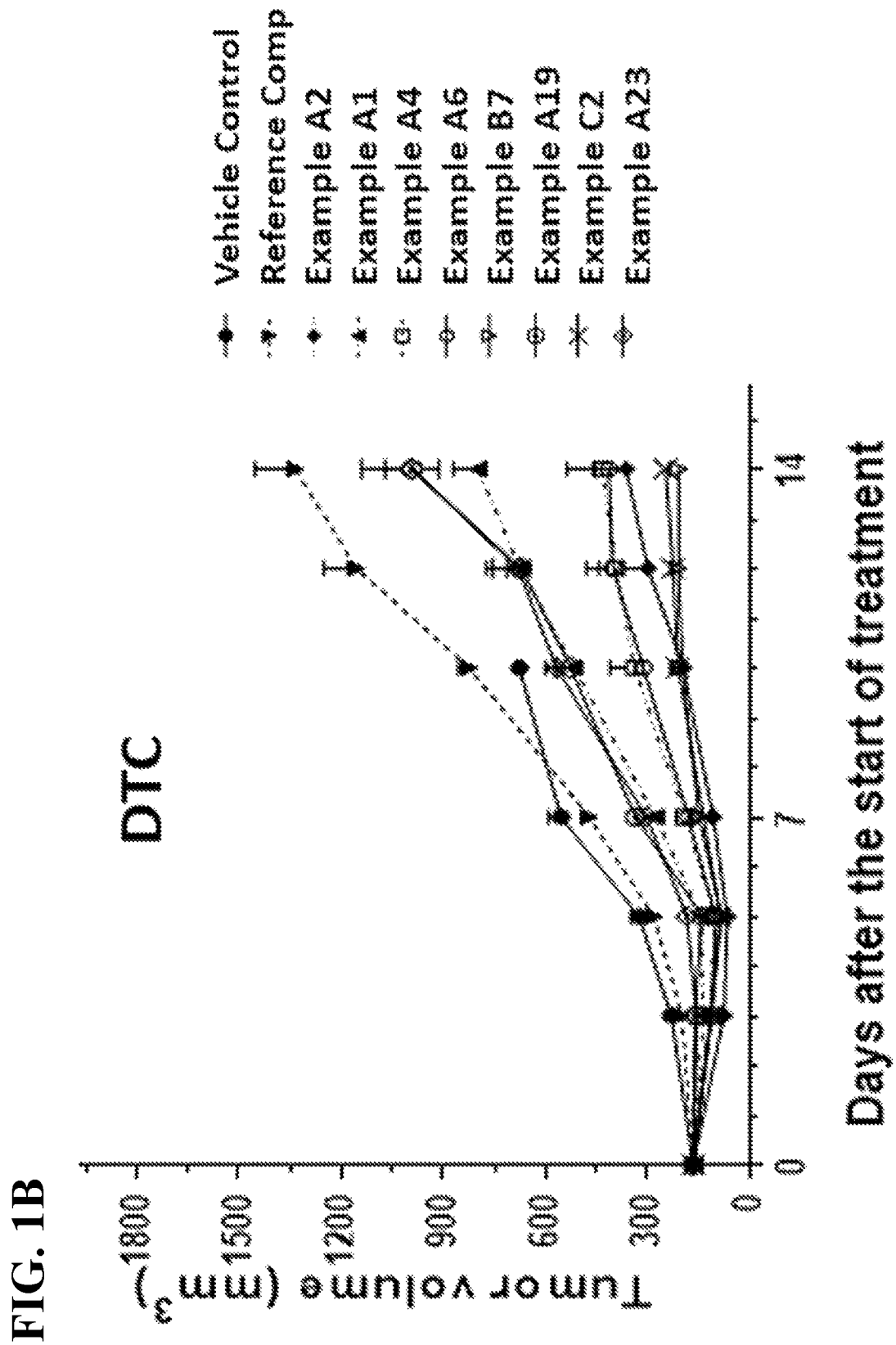
Figure 2A:
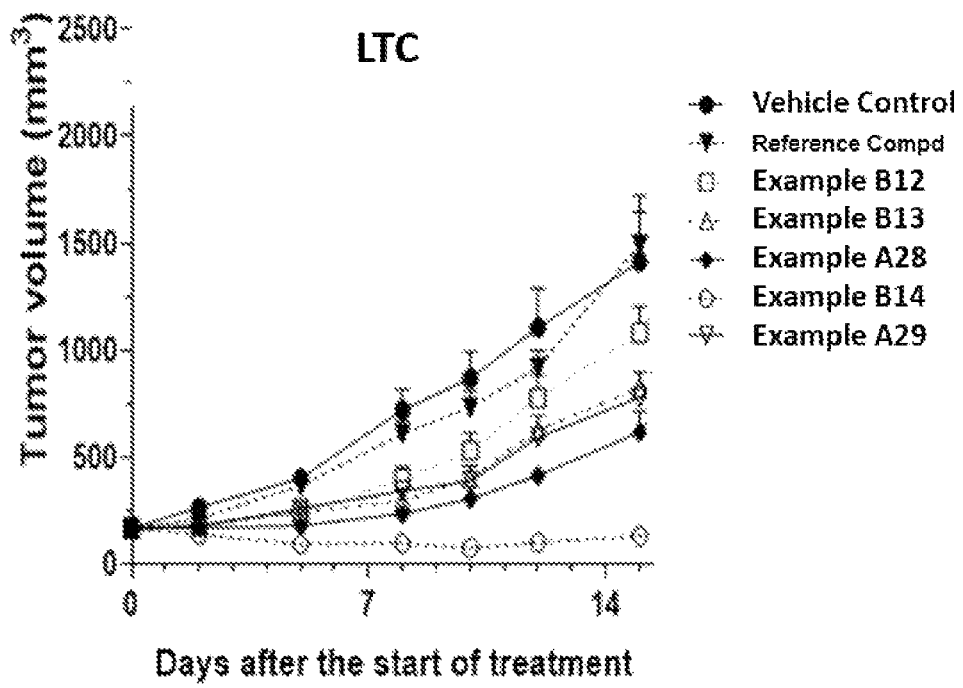
FIGS. 2A-5B show tumor growth curves of different treatment groups of female NOD-SCID mice bearing Ba/F3 EGFR L/T/C murine pro-B cell established tumors (LTC) and mice bearing Ba/F3 EGFR D/T/C murine pro-B cell tumor models (DTC). Data points represent group mean, error bars represent standard error of the mean (SEM).
Figure 2B:
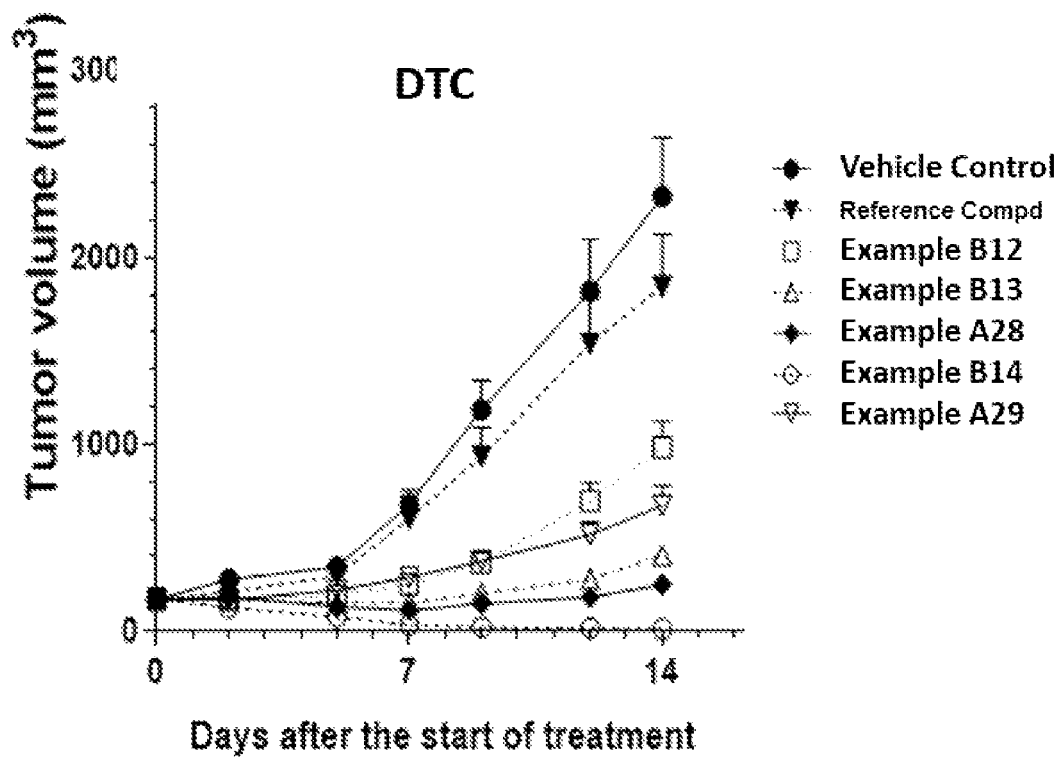
Figure 3A:
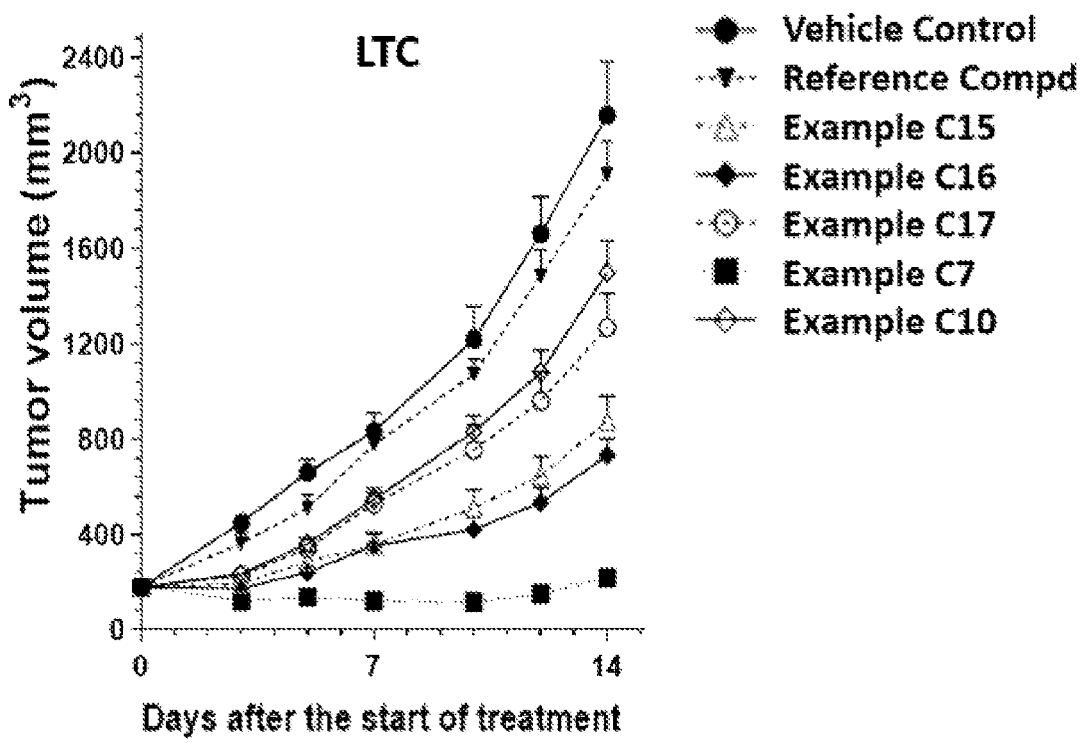
Figure 3B:
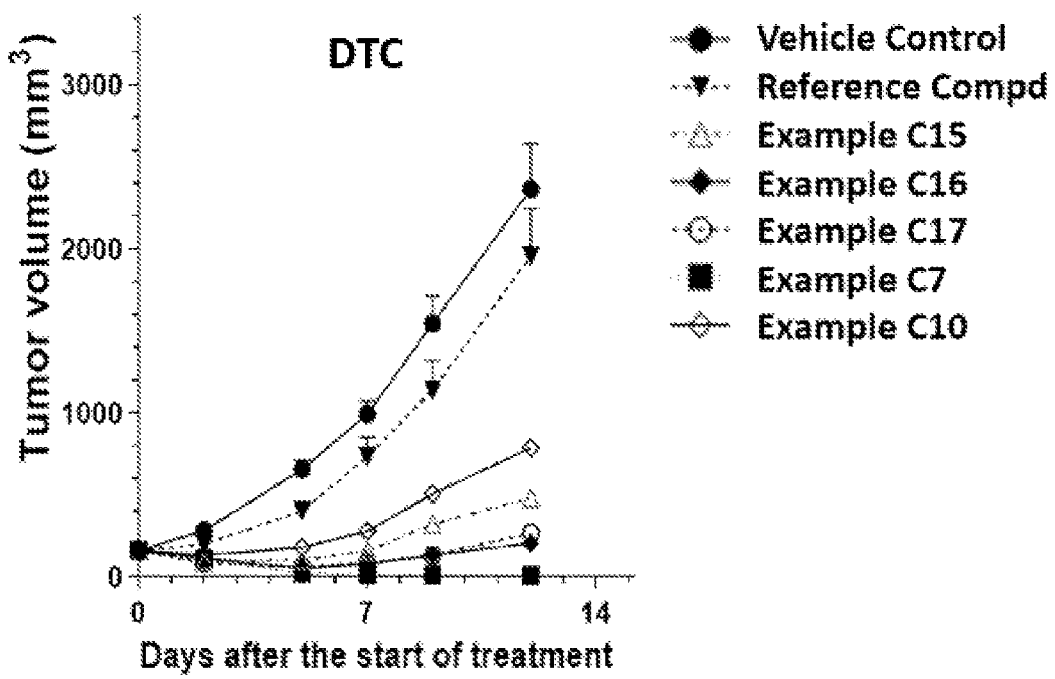
Figure 4A:
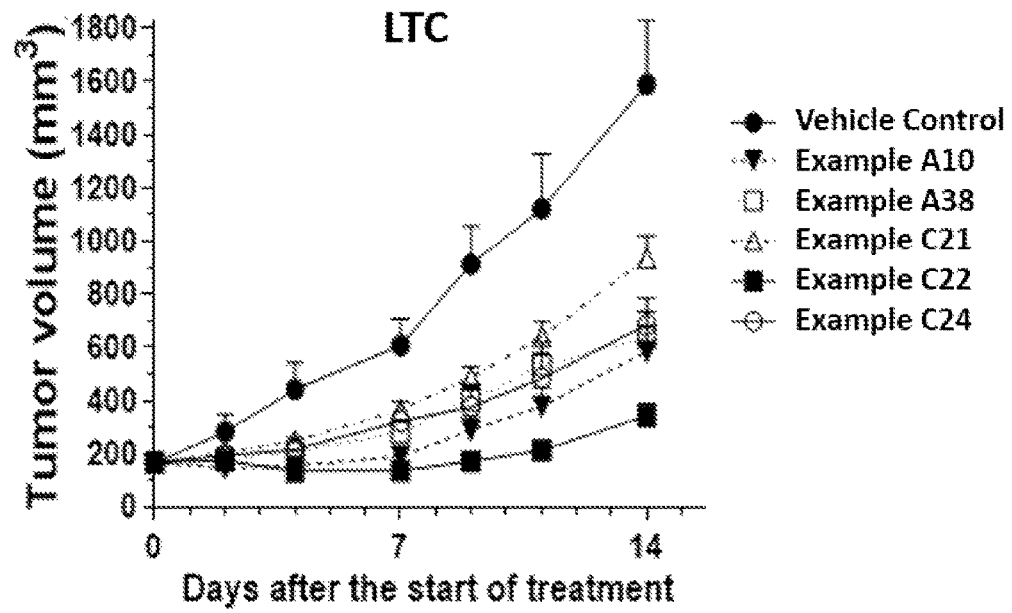
Figure 4B:
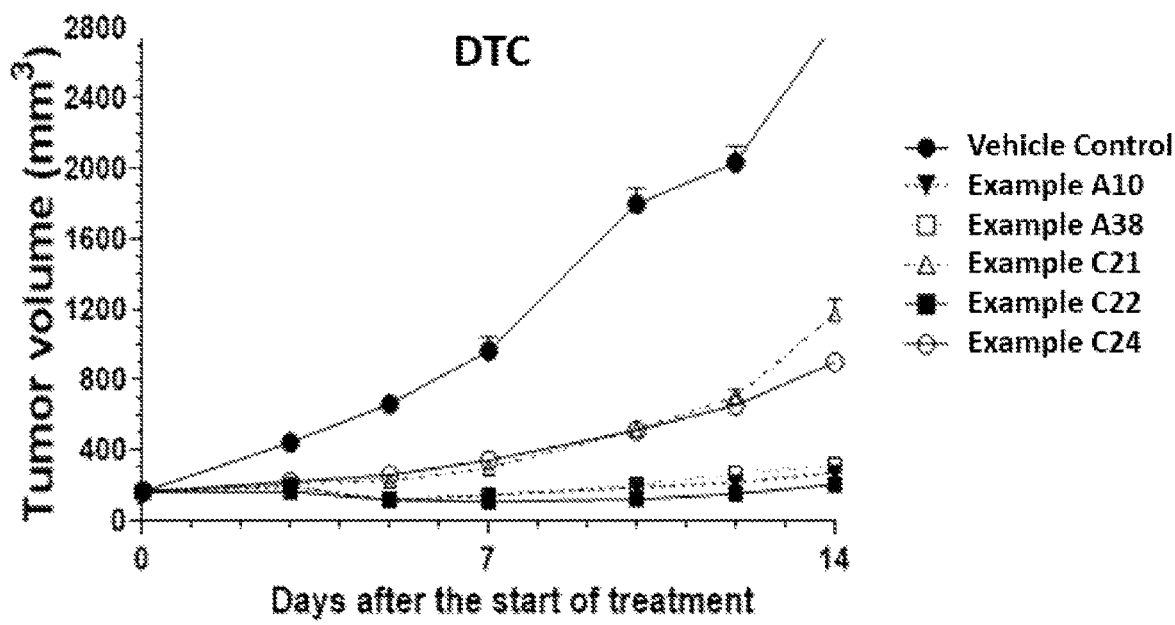
Figure 5A:
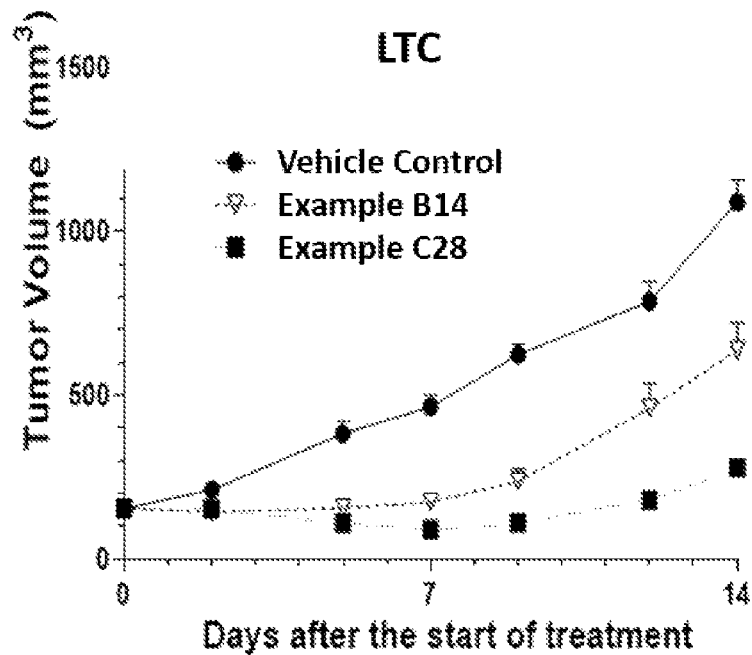
Figure 5B:
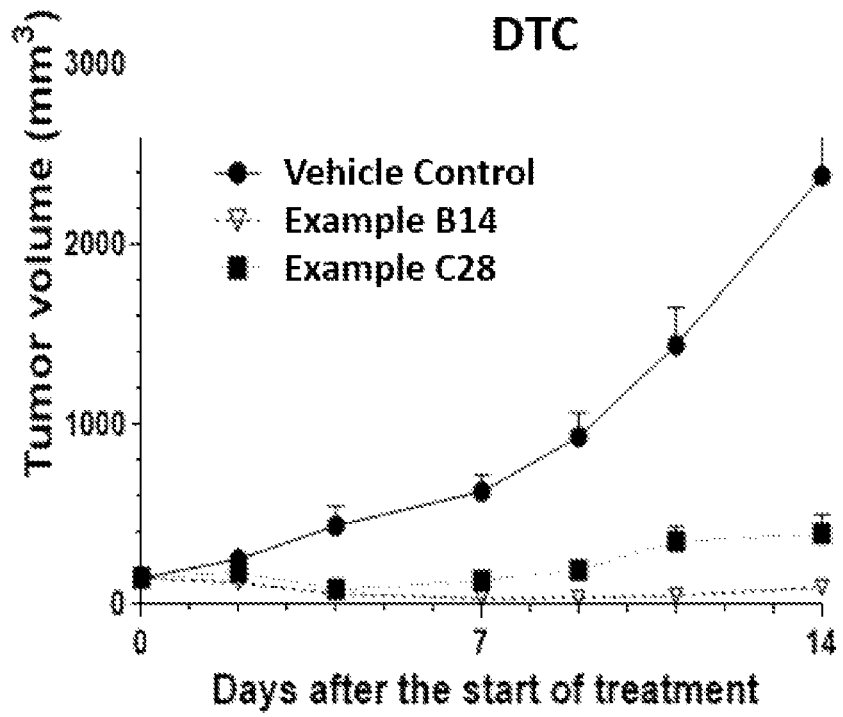

FIG. 1A and FIG. 1B show tumor growth curves of different treatment groups of female BALB/c nude mice bearing Ba/F3 EGFR L/T/C murine pro-B cell tumor models (FIG. 1A) and Ba/F3 EGFR D/T/C murine pro-B cell tumor models (FIG. 1B). Data points represent group mean, error bars represent standard error of the mean (SEM).

FIGS. 2A-5B show tumor growth curves of different treatment groups of female NOD-SCID mice bearing Ba/F3

TABLE 6

Description of experimental design

| Study set | Treatment group | n/Group | Dose (mg/kg) | Dosing Route | Schedule** |
|---|---|---|---|---|---|
| Set A | Vehicle Control *, Reference Compound ***, Example A2, A1, A4, A6, B7, A19, C2, A23 | 5 | 30 | p.o. | QD × 14 days |
| Set B | Vehicle Control, Reference Compound, Example B12, B13, A28, B14, A29 | 5 | 30 | p.o. | QD × 14-19 days |
| Set C | Vehicle Control, Reference Compound, Example C14, C15, C16, C17, C7, C10 | 5 | 30 | p.o. | QD × 13-14 days |
| Set D | Vehicle Control, Example A10, A38, C21, C22, C24 | 5 | 15 | p.o. | QD × 14-15 days |
| Set E | Vehicle Control, Example C28, B14 | 5 | 15 | p.o. | QD × 15 days |

In Table 6 above,
*: Vehicle control administered 10 µL/g of 5% DMSO, 20% PEG400, and 75% pH4.0 citrate buffer.
**QD = every day
***: Reference Compound: N-(2-((5-chloro-2-((2-methoxy-4-(4-(4-methylpiperazin-1-yl)piperidin-1-yl)phenyl)amino)pyrimidin-4-yl)amino)phenyl)methanesulfonamide After inoculation, the animals were checked daily for morbidity and mortality. At the time of routine monitoring, the animals were checked for any effects of tumor growth and treatments on normal behavior such as mobility, food and water consumption, body weight gain/loss (body weights was measured 3 times weekly), eye/hair matting and any other abnormal effect. Death and observed clinical signs were recorded based on the numbers of animals within each subset.

The major endpoint was to observe the tumor growth inhibition or complete remission of the inoculated tumor. Tumor sizes were measured 3 times weekly in two dimensions using a caliper, and the volume was expressed in $mm^3$ EGFR L/T/C murine pro-B cell established tumors (LTC) and mice bearing Ba/F3 EGFR D/T/C murine pro-B cell tumor models (DTC). Data points represent group mean, error bars represent standard error of the mean (SEM).

As shown in FIGS. 1A-5B, some candidates represented by Formula 1 showed potent inhibition against Ba/F3 EGFR L858R/T790M/C797S and Ba/F3 EGFR Del19/T790M/C797S murine pro-B cell tumor models of female BALB/c nude mice or NOD-SCID mice.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A compound selected from the following Compounds C1 through C32:

Example C1

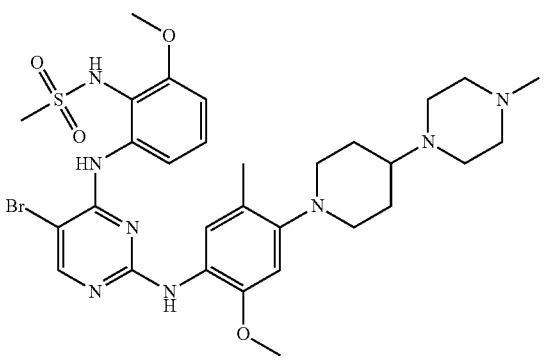

Example C2

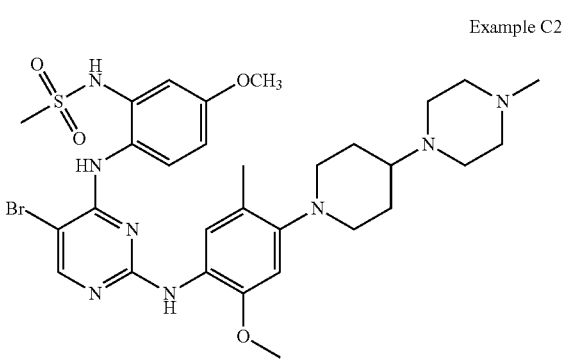

Example C3

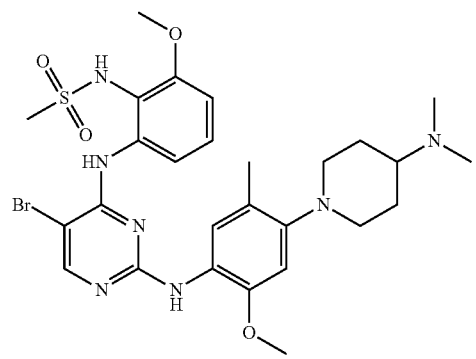

Example C4

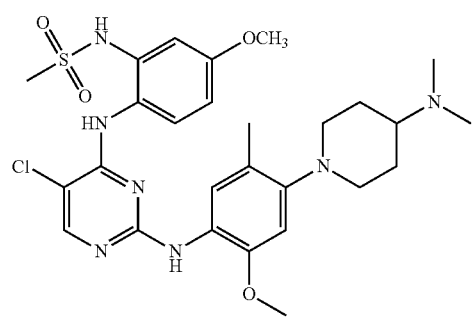

Example C5

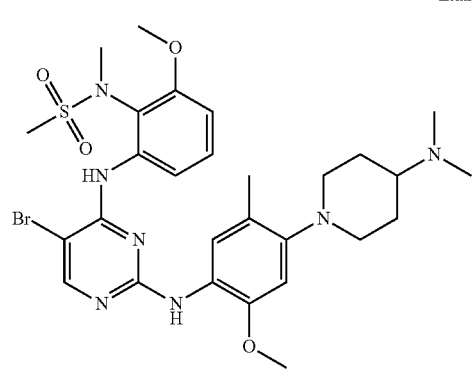

Example C6

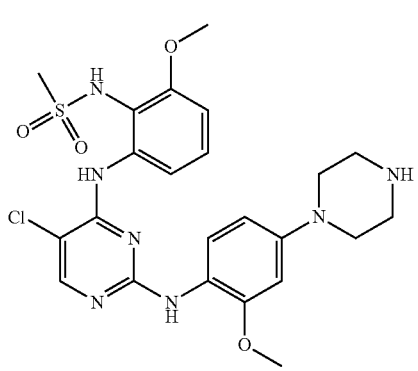

Example C7
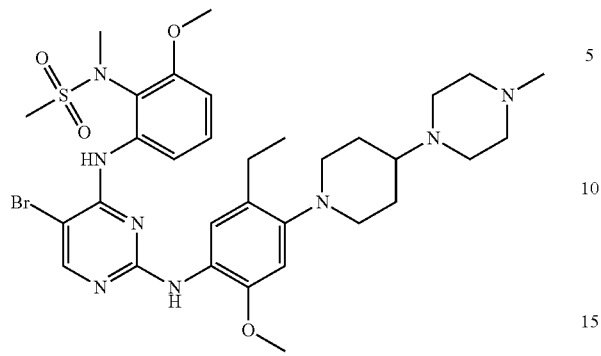
Example C11
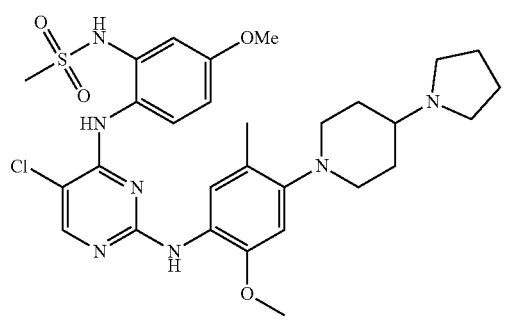
Example C8
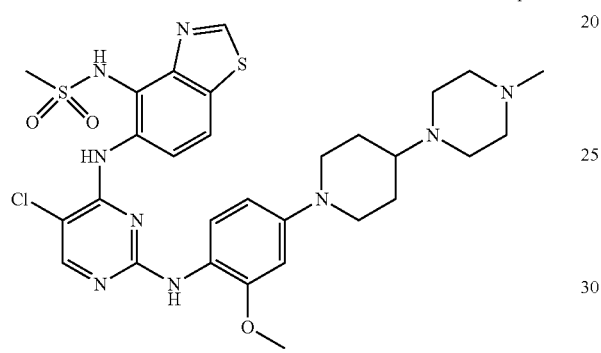
Example C12
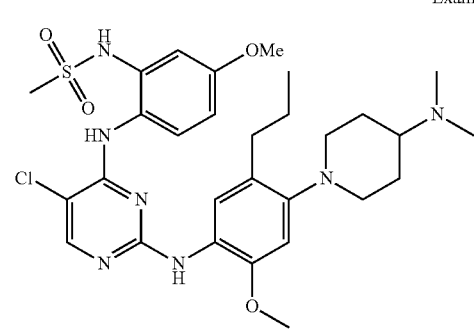
Example C9
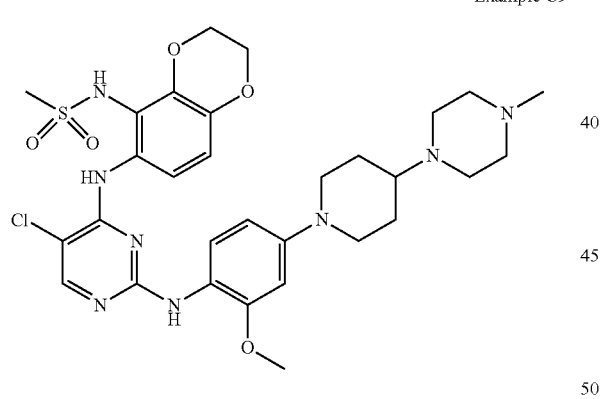
Example C13
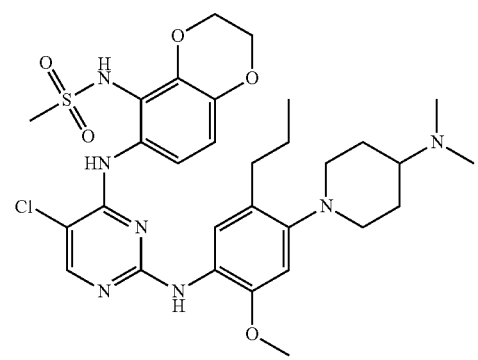
Example C10
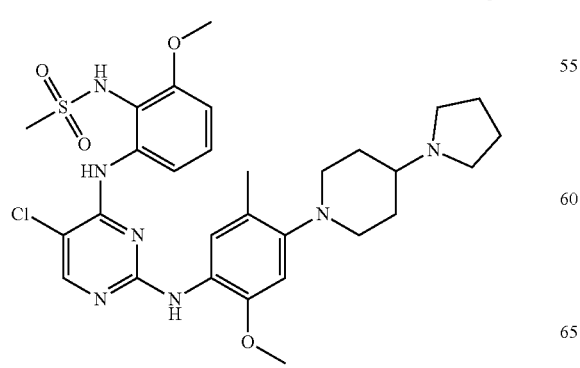
Example C14
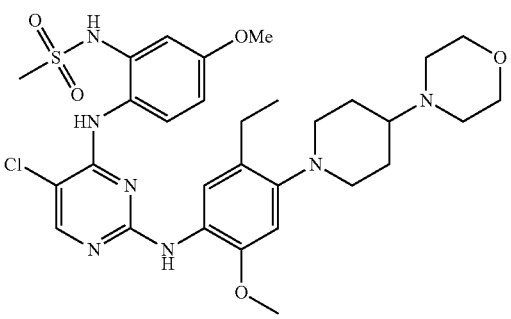

Example C15
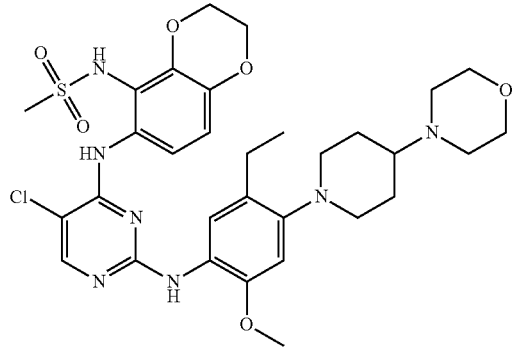
Example C16
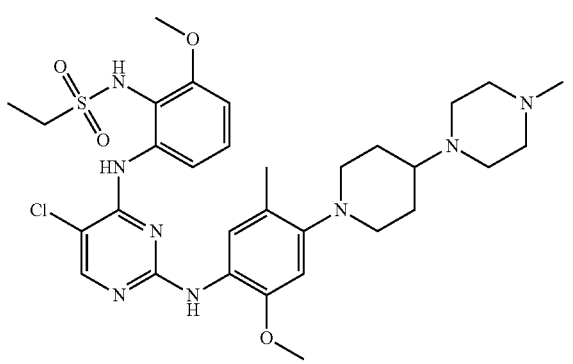
Example C17
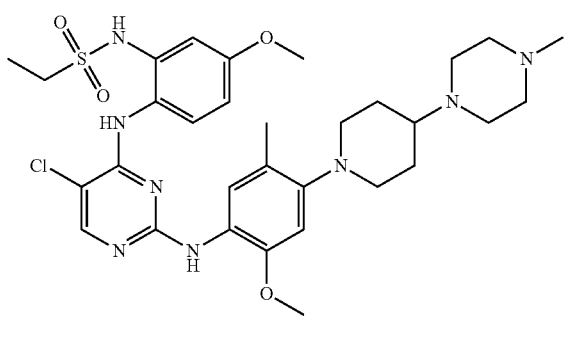
Example C18
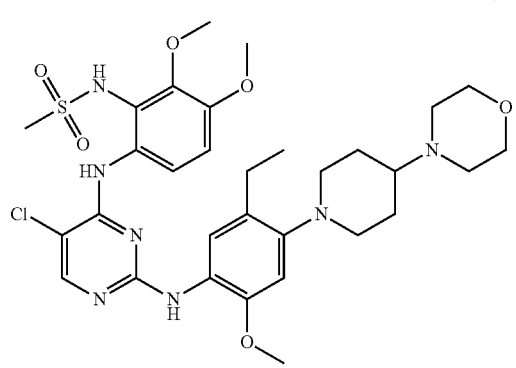
Example C19
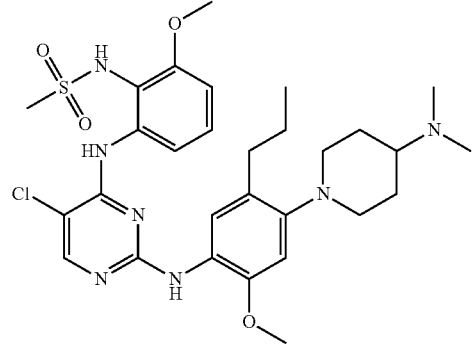
Example C20
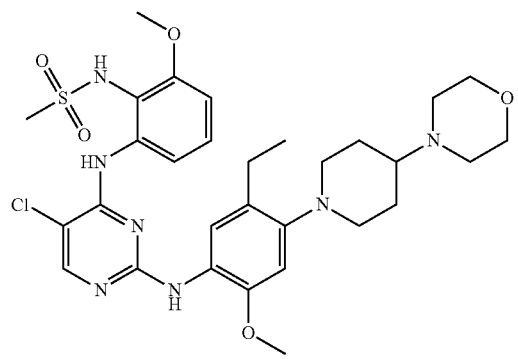
Example C21
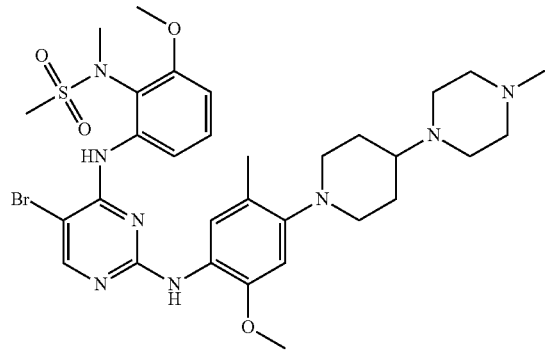
Example C22
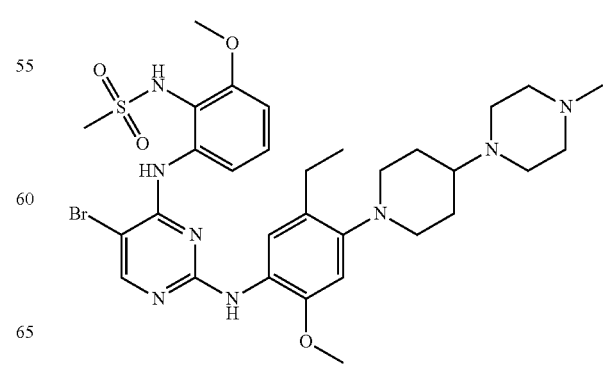

Example C23
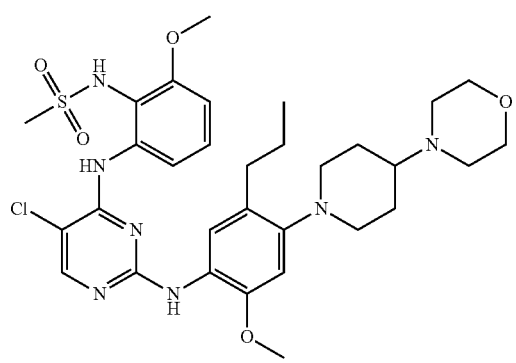
Example C27
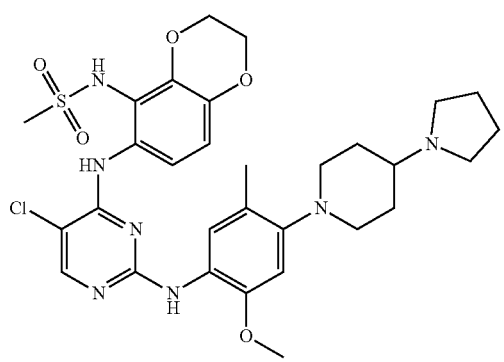
Example C24
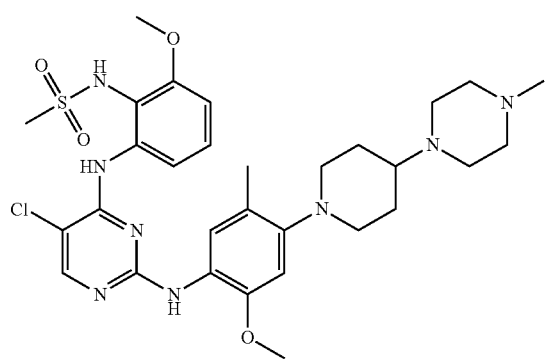
Example C28
Example C25
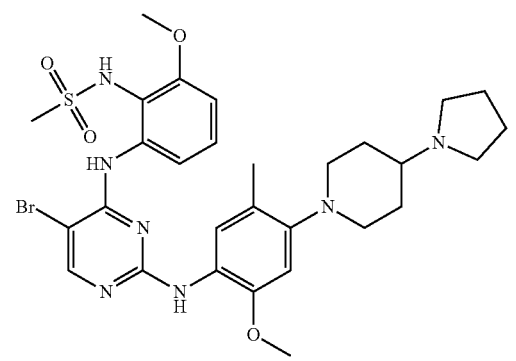
Example C29
Example C26
Example C30
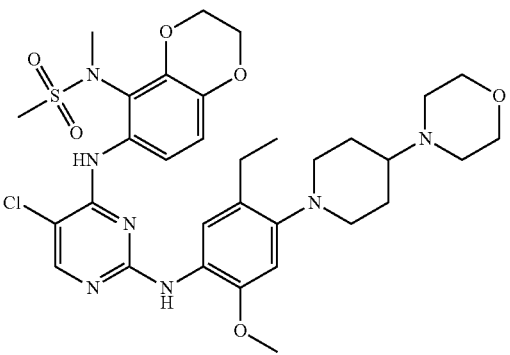

-continued

Example C31

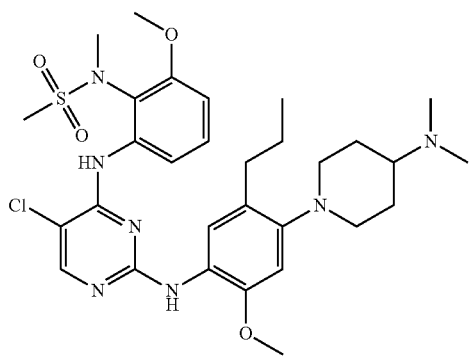

Example C32

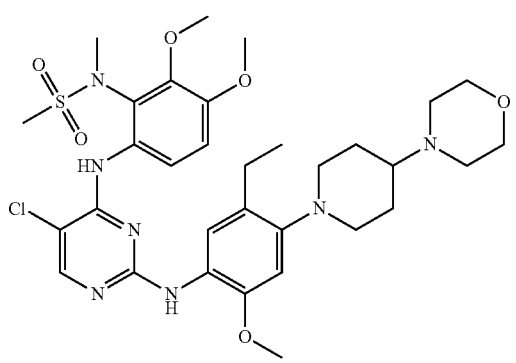

a prodrug thereof, a hydrate thereof, a solvate thereof, a stereoisomer thereof, an isotope labeled thereof, or a pharmaceutically acceptable salt thereof.

2. A composition comprising the compound, a prodrug thereof, a hydrate thereof, a solvate thereof, a stereoisomer thereof, an isotope labeled thereof, or a pharmaceutically acceptable salt thereof according to claim 1 as an active ingredient.

3. The composition according to claim 2, wherein the composition is a pharmaceutical composition and further comprises a pharmaceutically acceptable carrier.

4. A method for treating cancer in a subject in need thereof, comprising administering an effective amount of the composition of claim 2 to the subject.

5. The method according to claim 4, wherein the subject has an epidermal growth factor receptor (EGFR) mutation.

6. The method according to claim 5, wherein the EGFR mutation is one or more selected from the group consisting of EGFR L858R, EGFR L858R/T790M, EGFR L858R/C797S, L858R/T790M/C797S, EGFR Del19, EGFR Del19/T790M, EGFR Del19/C797S, and EGFR Del19/T790M/C797S.

7. The method according to claim 6, wherein the cancer is one or more selected from the group consisting of pseudomyxoma, intrahepatic cholangiocarcinoma, hepatoblastoma, liver cancer, thyroid cancer, colon cancer, testis cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian seminoma, male breast cancer, brain cancer, pituitary adenoma, multiple myeloma, gallbladder cancer, cholangiocarcinoma, colorectal cancer, chronic myeloid leukemia, chronic lymphocytic leukemia, retinoblastoma, choroidal melanoma, ampullar of vater cancer, bladder cancer, peritoneal cancer, parathyroid cancer, adrenal cancer, nasal and paranasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal tumor, Wilms' tumor, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, hematologic malignancy, and thymic cancer.

8. The method according to claim 2, further comprising administering another anticancer agent to the subject.

* * * * *